United States Patent
Keilhack et al.

(10) Patent No.: US 11,026,949 B2
(45) Date of Patent: *Jun. 8, 2021

(54) COMBINATION THERAPY FOR TREATING CANCER

(71) Applicants: Epizyme, Inc., Cambridge, MA (US); Health Research, Inc., Buffalo, NY (US)

(72) Inventors: Heike Keilhack, Belmont, MA (US); Roberto Pili, Indianapolis, IN (US)

(73) Assignees: Epizyme, Inc., Cambridge, MA (US); Health Research, Inc., Buffalo, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/562,683

(22) Filed: Sep. 6, 2019

(65) Prior Publication Data

US 2020/0101081 A1    Apr. 2, 2020

Related U.S. Application Data

(63) Continuation of application No. 15/567,838, filed as application No. PCT/US2016/028425 on Apr. 20, 2016, now Pat. No. 10,456,407.

(60) Provisional application No. 62/150,185, filed on Apr. 20, 2015.

(51) Int. Cl.
| | |
|---|---|
| *A61K 31/5377* | (2006.01) |
| *A61K 31/404* | (2006.01) |
| *A61K 31/444* | (2006.01) |
| *A61K 31/506* | (2006.01) |
| *A61K 31/517* | (2006.01) |
| *A61K 31/4412* | (2006.01) |
| *A61K 31/44* | (2006.01) |
| *A61K 45/06* | (2006.01) |
| *A61P 35/00* | (2006.01) |
| *A61K 31/496* | (2006.01) |

(52) U.S. Cl.
CPC ........ *A61K 31/5377* (2013.01); *A61K 31/404* (2013.01); *A61K 31/44* (2013.01); *A61K 31/444* (2013.01); *A61K 31/4412* (2013.01); *A61K 31/496* (2013.01); *A61K 31/506* (2013.01); *A61K 31/517* (2013.01); *A61K 45/06* (2013.01); *A61P 35/00* (2018.01)

(58) Field of Classification Search
CPC ............................ A61K 31/5377; A61P 35/00
See application file for complete search history.

(56) References Cited

U.S. PATENT DOCUMENTS

| | | | |
|---|---|---|---|
| 7,799,782 B2 | 9/2010 | Munson et al. | |
| 9,175,331 B2 | 11/2015 | Kuntz et al. | |
| 10,456,407 B2 * | 10/2019 | Keilhack | A61K 31/404 |
| 2012/0264734 A1 | 10/2012 | Kuntz et al. | |
| 2014/0378470 A1 | 12/2014 | Creasy et al. | |

FOREIGN PATENT DOCUMENTS

| | | |
|---|---|---|
| WO | WO 2012/034132 A2 | 3/2012 |
| WO | WO 2012/118812 A2 | 9/2012 |
| WO | WO 2012/142504 A1 | 10/2012 |
| WO | WO 2012/142513 A1 | 10/2012 |
| WO | WO 2013/155317 A1 | 10/2013 |
| WO | WO 2013/155464 | * 10/2013 |
| WO | WO 2013/155464 A1 | 10/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/100646 A1 | 6/2014 |
| WO | WO 2014/100665 A1 | 6/2014 |
| WO | WO 2014/144747 A1 | 9/2014 |
| WO | WO 2014/153030 A2 | 9/2014 |
| WO | WO 2014/168975 A1 | 10/2014 |
| WO | WO 2014/172044 A1 | 10/2014 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/085325 A1 | 6/2015 |
| WO | WO 2015/195848 A1 | 12/2015 |
| WO | WO 2015/200650 A9 | 12/2015 |
| WO | WO 2016/061507 A1 | 4/2016 |
| WO | WO 2016/081523 A1 | 5/2016 |

OTHER PUBLICATIONS

Hutson's CAS: 150: 437451,2008.*
Gershtein et al. CAS: 159:665429, 2013.*
Adelaiye, R. et al. (Feb. 2015) "Sunitinib Dose Escalation Overcomes Transient Resistance in Clear Cell Renal Cell Carcinoma and Is Associated with Epigenetic Modifications" *Molecular Cancer Therapeutics*, 14:513-522. First published online Dec. 17, 2014.
Huston, T.E. (2008) "Sunitinib (SUTENT) for the treatment of metastatic renal cell carcinoma" *Expert Review of Anticancer Therapy*, 8(11):1723-1731 (abstract) CAPLUS [online]. Retrieved from: STN, Accession No. 2008:1334644, Document No. 150:437451, 1 page.
Gershtein et al. (2013) "Vascular endothelial growth factor as a key angiogenesis regulator and clinically valuable marker in different malignant neoplasms" *Tekhnologii Zhivykh Sistem*, 10(2):18-33 (abstract) CAPLUS [online]. Retrieved from: STN, Accession No. 2013:1487642, Document No. 159: 665429, 1 page.
Garapaty-Rao, S. et al. (Nov. 2013) "Identification of EZH2 and EZH1 Small Molecule Inhibitors with Selective Impact on Diffuse Large B Cell Lymphoma Cell Growth" *Chem Biol*, 20:1329-1339.

(Continued)

*Primary Examiner* — Rei Tsang Shiao
(74) *Attorney, Agent, or Firm* — Cooley LLP; Heidi A. Erlacher; Christine C. Pemberton

(57) ABSTRACT

The present disclosure relates to compositions comprising inhibitors of human histone methyltransferase EZH2 and one or more other therapeutic agents (such as tyrosine kinase inhibitors or VEGF/VEGFR inhibitors), particularly anticancer agents such as sunitinib, and methods of combination therapy for administering to subjects in need thereof for the treatment of cancer.

20 Claims, 22 Drawing Sheets

Specification includes a Sequence Listing.

(56) References Cited

OTHER PUBLICATIONS

Knutson, S.K. et al. (2012) "A Selective Inhibitor of EZH2 Blocks H3K27 Methylation and Kills Mutant Lymphoma Cells" *Nat Chem Biol*, 8:890-896.
Qi, W. et al. (2012) "Selective inhibition of Ezh2 by a small molecule inhibitor blocks tumor cells proliferation" *Proc Natl Acad Sci USA*, vol. 109, No. 52, p. 21360-21365.
Varambally, S. et at (2002) "The Polycomb Group Protein EZH2 Is Involved in Progression of Prostate Cancer" *Nature*, 419:624-629.

* cited by examiner

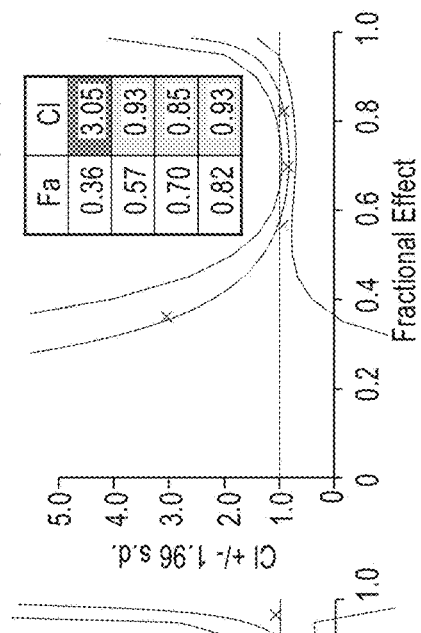
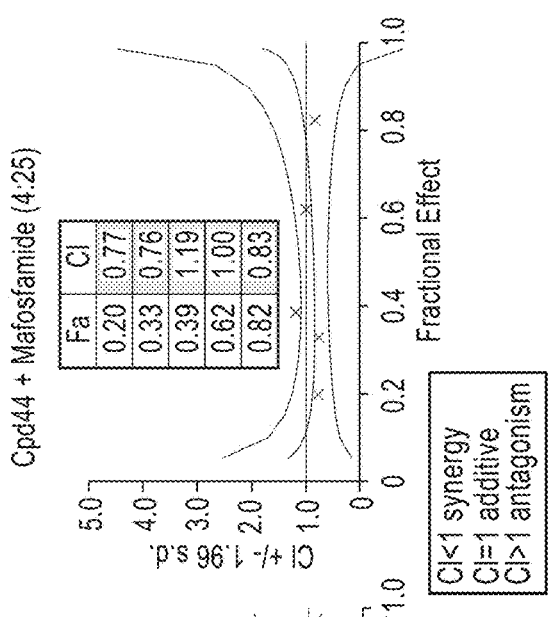
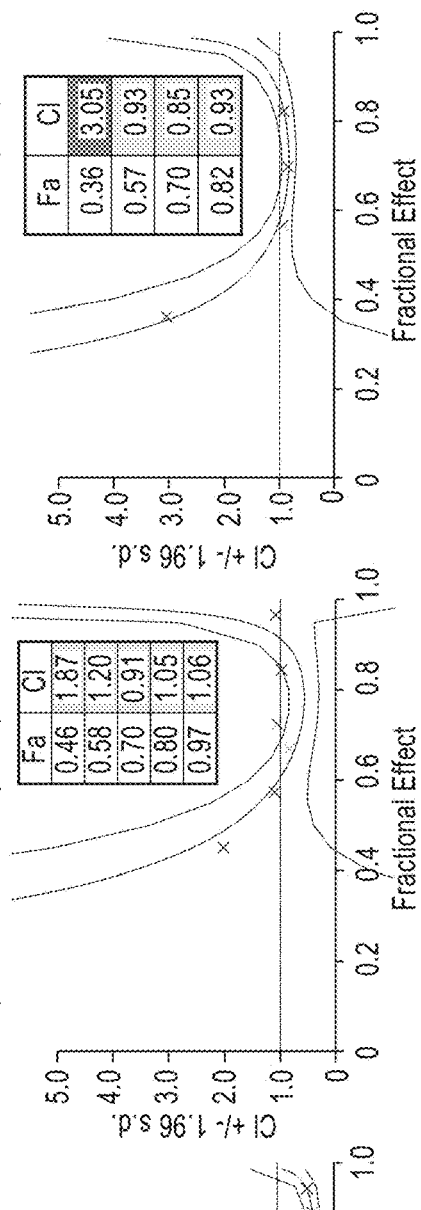
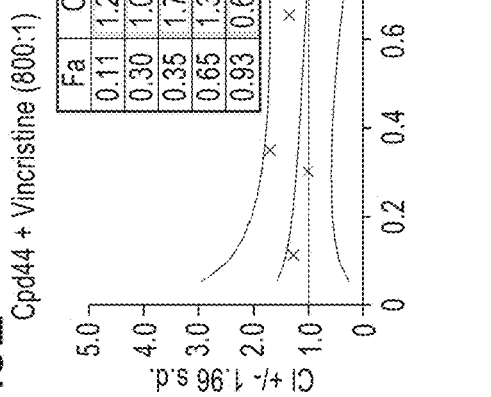
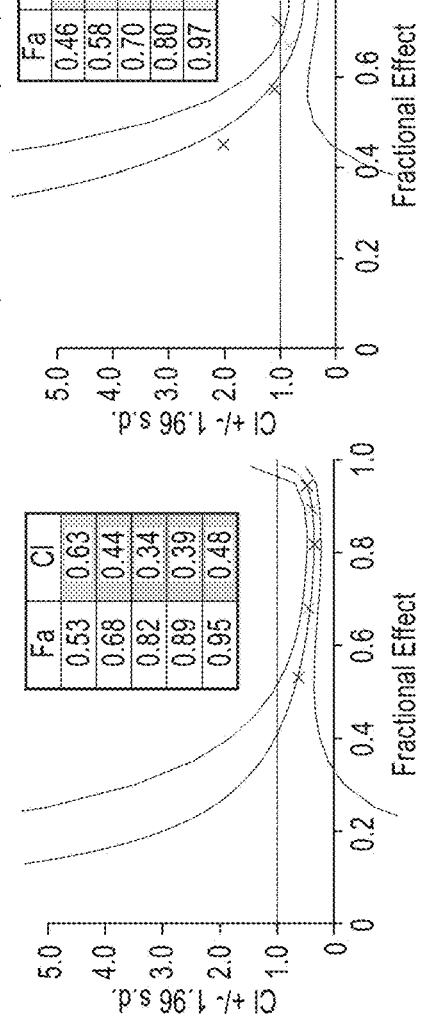
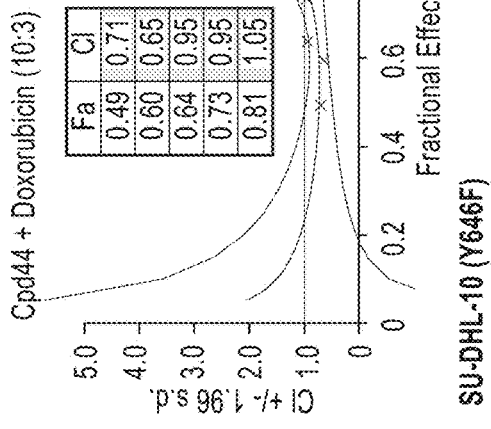

WSU-DLCL2 (Y646F)

Cpd44 + Prednisolone

Cpd44 + Dexamethasone

SU-DHL-10 (Y646F)

Cpd44 + Prednisolone

Cpd44 + Dexamethasone

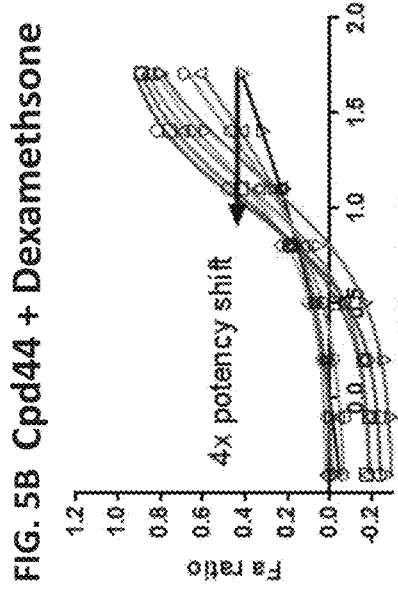
FIG. 5A Cpd44+ Prednisolone
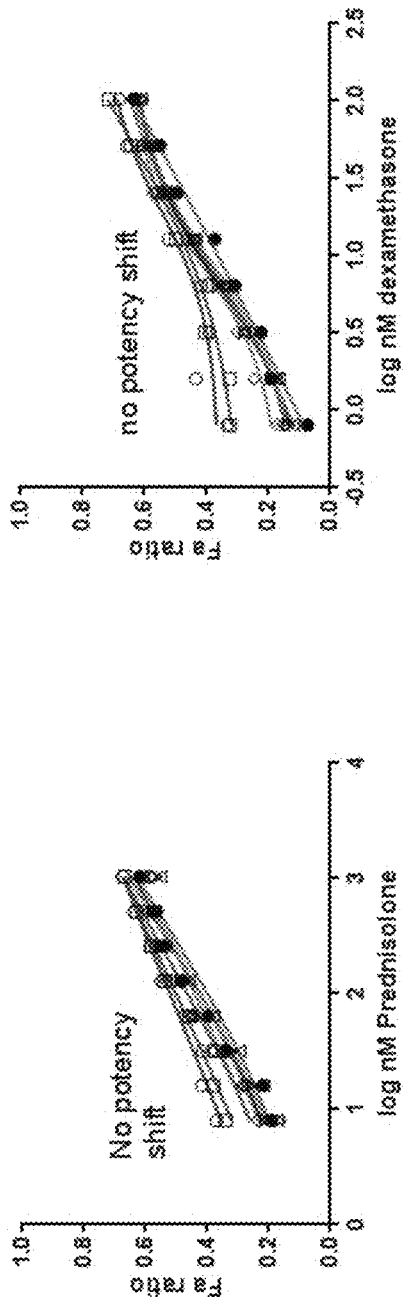
FIG. 5B Cpd44 + Dexamethsone
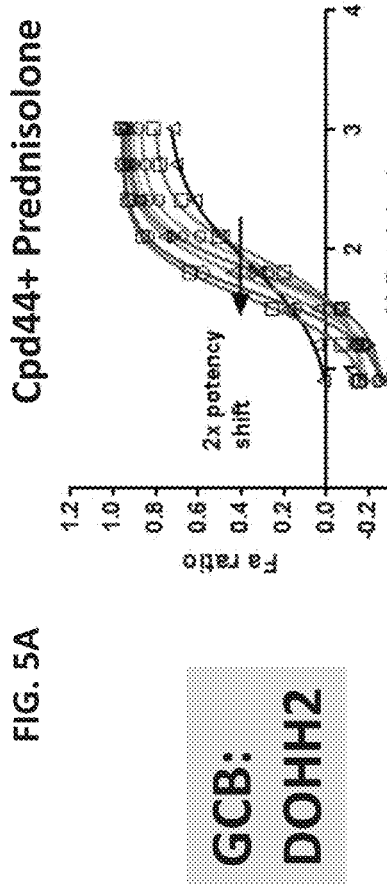
FIG. 5C Cpd44 + Prednisolone
FIG. 5D Cpd44 + Dexamethasone
GCB: DOHH2
ABC: Toledo

| Cell Line | 4 Day Cpd44 IC$_{50}$ (uM) | | 7 Day Cpd44 IC$_{50}$ (uM) | | |
|---|---|---|---|---|---|
| | Cpd44 Alone | Cpd44 Co-treatment | 4d Cpd44 Pre/ 3d Co-treat | 4d Pred Pre/ 3d Co-treat | 7d Co-treatment |
| WSU (Y646-Sens) | 0.53 +/- 0.014 | 0.020 +/- 0.021 | 0.011 +/- 0.0062 | >1 | 0.014 +/- 0.0049 |
| SU-DHL10 (Y646-Sens) | 0.64 +/- 0.26 | 0.0092 +/- 0.0044 | 0.0027 +/- 0.0013 | 0.52, >1 | 0.020 +/- 0.0057 |
| RL (Y646-Res) | >1 | 0.0096 +/- 0.0066 | <<0.004 | 0.38 | <0.004 |
| SU-DHL4 (Y646-Res) | >1 | >1, 0.2, >1 | 0.035 +/- 0.043 | >1 | 0.51 +/- 0.35 |
| DOHH2 (WT) | >1 | 0.20 +/- 0.25 | >1, 0.03, >1 | >1 | 0.34 +/- 0.078 |
| OCI-Ly19 (WT) | >1 | 0.19 +/- 0.11 | 0.0055 +/- 0.0047 | >1 | 0.026, <0.004 |

FIG. 6

| | | WSU-DLCL2 (EZH2 mutant GCB) | SU-DHL-10 (EZH2 mutant GCB) | Toledo (WT EZH2 ABC) | DOHH2 (WT EZH2 GCB) |
|---|---|---|---|---|---|
| Standard of Care DLBCL | Prednisolone | 7x potency enhancement | 2x potency enhancement | no effect | 2x potency enhancement |
| | Doxorubicin | synergy | additive | no effect | no effect |
| | Mafosfamide | additive | additive | no effect | no effect |
| | Vincristine | additive | additive | no effect | no effect |
| | Cisplatin | synergy | additive | no effect | no effect |
| | AraC | synergy | additive | no effect | no effect |
| | Vorinostat | additive | additive | no effect | no effect |
| Epigenetic Drugs | Panobinostat* | additive | Not tested | Not tested | Not tested |
| | Azacytadine* | additive | Not tested | Not tested | Not tested |
| | Everolimus | very strong synergy | strong synergy | no effect | no effect |
| Other Therapies | Dexamethasone | 15x potency enhancement | 5x potency enhancement | no effect | 4x potency enhancement |
| | Navitoclax | very strong synergy | 2x potency enhancement | Not tested | No effect |
| | Obatoclax | additive | additive | No effect | No effect |

CI < 1 synergy
CI = 1 additive
CI > 1 antagonism

No effect = No change in drug IC$_{50}$ upon addition of Cpd44.
* Experiments were performed with EZH2i tool compound instead of Cpd44.

FIG. 8

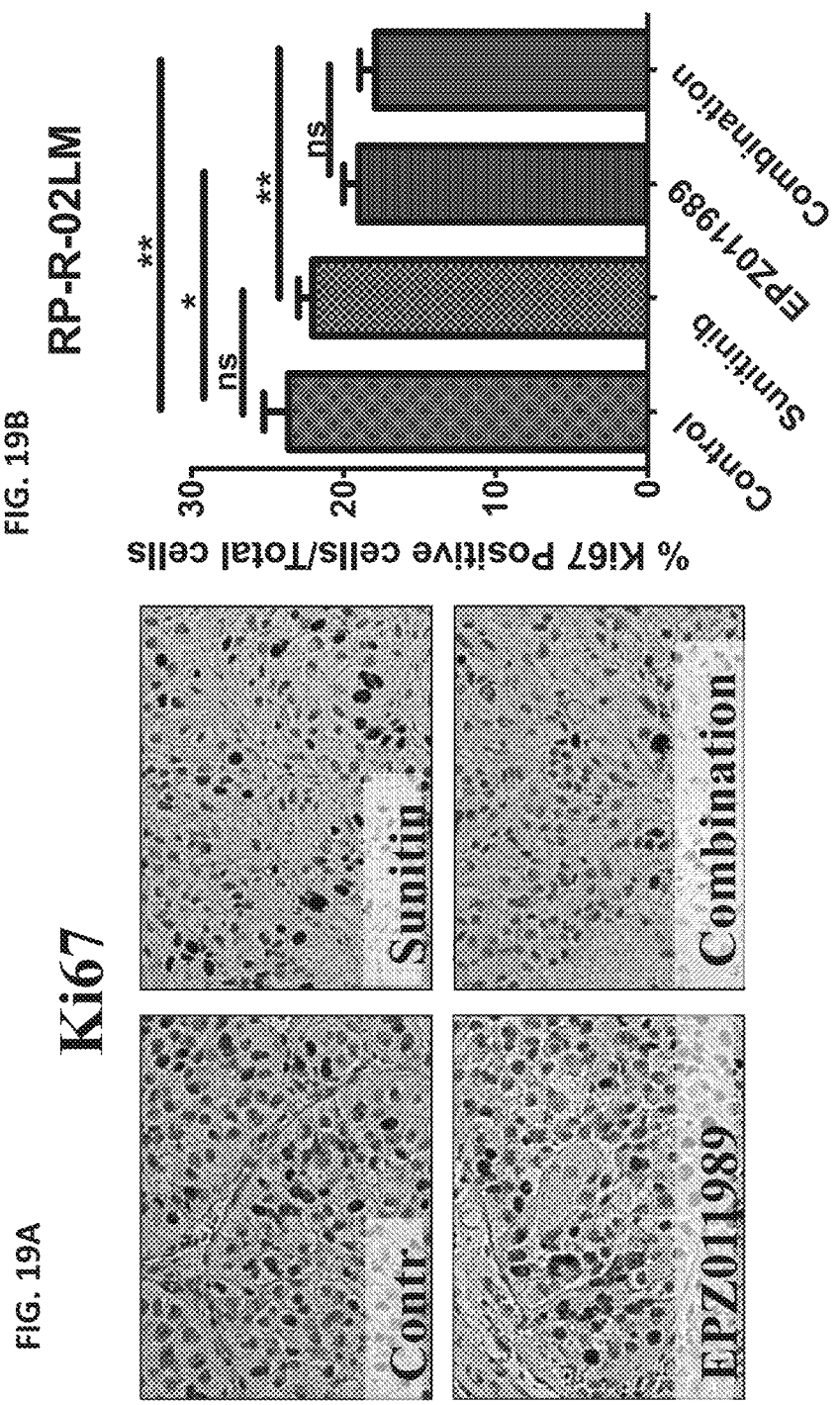

SEQUENCE LISTING

<160> NUMBER OF SEQ ID NOS: 12

<210> SEQ ID NO 1
<211> LENGTH: 746
<212> TYPE: PRT
<213> ORGANISM: Homo sapiens

<400> SEQUENCE: 1

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
```

```
                50             55              60
Ile Gln Pro Val His Ile Leu Thr Ser Val Ser Ser Leu Arg Gly Thr
 65                  70                  75                  80

Arg Glu Cys Ser Val Thr Ser Asp Leu Asp Phe Pro Thr Gln Val Ile
                 85                  90                  95

Pro Leu Lys Thr Leu Asn Ala Val Ala Ser Val Pro Ile Met Tyr Ser
                100                 105                 110

Trp Ser Pro Leu Gln Gln Asn Phe Met Val Glu Asp Glu Thr Val Leu
                115                 120                 125

His Asn Ile Pro Tyr Met Gly Asp Glu Val Leu Asp Gln Asp Gly Thr
                130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
                180                 185                 190

Pro Glu Glu Arg Glu Glu Lys Gln Lys Asp Leu Glu Asp His Arg Asp
                195                 200                 205

Asp Lys Glu Ser Arg Pro Pro Arg Lys Phe Pro Ser Asp Lys Ile Phe
                210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
                260                 265                 270

Gln Arg Glu Gln Ser Leu His Ser Phe His Thr Leu Phe Cys Arg Arg
                275                 280                 285

Cys Phe Lys Tyr Asp Cys Phe Leu His Pro Phe His Ala Thr Pro Asn
                290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
                325                 330                 335

Ala Leu Thr Ala Glu Arg Ile Lys Thr Pro Pro Lys Arg Pro Gly Gly
                340                 345                 350

Arg Arg Arg Gly Arg Leu Pro Asn Asn Ser Ser Arg Pro Ser Thr Pro
                355                 360                 365

Thr Ile Asn Val Leu Glu Ser Lys Asp Thr Asp Ser Asp Arg Glu Ala
                370                 375                 380

Gly Thr Glu Thr Gly Gly Glu Asn Asn Asp Lys Glu Glu Glu Glu Lys
385                 390                 395                 400

Lys Asp Glu Thr Ser Ser Ser Glu Ala Asn Ser Arg Cys Gln Thr
                405                 410                 415

Pro Ile Lys Met Lys Pro Asn Ile Glu Pro Pro Glu Asn Val Glu Trp
                420                 425                 430

Ser Gly Ala Glu Ala Ser Met Phe Arg Val Leu Ile Gly Thr Tyr Tyr
                435                 440                 445

Asp Asn Phe Cys Ala Ile Ala Arg Leu Ile Gly Thr Lys Thr Cys Arg
                450                 455                 460

Gln Val Tyr Glu Phe Arg Val Lys Glu Ser Ser Ile Ile Ala Pro Ala
465                 470                 475                 480
```

```
Pro Ala Glu Asp Val Asp Thr Pro Arg Lys Lys Arg Lys His
            485                 490                 495

Arg Leu Trp Ala Ala His Cys Arg Lys Ile Gln Leu Lys Lys Asp Gly
        500                 505                 510

Ser Ser Asn His Val Tyr Asn Tyr Gln Pro Cys Asp His Pro Arg Gln
            515                 520                 525

Pro Cys Asp Ser Ser Cys Pro Cys Val Ile Ala Gln Asn Phe Cys Glu
        530                 535                 540

Lys Phe Cys Gln Cys Ser Ser Glu Cys Gln Asn Arg Phe Pro Gly Cys
545                 550                 555                 560

Arg Cys Lys Ala Gln Cys Asn Thr Lys Gln Cys Pro Cys Tyr Leu Ala
            565                 570                 575

Val Arg Glu Cys Asp Pro Asp Leu Cys Leu Thr Cys Gly Ala Ala Asp
        580                 585                 590

His Trp Asp Ser Lys Asn Val Ser Cys Lys Asn Cys Ser Ile Gln Arg
        595                 600                 605

Gly Ser Lys Lys His Leu Leu Leu Ala Pro Ser Asp Val Ala Gly Trp
        610                 615                 620

Gly Ile Phe Ile Lys Asp Pro Val Gln Lys Asn Glu Phe Ile Ser Glu
625                 630                 635                 640

Tyr Cys Gly Glu Ile Ile Ser Gln Asp Glu Ala Asp Arg Arg Gly Lys
            645                 650                 655

Val Tyr Asp Lys Tyr Met Cys Ser Phe Leu Phe Asn Leu Asn Asn Asp
            660                 665                 670

Phe Val Val Asp Ala Thr Arg Lys Gly Asn Lys Ile Arg Phe Ala Asn
        675                 680                 685

His Ser Val Asn Pro Asn Cys Tyr Ala Lys Val Met Met Val Asn Gly
        690                 695                 700

Asp His Arg Ile Gly Ile Phe Ala Lys Arg Ala Ile Gln Thr Gly Glu
705                 710                 715                 720

Glu Leu Phe Phe Asp Tyr Arg Tyr Ser Gln Ala Asp Ala Leu Lys Tyr
                725                 730                 735

Val Gly Ile Glu Arg Glu Met Glu Ile Pro
            740                 745

<210> SEQ ID NO 2
<211> LENGTH: 2723
<212> TYPE: DNA
<213> ORGANISM: Homo sapiens

<400> SEQUENCE: 2
ggcggcgctt gattgggctg gggggggccaa ataaaagcga tggcgattgg gctgccgcgt      60
ttggcgctcg gtccggtcgc gtccgacacc cggtgggact cagaaggcag tggagccccg     120
gcggcggcgg cggcggcgcg cggggggcgac gcgcgggaac aacgcgagtc ggcgcgcggg     180
acgaagaata atcatgggcc agactgggaa gaaatctgag aagggaccag tttgttggcg     240
gaagcgtgta aaatcagagt acatgcgact gagacagctc aagaggttca gacgagctga     300
tgaagtaaag agtatgttta gttccaatcg tcagaaaatt ttggaaagaa cggaaatctt     360
aaaccaagaa tggaaacagc gaaggataca gcctgtgcac atcctgactt ctgtgagctc     420
attgcgcggg actagggagt gttcggtgac cagtgacttg gatttttccaa cacaagtcat     480 cccattaaag actctgaatg cagttgcttc agtaccccata atgtattctt ggtctcccct     540
acagcagaat tttatggtgg aagatgaaac tgttttacat aacattcctt atatgggaga     600
```

```
tgaagttttta gatcaggatg gtactttcat tgaagaacta ataaaaaatt atgatgggaa      660
agtacacggg gatagagaat gtgggtttat aaatgatgaa atttttgtgg agttggtgaa      720
tgcccttggt caatataatg atgatgacga tgatgatgat ggagacgatc ctgaagaaag      780
agaagaaaag cagaaagatc tggaggatca ccgagatgat aaagaaagcc gcccacctcg      840
gaaatttcct tctgataaaa ttttttgaagc catttcctca atgtttccag ataagggcac      900
agcagaagaa ctaaaggaaa aatataaaga actcaccgaa cagcagctcc caggcgcact      960
tcctcctgaa tgtaccccca acatagatgg accaaatgct aaatctgttc agagagagca     1020
aagcttacac tcctttcata cgcttttctg taggcgatgt tttaaatatg actgcttcct     1080
acatcgtaag tgcaattatt cttttcatgc aacacccaac acttataagc ggaagaacac     1140
agaaacagct ctagacaaca aaccttgtgg accacagtgt taccagcatt tggagggagc     1200
aaaggagttt gctgctgctc tcaccgctga gcggataaag accccaccaa aacgtccagg     1260
aggccgcaga agaggacggc ttcccaataa cagtagcagg cccagcaccc ccaccattaa     1320
tgtgctggaa tcaaaggata cagacagtga tagggaagca gggactgaaa cggggggaga     1380
gaacaatgat aaagaagaag aagagaagaa agatgaaact tcgagctcct ctgaagcaaa     1440
ttctcggtgt caaacaccaa taaagatgaa gccaaatatt gaacctcctg agaatgtgga     1500
gtggagtggt gctgaagcct caatgtttag agtcctcatt ggcacttact atgacaattt     1560
ctgtgccatt gctaggttaa ttgggaccaa acatgtaga caggtgtatg agtttagagt     1620
caaagaatct agcatcatag ctccagctcc cgctgaggat gtggatactc ctccaaggaa     1680
aaagaagagg aaacaccggt tgtgggctgc acactgcaga aagatacagc tgaaaaagga     1740
cggctcctct aaccatgttt acaactatca accctgtgat catccacggc agccttgtga     1800
cagttcgtgc ccttgtgtga tagcacaaaa ttttttgtgaa aagttttgtc aatgtagttc     1860
agagtgtcaa aaccgctttc cgggatgccg ctgcaaagca cagtgcaaca ccaagcagtg     1920
cccgtgctac ctggctgtcc gagagtgtga ccctgacctc tgtcttactt gtggagccgc     1980
tgaccattgg gacagtaaaa atgtgtcctg caagaactgc agtattcagc ggggctccaa     2040
aaagcatcta ttgctggcac catctgacgt ggcaggctgg gggattttta tcaaagatcc     2100
tgtgcagaaa aatgaattca tctcagaata ctgtggagag attatttctc aagatgaagc     2160
tgacagaaga gggaaagtgt atgataaata catgtgcagc tttctgttca acttgaacaa     2220
tgattttgtg gtggatgcaa cccgcaaggg taacaaaatt cgttttgcaa atcattcggt     2280
aaatccaaac tgctatgcaa aagttatgat ggttaacggt gatcacagga taggtatttt     2340
tgccaagaga gccatccaga ctggcgaaga gctgttttt gattacagat acagccaggc     2400
tgatgccctg aagtatgtcg gcatcgaaag agaaatggaa atcccttgac atctgctacc     2460 tcctccccc tcctctgaaa cagctgcctt agcttcagga acctcgagta ctgtgggcaa     2520
tttagaaaaa gaacatgcag tttgaaattc tgaatttgca aagtactgta agaataattt     2580
atagtaatga gtttaaaaat caacttttta ttgccttctc accagctgca aagtgttttg     2640
taccagtgaa tttttgcaat aatgcagtat ggtacatttt tcaactttga ataaagaata     2700
cttgaacttg tccttgttga atc                                             2723
```

<210> SEQ ID NO 3
<211> LENGTH: 751
<212> TYPE: PRT
<213> ORGANISM: Homo sapiens

```
<400> SEQUENCE: 3

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Gly Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Arg Lys Cys Asn Tyr Ser Phe
290                 295                 300

His Ala Thr Pro Asn Thr Tyr Lys Arg Lys Asn Thr Glu Thr Ala Leu
305                 310                 315                 320

Asp Asn Lys Pro Cys Gly Pro Gln Cys Tyr Gln His Leu Glu Gly Ala
                325                 330                 335

Lys Glu Phe Ala Ala Ala Leu Thr Ala Glu Arg Ile Lys Thr Pro Pro
            340                 345                 350

Lys Arg Pro Gly Gly Arg Arg Gly Arg Leu Pro Asn Asn Ser Ser
        355                 360                 365

Arg Pro Ser Thr Pro Thr Ile Asn Val Leu Glu Ser Lys Asp Thr Asp
370                 375                 380

Ser Asp Arg Glu Ala Gly Thr Glu Thr Gly Gly Glu Asn Asn Asp Lys
385                 390                 395                 400

Glu Glu Glu Glu Lys Lys Asp Glu Thr Ser Ser Ser Glu Ala Asn
                405                 410                 415
```

```
Ser Arg Cys Gln Thr Pro Ile Lys Met Lys Pro Asn Ile Glu Pro Pro
            420                 425                 430

Glu Asn Val Glu Trp Ser Gly Ala Glu Ala Ser Met Phe Arg Val Leu
        435                 440                 445

Ile Gly Thr Tyr Tyr Asp Asn Phe Cys Ala Ile Ala Arg Leu Ile Gly
    450                 455                 460

Thr Lys Thr Cys Arg Gln Val Tyr Glu Phe Arg Val Lys Glu Ser Ser
465                 470                 475                 480

Ile Ile Ala Pro Ala Pro Ala Glu Asp Val Asp Thr Pro Pro Arg Lys
                485                 490                 495

Lys Lys Arg Lys His Arg Leu Trp Ala Ala His Cys Arg Lys Ile Gln
            500                 505                 510

Leu Lys Lys Asp Gly Ser Ser Asn His Val Tyr Asn Tyr Gln Pro Cys
        515                 520                 525

Asp His Pro Arg Gln Pro Cys Asp Ser Ser Cys Pro Cys Val Ile Ala
    530                 535                 540

Gln Asn Phe Cys Glu Lys Phe Cys Gln Cys Ser Ser Glu Cys Gln Asn
545                 550                 555                 560

Arg Phe Pro Gly Cys Arg Cys Lys Ala Gln Cys Asn Thr Lys Gln Cys
                565                 570                 575

Pro Cys Tyr Leu Ala Val Arg Glu Cys Asp Pro Asp Leu Cys Leu Thr
            580                 585                 590

Cys Gly Ala Ala Asp His Trp Asp Ser Lys Asn Val Ser Cys Lys Asn
        595                 600                 605

Cys Ser Ile Gln Arg Gly Ser Lys Lys His Leu Leu Leu Ala Pro Ser
    610                 615                 620

Asp Val Ala Gly Trp Gly Ile Phe Ile Lys Asp Pro Val Gln Lys Asn
625                 630                 635                 640

Glu Phe Ile Ser Glu Tyr Cys Gly Glu Ile Ile Ser Gln Asp Glu Ala
                645                 650                 655

Asp Arg Arg Gly Lys Val Tyr Asp Lys Tyr Met Cys Ser Phe Leu Phe
            660                 665                 670

Asn Leu Asn Asn Asp Phe Val Val Asp Ala Thr Arg Lys Gly Asn Lys
        675                 680                 685

Ile Arg Phe Ala Asn His Ser Val Asn Pro Asn Cys Tyr Ala Lys Val
    690                 695                 700

Met Met Val Asn Gly Asp His Arg Ile Gly Ile Phe Ala Lys Arg Ala
705                 710                 715                 720

Ile Gln Thr Gly Glu Glu Leu Phe Phe Asp Tyr Arg Tyr Ser Gln Ala
                725                 730                 735

Asp Ala Leu Lys Tyr Val Gly Ile Glu Arg Glu Met Glu Ile Pro
            740                 745                 750

<210> SEQ ID NO 4
<211> LENGTH: 2591
<212> TYPE: DNA
<213> ORGANISM: Homo sapiens

<400> SEQUENCE: 4
ggcggcgctt gattgggctg gggggggccaa ataaaagcga tggcgattgg gctgccgcgt      60
ttggcgctcg gtccggtcgc gtccgacacc cggtgggact cagaaggcag tggagccccg     120
gcggcggcgg cggcggcgcg cggggggcgac gcgcgggaac aacgcgagtc ggcgcgcggg     180
acgaagaata atcatggggcc agactgggaa gaaatctgag aagggaccag tttgttggcg     240
```

```
gaagcgtgta aaatcagagt acatgcgact gagacagctc aagaggttca gacgagctga      300
tgaagtaaag agtatgttta gttccaatcg tcagaaaatt ttggaaagaa cggaaatctt      360
aaaccaagaa tggaaacagc gaaggataca gcctgtgcac atcctgactt ctgtgagctc      420
attgcgcggg actagggagg tggaagatga aactgtttta cataacattc cttatatggg      480
agatgaagtt ttagatcagg atggtacttt cattgaagaa ctaataaaaa attatgatgg      540
gaaagtacac ggggatagag aatgtgggtt tataaatgat gaattttttg tggagttggt      600
gaatgccctt ggtcaatata atgatgatga cgatgatgat gatggagacg atcctgaaga      660
aagagaagaa aagcagaaag atctggagga tcaccgagat gataaagaaa gccgcccacc      720
tcggaaattt ccttctgata aaattttttga agccatttcc tcaatgtttc cagataaggg      780
cacagcagaa gaactaaagg aaaaatataa agaactcacc gaacagcagc tcccaggcgc      840
acttcctcct gaatgtaccc ccaacataga tggaccaaat gctaaatctg ttcagagaga      900
gcaaagctta cactccttc atacgctttt ctgtaggcga tgttttaaat atgactgctt      960
cctacatcct tttcatgcaa cacccaacac ttataagcgg aagaacacag aaacagctct     1020
agacaacaaa ccttgtggac cacagtgtta ccagcatttg gagggagcaa aggagtttgc     1080
tgctgctctc accgctgagc ggataaagac cccaccaaaa cgtccaggag gccgcagaag     1140
aggacggctt cccaataaca gtagcaggcc cagcaccccc accattaatg tgctggaatc     1200
aaaggataca gacagtgata gggaagcagg gactgaaacg gggggagaga acaatgataa     1260
agaagaagaa gagaagaaag atgaaacttc gagctcctct gaagcaaatt ctcggtgtca     1320
aacaccaata aagatgaagc caaatattga acctcctgag aatgtggagt ggagtggtgc     1380
tgaagcctca atgtttagag tcctcattgg cacttactat gacaatttct gtgccattgc     1440
taggttaatt gggaccaaaa catgtagaca ggtgtatgag tttagagtca agaatctag      1500 catcatagct ccagctcccg ctgaggatgt ggatactcct ccaaggaaaa agaagaggaa     1560
acaccggttg tgggctgcac actgcagaaa gatacagctg aaaaaggacg gctcctctaa     1620
ccatgtttac aactatcaac cctgtgatca tccacggcag ccttgtgaca gttcgtgccc     1680
ttgtgtgata gcacaaaatt tttgtgaaaa gttttgtcaa tgtagttcag agtgtcaaaa     1740
ccgctttccg ggatgccgct gcaaagcaca gtgcaacacc aagcagtgcc cgtgctacct     1800
ggctgtccga gagtgtgacc ctgacctctg tcttacttgt ggagccgctg accattggga     1860
cagtaaaaat gtgtcctgca agaactgcag tattcagcgg ggctccaaaa agcatctatt     1920
gctggcacca tctgacgtgg caggctgggg attttttatc aaagatcctg tgcagaaaaa     1980
tgaattcatc tcagaatact gtggagagat tatttctcaa gatgaagctg acagaagagg     2040
gaaagtgtat gataaataca tgtgcagctt tctgttcaac ttgaacaatg atttgtggt     2100 ggatgcaacc cgcaagggta acaaaattcg ttttgcaaat cattcggtaa atccaaactg     2160
ctatgcaaaa gttatgatgg ttaacggtga tcacaggata ggtattttg ccaagagagc     2220 catccagact ggcgaagagc tgtttttga ttacagatac agccaggctg atgccctgaa     2280
gtatgtcggc atcgaaagag aaatggaaat cccttgacat ctgctacctc ctccccctc      2340 ctctgaaaca gctgccttag cttcaggaac ctcgagtact gtgggcaatt tagaaaaaga     2400
acatgcagtt tgaaattctg aatttgcaaa gtactgtaag aataatttat agtaatgagt     2460
ttaaaaatca acttttttatt gccttctcac cagctgcaaa gtgttttgta ccagtgaatt     2520
tttgcaataa tgcagtatgg tacattttc aactttgaat aaagaatact tgaacttgtc      2580
```
cttgttgaat c                                                                 2591

<210> SEQ ID NO 5
<211> LENGTH: 707
<212> TYPE: PRT
<213> ORGANISM: Homo sapiens

<400> SEQUENCE: 5

Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Val Glu Asp Glu Thr Val Leu His Asn Ile Pro Tyr Met Gly
                85                  90                  95

Asp Glu Val Leu Asp Gln Asp Gly Thr Phe Ile Glu Glu Leu Ile Lys
            100                 105                 110

Asn Tyr Asp Gly Lys Val His Gly Asp Arg Glu Cys Gly Phe Ile Asn
        115                 120                 125

Asp Glu Ile Phe Val Glu Leu Val Asn Ala Leu Gly Gln Tyr Asn Asp
    130                 135                 140

Asp Asp Asp Asp Asp Gly Asp Asp Pro Glu Glu Arg Glu Glu Lys
145                 150                 155                 160

Gln Lys Asp Leu Glu Asp His Arg Asp Asp Lys Glu Ser Arg Pro Pro
                165                 170                 175

Arg Lys Phe Pro Ser Asp Lys Ile Phe Glu Ala Ile Ser Ser Met Phe
            180                 185                 190

Pro Asp Lys Gly Thr Ala Glu Glu Leu Lys Glu Lys Tyr Lys Glu Leu
        195                 200                 205

Thr Glu Gln Gln Leu Pro Gly Ala Leu Pro Pro Glu Cys Thr Pro Asn
    210                 215                 220

Ile Asp Gly Pro Asn Ala Lys Ser Val Gln Arg Glu Gln Ser Leu His
225                 230                 235                 240

Ser Phe His Thr Leu Phe Cys Arg Arg Cys Phe Lys Tyr Asp Cys Phe
                245                 250                 255

Leu His Pro Phe His Ala Thr Pro Asn Thr Tyr Lys Arg Lys Asn Thr
            260                 265                 270

Glu Thr Ala Leu Asp Asn Lys Pro Cys Gly Pro Gln Cys Tyr Gln His
        275                 280                 285

Leu Glu Gly Ala Lys Glu Phe Ala Ala Ala Leu Thr Ala Glu Arg Ile
    290                 295                 300

Lys Thr Pro Pro Lys Arg Pro Gly Gly Arg Arg Arg Gly Arg Leu Pro
305                 310                 315                 320

Asn Asn Ser Ser Arg Pro Ser Thr Pro Thr Ile Asn Val Leu Glu Ser
                325                 330                 335

Lys Asp Thr Asp Ser Asp Arg Glu Ala Gly Thr Glu Thr Gly Gly Glu
            340                 345                 350

Asn Asn Asp Lys Glu Glu Glu Glu Lys Lys Asp Glu Thr Ser Ser Ser
        355                 360                 365

```
Ser Glu Ala Asn Ser Arg Cys Gln Thr Pro Ile Lys Met Lys Pro Asn
    370                 375                 380
Ile Glu Pro Pro Glu Asn Val Glu Trp Ser Gly Ala Glu Ala Ser Met
385                 390                 395                 400
Phe Arg Val Leu Ile Gly Thr Tyr Tyr Asp Asn Phe Cys Ala Ile Ala
                405                 410                 415
Arg Leu Ile Gly Thr Lys Thr Cys Arg Gln Val Tyr Glu Phe Arg Val
            420                 425                 430
Lys Glu Ser Ser Ile Ile Ala Pro Ala Pro Ala Glu Asp Val Asp Thr
        435                 440                 445
Pro Pro Arg Lys Lys Lys Arg Lys His Arg Leu Trp Ala Ala His Cys
450                 455                 460
Arg Lys Ile Gln Leu Lys Lys Asp Gly Ser Ser Asn His Val Tyr Asn
465                 470                 475                 480
Tyr Gln Pro Cys Asp His Pro Arg Gln Pro Cys Asp Ser Ser Cys Pro
                485                 490                 495
Cys Val Ile Ala Gln Asn Phe Cys Glu Lys Phe Cys Gln Cys Ser Ser
            500                 505                 510
Glu Cys Gln Asn Arg Phe Pro Gly Cys Arg Cys Lys Ala Gln Cys Asn
        515                 520                 525
Thr Lys Gln Cys Pro Cys Tyr Leu Ala Val Arg Glu Cys Asp Pro Asp
    530                 535                 540
Leu Cys Leu Thr Cys Gly Ala Ala Asp His Trp Asp Ser Lys Asn Val
545                 550                 555                 560
Ser Cys Lys Asn Cys Ser Ile Gln Arg Gly Ser Lys Lys His Leu Leu
                565                 570                 575
Leu Ala Pro Ser Asp Val Ala Gly Trp Gly Ile Phe Ile Lys Asp Pro
            580                 585                 590
Val Gln Lys Asn Glu Phe Ile Ser Glu Tyr Cys Gly Glu Ile Ile Ser
        595                 600                 605
Gln Asp Glu Ala Asp Arg Arg Gly Lys Val Tyr Asp Lys Tyr Met Cys
    610                 615                 620
Ser Phe Leu Phe Asn Leu Asn Asn Asp Phe Val Val Asp Ala Thr Arg
625                 630                 635                 640
Lys Gly Asn Lys Ile Arg Phe Ala Asn His Ser Val Asn Pro Asn Cys
                645                 650                 655
Tyr Ala Lys Val Met Met Val Asn Gly Asp His Arg Ile Gly Ile Phe
            660                 665                 670
Ala Lys Arg Ala Ile Gln Thr Gly Glu Glu Leu Phe Phe Asp Tyr Arg
        675                 680                 685
Tyr Ser Gln Ala Asp Ala Leu Lys Tyr Val Gly Ile Glu Arg Glu Met
    690                 695                 700
Glu Ile Pro
705

<210> SEQ ID NO 6
<211> LENGTH: 200
<212> TYPE: PRT
<213> ORGANISM: Homo sapiens

<400> SEQUENCE: 6

Ser Cys Pro Cys Val Ile Ala Gln Asn Phe Cys Glu Lys Phe Cys Gln
1               5                   10                  15
Cys Ser Ser Glu Cys Gln Asn Arg Phe Pro Gly Cys Arg Cys Lys Ala
            20                  25                  30
```

Gln Cys Asn Thr Lys Gln Cys Pro Cys Tyr Leu Ala Val Arg Glu Cys
            35                  40                  45

Asp Pro Asp Leu Cys Leu Thr Cys Gly Ala Ala His Trp Asp Ser
    50                  55                  60

Lys Asn Val Ser Cys Lys Asn Cys Ser Ile Gln Arg Gly Ser Lys Lys
65                  70                  75                  80

His Leu Leu Leu Ala Pro Ser Asp Val Ala Gly Trp Gly Ile Phe Ile
                85                  90                  95

Lys Asp Pro Val Gln Lys Asn Glu Phe Ile Ser Glu Tyr Cys Gly Glu
            100                 105                 110

Ile Ile Ser Gln Asp Glu Ala Asp Arg Arg Gly Lys Val Tyr Asp Lys
            115                 120                 125

Tyr Met Cys Ser Phe Leu Phe Asn Leu Asn Asn Asp Phe Val Val Asp
            130                 135                 140

Ala Thr Arg Lys Gly Asn Lys Ile Arg Phe Ala Asn His Ser Val Asn
145                 150                 155                 160

Pro Asn Cys Tyr Ala Lys Val Met Met Val Asn Gly Asp His Arg Ile
                165                 170                 175

Gly Ile Phe Ala Lys Arg Ala Ile Gln Thr Gly Glu Glu Leu Phe Phe
            180                 185                 190

Asp Tyr Arg Tyr Ser Gln Ala Asp
            195                 200

<210> SEQ ID NO 7
<211> LENGTH: 114
<212> TYPE: PRT
<213> ORGANISM: Homo sapiens

<400> SEQUENCE: 7

His Leu Leu Leu Ala Pro Ser Asp Val Ala Gly Trp Gly Ile Phe Ile
1               5                   10                  15

Lys Asp Pro Val Gln Lys Asn Glu Phe Ile Ser Glu Tyr Cys Gly Glu
            20                  25                  30

Ile Ile Ser Gln Asp Glu Ala Asp Arg Arg Gly Lys Val Tyr Asp Lys
            35                  40                  45

Tyr Met Cys Ser Phe Leu Phe Asn Leu Asn Asn Asp Phe Val Val Asp
        50                  55                  60

Ala Thr Arg Lys Gly Asn Lys Ile Arg Phe Ala Asn His Ser Val Asn
65                  70                  75                  80

Pro Asn Cys Tyr Ala Lys Val Met Met Val Asn Gly Asp His Arg Ile
                85                  90                  95

Gly Ile Phe Ala Lys Arg Ala Ile Gln Thr Gly Glu Glu Leu Phe Phe
            100                 105                 110

Asp Tyr

<210> SEQ ID NO 8
<211> LENGTH: 342
<212> TYPE: DNA
<213> ORGANISM: Homo sapiens

<400> SEQUENCE: 8
catctattgc tggcaccatc tgacgtggca ggctggggga ttttatcaa agatcctgtg      60 cagaaaaatg aattcatctc agaatactgt ggagagatta tttctcaaga tgaagctgac    120
agaagaggga agtgtatga taaatacatg tgcagctttc tgttcaactt gaacaatgat    180

-continued

```
tttgtggtgg atgcaacccg caagggtaac aaaattcgtt ttgcaaatca ttcggtaaat    240
ccaaactgct atgcaaaagt tatgatggtt aacggtgatc acaggatagg tattttttgcc   300 aagagagcca tccagactgg cgaagagctg ttttttgatt ac                       342
```

<210> SEQ ID NO 9
<211> LENGTH: 746
<212> TYPE: PRT
<213> ORGANISM: Homo sapiens
<220> FEATURE:
<221> NAME/KEY: MISC_FEATURE
<222> LOCATION: (641)..(641)
<223> OTHER INFORMATION: X is any amino acid other than tyrosine (Y).

<400> SEQUENCE: 9

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
    210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys Arg Arg
        275                 280                 285

Cys Phe Lys Tyr Asp Cys Phe Leu His Pro Phe His Ala Thr Pro Asn
    290                 295                 300

Thr Tyr Lys Arg Lys Asn Thr Glu Thr Ala Leu Asp Asn Lys Pro Cys
305                 310                 315                 320

Gly Pro Gln Cys Tyr Gln His Leu Glu Gly Ala Lys Glu Phe Ala Ala
```

-continued

```
                325                 330                 335
Ala Leu Thr Ala Glu Arg Ile Lys Thr Pro Pro Lys Arg Pro Gly Gly
            340                 345                 350
Arg Arg Arg Gly Arg Leu Pro Asn Asn Ser Ser Arg Pro Ser Thr Pro
            355                 360                 365
Thr Ile Asn Val Leu Glu Ser Lys Asp Thr Asp Ser Asp Arg Glu Ala
            370                 375                 380
Gly Thr Glu Thr Gly Gly Glu Asn Asn Asp Lys Glu Glu Glu Glu Lys
385                 390                 395                 400
Lys Asp Glu Thr Ser Ser Ser Glu Ala Asn Ser Arg Cys Gln Thr
            405                 410                 415
Pro Ile Lys Met Lys Pro Asn Ile Glu Pro Pro Glu Asn Val Glu Trp
            420                 425                 430
Ser Gly Ala Glu Ala Ser Met Phe Arg Val Leu Ile Gly Thr Tyr Tyr
            435                 440                 445
Asp Asn Phe Cys Ala Ile Ala Arg Leu Ile Gly Thr Lys Thr Cys Arg
            450                 455                 460
Gln Val Tyr Glu Phe Arg Val Lys Glu Ser Ser Ile Ile Ala Pro Ala
465                 470                 475                 480
Pro Ala Glu Asp Val Asp Thr Pro Pro Arg Lys Lys Lys Arg Lys His
                485                 490                 495
Arg Leu Trp Ala Ala His Cys Arg Lys Ile Gln Leu Lys Lys Asp Gly
            500                 505                 510
Ser Ser Asn His Val Tyr Asn Tyr Gln Pro Cys Asp His Pro Arg Gln
            515                 520                 525
Pro Cys Asp Ser Ser Cys Pro Cys Val Ile Ala Gln Asn Phe Cys Glu
            530                 535                 540
Lys Phe Cys Gln Cys Ser Ser Glu Cys Gln Asn Arg Phe Pro Gly Cys
545                 550                 555                 560
Arg Cys Lys Ala Gln Cys Asn Thr Lys Gln Cys Pro Cys Tyr Leu Ala
                565                 570                 575
Val Arg Glu Cys Asp Pro Asp Leu Cys Leu Thr Cys Gly Ala Ala Asp
            580                 585                 590
His Trp Asp Ser Lys Asn Val Ser Cys Lys Asn Cys Ser Ile Gln Arg
            595                 600                 605
Gly Ser Lys Lys His Leu Leu Leu Ala Pro Ser Asp Val Ala Gly Trp
            610                 615                 620
Gly Ile Phe Ile Lys Asp Pro Val Gln Lys Asn Glu Phe Ile Ser Glu
625                 630                 635                 640
Xaa Cys Gly Glu Ile Ile Ser Gln Asp Glu Ala Asp Arg Arg Gly Lys
                645                 650                 655
Val Tyr Asp Lys Tyr Met Cys Ser Phe Leu Phe Asn Leu Asn Asn Asp
            660                 665                 670
Phe Val Val Asp Ala Thr Arg Lys Gly Asn Lys Ile Arg Phe Ala Asn
            675                 680                 685
His Ser Val Asn Pro Asn Cys Tyr Ala Lys Val Met Met Val Asn Gly
            690                 695                 700
Asp His Arg Ile Gly Ile Phe Ala Lys Arg Ala Ile Gln Thr Gly Glu
705                 710                 715                 720
Glu Leu Phe Phe Asp Tyr Arg Tyr Ser Gln Ala Asp Ala Leu Lys Tyr
                725                 730                 735
Val Gly Ile Glu Arg Glu Met Glu Ile Pro
            740                 745
```

<210> SEQ ID NO 10
<211> LENGTH: 24
<212> TYPE: PRT
<213> ORGANISM: Homo sapiens

<400> SEQUENCE: 10

```
Leu Ala Thr Lys Ala Ala Arg Lys Ser Ala Pro Ala Thr Gly Gly Val
1               5                   10                  15

Lys Lys Pro His Arg Tyr Arg Pro
            20
```

<210> SEQ ID NO 11
<211> LENGTH: 695
<212> TYPE: PRT
<213> ORGANISM: Homo sapiens

<400> SEQUENCE: 11

```
Met Gly Gln Thr Gly Lys Lys Ser Glu Lys Gly Pro Val Cys Trp Arg
1               5                   10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Cys Ser Val Thr Ser Asp Leu
65                  70                  75                  80

Asp Phe Pro Thr Gln Val Ile Pro Leu Lys Thr Leu Asn Ala Val Ala
                85                  90                  95

Ser Val Pro Ile Met Tyr Ser Trp Ser Pro Leu Gln Gln Asn Phe Met
            100                 105                 110

Val Glu Asp Glu Thr Val Leu His Asn Ile Pro Tyr Met Gly Asp Glu
        115                 120                 125

Val Leu Asp Gln Asp Gly Thr Phe Ile Glu Glu Leu Ile Lys Asn Tyr
130                 135                 140

Asp Gly Lys Val His Gly Asp Arg Glu Cys Gly Phe Ile Asn Asp Glu
145                 150                 155                 160

Ile Phe Val Glu Leu Val Asn Ala Leu Gly Gln Tyr Asn Asp Asp Asp
                165                 170                 175

Asp Asp Asp Asp Gly Asp Pro Glu Glu Arg Glu Glu Lys Gln Lys
            180                 185                 190

Asp Leu Glu Asp His Arg Asp Asp Lys Glu Ser Arg Pro Pro Arg Lys
        195                 200                 205

Phe Pro Ser Asp Lys Ile Phe Glu Ala Ile Ser Ser Met Phe Pro Asp
210                 215                 220

Lys Gly Thr Ala Glu Glu Leu Lys Glu Lys Tyr Lys Glu Leu Thr Glu
225                 230                 235                 240

Gln Gln Leu Pro Gly Ala Leu Pro Pro Glu Cys Thr Pro Asn Ile Asp
                245                 250                 255

Gly Pro Asn Ala Lys Ser Val Gln Arg Glu Gln Ser Leu His Ser Phe
            260                 265                 270

His Thr Leu Phe Cys Arg Arg Cys Phe Lys Tyr Asp Cys Phe Leu His
        275                 280                 285

Pro Phe His Ala Thr Pro Asn Thr Tyr Lys Arg Lys Asn Thr Glu Thr
290                 295                 300
```

```
Ala Leu Asp Asn Lys Pro Cys Gly Pro Gln Cys Tyr Gln His Leu Glu
305                 310                 315                 320

Gly Ala Lys Glu Phe Ala Ala Leu Thr Ala Glu Arg Ile Lys Thr
            325                 330                 335

Pro Pro Lys Arg Pro Gly Gly Arg Arg Gly Arg Leu Pro Asn Asn
            340                 345                 350

Ser Ser Arg Pro Ser Thr Pro Thr Ile Asn Val Leu Glu Ser Lys Asp
        355                 360                 365

Thr Asp Ser Asp Arg Glu Ala Gly Thr Glu Thr Gly Gly Glu Asn Asn
        370                 375                 380

Asp Lys Glu Glu Glu Lys Lys Asp Glu Thr Ser Ser Ser Ser Glu
385                 390                 395                 400

Ala Asn Ser Arg Cys Gln Thr Pro Ile Lys Met Lys Pro Asn Ile Glu
            405                 410                 415

Pro Pro Glu Asn Val Glu Trp Ser Gly Ala Glu Ala Ser Met Phe Arg
            420                 425                 430

Val Leu Ile Gly Thr Tyr Tyr Asp Asn Phe Cys Ala Ile Ala Arg Leu
            435                 440                 445

Ile Gly Thr Lys Thr Cys Arg Gln Val Tyr Glu Phe Arg Val Lys Glu
        450                 455                 460

Ser Ser Ile Ile Ala Pro Ala Pro Ala Glu Asp Val Asp Thr Pro Pro
465                 470                 475                 480

Arg Lys Lys Lys Arg Lys His Arg Leu Trp Ala Ala His Cys Arg Lys
                485                 490                 495

Ile Gln Leu Lys Lys Gly Gln Asn Arg Phe Pro Gly Cys Arg Cys Lys
            500                 505                 510

Ala Gln Cys Asn Thr Lys Gln Cys Pro Cys Tyr Leu Ala Val Arg Glu
        515                 520                 525

Cys Asp Pro Asp Leu Cys Leu Thr Cys Gly Ala Ala Asp His Trp Asp
        530                 535                 540

Ser Lys Asn Val Ser Cys Lys Asn Cys Ser Ile Gln Arg Gly Ser Lys
545                 550                 555                 560

Lys His Leu Leu Leu Ala Pro Ser Asp Val Ala Gly Trp Gly Ile Phe
            565                 570                 575

Ile Lys Asp Pro Val Gln Lys Asn Glu Phe Ile Ser Glu Tyr Cys Gly
            580                 585                 590

Glu Ile Ile Ser Gln Asp Glu Ala Asp Arg Arg Gly Lys Val Tyr Asp
        595                 600                 605

Lys Tyr Met Cys Ser Phe Leu Phe Asn Leu Asn Asn Asp Phe Val Val
        610                 615                 620

Asp Ala Thr Arg Lys Gly Asn Lys Ile Arg Phe Ala Asn His Ser Val
625                 630                 635                 640

Asn Pro Asn Cys Tyr Ala Lys Val Met Met Val Asn Gly Asp His Arg
            645                 650                 655

Ile Gly Ile Phe Ala Lys Arg Ala Ile Gln Thr Gly Glu Glu Leu Phe
            660                 665                 670

Phe Asp Tyr Arg Tyr Ser Gln Ala Asp Ala Leu Lys Tyr Val Gly Ile
            675                 680                 685

Glu Arg Glu Met Glu Ile Pro
690                 695

<210> SEQ ID NO 12
<211> LENGTH: 2682
```

<212> TYPE: DNA
<213> ORGANISM: Homo sapiens

<400> SEQUENCE: 12

```
gacgacgttc gcggcgggga actcggagta gcttcgcctc tgacgtttcc ccacgacgca      60
ccccgaaatc cccctgagct ccggcggtcg cgggctgccc tcgccgcctg gtctggcttt     120
atgctaagtt tgagggaaga gtcgagctgc tctgctctct attgattgtg tttctggagg     180
gcgtcctgtt gaattcccac ttcattgtgt acatccccht ccgttccccc caaaaatctg     240
tgccacaggg ttactttttg aaagcgggag gaatcgagaa gcacgatctt ttggaaaact     300
tggtgaacgc ctaaataatc atgggccaga ctgggaagaa atctgagaag ggaccagttt     360
gttggcggaa gcgtgtaaaa tcagagtaca tgcgactgag acagctcaag aggttcagac     420
gagctgatga agtaaagagt atgtttagtt ccaatcgtca gaaaattttg gaaagaacgg     480
aaatcttaaa ccaagaatgg aaacagcgaa ggatacagcc tgtgcacatc ctgacttctt     540
gttcggtgac cagtgacttg gattttccaa cacaagtcat cccattaaag actctgaatg     600
cagttgcttc agtacccata atgtattctt ggtctcccct acagcagaat tttatggtgg     660
aagatgaaac tgttttacat aacattcctt atatgggaga tgaagttta gatcaggatg     720
gtactttcat tgaagaacta ataaaaaatt atgatgggaa agtacacggg gatagagaat     780
gtgggtttat aaatgatgaa attttgtgtg gtgg taa tgccctggt caatataatg     840
atgatgacga tgatgatgat ggagacgatc ctgaagaaag agaagaaaag cagaaagatc     900
tggaggatca ccgagatgat aaagaaagcc gcccacctcg gaaatttcct tctgataaaa     960
ttttgaagc catttcctca atgtttccag ataagggcac agcagaagaa ctaaaggaaa    1020
aatataaaga actcaccgaa cagcagctcc caggcgcact tcctcctgaa tgtacccca    1080
acatagatgg accaaatgct aaatctgttc agagagagca aagcttacac tcctttcata    1140
cgcttttctg taggcgatgt tttaaatatg actgcttcct acatccttt catgcaacac    1200
ccaacactta taagcggaag aacacagaaa cagctctaga caacaaaccct tgtggaccac    1260
agtgttacca gcatttggag ggagcaaagg agttttgctgc tgctctcacc gctgagcgga    1320
taaagacccc accaaaacgt ccaggaggcc gcagaagagg acggcttccc aataacagta    1380
gcaggcccag cacccccacc attaatgtgc tggaatcaaa ggatacagac agtgataggg    1440
aagcagggac tgaaacgggg ggagagaaca atgataaaga agaagaagag aagaaagatg    1500
aaacttcgag ctcctctgaa gcaaattctc ggtgtcaaac accaataaag atgaagccaa    1560
atattgaacc tcctgagaat gtggagtgga gtggtgctga agcctcaatg tttagagtcc    1620
tcattggcac ttactatgac aatttctgtg ccattgctag gttaattggg accaaaacat    1680
gtagacaggt gtatgagttt agagtcaaag aatctagcat catagctcca gctcccgctg    1740
aggatgtgga tactcctcca aggaaaaaga gaggaaaaca ccggttgtgg gctgcacact    1800
gcagaaagat acagctgaaa aagggtcaaa accgcttttcc gggatgccgc tgcaaagcac    1860
agtgcaacac caagcagtgc ccgtgctacc tggctgtccg agagtgtgac cctgacctct    1920
gtcttacttg tggagccgct gaccattggg acagtaaaaa tgtgtcctgc aagaactgca    1980
gtattcagcg gggctccaaa aagcatctat tgctggcacc atctgacgtg gcaggctggg    2040
ggatttttat caaagatcct gtgcagaaaa atgaattcat ctcagaatac tgtggagaga    2100
ttatttctca agatgaagct gacagaagag ggaaagtgta tgataaatac atgtgcagct    2160
ttctgttcaa cttgaacaat gattttgtgg tggatgcaac ccgcaagggt aacaaaattc    2220
```

-continued

```
gttttgcaaa tcattcggta aatccaaact gctatgcaaa agttatgatg gttaacggtg    2280
atcacaggat aggtatttt  gccaagagag ccatccagac tggcgaagag ctgtttttg     2340 attacagata cagccaggct gatgccctga agtatgtcgg catcgaaaga gaaatggaaa    2400
tcccttgaca tctgctacct cctcccccct cctctgaaac agctgcctta gcttcaggaa   2460
cctcgagtac tgtgggcaat ttagaaaaag aacatgcagt ttgaaattct gaatttgcaa   2520
agtactgtaa gaataattta tagtaatgag tttaaaaatc aactttttat tgccttctca   2580
ccagctgcaa agtgttttgt accagtgaat ttttgcaata atgcagtatg gtacattttt   2640
caactttgaa taaagaatac ttgaacttgt ccttgttgaa tc                      2682
```

COMBINATION THERAPY FOR TREATING CANCER

RELATED APPLICATIONS

This application is a continuation of U.S. application Ser. No. 15/567,838, filed Oct. 19, 2017 (now U.S. Pat. No. 10,456,407), which is a U.S. National Phase application, filed under 35 U.S.C. § 371, of International Application No. PCT/US2016/028425, filed Apr. 20, 2016, which claims priority to, and the benefit of, U.S. Provisional Application No. 62/150,185, filed Apr. 20, 2015, the entire contents of each of which are incorporated herein by reference in their entireties.

INCORPORATION-BY-REFERENCE OF SEQUENCE LISTING

The contents of the text file named "EPIZ048N01USSequenceListing.txt", which was created on Mar. 29, 2018, and is 46,146 bytes in size, are incorporated herein by reference in their entireties.

FIELD OF THE DISCLOSURE

This disclosure relates to compositions comprising inhibitors of human histone methyltransferase EZH2, the catalytic subunit of the PRC2 complex which catalyzes the mono- through tri-methylation of lysine 27 on histone H3 (H3-K27), and one or more other therapeutic agents, particularly anticancer agents, and methods of combination therapy for treating cancer.

BACKGROUND

Combination-therapy treatments for cancer have become more common, in part due to the perceived advantage of attacking the disease via multiple avenues. Although many effective combination-therapy treatments have been identified over the past few decades; in view of the continuing high number of deaths each year resulting from cancer, a continuing need exists to identify effective therapeutic regimens for use in anticancer treatment.

SUMMARY

The instant disclosure is based partially upon the discovery that EZH2 inhibition increases sensitivity to anti-VEGF agent such as sunitinib. Accordingly, one aspect of this disclosure relates to a method for treating cancer in a subject (e.g., a patient) in need thereof, by administering a therapeutically effective amount of an EZH2 inhibitor and one or more tyrosine kinase inhibitors or VEGF/VEGFR inhibitors. For example, the cancer is resistant to tyrosine kinase inhibitor treatment or resistant to VEGF/VEGFR inhibitor treatment. For example, the cancer is renal cell carcinoma (e.g., advanced clear cell renal cell carcinoma).

The instant disclosure is based partially upon the discovery that EZH2 inhibitors, such as Compound 44 and glucocorticoid receptor agonists (GRags), such as Prednisone, Prednisolone or Dexamethasone, cooperate to dramatically enhance therapeutic activity in cancer. The combination of Compound 44 and prednisolone extends the range of cells that are sensitive to EZH2 inhibition, from mutant-bearing only to all GCB NHL cells.

The present disclosure directs to methods for treating cancer in a patient in need thereof by administering a therapeutically effective amount of an EZH2 inhibitor and one or more therapeutic agents selected from the group consisting of a glucocorticoid receptor agonist (GRag), CHOP and a BCL2 inhibitor. For example, the BCL2 inhibitor is navitoclax.

In some embodiments, the cancer is NHL of the germinal center B subtype.

In some embodiments, the cancer is an EZH2 mutant cancer. Alternatively, the cancer is an EZH2 wild type cancer.

In some embodiments, the cancer is an EZH2 inhibitor resistant or refractory cancer.

The EZH2 inhibitor and the GRag may be administered simultaneously or sequentially. For example, the EZH2 inhibitor is administered prior to administration of the GRag.

In one aspect of the disclosure, the combination therapies described here induce a modulation in the expression of specific genes, for example, glucocorticoid target genes. As used herein, glucocorticoid target genes refer to genes that are directly or indirectly regulated by glucocorticoid. In certain embodiments a gene is upregulated following the combination therapies described herein. In certain embodiments the gene is Sestrin, TNF and/or GILZ. In certain embodiments these genes can be used as biomarkers, i.e., the gene expression profile can be used to identify patients suitable for the combination therapies described herein. In certain embodiments, the gene expression can be used to monitor or evaluate the dosage or efficacy of the combination therapies described herein.

In one embodiment the cancer is a hematological cancer. In a certain embodiment the cancer is a lymphoma. In a certain embodiment the cancer is a Non-Hodgkin's Lymphoma (NHL) or Diffuse Large B-cell Lymphoma (DLBCL) of the germinal center B subtype (GCB).

In one embodiment the therapeutic activity of the EZH2 inhibitor is enhanced by the GRag in EZH2 mutant bearing cells.

In one aspect of the disclosure, the EZH2 inhibitors enhance the GRag therapeutic activity in WT EZH2 cells. In one embodiment, the cells are WT GCB EZH2 cells. In a certain embodiment of the disclosure, the EZH2 inhibitor is Compound 44 and the GRag is Prednisone.

One aspect of the disclosure is based upon the discovery that the combination of the EZH2 inhibitor and the GRag reverses the insensitivity in EZH2-inhibitor resistant or refractory mutant cells, including EZH2 mutation bearing cells.

In mutant EZH2 GCB lymphoma cells, combination benefit was also observed with all the single components of the CHOP chemotherapy regime. In addition, in two different EZH2 mutant xenograft models, strong combination benefit with CHOP, and this effect was preserved in a study in a third EZH2 mutant xenograft model in which doxorubicin was omitted from the chemotherapy regime.

The present disclosure is based upon the discovery that EZH2 histone methyltransferase inhibitors and other anticancer agents can be used in combination to treat certain tumors with superior results than those achieved by treating tumors with EZH2 histone methyltransferase inhibitors and the anti-cancer agents alone. Accordingly, the present disclosure provides a composition comprising an EZH2 histone methyltransferase inhibitor and one or more other therapeutic agents, and methods for their use to treat diseases the course of which can be influenced by modulating the methylation status of histones or other proteins, e.g., cancer. In a certain embodiment, the present disclosure features a composition comprising Compound 44 and prednisone. In certain embodiments, the present disclosure features a combination therapy comprising Compound 44 and navitoclax. The present disclosure also includes methods for combination therapies comprising EZH2 histone methyltransferase inhibitor and one or more therapeutic agents, such as a Compound 44 and prednisone, to treat cancer, e.g., GCB lymphoma, follicular lymphoma (FL) and diffuse cell large B-cell lymphoma (DCLBL). Specifically, the methods of the present disclosure are useful for treating or preventing cancer or inhibiting cancer cell proliferation.

In one aspect, the present disclosure features a composition comprising a compound of Formula (VIa) below and one or more other therapeutic agents (such as tyrosine kinase inhibitors) or a pharmaceutically acceptable salt or ester thereof.

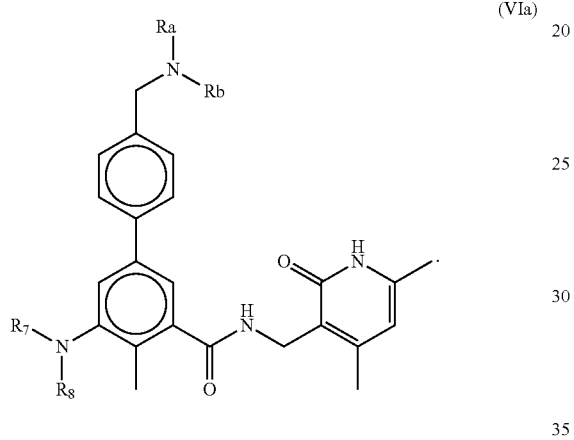

(VIa)

The compounds of Formula (VIa) can include one or more of the following features:

Each of $R_a$ and $R_b$, independently is H or $C_1$-$C_6$ alkyl.

$R_a$ and $R_b$, together with the N atom to which they are attached, is a 4 to 7-membered heterocycloalkyl ring having 0 or 1 additional heteroatom, the $C_1$-$C_6$ alkyl and the 4 to 12-membered (e.g., 4 to 7-membered) heterocycloalkyl ring being optionally substituted with one or more -$Q_3$-$T_3$.

$Q_3$ is a bond or unsubstituted or substituted $C_1$-$C_3$ alkyl linker.

$T_3$ is H, halo, 4 to 7-membered heterocycloalkyl, $C_1$-$C_3$ alkyl, $OR_d$, $COOR_d$, —$S(O)_2R_d$, or —$NR_dR_e$, each of $R_d$ and $R_e$ independently being H or $C_1$-$C_6$ alkyl.

$R_7$ is $C_1$-$C_6$ alkyl, $C_3$-$C_5$ cycloalkyl or 4 to 12-membered (e.g., 4 to 7-membered) heterocycloalkyl, each optionally substituted with one or more -$Q_5$-$T_5$. For example, $R_7$ is not H.

$R_7$ is 4 to 7-membered heterocycloalkyl optionally substituted with one or more -$Q_5$-$T_5$.

$R_7$ is piperidinyl, tetrahydropyran, cyclopentyl, or cyclohexyl, each optionally substituted with one -$Q_5$-$T_5$.

$T_5$ is H, halo, $C_1$-$C_6$ alkyl, $C_1$-$C_6$ alkoxyl, $C_3$-$C_5$ cycloalkyl, $C_6$-$C_{10}$ aryl, or 4 to 12-membered (e.g., 4 to 7-membered) heterocycloalkyl.

$Q_5$ is a bond and $T_5$ is $C_1$-$C_6$ alkyl, $C_3$-$C_5$ cycloalkyl, or 4 to 12-membered (e.g., 4 to 7-membered) heterocycloalkyl.

$Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 12-membered (e.g., 4 to 7-membered) heterocycloalkyl.

$Q_5$ is $C_1$-$C_3$ alkyl linker and $T_5$ is H or $C_6$-$C_{10}$ aryl.

$Q_5$ is $C_1$-$C_3$ alkyl linker and $T_5$ is $C_3$-$C_8$ cycloalkyl, 4 to 7-membered heterocycloalkyl, or $S(O)_qR_q$.

$R_7$ is cyclopentyl or cyclohexyl, each optionally substituted with one -$Q_5$-$T_5$.

$Q_5$ is NHC(O) and $T_5$ is $C_1$-$C_6$ alkyl or $C_1$-$C_6$ alkoxy.

$R_7$ is isopropyl.

Each of $R_2$ and $R_4$, independently is H or $C_1$-$C_6$ alkyl optionally substituted with amino, mono-$C_1$-$C_6$ alkylamino, di-$C_1$-$C_6$ alkylamino, or $C_6$-$C_{10}$ aryl.

$R_8$ is H, methyl, or ethyl.

$R_8$ is methyl.

$R_8$ is ethyl.

$R_8$ is 4 to 7-heterocycloalkyl, e.g., tetrahydropyran.

The present disclosure features a composition comprising a compound selected from Table 1 or a pharmaceutically acceptable salt or ester thereof and one or more other therapeutic agents.

For example, the EZH2 inhibitor is Compound 44 (also known as EPZ-6438, E7438) having the following formula:

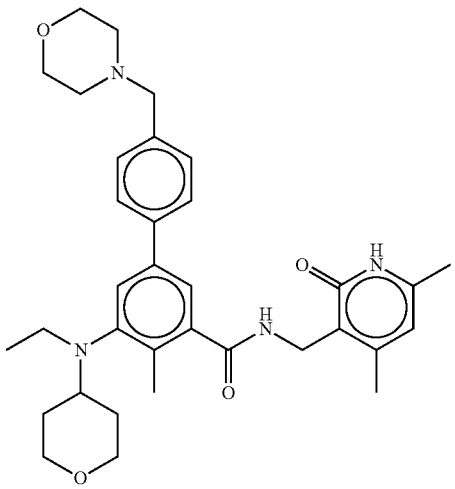

or a pharmaceutically acceptable salt or solvate thereof and one or more other therapeutic agents.

For example, the EZH2 inhibitor is Compound A having the following formula:

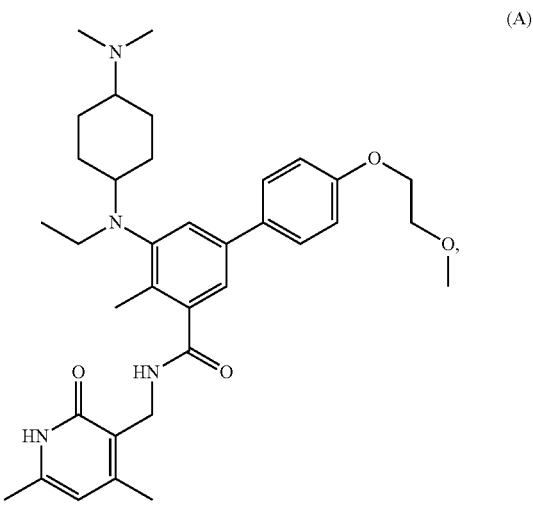

(A)

stereoisomers thereof, or pharmaceutically acceptable salts or solvates thereof.

For example, the EZH2 inhibitor is Compound B (also known as EPZ011989) having the following formula:

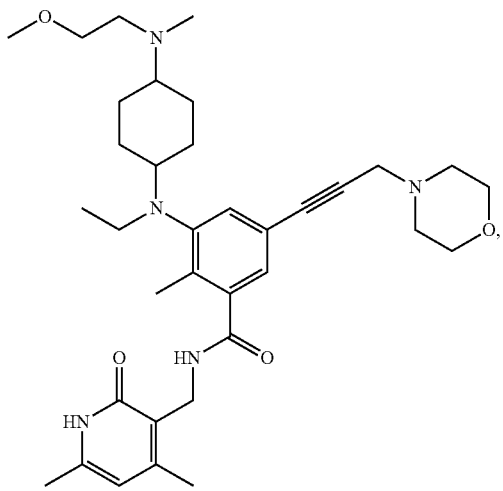

(B)

stereoisomers thereof, or pharmaceutically acceptable salts or solvates thereof.

For example, the EZH2 inhibitor is Compound C having the following formula:

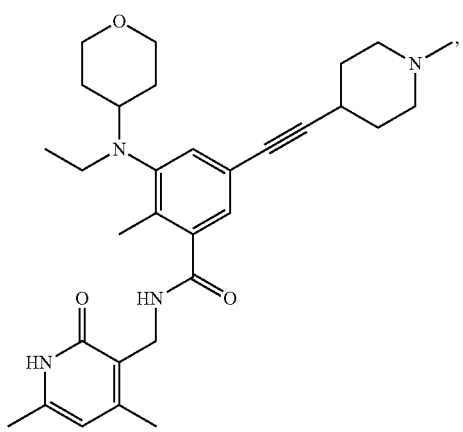

(C)

stereoisomers thereof, or pharmaceutically acceptable salts or solvates thereof.

For example, the EZH2 inhibitor is GSK-126 having the following formula:

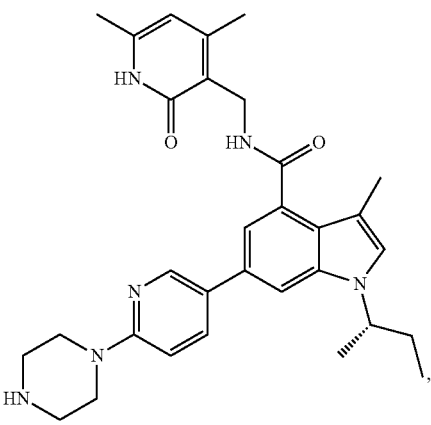 [SMILES: CC[C@H](C)n1cc(C)c2c(C(=O)NCc3c(C)cc(C)[nH]c3=O)cc(-c3ccc(N4CCNCC4)nc3)cc21]

stereoisomers thereof, or pharmaceutically acceptable salts or solvates thereof.

In this and other aspects of the disclosure, in one embodiment the other therapeutic agents are anticancer agents.

In this and other aspects of the disclosure, in one embodiment the other therapeutic agents are tyrosine kinase inhibitors. For example, the EZH2 inhibitor and the one or more tyrosine kinase inhibitors are administered simultaneously or sequentially. For example, the EZH2 inhibitor is administered prior to administration of the one or more tyrosine kinase inhibitors.

In this and other aspects of the disclosure, in one embodiment the other therapeutic agents are or VEGF/VEGFR inhibitors. For example, the EZH2 inhibitor and the one or more VEGF/VEGFR inhibitors are administered simultaneously or sequentially. For example, the EZH2 inhibitor is administered prior to administration of the one or more VEGF/VEGFR inhibitors.

In this and other aspects of the disclosure, in one embodiment the other therapeutic agents are glucocorticoids.

In this and other aspects of the disclosure, in one embodiment the other therapeutic agents are selected from prednisone, prednisolone, cyclophosphamide, vincristine, doxorubicin, mafosfamide, cisplatin, AraC, everolimus, decitabine, dexamethasone, and analogs, derivatives, or combinations thereof.

In this and other aspects of the disclosure, in one embodiment the other therapeutic agent is prednisone, or an analog or derivative thereof.

The present disclosure also provides pharmaceutical compositions comprising a compound selected from those of Formulae (I)-(VIa) disclosed herein or pharmaceutical acceptable salts thereof and one or more therapeutic agents, and a pharmaceutically acceptable carrier.

The present disclosure also provides pharmaceutical compositions comprising a compound selected from Table I, one or more other therapeutic agents, or pharmaceutically acceptable salts thereof, and a pharmaceutically acceptable carrier.

The present disclosure also provides pharmaceutical compositions comprising a compound selected from those of Formulae (I)-(VIa) disclosed herein or pharmaceutically acceptable salts thereof, one or more other therapeutic agents, and a pharmaceutically acceptable carrier.

Another aspect of this disclosure is a method for treating or preventing a disease by administering to a subject in need thereof a therapeutically effective amount of a composition comprising a compound of Formulae (I)-(VIa), or a pharmaceutically acceptable salt thereof, and one or more additional therapeutic agents. The disease of the present disclosure can be influenced, treated, or prevented by modulating the methylation status of histones or other proteins. For example, the disease is cancer, a precancerous condition, or a neurological disease. Preferably, the lymphoma is non-Hodgkin lymphoma, follicular lymphoma or diffuse large B-cell lymphoma. Alternatively, the leukemia is chronic myelogenous leukemia (CML). The precancerous condition is, e.g., myelodysplastic syndromes (MDS, formerly known as preleukemia).

The subject of the present disclosure includes any human subject who has been diagnosed with, has symptoms of, or is at risk of developing a cancer or a precancerous condition. The subject of the present disclosure includes any human subject expressing a mutant EZH2. For example, a mutant EZH2 comprises one or more mutations, wherein the mutation is a substitution, a point mutation, a nonsense mutation, a missense mutation, a deletion, or an insertion. A mutant EZH2 of the present disclosure may comprise a mutation in the substrate pocket domain as defined in SEQ ID NO: 6. A mutant EZH2 may have a substitution at amino acid Y641. Preferably, the mutant EZH2 has one of the following mutations: substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); and a substitution of cysteine (C) for the wild type residue tyrosine (Y) at amino acid position 641 of SEQ ID NO: 1 (Y641C).

Other mutations of EZH2 may include, but are not limited to: a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of serine (S) for the wild type residue asparagine (N) at amino acid position 322 of SEQ ID NO: 3 (N322S), a substitution of glutamine (Q) for the wild type residue arginine (R) at amino acid position 288 of SEQ ID NO: 3 (R288Q), a substitution of isoleucine (I) for the wild type residue threonine (T) at amino acid position 573 of SEQ ID NO: 3 (T573I), a substitution of glutamic acid (E) for the wild type residue aspartic acid (D) at amino acid position 664 of SEQ ID NO: 3 (D664E), a substitution of glutamine (Q) for the wild type residue arginine (R) at amino acid position 458 of SEQ ID NO: 5 (R458Q), a substitution of lysine (K) for the wild type residue glutamic acid (E) at amino acid position 249 of SEQ ID NO: 3 (E249K), a substitution of cysteine (C) for the wild type residue arginine (R) at amino acid position 684 of SEQ ID NO: 3 (R684C), a substitution of histidine (H) for the wild type residue arginine (R) at amino acid position 628 of SEQ ID NO: 11 (R628H), a substitution of histidine (H) for the wild type residue glutamine (Q) at amino acid position 501 of SEQ ID NO: 5 (Q501H), a substitution of asparagine (N) for the wild type residue aspartic acid (D) at amino acid position 192 of SEQ ID NO: 3 (D192N), a substitution of valine (V) for the wild type residue aspartic acid (D) at amino acid position 664 of SEQ ID NO: 3 (D664V), a substitution of leucine (L) for the wild type residue valine (V) at amino acid position 704 of SEQ ID NO: 3 (V704L), a substitution of serine (S) for the wild type residue proline (P) at amino acid position 132 of SEQ ID NO: 3 (P132S), a substitution of lysine (K) for the wild type residue glutamic acid (E) at amino acid position 669 of SEQ ID NO: 11 (E669K), a substitution of threonine (T) for the wild type residue alanine (A) at amino acid position 255 of SEQ ID NO: 3 (A255T), a substitution of valine (V) for the wild type residue glutamic acid (E) at amino acid position 726 of SEQ ID NO: 3 (E726V), a substitution of tyrosine (Y) for the wild type residue cysteine (C) at amino acid position 571 of SEQ ID NO: 3 (C571Y), a substitution of cysteine (C) for the wild type residue phenylalanine (F) at amino acid position 145 of SEQ ID NO: 3 (F145C), a substitution of threonine (T) for the wild type residue asparagine (N) at amino acid position 693 of SEQ ID NO: 3 (N693T), a substitution of serine (S) for the wild type residue phenylalanine (F) at amino acid position 145 of SEQ ID NO: 3 (F145S), a substitution of histidine (H) for the wild type residue glutamine (Q) at amino acid position 109 of SEQ ID NO: 11 (Q109H), a substitution of cysteine (C) for the wild type residue phenylalanine (F) at amino acid position 622 of SEQ ID NO: 11 (F622C), a substitution of arginine (R) for the wild type residue glycine (G) at amino acid position 135 of SEQ ID NO: 3 (G135R), a substitution of glutamine (Q) for the wild type residue arginine (R) at amino acid position 168 of SEQ ID NO: 5 (R168Q), a substitution of arginine (R) for the wild type residue glycine (G) at amino acid position 159 of SEQ ID NO: 3 (G159R), a substitution of cysteine (C) for the wild type residue arginine (R) at amino acid position 310 of SEQ ID NO: 5 (R310C), a substitution of histidine (H) for the wild type residue arginine (R) at amino acid position 561 of SEQ ID NO: 3 (R561H), a substitution of histidine (H) for the wild type residue arginine (R) at amino acid position 634 of SEQ ID NO: 11 (R634H), a substitution of arginine (R) for the wild type residue glycine (G) at amino acid position 660 of SEQ ID NO: 3 (G660R), a substitution of cysteine (C) for the wild type residue tyrosine (Y) at amino acid position 181 of SEQ ID NO: 3 (Y181C), a substitution of arginine (R) for the wild type residue histidine (H) at amino acid position 297 of SEQ ID NO: 3 (H297R), a substitution of serine (S) for the wild type residue cysteine (C) at amino acid position 612 of SEQ ID NO: 11 (C612S), a substitution of tyrosine (Y) for the wild type residue histidine (H) at amino acid position 694 of SEQ ID NO: 3 (H694Y), a substitution of alanine (A) for the wild type residue aspartic acid (D) at amino acid position 664 of SEQ ID NO: 3 (D664A), a substitution of threonine (T) for the wild type residue isoleucine (I) at amino acid position 150 of SEQ ID NO: 3 (I150T), a substitution of arginine (R) for the wild type residue isoleucine (I) at amino acid position 264 of SEQ ID NO: 3 (I264R), a substitution of leucine (L) for the wild type residue proline (P) at amino acid position 636 of SEQ ID NO: 3 (P636L), a substitution of threonine (T) for the wild type residue isoleucine (I) at amino acid position 713 of SEQ ID NO: 3 (I713T), a substitution of proline (P) for the wild type residue glutamine (Q) at amino acid position 501 of SEQ ID NO: 5 (Q501P), a substitution of glutamine (Q) for the wild type residue lysine (K) at amino acid position 243 of SEQ ID NO: 3 (K243Q), a substitution of aspartic acid (D) for the wild type residue glutamic acid (E) at amino acid position 130 of SEQ ID NO: 5 (E130D), a substitution of glycine (G) for the wild type residue arginine (R) at amino acid position 509 of SEQ ID NO: 3 (R509G), a substitution of histidine (H) for the wild type residue arginine (R) at amino acid position 566 of SEQ ID NO: 3 (R566H), a substitution of histidine (H) for the wild type residue aspartic acid (D) at amino acid position 677 of SEQ ID NO: 3 (D677H), a substitution of asparagine (N) for the wild type residue lysine (K) at amino acid position 466 of SEQ ID NO: 5 (K466N), a substitution of histidine (H) for the wild type residue arginine (R) at amino acid position 78 of SEQ ID NO: 3 (R78H), a substitution of methionine (M) for the wild type residue lysine (K) at amino acid position 1 of SEQ ID NO: 6 (K6M), a substitution of leucine (L) for the wild type residue serine (S) at amino acid position 538 of SEQ ID NO: 3 (S538L), a substitution of glutamine (Q) for the wild type residue leucine (L) at amino acid position 149 of SEQ ID NO: 3 (L149Q), a substitution of valine (V) for the wild type residue leucine (L) at amino acid position 252 of SEQ ID NO: 3 (L252V), a substitution of valine (V) for the wild type residue leucine (L) at amino acid position 674 of SEQ ID NO: 3 (L674V), a substitution of valine (V) for the wild type residue alanine (A) at amino acid position 656 of SEQ ID NO: 3 (A656V), a substitution of aspartic acid (D) for the wild type residue alanine (A) at amino acid position 731 of SEQ ID NO: 3 (Y731D), a substitution of threonine (T) for the wild type residue alanine (A) at amino acid position 345 of SEQ ID NO: 3 (A345T), a substitution of aspartic acid (D) for the wild type residue alanine (A) at amino acid position 244 of SEQ ID NO: 3 (Y244D), a substitution of tryptophan (W) for the wild type residue cysteine (C) at amino acid position 576 of SEQ ID NO: 3 (C576W), a substitution of lysine (K) for the wild type residue asparagine (N) at amino acid position 640 of SEQ ID NO: 3 (N640K), a substitution of lysine (K) for the wild type residue asparagine (N) at amino acid position 675 of SEQ ID NO: 3 (N675K), a substitution of tyrosine (Y) for the wild type residue aspartic acid (D) at amino acid position 579 of SEQ ID NO: 11 (D579Y), a substitution of isoleucine (I) for the wild type residue asparagine (N) at amino acid position 693 of SEQ ID NO: 3 (N693I), and a substitution of lysine (K) for the wild type residue asparagine (N) at amino acid position 693 of SEQ ID NO: 3 (N693K).

Other mutations of EZH2 can include: a frameshift at amino acid position 730, 391, 461, 441, 235, 254, 564, 662, 715, 405, 685, 64, 73, 656, 718, 374, 592, 505, 730, or 363 of SEQ ID NO: 3, 5 or 11 or the corresponding nucleotide positions encoding the amino acid sequences mentioned above; a deletion of glutamic acid (E) and leucine (L) at amino acid positions 148 and 149 of SEQ ID NO: 3, 5 or 11, or a nonsense mutation at amino acid position 733, 25, 317, 62, 553, 328, 58, 207, 123, 63, 137, or 60 of SEQ ID NO: 3, 5 or 11.

A subject of the present disclosure may have resistance to any one or more other therapeutic agents or any of the compounds described herein. For example, the subject may have resistance to EZH inhibitors or prednisone.

The present disclosure features a method for inhibiting cancer cell proliferation comprising contacting said cancer cells with a composition comprising any compound of Formulae (I)-(VIa) or pharmaceutically acceptable salt thereof, and one or more additional therapeutic agent. Inhibiting cancer cell proliferation includes delaying cancer cell growth, inducing cell death, reducing cancer cell viability, inhibiting or delaying tumor growth, or reducing tumor size.

The present disclosure features methods of combination therapy wherein any compound of Formulae (I)-(VIa), or pharmaceutically acceptable salt thereof, and one or more other therapeutic agents are administered simultaneously or sequentially. For example, any compound of Formulae (I)-(VIa) or pharmaceutically acceptable salt thereof may be administered prior to administration of one or more other therapeutic agents. For example, any compound of Formulae (I)-(VIa) or pharmaceutically acceptable salt there or may be administered prior to administration of a composition comprising any compound of Formulae (I)-(VIa) or pharmaceutically acceptable salt thereof and one or more other therapeutic agents. Concurrent or sequential administration of any compound of Formulae (I)-(VIa) and/or each therapeutic agent can be effected by any appropriate route including, but not limited to, oral routes, intravenous routes, intramuscular routes, and direct absorption through mucous membrane tissues. The therapeutic agents can be administered by the same route or by different routes.

The methods of combination therapy featured in the present disclosure may result in a synergistic effect, wherein the effect of a combination of compounds or other therapeutic agents is greater than the sum of the effects resulting from administration of any of the compounds or other therapeutic agents as single agents. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

Compositions of the present disclosure can be administered at a dosage of 0.01 mg/kg per day to about 1000 mg/kg per day. Any compound of Formulae (I)-(VIa) or pharmaceutically acceptable salt thereof may be administered at a dosage of 0.01 mg/kg per day to about 1000 mg/kg per day. Any other therapeutic agent may be administered at a dosage of 0.01 mg/kg per day to about 1000 mg/kg per day.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTIONS OF FIGURES

FIG. 1 is a scheme showing the design of in vitro combination assays. Pre-treatment model A: Lymphoma cells were pretreated in flasks with 7 doses of Compound 44 (also called EZH-6438) or DMSO for 4 days. Cells were normalized and co-treated with Compound 44 and compound of interest (3 replicate plates in matrix of two compound combinations in a constant ratio) using the HP D300 digital dispenser. After 3 days of co-treatment, cell viability was measured via ATP content using CellTiter-Glo®.

Pre-treatment models B and C: Lymphoma cells were pre-treated with 1 dose of compound of interest or 7 doses of Compound 44 and DMSO for 4 days. Cells were then normalized and co-treated with 1 dose of compound of interest and 7 doses of Compound 44 and DMSO for 3 days. Viability was determined using Guava ViaCount® Reagent. Co-treatment Model: Lymphoma cells were treated with 7 doses of Compound 44 and 1 dose of compound of interest for either 4 or 7 days. Viability was determined using Guava ViaCount® Reagent.

FIG. 2 is a scheme showing the data analysis using Chou-Talalay method. Synergy quantification is performed using the Chou-Talalay method[3] for drug combination. The Combination Index (CI) equation offers a quantitative definition for additivity (CI=1), synergism (CI<1), and antagonism (CI>1). This equation used Fa values from a constant ratio of drug combination to determine CI values. The resulting plot (Fa-CI) plot shows the resultant CI values bracketed by 95% confidence intervals. These Fa-CI plots are generated using the Calcusyn software. Statistically significant CI values for synergy are for example those CI value<1 with the confidence interval lines also below 1.

FIGS. 3A-3F are a series of Fa-Cl plots demonstrating combination benefit with CHOP components and Compound 44 in mutant EZH2 germinal center B-cell lymphoma cell lines. Compound 44 and doxorubicin act synergistically in the WSU-DLCL2 cells (FIG. 3A) and produce an additive effect in SU-DHL-10 cells (FIG. 3D). Combination benefit is observed with mafosfamide in WSU-DLCL2 cells (FIG. 3C) and SU-DHL-10 cells (FIG. 3F). Combination benefit is also observed with vincristine in both EZH2 Y646 mutant cell lines: WSU-DLCL2 cells (FIG. 3B) and SU-DHL-10 cells (FIG. 3E). In WSU-DLCL2 doses ranged from 0.16-20 nM for doxorubicin, 0.04-5 nM for vincristine, 0.156-10 μM for mafosfamide, and 15-1000 nM for Compound 44. In SU-DHL-10 cells doses ranged from 0.5-60 nM for doxorubicin, 0.016-2 nM for vincristine, 0.156-10 μM for mafosfamide, and 1.56-100 nM for Compound 44. Cells were treated according to pretreatment model A, and data analyzed with the Calcusyn software.

FIGS. 4A-4D are a series of plots demonstrating that glucocorticoid agonists enhance potency of Compound 44 in EZH2 mutant lymphoma lines. Potency of Compound 44 is dramatically increased when combined with glucocorticoid agonists. The addition of prednisolone (FIG. 4A, FIG. 4C) or dexamethasone (FIG. 4B, FIG. 4D) in 2 EZH2 Y646F mutant DLBCL lines according to pre-treatment model A produces a dose dependent shift in the $IC_{50}$ of Compound 44. Doses ranged from 15 nM-1000 nM for prednisolone and 1.5 nM-100 nM for dexamethasone in both cell lines. Doses of Compound 44 ranged from 15-1000 nM in WSU-DLCL2 cells and 1.5-100 nM in SU-DHL-10 cells.

FIGS. 5A-5D are a series of plots demonstrating combination benefit of Compound 44 with glucocorticoid agonists in EZH2 WT germinal center but not activated B-Cell lymphoma lines. Combination benefit was observed in DOHH2 EZH2 wild type GCB cells upon treatment with Compound 44 and prednisolone (FIG. 5A) or dexamethasone (FIG. 5B), according to pretreatment model A. In contrast, no combination benefit was observed in Toledo cells (in FIGS. 5C and 5D for Cpd44+ Prednisolone and Cpd44+Dexamethasone, respectively), an EZH2 wild type ABC lymphoma line. Doses ranged from 15 nM-1000 nM for prednisolone and from 1.5 nM-100 nM for dexamethasone in both cells lines. Compound 44 ranged from 0.16-10 μM in DOHH2 cells and 15.6-1000 nM in Toledo cells.

FIG. 6 is a summary table showing that Compound 44/glucocorticoid agonist combination overcomes EZH2 inhibitors (EZH2i) insensitivity in cell lines resistant to EZH2 inhibitors. Overall, a combination of prednisolone and Compound 44 leads to greater sensitivity in all GCB cell lines tested, not just EZH2i sensitive cell lines. Except for RL cells, where sequence of drug addition is crucial as preincubation with prednisolone, followed by Compound 44, is not effective.

FIGS. 7A and 7B are two plots showing very strong synergy observed in EZH2 mutant lymphoma cell line with combination of Compound 44 and other targeted therapies. Very strong synergy is observed when Compound 44 is combined with the BCL2 inhibitor Navitoclax (in FIG. 7A), as well as with mTOR inhibitor everolimus (in FIG. 7B). Dose ranges for Navitoclax are 0.16-10 μM, 0.04-5 nM for Everolimus, and 31-2000 nM for Compound 44. These data were generated in the pretreatment model A and data analyzed with Calcusyn software.

FIG. 8 is a summary table of combinations with Compound 44. Combination benefit with Compound 44 is achieved with all drugs tested in EZH2 mutant lymphoma lines. Glucocorticoid agonists demonstrate combination benefit with EZH2 WT and mutant GCB lymphoma lines, but not in an ABC lymphoma cell line.

FIGS. 9A-9C are a series of plots demonstrating that Compound 44-CHOP combinations show enhanced antitumor activity compared to single agents in several EZH2 mutant lymphoma xenograft models. (FIG. 9A). WSU-DLCL2 (EZH2 Y646F) xenografts were treated with Compound 44, CHOP, or the combination for 28 days, as specified in the methods. Mean tumor volumes+/– SEM are plotted. Both doses of Compound 44 at 150 mg/kg TID and 225 mg/kg BID were statistically more significant in tumor growth inhibition than vehicle alone (*p value<0.05). Treatment with Compound 44 at 225 mg/kg BID plus CHOP resulted in greater tumor regression than with any single agent alone (***p value<0.001 versus vehicle). Statistics calculated by repeated measures ANOVA. (FIG. 9B). SU-DHL6 (EZH2 Y646N) xenografts were treated with Compound 44, CHOP, or the combination for 28 days, as specified in the methods. Mean tumor volumes+/– SEM are plotted in top panel. CHOP or single agent Compound 44 alone had no effect on tumor growth, but treatment with Compound 44 at 225 mg/kg BID plus CHOP resulted in tumor growth regression during the treatment period of 28 days, while also maintaining tumor growth delay after 32 days of dosing cessation (*p value<0.0001). Survival curves (bottom panel) out to 60 days demonstrate significant tumor growth delay in animals treated with Compound 44+CHOP (**p value<0.05). Statistics calculated by two-tailed t-test. (FIG. 9C). SUDHL-10 (EZH2 Y646F) xenografts were treated with Compound 44, COP (SOC without the doxorubicin component), or the combination for 28 days, as specified in the methods. Mean tumor volumes+/– SEM are plotted in top panel. Percent survival out to 60 days in a tumor growth delay study is plotted in the middle panel (Note: 500 mg/kg and 250 mg/kg+COP survival curves are overlapping). Mean tumor weights are compared in the bottom panel, demonstrating the significant differences in tumor weight between groups (*p value<0.05, p value<0.01, **p value<0.0001).

FIGS. 10A-10C are panels showing that glucocorticoid target genes are up-regulated by prednisolone+Compound 44 combination in EZH2 mutant cell lines. Expression levels of (FIG. 10A). Sestrin; (FIG. 10B). TNF and (FIG. 10C) GILZ normalized to DMSO controls for each cell line with the indicated single agent or combination. Fold change values were quantified using the ΔΔCt method and RPLPO as the housekeeping gene.

FIGS. 11A and 11B are panels showing that global H3K27 acetylation and trimethylation are unaffected by prednisolone or combination treatment. Cells were treated for 4 days with increasing doses of prednisolone, Compound 44, or a combination of Compound 44+a constant dose of prednisolone. Acid extracted histones were analyzed by ELISA for H3K27me3 levels (FIG. 11A) (Prednisolone, left panel; Compound 44 and combination, right panel, with IC50 values as insets of each graph) or western blot for H3K27 ac levels (FIG. 11B). For prednisolone treatment, H3K27me3 values are represented as a bar graph as there was no dose dependent changes were observed with this compound.

Figure 15A:
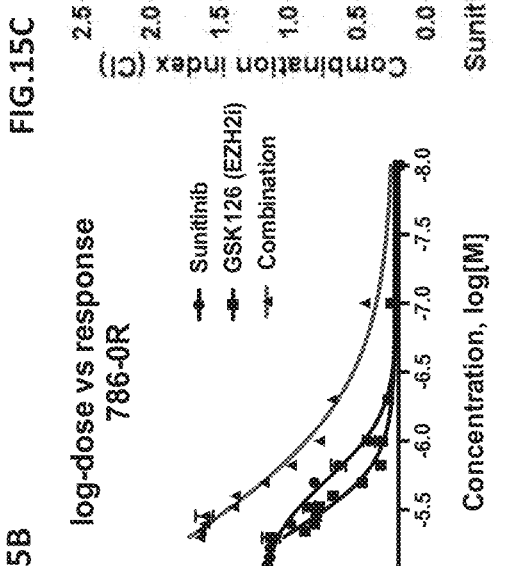
Figure 15B:
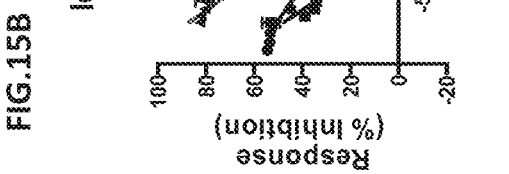
Figure 15C:
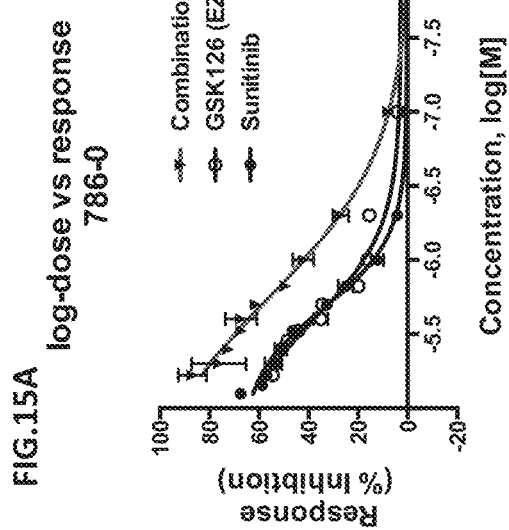
Figure 15D:
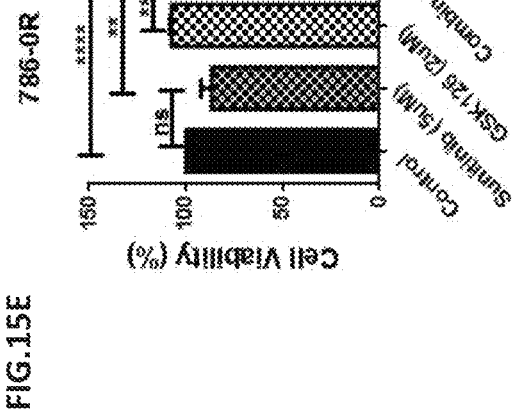
Figure 15E:
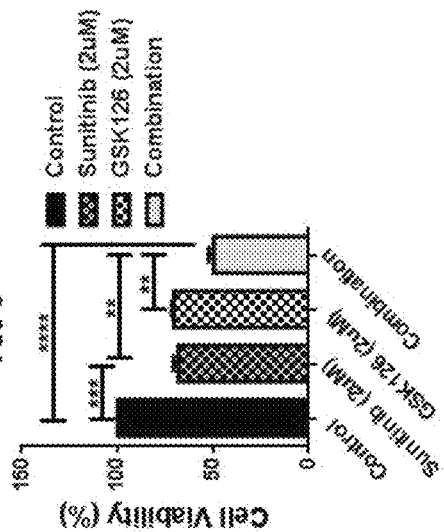

FIGS. 15A-15E are a series of plots demonstrating that inhibition of EZH2 increases sensitivity to sunitinib in ccRCC cell lines. FIGS. 15A-15B: Cell inhibition assay with single agents and combination. FIG. 15C: Combination index values indicating concentrations of sunitinib and GSK126 combination with synergy. FIGS. 15D-15E: ccRCC cell lines treated with either sunitinib, GSK126 or both for 48 hr. Bar chart indicates significant decrease in cell viability in combination treatment arm as compared to the single agents alone.

Figure 16B:
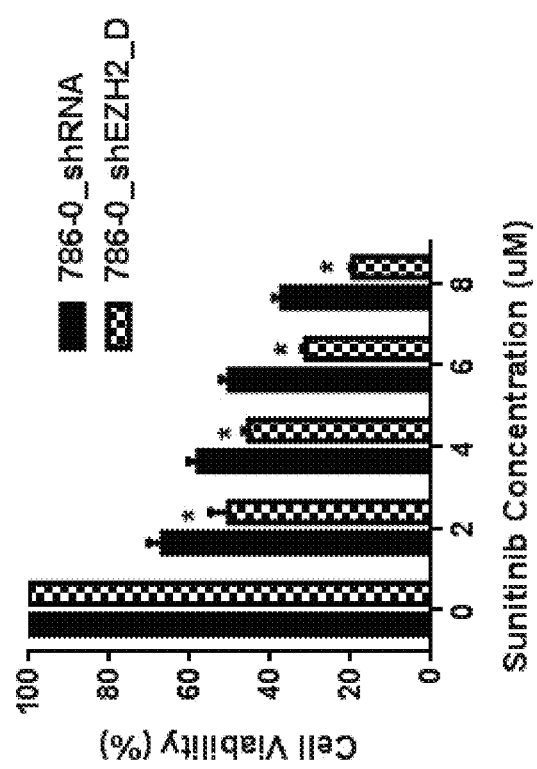
Figure 16A:
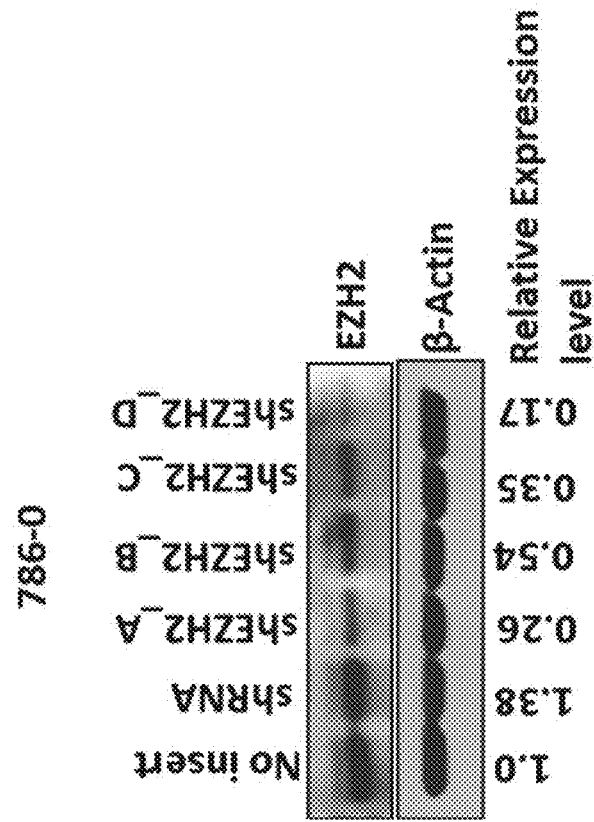

FIGS. 16A-16B are a series of plots demonstrating that knockdown of EZH2 increases sensitivity to sunitinib in ccRCC cell line. FIG. 16A: Western blot analysis showing the efficiency of EZH2 knockdown in 786-0 cell line. FIG. 16B: Specific knockdown of EZH2 in 786-0 cells are more sensitive to sunitinib as compare to the scrambled template control, 786-0_shRNA.

Figure 17A:
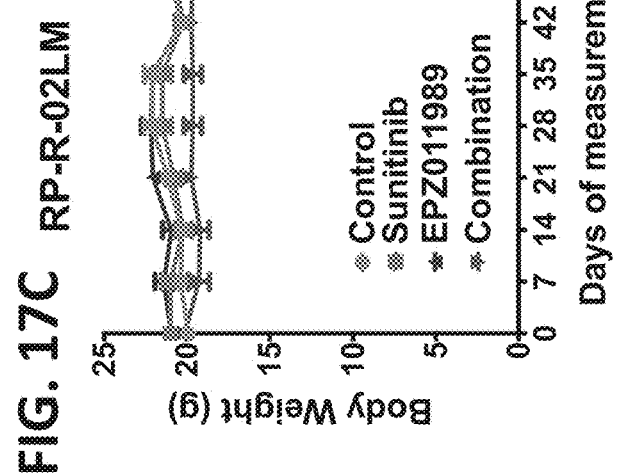
Figure 17B:
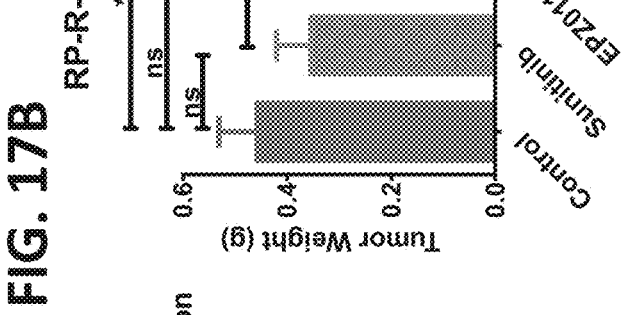
Figure 17C:
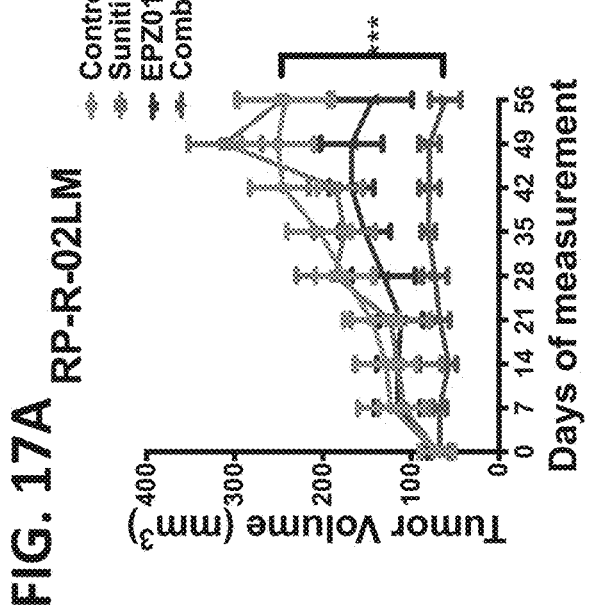

FIGS. 17A-17C are a series of plots demonstrating that EZH2 inhibition sensitizes tumors to sunitinib in RP-R-02LM ccRCC PDX model. Tumor growth curve shows a significant decrease in tumor growth in combination group as compared to sunitinib alone (FIGS. 17A and 17B). Body weight curve overt time indicates that mice tolerated well to both drugs and dosing schedule (FIG. 17C).

Figure 18B:
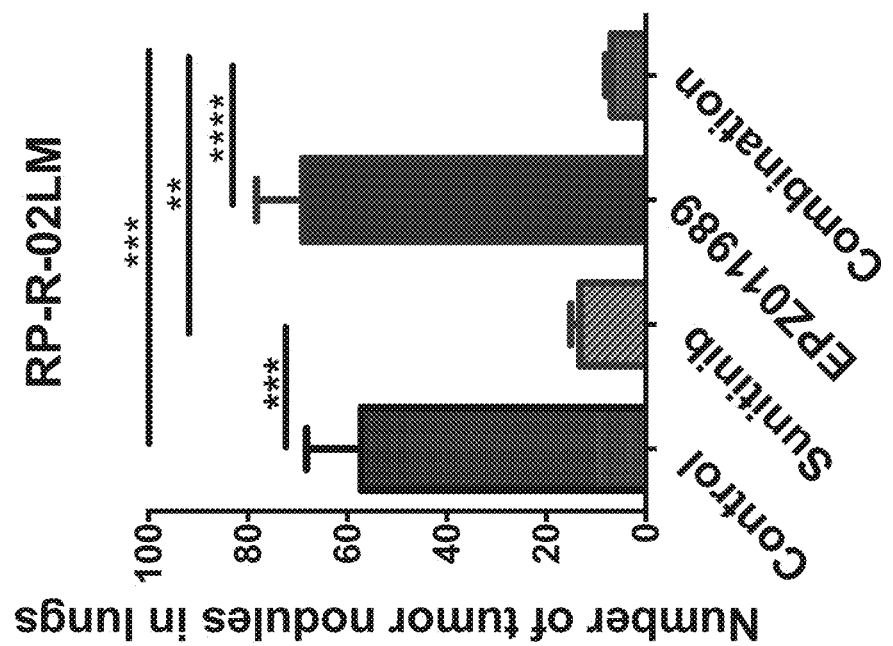
Figure 18A:
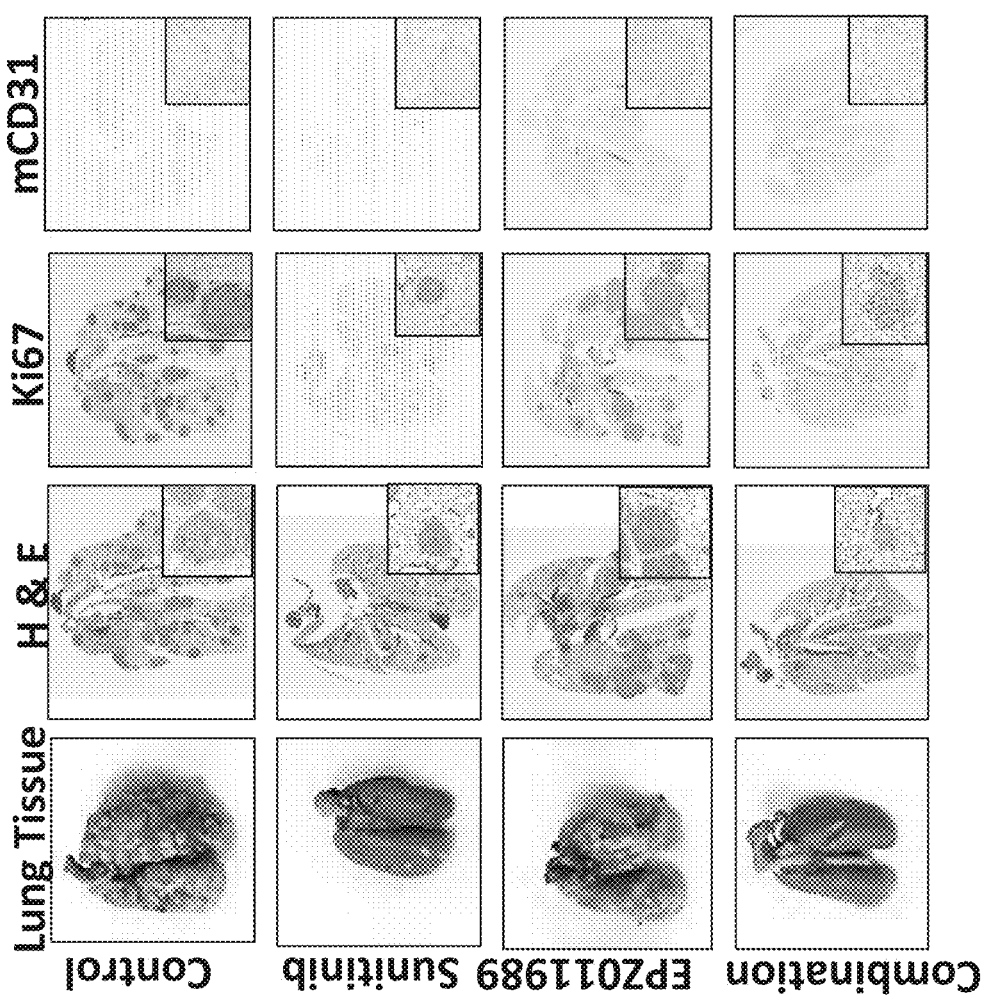

FIGS. 18A-18B are a series of plots demonstrating that combination of sunitinib and Compound B shows increased anti-metastatic effect compared to single agents alone. FIG. 18A includes representative pictures of lung tissues and H&E stain indicating a decrease in metastasis in sunitinib treated group which is increased in the combination group. There were no differences in expression of Ki67 and CD31 levels in tumor cells present in the lungs between treatment groups. FIG. 18B is a plot of number of tumor nodules in lungs with various treatments.

Figure 20B:
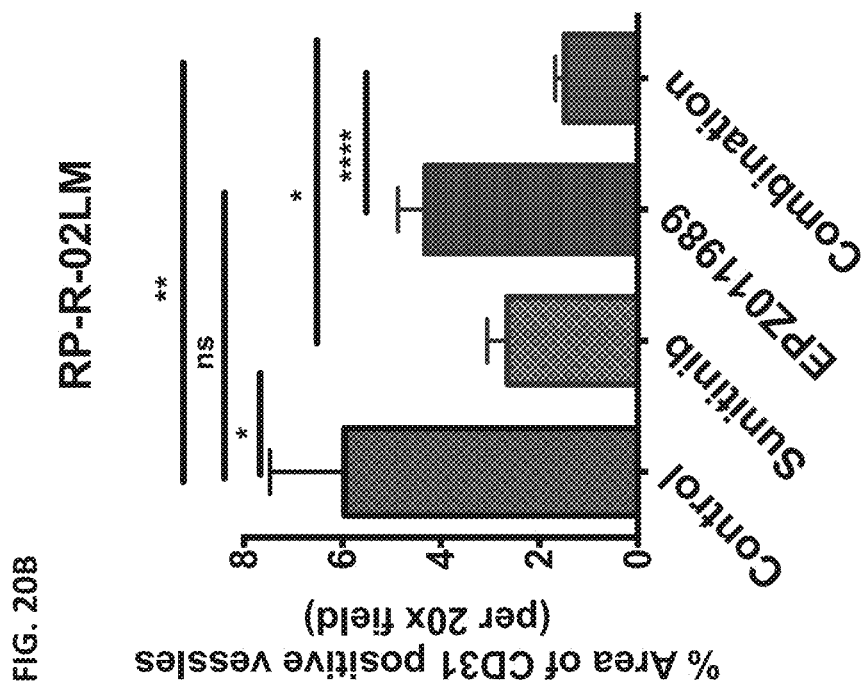
Figure 20A:
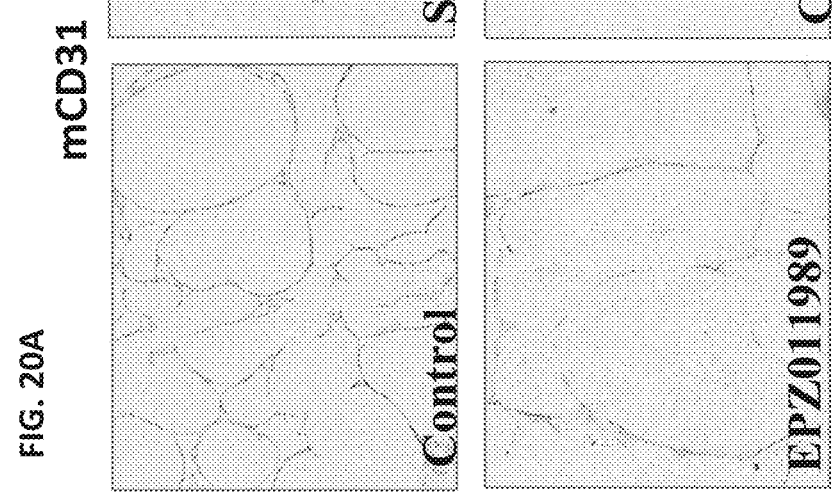
Figure 21:
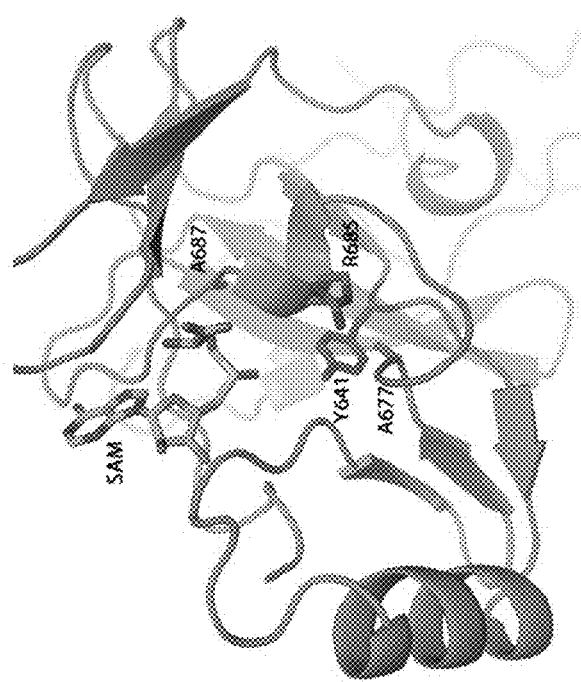

FIGS. 19A-19B are a series of plots demonstrating that combination of sunitinib and Compound B decreases cell proliferation in ccRCC PDX model. Decreased cell proliferation in combination treatment and Compound B treated tumors was observed in tumors at primary site as indicated Ki67 stain (FIG. 19A) and quantification (FIG. 19B). *p<0.05, **p, 0.001, ns=not significant FIGS. 20A-20B are a series of plots demonstrating that combination of sunitinib and Compound B decreases vascular density as in ccRCC PDX model. Significant decreased in vessel density was observed was in sunitinib and combination treated group in tumors at primary site as indicated by mCD31 stain (FIG. 20A) and quantification (FIG. 20B). *p<0.05, p<0.001, *p<0.0001, ns=not significant FIG. 21 is an illustration of the EZH2 protein structure.

DETAILED DESCRIPTION

The present disclosure is based partially upon the discovery that EZH2 histone methyltransferase inhibitors and other anti-cancer agents can be used in combination to treat certain tumors with superior results than those achieved by treating tumors with EZH2 histone methyltransferase inhibitors and the anti-cancer agents alone. Accordingly, the present disclosure provides a composition comprising an EZH2 histone methyltransferase inhibitor and one or more other therapeutic agents, and methods for their use to treat diseases the course of which can be influenced by modulating the methylation status of histones or other proteins, e.g., cancer. In a certain embodiment, the present disclosure features a composition comprising a compound of Formulae (I)-(VIa) and a tyrosine kinase inhibitor such as sunitinib. In a certain embodiment, the present disclosure features a composition comprising a compound of Formulae (I)-(VIa) and an anti-VEGF agent such as sunitinib. In a certain embodiment, the present disclosure features a composition comprising a compound of Formulae (I)-(VIa) and prednisone. The present disclosure also includes methods for combination therapies comprising EZH2 histone methyltransferase inhibitor and one or more therapeutic agents, such as a compound of Formulae (I)-(VIa) and sunitinib or prednisone, to treat cancer, e.g., renal cell carcinoma, follicular lymphoma (FL) and diffuse cell large B-cell lymphoma (DCLBL). Specifically, the methods of the present disclosure are useful for treating or preventing cancer or inhibiting cancer cell proliferation.

EZH2 is a histone methyltransferase that is the catalytic subunit of the PRC2 complex which catalyzes the mono-through tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). Other studies provided evidence for a functional link between dysregulated EZH2 expression, transcriptional repression, and neoplastic transformation. Varambally et al. (2002) *Nature* 419(6907):624-9 Kleer et al. (2003) *Proc Natl Acad Sci USA* 100(20):11606-11.

Response to anti-VEGF therapy continues to be a challenge in patients with metastatic renal cell carcinoma as patients who initially respond to treatment eventually develop resistance and progress. Epigenetic changes such as the overexpression of Enhancer of zeste homologue (EZH2) which is a histone methyltransferase has been shown to be frequently overexpressed in human malignancies, involved in epigenetic silencing of a number of genes and the regulation tumor angiogenesis. EZH2 has been recently reported to be involved in drug resistance. See, e.g., Herranz, Nicolás, et al. "Polycomb complex 2 is required for E-cadherin repression by the Snail1 transcription factor." Molecular and cellular biology 28.15 (2008): 4772-4781; and Adelaiye, Remi, et al. "Sunitinib dose-escalation overcomes transient resistance in clear cell renal cell carcinoma and is associated with epigenetic modifications." Molecular cancer therapeutics (2014): molcanther-0208. Accordingly, inhibition of EZH2 can re-sensitize tumors to anti-VEGF agents.

An aspect of the present disclosure relates to methods for treating or alleviating a symptom of cancer or precancerous condition in a subject by administering to a subject expressing a mutant EZH2 a therapeutically effective amount of an EZH2 inhibitor and one or more other therapeutic agents (such as a tyrosine kinase inhibitor or an anti-VEGF agent). The mutant EZH2 of the present disclosure refers to a mutant EZH2 polypeptide or a nucleic acid sequence encoding a mutant EZH2 polypeptide. In certain embodiments the mutant EZH2 comprises one or more mutations in its substrate pocket domain as defined in SEQ ID NO: 6. For example, the mutation may be a substitution, a point mutation, a nonsense mutation, a misssense mutation, a deletion, or an insertion.

Human EZH2 nucleic acids and polypeptides have previously been described. See, e.g., Chen et al. (1996) *Genomics* 38:30-7 [746 amino acids]; Swiss-Prot Accession No. Q15910 [746 amino acids]; GenBank Accession Nos. NM_004456 and NP_004447 (isoform a [751 amino acids]); and GenBank Accession Nos. NM_152998 and NP_694543 (isoform b [707 amino acids]), each of which is incorporated herein by reference in its entirety.

```
Amino acid sequence of human EZH2 (Swiss-Prot
Accession No. Q15910)
                                        (SEQ ID NO: 1)
MGQTGKKSEKGPVCWRKRVKSEYMRLRQLKRFRRADEVKSMFSSNRQKIL

ERTEILNQEWKQRRIQPVHILTSVSSLRGTRECSVTSDLDFPTQVIPLKT

LNAVASVPIMYSWSPLQQNFMVEDETVLHNIPYMGDEVLDQDGTFIEELI

KNYDGKVHGDRECGFINDEIFVELVNALGQYNDDDDDDGDDPEEREEKQ

KDLEDHRDDKESRPPRKFPSDKIFEAISSMFPDKGTAEELKEKYKELTEQ

QLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRP

GGRRRGRLPNNSSRPSTPTINVLESKDTDSDREAGTETGGENNDKEEEEK

KDETSSSSEANSRCQTPIKMKPNIEPPENVEWSGAEASMFRVLIGTYYDN

FCAIARLIGTKTCRQVYEFRVKESSIIAPAPAEDVDTPPRKKKRKHRLWA

AHCRKIQLKKDGSSNHVYNYQPCDHPRQPCDSSCPCVIAQNFCEKFCQCS

SECQNRFPGCRCKAQCNTKQCPCYLAVRECDPDLCLTCGAADHWDSKNVS

CKNCSIQRGSKKHLLLAPSDVAGWGIFIKDPVQKNEFISEYCGEIISQDE

ADRRGKVYDKYMCSFLFNLNNDFVVDATRKGNKIRFANHSVNPNCYAKVM

MVNGDHRIGIFAKRAIQTGEELFFDYRYSQADALKYVGIEREMEIP

Nucleotide sequence of human EZH2, transcript
variant 1 (GenBank Accession No. NM_004456)
                                        (SEQ ID NO: 2)
ggcggcgcttgattgggctggggggggccaaataaaagcgatggcgattgg gctgccgcgtttggcgctcggtccggtcgcgtccgacacccggtgggact cagaaggcagtggagccccggcggcggcggcggcggcgcggggggcgac gcgcgggaacaacgcgagtcggcgcgcgggacgaagaataatcatgggcc agactggggaagaaatctgagaagggaccagtttgttggcggaagcgtgta aaatcagagtacatgcgactgagacagctcaagaggttcagacgagctga tgaagtaaagagtatgtttagttccaatcgtcagaaaattttggaaagaa cggaaatcttaaaccaagaatggaaacagcgaaggatacagcctgtgcac atcctgacttctgtgagctcattgcgcgggactagggagtgttcggtgac cagtgacttggattttccaacacaagtcatcccattaaagactctgaatg cagttgcttcagtacccataatgtattcttggtctcccctacagcagaat tttatggtggaagatgaaactgttttacataacattccttatatgggaga tgaagttttagatcaggatggtacttcattgaagaactaataaaaaatt atgatgggaaagtacacgggatagagaatgtgggtttataaatgatgaa atttttgtggagttggtgaatgcccttggtcaatataatgatgatgacga tgatgatgatggagacgatcctgaagaaagagaagaaaagcagaaagatc tggaggatcaccgagatgataaagaaagccgcccacctcggaaatttcct tctgataaaattttttgaagccatttcctcaatgtttccagataagggcac agcagaagaactaaaggaaaaatataaagaactcaccgaacagcagctcc caggcgcacttcctcctgaatgtacccccaacatagatggaccaaatgct aaatctgttcagagagagcaaagcttacactccttcatacgcttttctg taggcgatgttttaaatatgactgcttcctacatcgtaagtgcaattatt cttttcatgcaacacccaacacttataagcggaagaacacagaaacagct ctagacaacaaaccttgtggaccacagtgttaccagcatttggagggagc aaaggagtttgctgctgctctcaccgctgagcggataaagaccccaccaa aacgtccaggaggccgcagaagaggacggcttcccaataacagtagcagg cccagcaccccaccattaatgtgctggaatcaaaggatacagacagtga tagggaagcagggactgaaacgggggagagaacaatgataaagaagaag aagagaagaaagatgaaacttcgagctcctctgaagcaaattctcggtgt caaacaccaataaagatgaagccaaatattgaacctcctgagaatgtgga gtggagtggtgctgaagcctcaatgtttagagtcctcattggcacttact atgacaatttctgtgccattgctaggttaattgggaccaaaacatgtaga caggtgtatgagtttagagtcaaagaatctagcatcatagctccagctcc cgctgaggatgtggatactcctccaaggaaaaagaagaggaaacaccggt tgtgggctgcacactgcagaaagatacagctgaaaaaggacggctcctct aaccatgtttacaactatcaaccctgtgatcatccacgcagccttgtga cagttcgtgcccttgtgtgatagcacaaaattttttgtgaaaagttttgtc aatgtagttcagagtgtcaaaaccgctttccgggatgccgctgcaaagca cagtgcaacaccaagcagtgcccgtgctacctggctgtccgagagtgtga ccctgacctctgtcttacttgtggagccgctgaccattgggacagtaaaa atgtgtcctgcaagaactgcagtattcagcggggctccaaaaagcatcta ttgctggcaccatctgacgtggcaggctgggggattttatcaaagatcc tgtgcagaaaatgaattcatctcagaatactgtggagagattatttctc aagatgaagctgacagaagagggaaagtgtatgataaatacatgtgcagc tttctgttcaacttgaacaatgattttgtggtggatgcaacccgcaaggg taacaaaattcgttttgcaaatcattcggtaaatccaaactgctatgcaa
```

-continued aagttatgatggttaacggtgatcacaggataggtatttttgccaagaga gccatccagactggcgaagagctgttttttgattacagatacagccaggc tgatgccctgaagtatgtcggcatcgaaagagaaatggaaatcccttgac atctgctacctcctcccccctcctctgaaacagctgccttagcttcagga acctcgagtactgtgggcaatttagaaaaagaacatgcagtttgaaattc tgaatttgcaaagtactgtaagaataatttatagtaatgagtttaaaaat caactttttattgccttctcaccagctgcaaagtgttttgtaccagtgaa ttttttgcaataatgcagtatggtacattttttcaacttttgaataaagaata cttgaacttgtccttgttgaatc Full amino acid sequence of EZH2, isoform a
(GenBank Accession No. NP_004447)
(SEQ ID NO: 3)
MGQTGKKSEKGPVCWRKRVKSEYMRLRQLKRFRRADEVKSMFSSNRQKIL

ERTEILNQEWKQRRIQPVHILTSVSSLRGTRECSVTSDLDFPTQVIPLKT

LNAVASVPIMYSWSPLQQNFMVEDETVLHNIPYMGDEVLDQDGTFIEELI

KNYDGKVHGDRECGFINDEIFVELVNALGQYNDDDDDDGDDPEEREEKQ

KDLEDHRDDKESRPPRKFPSDKIFEAISSMFPDKGTAEELKEKYKELTEQ

QLPGALPPECTPNIDGPNAKSVQREQSLHSFHTLFCRRCFKYDCFLHRKC

NYSFHATPNTYKRKNTETALDNKPCGPQCYQHLEGAKEFAAALTAERIKT

PPKRPGGRRRGRLPNNSSRPSTPTINVLESKDTDSDREAGTETGGENNDK

EEEEKKDETSSSSEANSRCQTPIKMKPNIEPPENVEWSGAEASMFRVLIG

TYYDNFCAIARLIGTKTCRQVYEFRVKESSIIAPAPAEDVDTPPRKKKRK

HRLWAAHCRKIQLKKDGSSNHVYNYQPCDHPRQPCDSSCPCVIAQNFCEK

FCQCSSECQNRFPGCRCKAQCNTKQCPCYLAVRECDPDLCLTCGAADHWD

SKNVSCKNCSIQRGSKKHLLLAPSDVAGWGIFIKDPVQKNEFISEYCGEI

ISQDEADRRGKVYDKYMCSFLFNLNNDFVVDATRKGNKIRFANHSVNPNC

YAKVMMVNGDHRIGIFAKRAIQTGEELFFDYRYSQADALKYVGIER

EMEIP

Nucleotide sequence of human EZH2, transcript
variant 2 (GenBank Accession No. NM_152998)
(SEQ ID NO: 4)
ggcggcgcttgattgggctggggggccaaataaaagcgatggcgattgg gctgccgcgtttggcgctcggtccggtcgcgtccgacacccggtgggact cagaaggcagtggagccccggcggcggcggcggcggcgcgcgggggcgac gcgcgggaacaacgcgagtcggcgcgcgggacgaagaataatcatgggcc agactgggaagaaatctgagaagggaccagtttgttggcggaagcgtgta aaatcagagtacatgcgactgagacagctcaagaggttcagacgagctga tgaagtaaagagtatgtttagttccaatcgtcagaaaattttggaaagaa cggaaatcttaaaccaagaatggaaacagcgaaggatacagcctgtgcac atcctgacttctgtgagctcattgcgcgggactaggaggtggaagatga aactgttttacataacattccttatatgggagatgaagtttagatcagg atggtactttcattgaagaactaataaaaaattatgatgggaaagtacac ggggatagagaatgtgggtttataaatgatgaaatttttgtggagttggt gaatgcccttggtcaatataatgatgatgacgatgatgatgatggagacg atcctgaagaaagagaagaaaagcagaaagatctggaggatcaccgagat gataaagaaagccgcccacctcggaaatttccttctgataaaattttttga agccatttcctcaatgtttccagataagggcacagcagaagaactaaagg aaaaatataaagaactcaccgaacagcagctcccaggcgcacttcctcct gaatgtacccccaacatagatggaccaaatgctaaatctgttcagagaga gcaaagcttacactccttcatacgcttttctgtaggcgatgttttaaat atgactgcttcctacatccttttcatgcaacacccaacacttataagcgg aagaacacagaaacagctctagacaacaaaccttgtggaccacagtgtta ccagcatttggagggagcaaaggagtttgctgctgctctcaccgctgagc ggataaagaccccaccaaaacgtccaggaggccgcagaagaggacggctt cccaataacagtagcaggcccagcaccccccaccattaatgtgctggaatc aaaggatacagacagtgataggaagcagggactgaaacggggggagaga acaatgataaagaagaagaagaagaagaaagatgaaacttcgagctcctct gaagcaaattctcggtgtcaaacaccaataaagatgaagccaaatattga acctcctgagaatgtggagtggagtggtgctgaagcctcaatgtttagag tcctcattggcacttactatgacaatttctgtgccattgctaggttaatt gggaccaaaacatgtagacaggtgtatgagtttagagtcaaagaatctag catcatagctccagctcccgctgaggatgtggatactcctccaaggaaaa agaagaggaaacaccggttgtgggctgcacactgcagaaagatacagctg aaaaaggacggctcctctaaccatgtttacaactatcaaccctgtgatca tccacggcagccttgtgacagttcgtgccttgtgtgatagcacaaaatt tttgtgaaaagttttgtcaatgtagttcagagtgtcaaaaccgctttccg ggatgccgctgcaaagcacagtgcaacaccaagcagtgcccgtgctacct ggctgtccgagagtgtgaccctgacctctgtcttacttgtggagccgctg accattgggacagtaaaaatgtgtcctgcaagaactgcagtattcagcgg ggctccaaaaagcatctattgctggcaccatctgacgtggcaggctgggg gattttttatcaaagatcctgtgcagaaaaatgaattcatctcagaatact gtggagagattattctcaagatgaagctgacagaagagggaaagtgtat gataaatacatgtgcagctttctgttcaacttgaacaatgattttgtggt ggatgcaacccgcaagggtaacaaaattcgttttgcaaatcattcggtaa atccaaactgctatgcaaaagttatgatggttaacggtgatcacaggata ggtatttttgccaagagagccatccagactggcgaagagctgttttttga ttacagatacagccaggctgatgccctgaagtatgtcggcatcgaaagag aaatggaaatcccttgacatctgctacctcctcccccctcctctgaaaca gctgccttagcttcaggaacctcgagtactgtgggcaatttagaaaaaga acatgcagtttgaaattctgaatttgcaaagtactgtaagaataatttat agtaatgagtttaaaaatcaactttttattgccttctcaccagctgcaaa gtgttttgtaccagtgaattttttgcaataatgcagtatggtacatttttc aacttttgaataaagaatacttgaacttgtccttgttgaatc Full amino acid sequence of EZH2, isoform b
(GenBank Accession No. NP_694543)
(SEQ ID NO: 5)
MGQTGKKSEKGPVCWRKRVKSEYMRLRQLKRFRRADEVKSMFSSNRQKIL
ERTEILNQEWKQRRIQPVHILTSVSSLRGTREVEDETVLHNIPYMGDEVL
DQDGTFIEELIKNYDGKVHGDRECGFINDEIFVELVNALGQYNDDDDDD
GDDPEEREEKQKDLEDHRDDKESRPPRKFPSDKIFEAISSMFPDKGTAEE
LKEKYKELTEQQLPGALPPECTPNIDGPNAKSVQREQSLHSFHTLFCRRC
FKYDCFLHPFHATPNTYKRKNTETALDNKPCGPQCYQHLEGAKEFAAALT
AERIKTPPKRPGGRRRGRLPNNSSRPSTPTINVLESKDTDSDREAGTETG
GENNDKEEEEKKDETSSSSEANSRCQTPIKMKPNIEPPENVEWSGAEASM
FRVLIGTYYDNFCAIARLIGTKTCRQVYEFRVKESSIIAPAPAEDVDTPP
RKKKRKHRLWAAHCRKIQLKKDGSSNHVYNYQPCDHPRQPCDSSCPCVIA
QNFCEKFCQCSSECQNRFPGCRCKAQCNTKQCPCYLAVRECDPDLCLTCG
AADHWDSKNVSCKNCSIQRGSKKHLLLAPSDVAGWGIFIKDPVQKNEFIS
EYCGEIISQDEADRRGKVYDKYMCSFLFNLNNDFVVDATRKGNKIRFANH
SVNPNCYAKVMMVNGDHRIGIFAKRAIQTGEELFFDYRYSQADALKYVGI
EREMEIP Full amino acid sequence of EZH2, isoform e
(GenBank Accession No. NP_001190178.1)
(SEQ ID NO: 11)
MGQTGKKSEKGPVCWRKRVKSEYMRLRQLKRFRRADEVKSMFSSNRQKIL
ERTEILNQEWKQRRIQPVHILTSCSVTSDLDFPTQVIPLKTLNAVASVPI
MYSWSPLQQNFMVEDETVLHNIPYMGDEVLDQDGTFIEELIKNYDGKVHG
DRECGFINDEIFVELVNALGQYNDDDDDDGDDPEEREEKQKDLEDHRDD
KESRPPRKFPSDKIFEAISSMFPDKGTAEELKEKYKELTEQQLPGALPPE
CTPNIDGPNAKSVQREQSLHSFHTLFCRRCFKYDCFLHPFHATPNTYKRK
NTETALDNKPCGPQCYQHLEGAKEFAAALTAERIKTPPKRPGGRRRGRLP
NNSSRPSTPTINVLESKDTDSDREAGTETGGENNDKEEEEKKDETSSSSE
ANSRCQTPIKMKPNIEPPENVEWSGAEASMFRVLIGTYYDNFCAIARLIG
TKTCRQVYEFRVKESSIIAPAPAEDVDTPPRKKKRKHRLWAAHCRKIQLK
KGQNRFPGCRCKAQCNTKQCPCYLAVRECDPDLCLTCGAADHWDSKNVSC
KNCSIQRGSKKHLLLAPSDVAGWGIFIKDPVQKNEFISEYCGEIISQDEA
DRRGKVYDKYMCSFLFNLNNDFVVDATRKGNKIRFANHSVNPNCYAKVMM
VNGDHRIGIFAKRAIQTGEELFFDYRYSQADALKYVGIEREMEIP Homo sapiens enhancer of zeste homolog 2
(Drosophila) (EZH2), transcript variant 5,
nucleotide sequence (GenBank Accession
No. NM_001203249.1)
(SEQ ID NO: 12)
GACGACGTTCGCGGCGGGGAACTCGGAGTAGCTTCGCCTCTGACGTTTCC
CCACGACGCACCCCGAAATCCCCCTGAGCTCCGGCGGTCGCGGGCTGCCC
TCGCCGCCTGGTCTGGCTTTATGCTAAGTTTGAGGGAAGAGTCGAGCTGC
TCTGCTCTCTATTGATTGTGTTTCTGGAGGGCGTCCTGTTGAATTCCCAC
TTCATTGTGTACATCCCCTTCCGTTCCCCCCAAAAATCTGTGCCACAGGG
TTACTTTTTGAAAGCGGGAGGAATCGAGAAGCACGATCTTTTGGAAAACT
TGGTGAACGCCTAAATAATCATGGGCCAGACTGGGAAGAAATCTGAGAAG
GGACCAGTTTGTTGGCGGAAGCGTGTAAAATCAGAGTACATGCGACTGAG
ACAGCTCAAGAGGTTCAGACGAGCTGATGAAGTAAAGAGTATGTTTAGTT
CCAATCGTCAGAAAATTTTGGAAAGAACGGAAATCTTAAACCAAGAATGG
AAACAGCGAAGGATACAGCCTGTGCACATCCTGACTTCTTGTTCGGTGAC
CAGTGACTTGGATTTTCCAACACAAGTCATCCCATTAAAGACTCTGAATG
CAGTTGCTTCAGTACCCATAATGTATTCTTGGTCTCCCCTACAGCAGAAT
TTTATGGTGGAAGATGAAACTGTTTTACATAACATTCCTTATATGGGAGA
TGAAGTTTTAGATCAGGATGGTACTTTCATTGAAGAACTAATAAAAAATT
ATGATGGGAAAGTACACGGGGATAGAGAATGTGGGTTTATAAATGATGAA
ATTTTTGTGGAGTTGGTGAATGCCCTTGGTCAATATAATGATGATGACGA
TGATGATGATGGAGACGATCCTGAAGAAAGAGAAGAAAAGCAGAAAGATC
TGGAGGATCACCGAGATGATAAAGAAAGCCGCCCACCTCGGAAATTTCCT
TCTGATAAAATTTTTGAAGCCATTTCCTCAATGTTTCCAGATAAGGGCAC
AGCAGAAGAACTAAAGGAAAAATATAAAGAACTCACCGAACAGCAGCTCC
CAGGCGCACTTCCTCCTGAATGTACCCCCAACATAGATGGACCAAATGCT
AAATCTGTTCAGAGAGAGCAAAGCTTACACTCCTTTCATACGCTTTTCTG
TAGGCGATGTTTTAAATATGACTGCTTCCTACATCCTTTTCATGCAACAC
CCAACACTTATAAGCGGAAGAACACAGAAACAGCTCTAGACAACAAACCT
TGTGGACCACAGTGTTACCAGCATTTGGAGGGAGCAAAGGAGTTTGCTGC
TGCTCTCACCGCTGAGCGGATAAAGACCCCACCAAAACGTCCAGGAGGCC
GCAGAAGAGGACGGCTTCCCAATAACAGTAGCAGGCCCAGCACCCCCACC
ATTAATGTGCTGGAATCAAAGGATACAGACAGTGATAGGGAAGCAGGGAC
TGAAACGGGGGAGAGAACAATGATAAAGAAGAAGAAGAGAAGAAAGATG
AAACTTCGAGCTCCTCTGAAGCAAATTCTCGGTGTCAAACACCAATAAAG
ATGAAGCCAAATATTGAACCTCCTGAGAATGTGGAGTGGAGTGGTGCTGA
AGCCTCAATGTTTAGAGTCCTCATTGGCACTTACTATGACAATTTCTGTG
CCATTGCTAGGTTAATTGGGACCAAAACATGTAGACAGGTGTATGAGTTT
AGAGTCAAAGAATCTAGCATCATAGCTCCAGCTCCCGCTGAGGATGTGGA
TACTCCTCCAAGGAAAAAGAAGAGGAAACACCGGTTGTGGGCTGCACACT
GCAGAAAGATACAGCTGAAAAAGGGTCAAAACCGCTTTCCGGGATGCCGC
TGCAAAGCACAGTGCAACACCAAGCAGTGCCCGTGCTACCTGGCTGTCCG
AGAGTGTGACCCTGACCTCTGTCTTACTTGTGGAGCCGCTGACCATTGGG
ACAGTAAAAATGTGTCCTGCAAGAACTGCAGTATTCAGCGGGGCTCCAAA
AAGCATCTATTGCTGGCACCATCTGACGTGGCAGGCTGGGGGATTTTTAT
CAAAGATCCTGTGCAGAAAAATGAATTCATCTCAGAATACTGTGGAGAGA
TTATTTCTCAAGATGAAGCTGACAGAAGAGGGAAAGTGTATGATAAATAC
ATGTGCAGCTTTCTGTTCAACTTGAACAATGATTTTGTGGTGGATGCAAC
CCGCAAGGGTAACAAAATTCGTTTTGCAAATCATTCGGTAAATCCAAACT
GCTATGCAAAAGTTATGATGGTTAACGGTGATCACAGGATAGGTATTTTT -continued
```
GCCAAGAGAGCCATCCAGACTGGCGAAGAGCTGTTTTTTGATTACAGATA

CAGCCAGGCTGATGCCCTGAAGTATGTCGGCATCGAAAGAGAAATGGAAA

TCCCTTGACATCTGCTACCTCCTCCCCCCTCCTCTGAAACAGCTGCCTTA

GCTTCAGGAACCTCGAGTACTGTGGGCAATTTAGAAAAAGAACATGCAGT

TTGAAATTCTGAATTTGCAAAGTACTGTAAGAATAATTTATAGTAATGAG

TTTAAAAATCAACTTTTTATTGCCTTCTCACCAGCTGCAAAGTGTTTTGT

ACCAGTGAATTTTTGCAATAATGCAGTATGGTACATTTTTCAACTTTGAA

TAAAGAATACTTGAACTTGTCCTTGTTGAATC
```

A structure model of partial EZH2 protein based on the A chain of nuclear receptor binding SET domain protein 1 (NSD1) is provided below. This model corresponds to amino acid residues 533-732 of EZH2 sequence of SEQ ID NO: 1.

The corresponding amino acid sequence of this structure model is provided below. The residues in the substrate pocket domain are underlined. The residues in the SET domain are shown italic.

```
                                               (SEQ ID NO: 6)
SCPCVIAQNFCEKFCQCSSECQNRFPGCRCKAQCNTKQCPCYLAVRECDP

DLCLTCGAADHWDSKNVSCKNCSIQRGSKKHLLLAPSDVAGWGIFIKDP

VQKNEFISEY⁶⁴¹CGEIISQDEADRRGKVYDKYMCSFLFNLNNDFV⁶⁷⁴VD

A⁶⁷⁷TRKGNKIR⁶⁸⁵FA⁶⁸⁷NHSVNPNCYAKVMMVNGDHRIGIFAKRAIQTG

EELFFDYRYSQAD
```

The catalytic site of EZH2 is believed to reside in a conserved domain of the protein known as the SET domain. The amino acid sequence of the SET domain of EZH2 is provided by the following partial sequence spanning amino acid residues 613-726 of Swiss-Prot Accession No. Q15910 (SEQ ID NO: 1):

```
                                               (SEQ ID NO: 7)
HLLLAPSDVAGWGIFIKDPVQKNEFISEYCGEIISQDEADRRGKVYDKYM

CSFLFNLNNDFVVDATRKGNKIRFANHSVNPNCYAKVMMVNGDHRIGIFA

KRAIQTGEELFFDY.
```

The tyrosine (Y) residue shown underlined in SEQ ID NO: 7 is Tyr641 (Y641) in Swiss-Prot Accession No. Q15910 (SEQ ID NO: 1).

The SET domain of GenBank Accession No. NP_004447 (SEQ ID NO: 3) spans amino acid residues 618-731 and is identical to SEQ ID NO:6. The tyrosine residue corresponding to Y641 in Swiss-Prot Accession No. Q15910 shown underlined in SEQ ID NO: 7 is Tyr646 (Y646) in GenBank Accession No. NP_004447 (SEQ ID NO: 3).

The SET domain of GenBank Accession No. NP_694543 (SEQ ID NO: 5) spans amino acid residues 574-687 and is identical to SEQ ID NO: 7. The tyrosine residue corresponding to Y641 in Swiss-Prot Accession No. Q15910 shown underlined in SEQ ID NO: 7 is Tyr602 (Y602) in GenBank Accession No. NP_694543 (SEQ ID NO: 5).

The nucleotide sequence encoding the SET domain of GenBank Accession No. NP_004447 is

```
                                               (SEQ ID NO: 8)
catctattgctggcaccatctgacgtggcaggctgggggattttatcaa agatcctgtgcagaaaaatgaattcatctcagaatactgtggagagatta tttctcaagatgaagctgacagaagagggaaagtgtatgataaatacatg tgcagctttctgttcaacttgaacaatgattttgtggtggatgcaacccg caagggtaacaaaattcgttttgcaaatcattcggtaaatccaaactgct atgcaaaagttatgatggttaacggtgatcacaggataggtatttttgcc aagagagccatccagactggcgaagagctgtttttgattac,
``` where the codon encoding Y641 is shown underlined.

For purposes of this application, amino acid residue Y641 of human EZH2 is to be understood to refer to the tyrosine residue that is or corresponds to Y641 in Swiss-Prot Accession No. Q15910.

```
Full amino acid sequence of Y641 mutant EZH2
                                               (SEQ ID NO: 9)
MGQTGKKSEKGPVCWRKRVKSEYMRLRQLKRFRRADEVKSMFSSNRQKIL

ERTEILNQEWKQRRIQPVHILTSVSSLRGTRECSVTSDLDFPTQVIPLKT

LNAVASVPIMYSWSPLQQNFMVEDETVLHNIPYMGDEVLDQDGTFIEELI

KNYDGKVHGDRECGFINDEIFVELVNALGQYNDDDDDDGDDPEEREEKQ

KDLEDHRDDKESRPPRKFPSDKIFEAISSMFPDKGTAEELKEKYKELTEQ

QLPGALPPECTPNIDGPNAKSVQREQSLHSFHTLFCRRCFKYDCFLHPFH

ATPNTYKRKNTETALDNKPCGPQCYQHLEGAKEFAAALTAERIKTPPKRP

GGRRRGRLPNNSSRPSTPTINVLESKDTDSDREAGTETGGENNDKEEEEK

KDETSSSSEANSRCQTPIKMKPNIEPPENVEWSGAEASMFRVLIGTYYDN

FCAIARLIGTKTCRQVYEFRVKESSIIAPAPAEDVDTPPRKKKRKHRLWA

AHCRKIQLKKDGSSNHVYNYQPCDHPRQPCDSSCPCVIAQNFCEKFCQCS

SECQNRFPGCRCKAQCNTKQCPCYLAVRECDPDLCLTCGAADHWDSKNVS

CKNCSIQRGSKKHLLLAPSDVAGWGIFIKDPVQKNEFISEXCGEIISQDE

ADRRGKVYDKYMCSFLFNLNNDFVVDATRKGNKIRFANHSVNPNCYAKVM

MVNGDHRIGIFAKRAIQTGEELFFDYRYSQADALKYVGIEREMEIP
Wherein x can be any amino acid
residue other than tyrosine (Y)
```

Also for purposes of this application, a Y641 mutant of human EZH2, and, equivalently, a Y641 mutant of EZH2, is to be understood to refer to a human EZH2 in which the amino acid residue corresponding to Y641 of wild-type human EZH2 is substituted by an amino acid residue other than tyrosine.

In one embodiment the amino acid sequence of a Y641 mutant of EZH2 differs from the amino acid sequence of wild-type human EZH2 only by substitution of a single amino acid residue corresponding to Y641 of wild-type human EZH2 by an amino acid residue other than tyrosine.

In one embodiment the amino acid sequence of a Y641 mutant of EZH2 differs from the amino acid sequence of wild-type human EZH2 only by substitution of phenylalanine (F) for the single amino acid residue corresponding to Y641 of wild-type human EZH2. The Y641 mutant of EZH2 according to this embodiment is referred to herein as a Y641F mutant or, equivalently, Y641F.

In one embodiment the amino acid sequence of a Y641 mutant of EZH2 differs from the amino acid sequence of wild-type human EZH2 only by substitution of histidine (H) for the single amino acid residue corresponding to Y641 of wild-type human EZH2. The Y641 mutant of EZH2 according to this embodiment is referred to herein as a Y641H mutant or, equivalently, Y641H.

In one embodiment the amino acid sequence of a Y641 mutant of EZH2 differs from the amino acid sequence of wild-type human EZH2 only by substitution of asparagine (N) for the single amino acid residue corresponding to Y641 of wild-type human EZH2. The Y641 mutant of EZH2 according to this embodiment is referred to herein as a Y641N mutant or, equivalently, Y641N.

In one embodiment the amino acid sequence of a Y641 mutant of EZH2 differs from the amino acid sequence of wild-type human EZH2 only by substitution of serine (S) for the single amino acid residue corresponding to Y641 of wild-type human EZH2. The Y641 mutant of EZH2 according to this embodiment is referred to herein as a Y641S mutant or, equivalently, Y641S.

In one embodiment the amino acid sequence of a Y641 mutant of EZH2 differs from the amino acid sequence of wild-type human EZH2 only by substitution of cysteine (C) for the single amino acid residue corresponding to Y641 of wild-type human EZH2. The Y641 mutant of EZH2 according to this embodiment is referred to herein as a Y641C mutant or, equivalently, Y641C.

In one embodiment the amino acid sequence of a A677 mutant of EZH2 differs from the amino acid sequence of wild-type human EZH2 only by substitution of a non-alanine amino acid, preferably glycine (G) for the single amino acid residue corresponding to A677 of wild-type human EZH2. The A677 mutant of EZH2 according to this embodiment is referred to herein as an A677 mutant, and preferably an A677G mutant or, equivalently, A677G.

In one embodiment the amino acid sequence of a A687 mutant of EZH2 differs from the amino acid sequence of wild-type human EZH2 only by substitution of a non-alanine amino acid, preferably valine (V) for the single amino acid residue corresponding to A687 of wild-type human EZH2. The A687 mutant of EZH2 according to this embodiment is referred to herein as an A687 mutant and preferably an A687V mutant or, equivalently, A687V.

In one embodiment the amino acid sequence of a R685 mutant of EZH2 differs from the amino acid sequence of wild-type human EZH2 only by substitution of a non-arginine amino acid, preferably histidine (H) or cysteine (C) for the single amino acid residue corresponding to R685 of wild-type human EZH2. The R685 mutant of EZH2 according to this embodiment is referred to herein as an R685 mutant and preferably an R685C mutant or an R685H mutant or, equivalently, R685H or R685C.

In one embodiment the amino acid sequence of a mutant of EZH2 differs from the amino acid sequence of wild-type human EZH2 in one or more amino acid residues in its substrate pocket domain as defined in SEQ ID NO: 6. The mutant of EZH2 according to this embodiment is referred to herein as an EZH2 mutant.

Other exemplary substitution amino acid mutation includes a substitution at amino acid position 677, 687, 674, 685, or 641 of SEQ ID NO: 1, such as, but is not limited to a substitution of glycine (G) for the wild type residue alanine (A) at amino acid position 677 of SEQ ID NO: 1 (A677G); a substitution of valine (V) for the wild type residue alanine (A) at amino acid position 687 of SEQ ID NO: 1 (A687V); a substitution of methionine (M) for the wild type residue valine (V) at amino acid position 674 of SEQ ID NO: 1 (V674M); a substitution of histidine (H) for the wild type residue arginine (R) at amino acid position 685 of SEQ ID NO: 1 (R685H); a substitution of cysteine (C) for the wild type residue arginine (R) at amino acid position 685 of SEQ ID NO: 1 (R685C); a substitution of phenylalanine (F) for the wild type residue tyrosine (Y) at amino acid position 641 of SEQ ID NO: 1 (Y641F); a substitution of histidine (H) for the wild type residue tyrosine (Y) at amino acid position 641 of SEQ ID NO: 1 (Y641H); a substitution of asparagine (N) for the wild type residue tyrosine (Y) at amino acid position 641 of SEQ ID NO: 1 (Y641N); a substitution of serine (S) for the wild type residue tyrosine (Y) at amino acid position 641 of SEQ ID NO: 1 (Y641S); or a substitution of cysteine (C) for the wild type residue tyrosine (Y) at amino acid position 641 of SEQ ID NO: 1 (Y641C).

The mutation of the present disclosure may also include a substitution of serine (S) for the wild type residue asparagine (N) at amino acid position 322 of SEQ ID NO: 3 (N322S), a substitution of glutamine (Q) for the wild type residue arginine (R) at amino acid position 288 of SEQ ID NO: 3 (R288Q), a substitution of isoleucine (I) for the wild type residue threonine (T) at amino acid position 573 of SEQ ID NO: 3 (T573I), a substitution of glutamic acid (E) for the wild type residue aspartic acid (D) at amino acid position 664 of SEQ ID NO: 3 (D664E), a substitution of glutamine (Q) for the wild type residue arginine (R) at amino acid position 458 of SEQ ID NO: 5 (R458Q), a substitution of lysine (K) for the wild type residue glutamic acid (E) at amino acid position 249 of SEQ ID NO: 3 (E249K), a substitution of cysteine (C) for the wild type residue arginine (R) at amino acid position 684 of SEQ ID NO: 3 (R684C), a substitution of histidine (H) for the wild type residue arginine (R) at amino acid position 628 of SEQ ID NO: 11 (R628H), a substitution of histidine (H) for the wild type residue glutamine (Q) at amino acid position 501 of SEQ ID NO: 5 (Q501H), a substitution of asparagine (N) for the wild type residue aspartic acid (D) at amino acid position 192 of SEQ ID NO: 3 (D192N), a substitution of valine (V) for the wild type residue aspartic acid (D) at amino acid position 664 of SEQ ID NO: 3 (D664V), a substitution of leucine (L) for the wild type residue valine (V) at amino acid position 704 of SEQ ID NO: 3 (V704L), a substitution of serine (S) for the wild type residue proline (P) at amino acid position 132 of SEQ ID NO: 3 (P132S), a substitution of lysine (K) for the wild type residue glutamic acid (E) at amino acid position 669 of SEQ ID NO: 11 (E669K), a substitution of threonine (T) for the wild type residue alanine (A) at amino acid position 255 of SEQ ID NO: 3 (A255T), a substitution of valine (V) for the wild type residue glutamic acid (E) at amino acid position 726 of SEQ ID NO: 3 (E726V), a substitution of tyrosine (Y) for the wild type residue cysteine (C) at amino acid position 571 of SEQ ID NO: 3 (C571Y), a substitution of cysteine (C) for the wild type residue phenylalanine (F) at amino acid position 145 of SEQ ID NO: 3 (F145C), a substitution of threonine (T) for the wild type residue asparagine (N) at amino acid position 693 of SEQ ID NO: 3 (N693T), a substitution of serine (S) for the wild type residue phenylalanine (F) at amino acid position 145 of SEQ ID NO: 3 (F145S), a substitution of histidine (H) for the wild type residue glutamine (Q) at amino acid position 109 of SEQ ID NO: 11 (Q109H), a substitution of cysteine (C) for the wild type residue phenylalanine (F) at amino acid position 622 of SEQ ID NO: 11 (F622C), a substitution of arginine (R) for the wild type residue glycine (G) at amino acid position 135 of SEQ ID NO: 3 (G135R), a substitution of glutamine (Q) for the wild type residue arginine (R) at amino acid position 168 of SEQ ID NO: 5 (R168Q), a substitution of arginine (R) for the wild type residue glycine (G) at amino acid position 159 of SEQ ID NO: 3 (G159R), a substitution of cysteine (C) for the wild type residue arginine (R) at amino acid position 310 of SEQ ID NO: 5 (R310C), a substitution of histidine (H) for the wild type residue arginine (R) at amino acid position 561 of SEQ ID NO: 3 (R561H), a substitution of histidine (H) for the wild type residue arginine (R) at amino acid position 634 of SEQ ID NO: 11 (R634H), a substitution of arginine (R) for the wild type residue glycine (G) at amino acid position 660 of SEQ ID NO: 3 (G660R), a substitution of cysteine (C) for the wild type residue tyrosine (Y) at amino acid position 181 of SEQ ID NO: 3 (Y181C), a substitution of arginine (R) for the wild type residue histidine (H) at amino acid position 297 of SEQ ID NO: 3 (H297R), a substitution of serine (S) for the wild type residue cysteine (C) at amino acid position 612 of SEQ ID NO: 11 (C612S), a substitution of tyrosine (Y) for the wild type residue histidine (H) at amino acid position 694 of SEQ ID NO: 3 (H694Y), a substitution of alanine (A) for the wild type residue aspartic acid (D) at amino acid position 664 of SEQ ID NO: 3 (D664A), a substitution of threonine (T) for the wild type residue isoleucine (I) at amino acid position 150 of SEQ ID NO: 3 (I150T), a substitution of arginine (R) for the wild type residue isoleucine (I) at amino acid position 264 of SEQ ID NO: 3 (I264R), a substitution of leucine (L) for the wild type residue proline (P) at amino acid position 636 of SEQ ID NO: 3 (P636L), a substitution of threonine (T) for the wild type residue isoleucine (I) at amino acid position 713 of SEQ ID NO: 3 (I713T), a substitution of proline (P) for the wild type residue glutamine (Q) at amino acid position 501 of SEQ ID NO: 5 (Q501P), a substitution of glutamine (Q) for the wild type residue lysine (K) at amino acid position 243 of SEQ ID NO: 3 (K243Q), a substitution of aspartic acid (D) for the wild type residue glutamic acid (E) at amino acid position 130 of SEQ ID NO: 5 (E130D), a substitution of glycine (G) for the wild type residue arginine (R) at amino acid position 509 of SEQ ID NO: 3 (R509G), a substitution of histidine (H) for the wild type residue arginine (R) at amino acid position 566 of SEQ ID NO: 3 (R566H), a substitution of histidine (H) for the wild type residue aspartic acid (D) at amino acid position 677 of SEQ ID NO: 3 (D677H), a substitution of asparagine (N) for the wild type residue lysine (K) at amino acid position 466 of SEQ ID NO: 5 (K466N), a substitution of histidine (H) for the wild type residue arginine (R) at amino acid position 78 of SEQ ID NO: 3 (R78H), a substitution of methionine (M) for the wild type residue lysine (K) at amino acid position 1 of SEQ ID NO: 6 (K6M), a substitution of leucine (L) for the wild type residue serine (S) at amino acid position 538 of SEQ ID NO: 3 (S538L), a substitution of glutamine (Q) for the wild type residue leucine (L) at amino acid position 149 of SEQ ID NO: 3 (L149Q), a substitution of valine (V) for the wild type residue leucine (L) at amino acid position 252 of SEQ ID NO: 3 (L252V), a substitution of valine (V) for the wild type residue leucine (L) at amino acid position 674 of SEQ ID NO: 3 (L674V), a substitution of valine (V) for the wild type residue alanine (A) at amino acid position 656 of SEQ ID NO: 3 (A656V), a substitution of aspartic acid (D) for the wild type residue alanine (A) at amino acid position 731 of SEQ ID NO: 3 (Y731D), a substitution of threonine (T) for the wild type residue alanine (A) at amino acid position 345 of SEQ ID NO: 3 (A345T), a substitution of aspartic acid (D) for the wild type residue alanine (A) at amino acid position 244 of SEQ ID NO: 3 (Y244D), a substitution of tryptophan (W) for the wild type residue cysteine (C) at amino acid position 576 of SEQ ID NO: 3 (C576W), a substitution of lysine (K) for the wild type residue asparagine (N) at amino acid position 640 of SEQ ID NO: 3 (N640K), a substitution of lysine (K) for the wild type residue asparagine (N) at amino acid position 675 of SEQ ID NO: 3 (N675K), a substitution of tyrosine (Y) for the wild type residue aspartic acid (D) at amino acid position 579 of SEQ ID NO: 11 (D579Y), a substitution of isoleucine (I) for the wild type residue asparagine (N) at amino acid position 693 of SEQ ID NO: 3 (N693I), and a substitution of lysine (K) for the wild type residue asparagine (N) at amino acid position 693 of SEQ ID NO: 3 (N693K).

The mutation of the present disclosure may be a frameshift at amino acid position 730, 391, 461, 441, 235, 254, 564, 662, 715, 405, 685, 64, 73, 656, 718, 374, 592, 505, 730, or 363 of SEQ ID NO: 3, 5 or 11 or the corresponding nucleotide position of the nucleic acid sequence encoding SEQ ID NO: 3, 5, or 21. The mutation of the EZH2 may also be an insertion of a glutamic acid (E) between amino acid positions 148 and 149 of SEQ ID NO: 3, 5 or 11. Another example of EZH2 mutation is a deletion of glutamic acid (E) and leucine (L) at amino acid positions 148 and 149 of SEQ ID NO: 3, 5 or 11. The mutant EZH2 may further comprise a nonsense mutation at amino acid position 733, 25, 317, 62, 553, 328, 58, 207, 123, 63, 137, or 60 of SEQ ID NO: 3, 5 or 11.

Cells heterozygous for EZH2 would be expected to display a malignant phenotype due to the efficient formation of H3-K27me1 by the WT enzyme and the efficient, subsequent transition of this progenitor species to H3-K27me2, and, especially, H3-K27me3, by the mutant enzyme form(s).

Previous results point to dependency on enzymatic coupling between enzymes that perform H3-K27 mono-methylation and certain mutant forms of EZH2 for pathogenesis in follicular lymphoma and diffuse large B-cell lymphoma. For example, cells expressing Y641 mutant EZH2 may be more sensitive to small molecule EZH2 inhibitors than cells expressing WT EZH2. Specifically, cells expressing Y641 mutant EZH2 show reduced growing, dividing or proliferation, or even undergo apoptosis or necrosis after the treatment of EZH2 inhibitors. In contrast, cells expressing WT EZH2 are not responsive to the anti-proliferative effect of the EZH2 inhibitors (U.S. patent application Ser. No. 13/230,703 (now U.S. Pat. No. 8,895,245); incorporated herein by reference in its entirety.)

An aspect of the present disclosure is a method for treating or alleviating a symptom of cancer or precancerous condition in a subject by administering to a subject expressing a mutant EZH2 comprising a mutation in the substrate pocket domain as defined in SEQ ID NO: 6 a therapeutically effective amount of an EZH2 inhibitor as described herein, e.g., a compound of Formulae (I)-(VIa) in combination with another agent suitable to be administered together simultaneously, sequentially, or in alternation.

Another aspect of the disclosure is a method for inhibiting in a subject conversion of H3-K27 to trimethylated H3-K27. The inhibition can involve inhibiting in a subject conversion of unmethylated H3-K27 to monomethylated H3-K27, conversion of monomethylated H3-K27 to dimethylated H3-K27, conversion of dimethylated H3-K27 to trimethylated H3-K27, or any combination thereof, including, for example, conversion of monomethylated H3-K27 to dimethylated H3-K27 and conversion of dimethylated H3-K27 to trimethylated H3-K27. As used herein, unmethylated H3-K27 refers to histone H3 with no methyl group covalently linked to the amino group of lysine 27. As used herein, monomethylated H3-K27 refers to histone H3 with a single methyl group covalently linked to the amino group of lysine 27. Monomethylated H3-K27 is also referred to herein as H3-K27me1. As used herein, dimethylated H3-K27 refers to histone H3 with two methyl groups covalently linked to the amino group of lysine 27. Dimethylated H3-K27 is also referred to herein as H3-K27me2. As used herein, trimethylated H3-K27 refers to histone H3 with three methyl groups covalently linked to the amino group of lysine 27. Trimethylated H3-K27 is also referred to herein as H3-K27me3.

Histone H3 is a 136 amino acid long protein, the sequence of which is known. See, for example, GenBank Accession No. CAB02546, the content of which is incorporated herein by reference. As disclosed further herein, in addition to full-length histone H3, peptide fragments of histone H3 comprising the lysine residue corresponding to K27 of full-length histone H3 can be used as substrate for EZH2 (and likewise for mutant forms of EZH2) to assess conversion of H3-K27m1 to H3-K27m2 and conversion of H3-K27m2 to H3-K27m3. In one embodiment, such peptide fragment corresponds to amino acid residues 21-44 of histone H3. Such peptide fragment has the amino acid sequence (SEQ ID NO: 10)
LATKAARKSAPATGGVKKPHRYRP.

A composition of the present disclosure comprises a compound of Formulae (I)-(VIa) and one or more other therapeutic agents, or a pharmaceutically acceptable salt thereof. The compounds of Formulae (I)-(VIa) are suitable for administration as part of a combination therapy with one or more other therapeutic agents or treatment modality, suitable to be administered together, sequentially, or in alternation. Other compounds of Formulae (I)-(VIa) suitable for the methods of the disclosure are described in U.S. Publication 20120264734, the contents of which are hereby incorporated by reference in their entireties.

A compound (i.e., an EZH2 inhibitor) that can be used in any methods described herein may have the following Formula I:

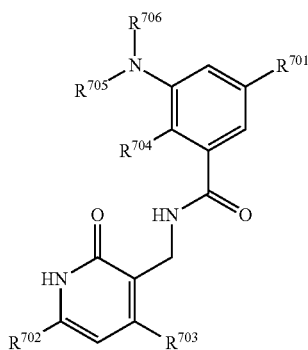

(I)

or a pharmaceutically acceptable salt thereof; wherein
$R^{701}$ is H, F, $OR^{707}$, $NHR^{707}$, $-(C\equiv C)-(CH_2)_{n7}-R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, $O-C_{1-6}$ alkyl, $NH-C_{1-6}$ alkyl, and, $C_{1-3}$ alkyl substituted with $C_{3-8}$ cycloalkyl or 4-7 membered heterocycloalkyl containing 1-3 heteroatoms, wherein each of the $O-C_{1-6}$ alkyl and $NH-C_{1-6}$ alkyl is optionally substituted with hydroxyl, $O-C_{1-3}$ alkyl or $NH-C_{1-3}$ alkyl, each of the $O-C_{1-3}$ alkyl and $NH-C_{1-3}$ alkyl being optionally further substituted with $O-C_{1-3}$ alkyl or $NH-C_{1-3}$ alkyl;

each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo;

each of $R^{704}$ and $R^{705}$, independently is $C_{1-4}$ alkyl;

$R^{706}$ is cyclohexyl substituted by $N(C_{1-4}$ alkyl$)_2$ wherein one or both of the $C_{1-4}$ alkyl is substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or $O-C_{1-6}$ alkyl, wherein the 4-7 membered heterocycloalkyl can be optionally further substituted with OH or $C_{1-6}$ alkyl; and $n_7$ is 0, 1 or 2.

For example, $R^{706}$ is cyclohexyl substituted by $N(C_{1-4}$ alkyl$)_2$ wherein one of the $C_{1-4}$ alkyl is unsubstituted and the other is substituted with methoxy.

For example, $R^{706}$ is

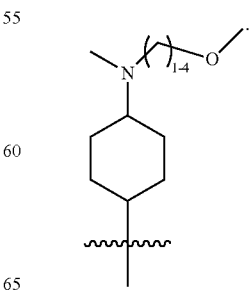

For example, the compound is of Formula II:

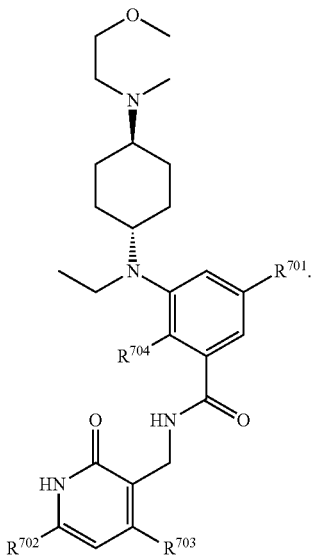

(II)

For example, $R^{702}$ is methyl or isopropyl and $R^{703}$ is methyl or methoxyl.

For example, $R^{704}$ is methyl.

For example, $R^{701}$ is $OR^{707}$ and $R^{707}$ is $C_{1-3}$ alkyl optionally substituted with $OCH_3$ or morpholine.

For example, $R^{701}$ is H or F.

For example, $R^{701}$ is tetrahydropyranyl, phenyl, pyridyl, pyrimidyl, pyrazinyl, imidazolyl, or pyrazolyl, each of which is optionally substituted with methyl, methoxy, ethyl substituted with morpholine, or —$OCH_2CH_2OCH_3$.

For example, $R^{708}$ is morpholine, piperidine, piperazine, pyrrolidine, diazepane, or azetidine, each of which is optionally substituted with OH or $C_{1-6}$ alkyl.

For example, $R^{708}$ is morpholine

For example, $R^{708}$ is piperazine substituted with $C_{1-6}$ alkyl.

For example, $R^{708}$ is methyl, t-butyl or $C(CH_3)_2OH$.

A compound (i.e., an EZH2 inhibitor) that can be used in any methods described herein may have the following Formula III:

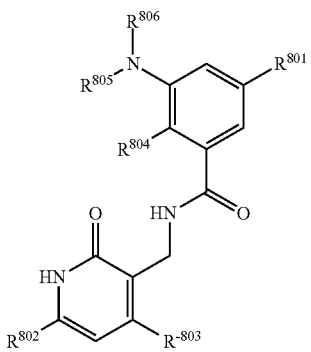

(III)

or a pharmaceutically acceptable salt thereof.

In this formula:

$R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl; or $R^{801}$ is phenyl substituted with -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is optionally substituted 4- to 12-membered heterocycloalkyl; and $R^{801}$ is optionally further substituted;

each of $R^{802}$ and $R^{803}$, independently is H, halo, $C_{1-4}$ alkyl, $C_{1-6}$ alkoxyl or $C_6$-$C_{10}$ aryloxy, each optionally substituted with one or more halo;

each of $R^{804}$ and $R^{805}$, independently is $C_{1-4}$ alkyl; and $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl.

For example, each of $Q_x$ and $Q_2$ independently is a bond or methyl linker, and each of $T_x$ and $T_2$ independently is tetrahydropyranyl, piperidinyl substituted by 1, 2, or 3 $C_1$-4 alkyl groups, or cyclohexyl substituted by $N(C_{1-4}$ alkyl$)_2$ wherein one or both of the $C_{1-4}$ alkyl is optionally substituted with $C_{1-6}$ alkoxy;

For example, $R^{806}$ is cyclohexyl substituted by $N(C_{1-4}$ alkyl$)_2$ or $R^{806}$ is tetrahydropyranyl.

For example, $R^{806}$ is

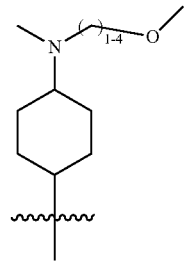

For example, $R^{801}$ is phenyl or 5- or 6-membered heteroaryl substituted with O—$C_{1-6}$ alkyl-$R_x$, or $R^{801}$ is phenyl, substituted with $CH_2$-tetrahydropyranyl.

For example, a compound of the present disclosure is of Formula IVa or IVb:

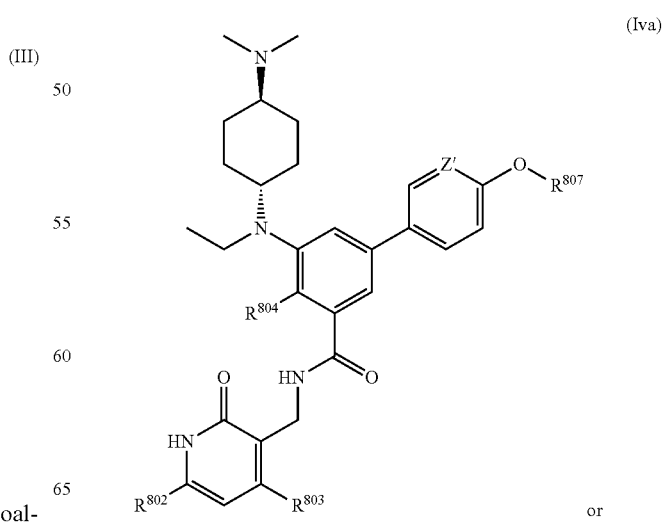

(Iva)

or

-continued (IVb)

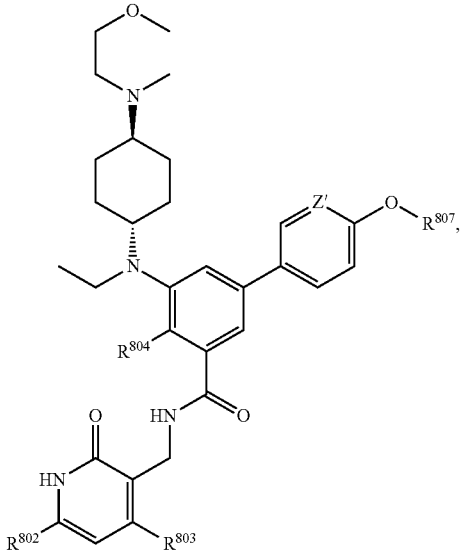

wherein Z' is CH or N, and $R^{807}$ is $C_{2-3}$ alkyl-$R_x$.

For example, $R^{807}$ is —$CH_2CH_2OH$, —$CH_2CH_2OCH_3$, or —$CH_2CH_2OCH_2CH_2OCH_3$.

For example, $R^{802}$ is methyl or isopropyl and $R^{803}$ is methyl or methoxyl.

For example, $R^{804}$ is methyl.

A compound of the present disclosure may have the following Formula (V):

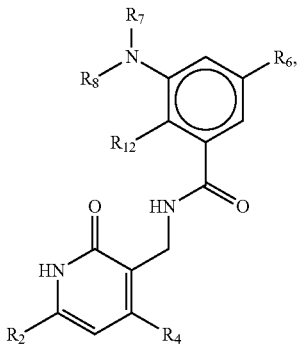

(V)

or a pharmaceutically acceptable salt or ester thereof.

In this Formula:

$R_2$, $R_4$ and $R_{12}$ are each, independently $C_{1-6}$ alkyl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_k$C(O), S(O)$_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_q R_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; and $R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, and the 4 to 11-membered heterocycloalkyl ring formed by $R_7$ and $R_8$ is optionally substituted with one or more -$Q_6$-$T_6$, wherein $Q_6$ is a bond, C(O), C(O)$NR_m$, $NR_m$C(O), S(O)$_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo.

For example, $R_6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —$OR_a$, —$NR_aR_b$, —$(NR_aR_bR_c)^+A^-$, —$C(O)NR_aR_b$, —$NR_bC(O)R_a$, —$S(O)_2R_a$, or $R_{S2}$, in which each of $R_a$ and $R_b$, independently is H or $R_{S3}$, each of $R_{S2}$ and $R_{S3}$, independently, is $C_1$-$C_6$ alkyl, or $R_a$ and $R_b$, together with the N atom to which they are attached, form a 4 to 7-membered heterocycloalkyl ring having 0 or 1 additional heteroatom, and each of $R_{S2}$, $R_{S3}$, and the 4 to 7-membered heterocycloalkyl ring formed by $R_a$ and $R_b$, is optionally, independently substituted with one or more -$Q_3$-$T_3$, wherein $Q_3$ is a bond or $C_1$-$C_3$ alkyl linker and $T_3$ is selected from the group consisting of halo, $C_1$-$C_6$ alkyl, 4 to 7-membered heterocycloalkyl, $OR_d$, —$S(O)_2R_d$, and —$NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S.

For example, the compound of the present disclosure is of Formula (VI):

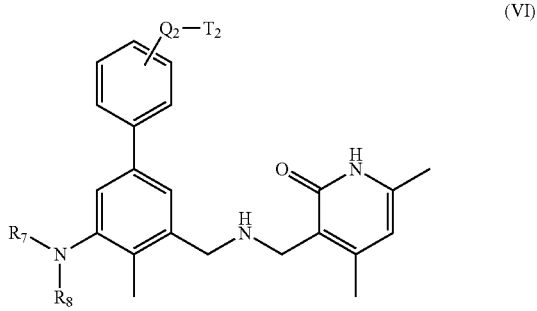

(VI)

or a pharmaceutically acceptable salt thereof, wherein $Q_2$ is a bond or methyl linker, $T_2$ is H, halo, —$OR_a$, —$NR_aR_b$, —$(NR_aR_bR_c)^+A^-$, or —$S(O)_2NR_aR_b$, $R_7$ is piperidinyl, tetrahydropyran, cyclopentyl, or cyclohexyl, each optionally substituted with one -$Q_5$-$T_5$ and $R_8$ is ethyl.

The present disclosure provides the compounds of Formula (VIa):

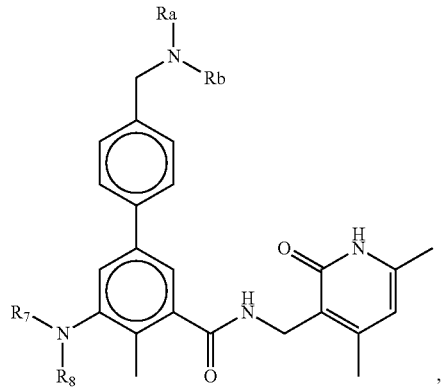

(VIa)

or a pharmaceutically acceptable salts or esters thereof, wherein $R_7$, $R_8$, $R_a$, and $R_b$ are defined herein.

The compounds of Formula (VIa) can include one or more of the following features:

For example, each of $R_a$ and $R_b$ independently is H or $C_1$-$C_6$ alkyl optionally substituted with one or more -$Q_3$-$T_3$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) and the ring is optionally substituted with one or more -$Q_3$-$T_3$.

For example, $R_a$ and $R_b$, together with the N atom to which they are attached, form azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, or morpholinyl, and the ring is optionally substituted with one or more -$Q_3$-$T_3$.

For example, one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_d$, $COOR_d$, —$S(O)_2R_d$, or —$NR_dR_e$.

For example, each of $R_d$ and $R_e$ independently being H or $C_1$-$C_6$ alkyl.

For example, $R_7$ is $C_3$-$C_8$ cycloalkyl or 4 to 7-membered heterocycloalkyl, each optionally substituted with one or more -$Q_5$-$T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more -$Q_5$-$T_5$.

For example, $R_7$ is cyclopentyl cyclohexyl or tetrahydro-2H-thiopyranyl, each of which is optionally substituted with one or more -$Q_5$-$T_5$.

For example, $Q_5$ is NHC(O) and $T_5$ is $C_1$-$C_6$ alkyl or $C_1$-$C_6$ alkoxy, each For example, one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1$-$C_6$ alkylamino, di-$C_1$-$C_6$ alkylamino.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

For example, $R_8$ is H, methyl, or ethyl.

In one embodiment, the compound of the disclosure is Compound 44

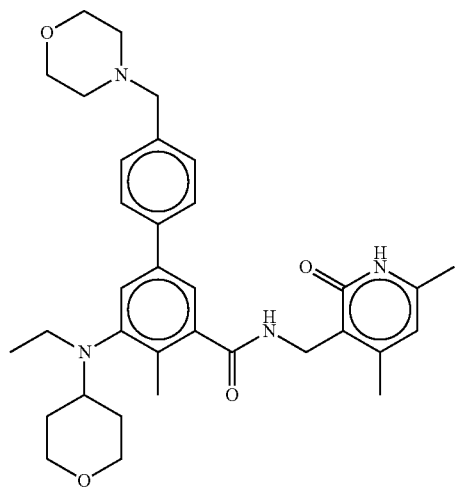

or a pharmaceutically acceptable salt thereof.

In some embodiments, a compound that can be used in any methods presented here is:

(A)

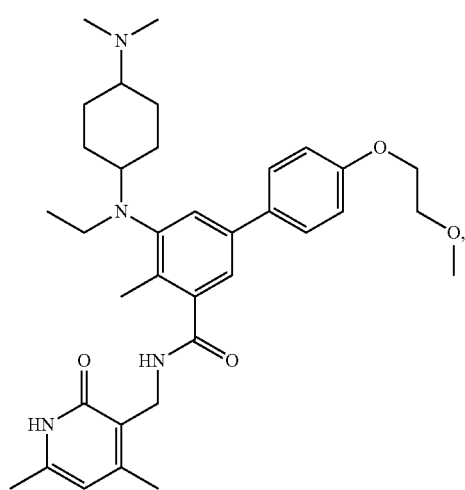

(B)

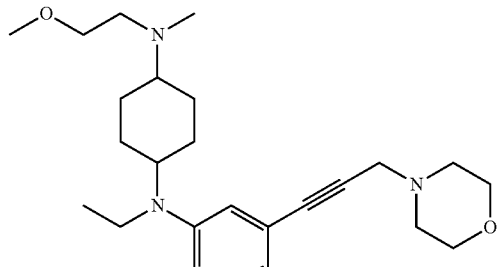

or (C)

stereoisomers thereof or pharmaceutically acceptable salts and solvates thereof.

In some embodiments, a compound that can be used in any methods presented here is GSK-126, stereoisomers thereof or pharmaceutically acceptable salts and solvates thereof.

In one embodiment, the compound of the disclosure is the compound itself, i.e., the free base or "naked" molecule. In another embodiment, the compound is a salt thereof, e.g., a mono-HCl or tri-HCl salt, mono-HBr or tri-HBr salt of the naked molecule.

Representative compounds of the present disclosure include compounds listed in Table 1.

In the table below, each occurrence of

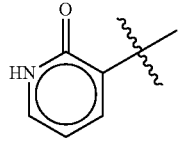

should be construed as

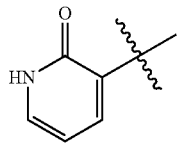

TABLE 1

| Compound Number | Structure | MS (M + 1)+ |
|---|---|---|
| 1 | 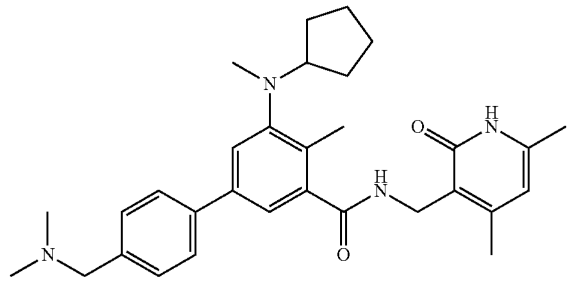 | 501.39 |
| 2 | 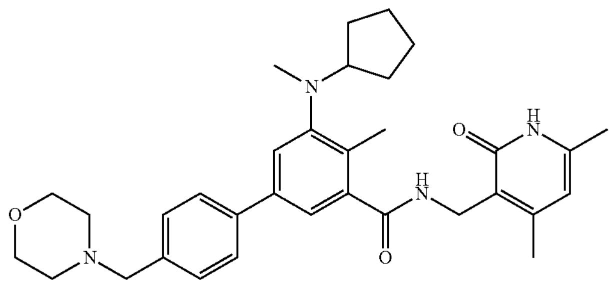 [SMILES: Cc1cc(C)c(CNC(=O)c2cc(-c3ccc(CN4CCOCC4)cc3)cc(N(C)C3CCCC3)c2C)c(=O)[nH]1] | 543.22 |
| 3 | 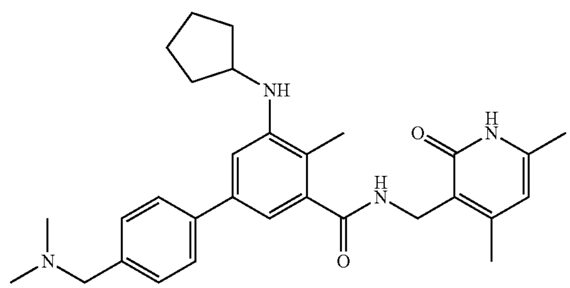 | 486.21 |
| 4 | 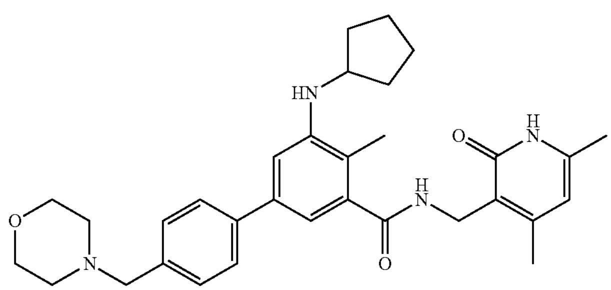 [SMILES: Cc1cc(C)c(CNC(=O)c2cc(-c3ccc(CN4CCOCC4)cc3)cc(NC3CCCC3)c2C)c(=O)[nH]1] | 529.30 |
| 11 | 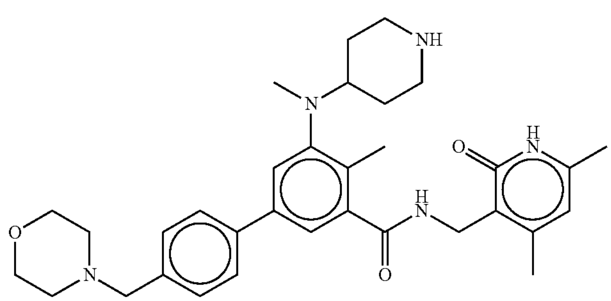 | 558.45 |

TABLE 1-continued

| Compound Number | Structure | MS (M + 1)+ |
|---|---|---|
| 12 | 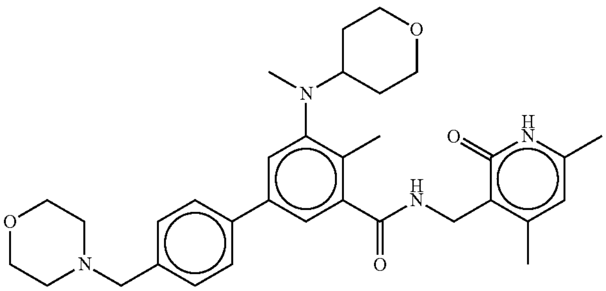 | 559.35 |
| 13 | 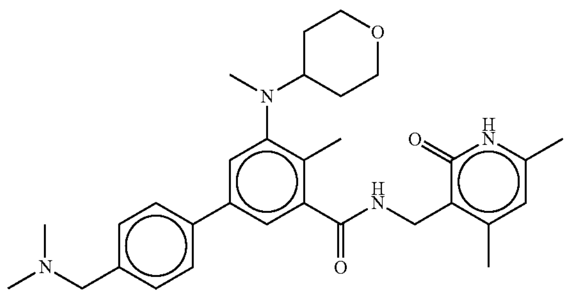 | 517.3 |
| 14 | 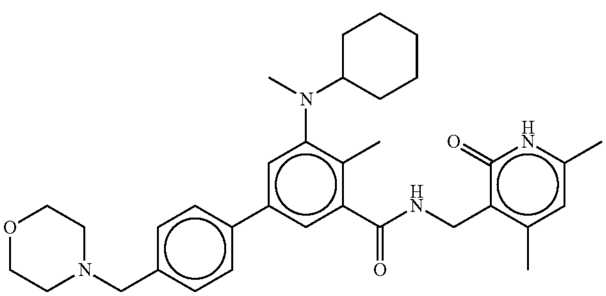 | 557.4 |
| 16 | 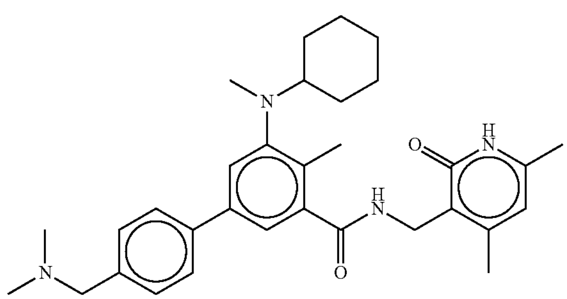 | 515.4 |
| 20 | 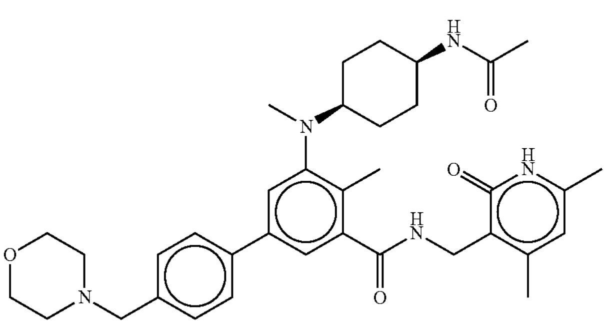 | 614.4 |

TABLE 1-continued

| Compound Number | Structure | MS (M + 1)+ |
|---|---|---|
| 21 | 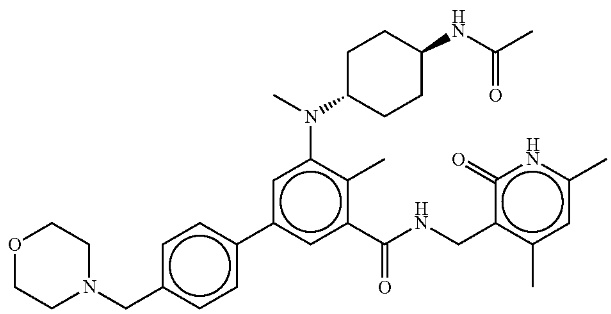 | 614.4 |
| 27 | 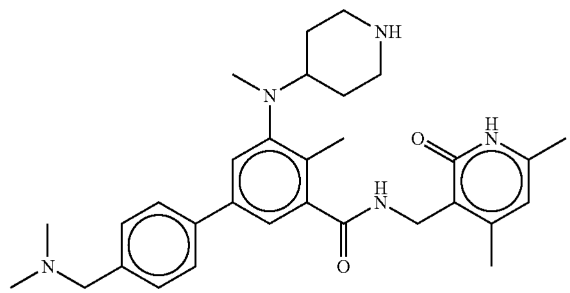 | 516.35 |
| 36 | 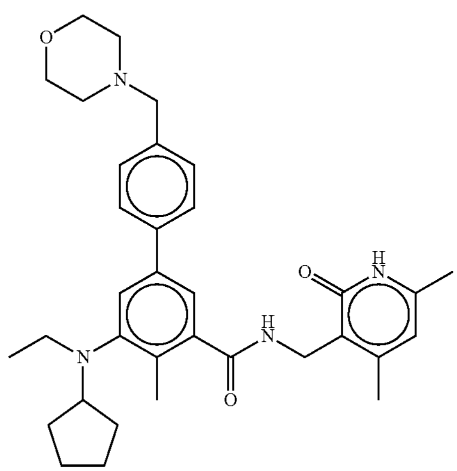 | 557.35 |
| 39 | 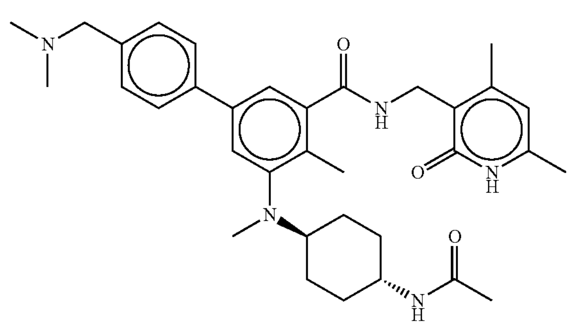 | 572.35 |

TABLE 1-continued

| Compound Number | Structure | MS (M + 1)+ |
|---|---|---|
| 40 | 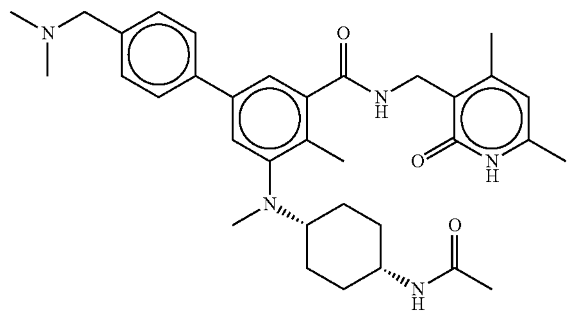 | 572.35 |
| 42 | 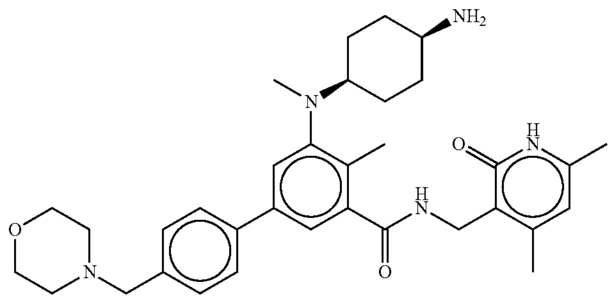 | 572.4 |
| 43 | 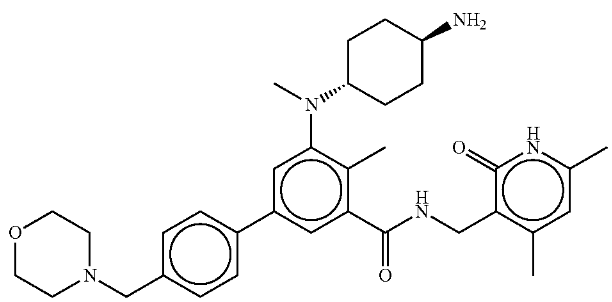 | 572.6 |
| 44 | 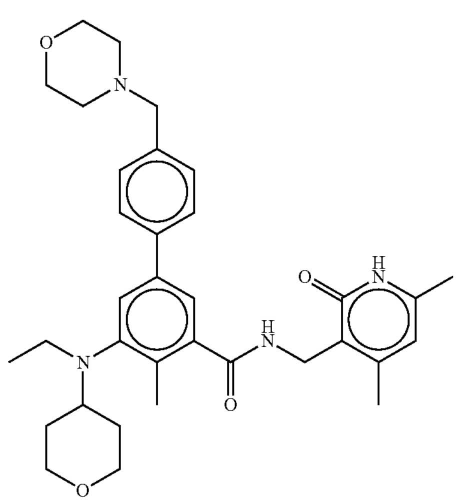 | 573.40 |

TABLE 1-continued

| Compound Number | Structure | MS (M + 1)+ |
|---|---|---|
| 47 | 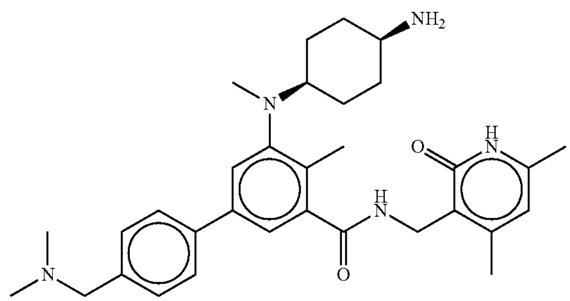 | 530.35 |
| 59 | 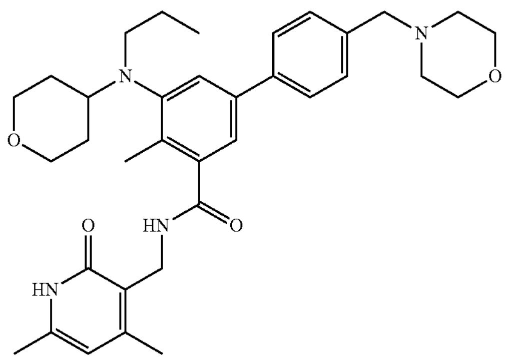 [SMILES: CCCN(c1cc(-c2ccc(CN3CCOCC3)cc2)cc(C(=O)NCc2c(C)cc(C)[nH]c2=O)c1C)C1CCOCC1] | 587.40 |
| 60 | 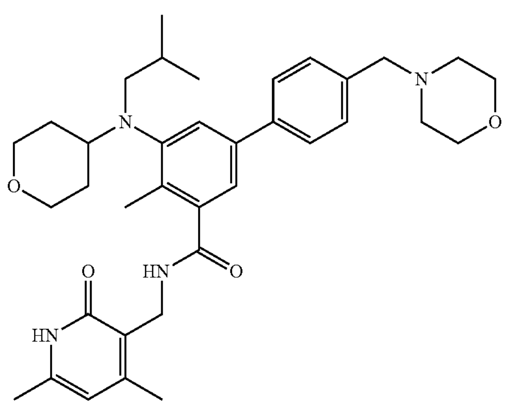 [SMILES: Cc1cc(C)c(CNC(=O)c2cc(-c3ccc(CN4CCOCC4)cc3)cc(N(CC(C)C)C3CCOCC3)c2C)c(=O)[nH]1] | 601.30 |
| 61 | 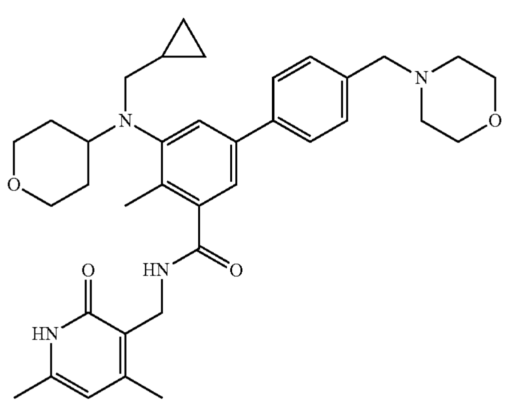 [SMILES: Cc1cc(C)c(CNC(=O)c2cc(-c3ccc(CN4CCOCC4)cc3)cc(N(CC3CC3)C3CCOCC3)c2C)c(=O)[nH]1] | 599.35 |

TABLE 1-continued

| Compound Number | Structure | MS (M + 1)+ |
|---|---|---|
| 62 | 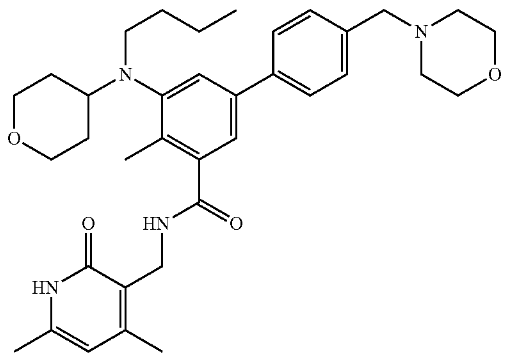 [SMILES: CCCCN(c1cc(-c2ccc(CN3CCOCC3)cc2)cc(C(=O)NCc2c(C)cc(C)[nH]c2=O)c1C)C1CCOCC1] | 601.35 |
| 63 | 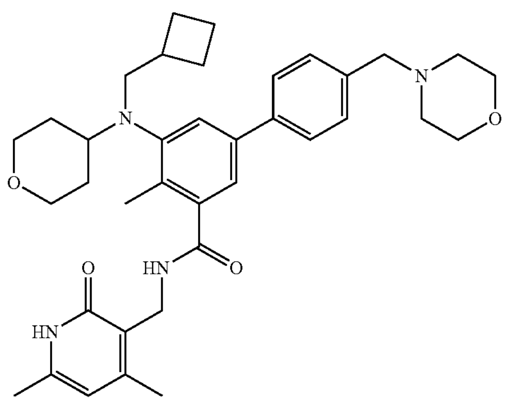 [SMILES: Cc1cc(C)c(CNC(=O)c2cc(-c3ccc(CN4CCOCC4)cc3)cc(N(CC3CCC3)C3CCOCC3)c2C)c(=O)[nH]1] | 613.35 |
| 65 | 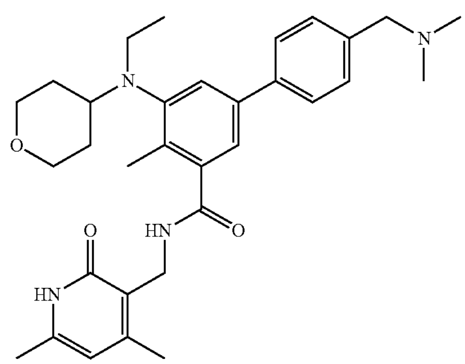 [SMILES: CCN(c1cc(-c2ccc(CN(C)C)cc2)cc(C(=O)NCc2c(C)cc(C)[nH]c2=O)c1C)C1CCOCC1] | 531.30 |
| 66 | 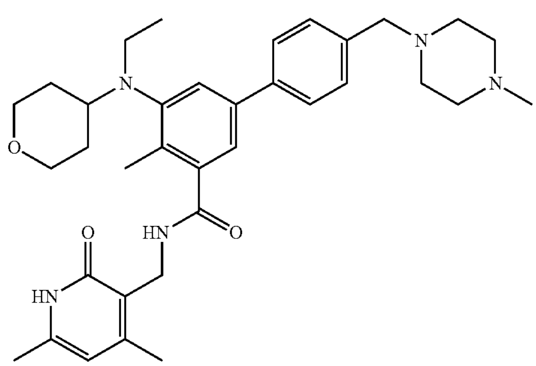 [SMILES: CCN(c1cc(-c2ccc(CN3CCN(C)CC3)cc2)cc(C(=O)NCc2c(C)cc(C)[nH]c2=O)c1C)C1CCOCC1] | 586.40 |

TABLE 1-continued

| Compound Number | Structure | MS (M + 1)+ |
|---|---|---|
| 67 | 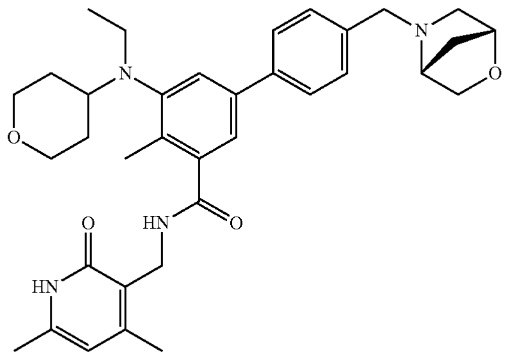 [SMILES: CCN(c1cc(-c2ccc(CN3C[C@H]4C[C@@H]3CO4)cc2)cc(C(=O)NCc2c(C)cc(C)[nH]c2=O)c1C)C1CCOCC1] | 585.25 |
| 68 | 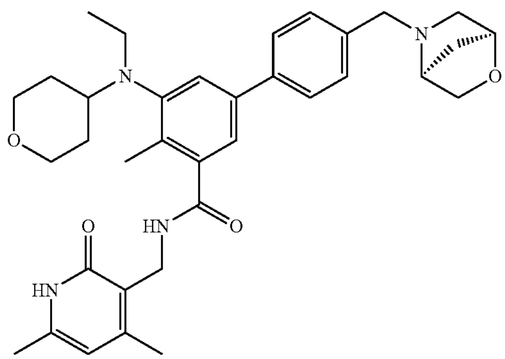 [SMILES: CCN(c1cc(-c2ccc(CN3C[C@@H]4C[C@H]3CO4)cc2)cc(C(=O)NCc2c(C)cc(C)[nH]c2=O)c1C)C1CCOCC1] | 585.35 |
| 69 | 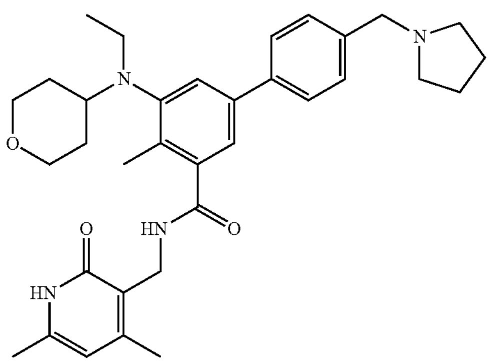 [SMILES: CCN(c1cc(-c2ccc(CN3CCCC3)cc2)cc(C(=O)NCc2c(C)cc(C)[nH]c2=O)c1C)C1CCOCC1] | 557.25 |
| 70 | 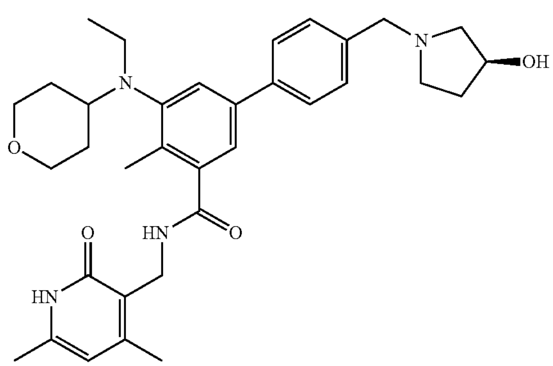 [SMILES: CCN(c1cc(-c2ccc(CN3CC[C@H](O)C3)cc2)cc(C(=O)NCc2c(C)cc(C)[nH]c2=O)c1C)C1CCOCC1] | 573.40 |

TABLE 1-continued

| Compound Number | Structure | MS (M + 1)+ |
|---|---|---|
| 71 | 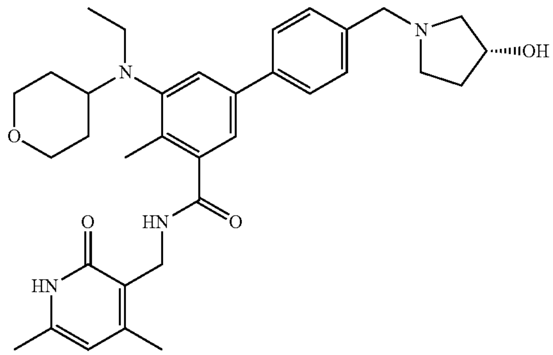 [SMILES: CCN(c1cc(-c2ccc(CN3CC[C@@H](O)C3)cc2)cc(C(=O)NCc2c(C)cc(C)[nH]c2=O)c1C)C1CCOCC1] | 573.40 |
| 72 | 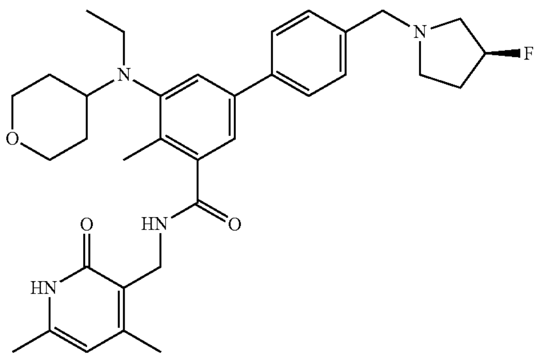 [SMILES: CCN(c1cc(-c2ccc(CN3CC[C@H](F)C3)cc2)cc(C(=O)NCc2c(C)cc(C)[nH]c2=O)c1C)C1CCOCC1] | 575.35 |
| 73 | 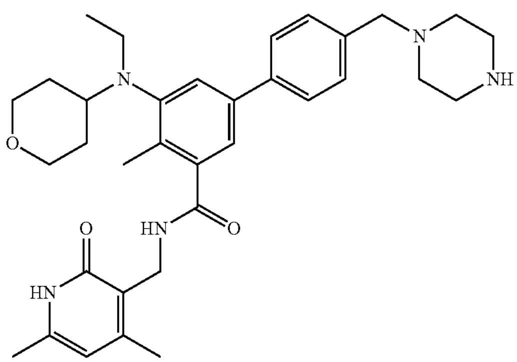 [SMILES: CCN(c1cc(-c2ccc(CN3CCNCC3)cc2)cc(C(=O)NCc2c(C)cc(C)[nH]c2=O)c1C)C1CCOCC1] | 572.10 |
| 74 | 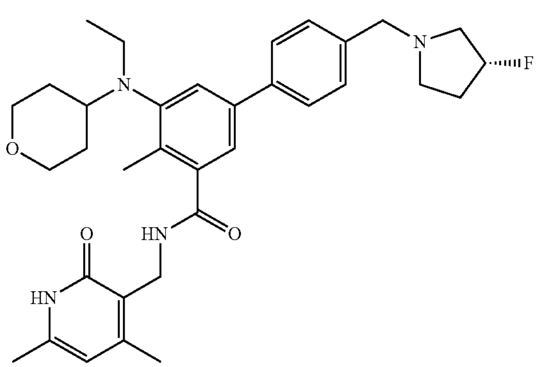 [SMILES: CCN(c1cc(-c2ccc(CN3CC[C@@H](F)C3)cc2)cc(C(=O)NCc2c(C)cc(C)[nH]c2=O)c1C)C1CCOCC1] | 575.35 |

TABLE 1-continued

| Compound Number | Structure | MS (M + 1)+ |
|---|---|---|
| 75 | 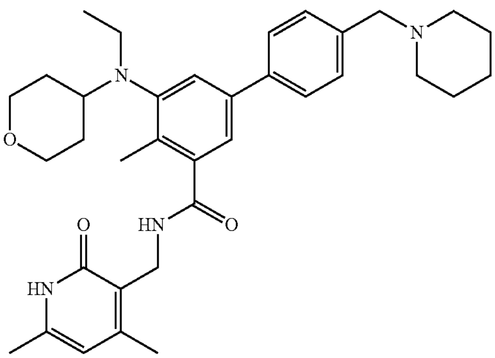 [SMILES: CCN(c1cc(-c2ccc(CN3CCCCC3)cc2)cc(C(=O)NCc2c(C)cc(C)[nH]c2=O)c1C)C1CCOCC1] | 571.25 |
| 76 | 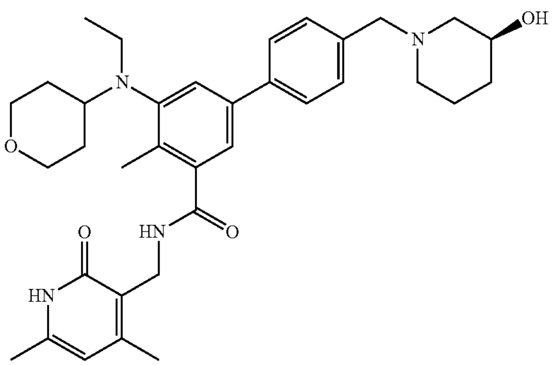 [SMILES: CCN(c1cc(-c2ccc(CN3CCC[C@H](O)C3)cc2)cc(C(=O)NCc2c(C)cc(C)[nH]c2=O)c1C)C1CCOCC1] | 587.40 |
| 77 | 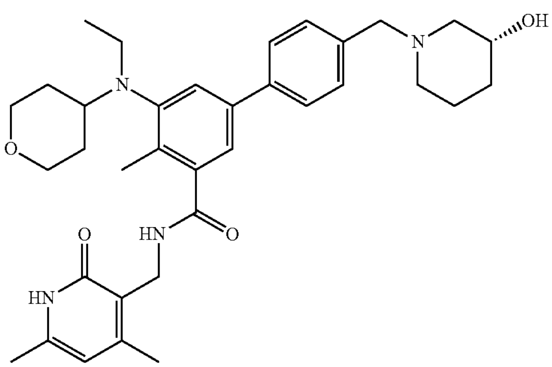 [SMILES: CCN(c1cc(-c2ccc(CN3CCC[C@@H](O)C3)cc2)cc(C(=O)NCc2c(C)cc(C)[nH]c2=O)c1C)C1CCOCC1] | 587.45 |
| 78 | 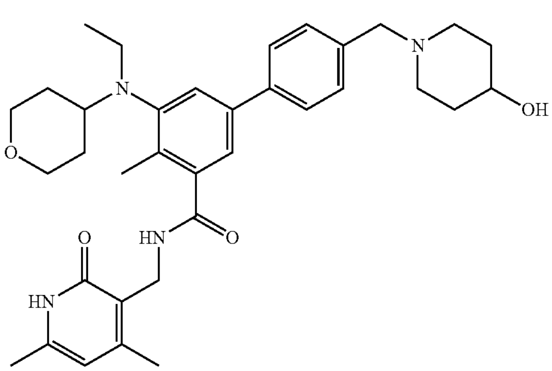 [SMILES: CCN(c1cc(-c2ccc(CN3CCC(O)CC3)cc2)cc(C(=O)NCc2c(C)cc(C)[nH]c2=O)c1C)C1CCOCC1] | 587.20 |

TABLE 1-continued

| Compound Number | Structure | MS (M + 1)+ |
|---|---|---|
| 79 | 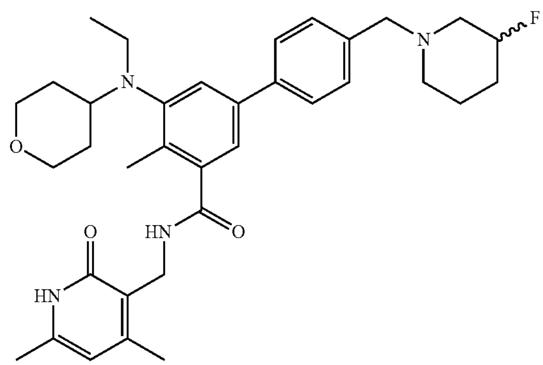 [SMILES: CCN(c1cc(-c2ccc(CN3CCCC(F)C3)cc2)cc(C(=O)NCc2c(C)cc(C)[nH]c2=O)c1C)C1CCOCC1] | 589.35 |
| 80 | 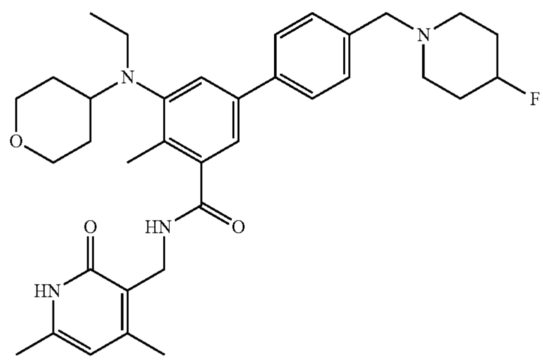 [SMILES: CCN(c1cc(-c2ccc(CN3CCC(F)CC3)cc2)cc(C(=O)NCc2c(C)cc(C)[nH]c2=O)c1C)C1CCOCC1] | 589.30 |
| 81 | 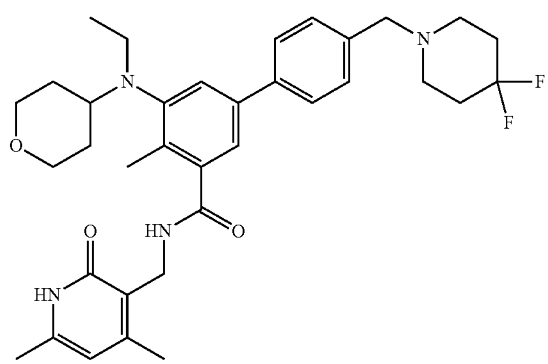 [SMILES: CCN(c1cc(-c2ccc(CN3CCC(F)(F)CC3)cc2)cc(C(=O)NCc2c(C)cc(C)[nH]c2=O)c1C)C1CCOCC1] | 607.35 |
| 82 | 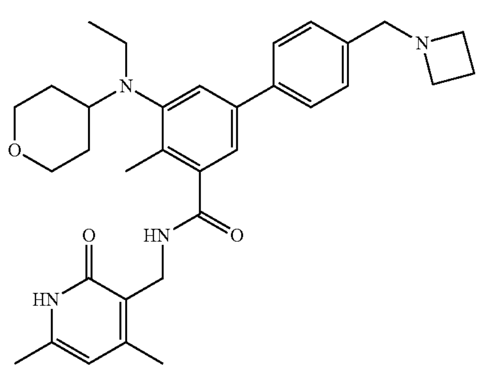 [SMILES: CCN(c1cc(-c2ccc(CN3CCC3)cc2)cc(C(=O)NCc2c(C)cc(C)[nH]c2=O)c1C)C1CCOCC1] | 543.40 |

TABLE 1-continued

| Compound Number | Structure | MS (M + 1)+ |
|---|---|---|
| 83 | 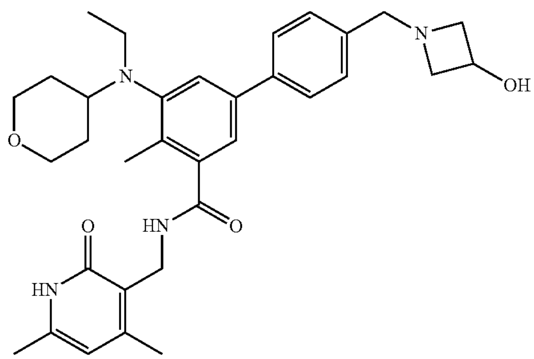 [SMILES: CCN(c1cc(-c2ccc(CN3CC(O)C3)cc2)cc(C(=O)NCc2c(C)cc(C)[nH]c2=O)c1C)C1CCOCC1] | 559.80 |
| 84 | 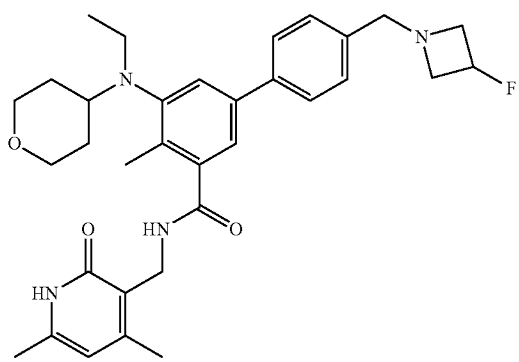 [SMILES: CCN(c1cc(-c2ccc(CN3CC(F)C3)cc2)cc(C(=O)NCc2c(C)cc(C)[nH]c2=O)c1C)C1CCOCC1] | 561.25 |
| 85 | 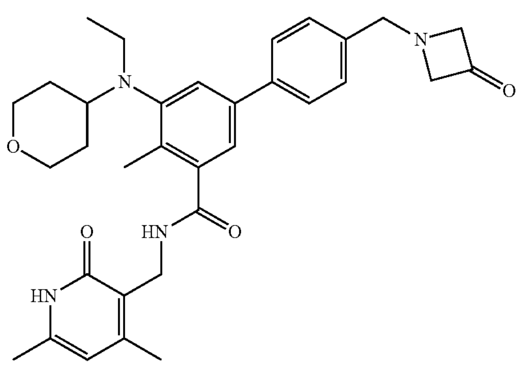 [SMILES: CCN(c1cc(-c2ccc(CN3CC(=O)C3)cc2)cc(C(=O)NCc2c(C)cc(C)[nH]c2=O)c1C)C1CCOCC1] | 563.00 |
| 86 | 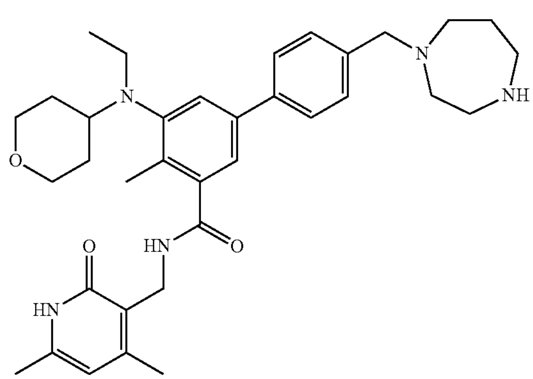 [SMILES: CCN(c1cc(-c2ccc(CN3CCCNCC3)cc2)cc(C(=O)NCc2c(C)cc(C)[nH]c2=O)c1C)C1CCOCC1] | 585.37 |

TABLE 1-continued

| Compound Number | Structure | MS (M + 1)+ |
|---|---|---|
| 87 | 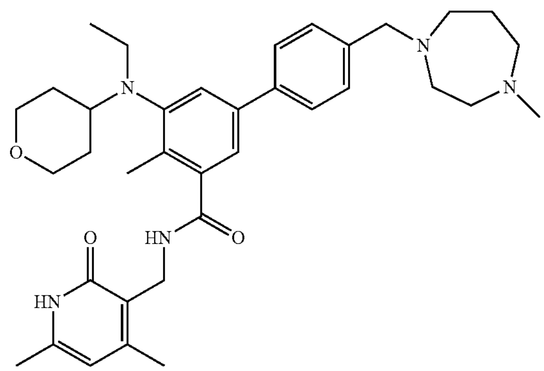 [SMILES: CCN(c1cc(-c2ccc(CN3CCCN(C)CC3)cc2)cc(C(=O)NCc2c(C)cc(C)[nH]c2=O)c1C)C1CCOCC1] | 600.30 |
| 88 | 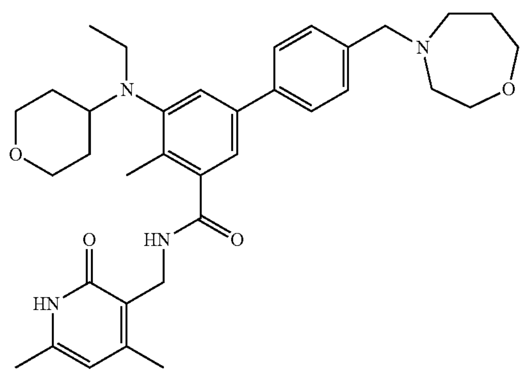 [SMILES: CCN(c1cc(-c2ccc(CN3CCCOCC3)cc2)cc(C(=O)NCc2c(C)cc(C)[nH]c2=O)c1C)C1CCOCC1] | 587.40 |
| 89 | 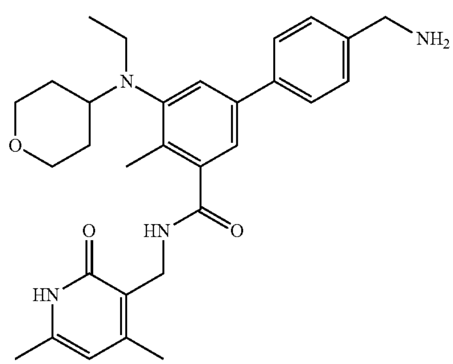 [SMILES: CCN(c1cc(-c2ccc(CN)cc2)cc(C(=O)NCc2c(C)cc(C)[nH]c2=O)c1C)C1CCOCC1] | 503.40 |
| 90 | 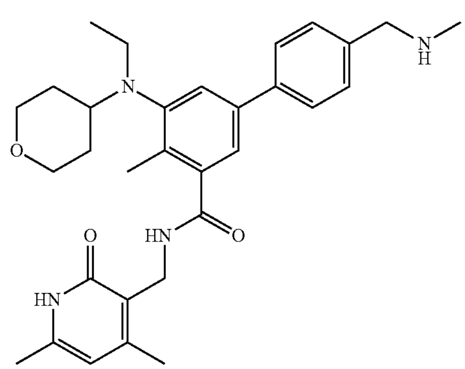 [SMILES: CCN(c1cc(-c2ccc(CNC)cc2)cc(C(=O)NCc2c(C)cc(C)[nH]c2=O)c1C)C1CCOCC1] | 517.30 |

TABLE 1-continued
| Compound Number | Structure | MS (M + 1)+ |
|---|---|---|
| 91 | 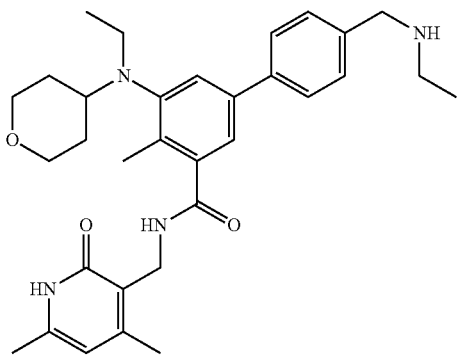 [SMILES: CCNCc1ccc(-c2cc(C(=O)NCc3c(C)cc(C)[nH]c3=O)c(C)c(N(CC)C3CCOCC3)c2)cc1] | 531.35 |
| 92 | 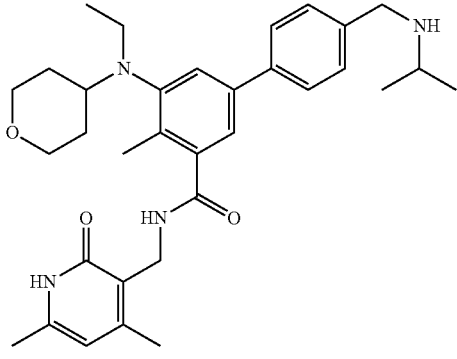 [SMILES: CCN(c1cc(-c2ccc(CNC(C)C)cc2)cc(C(=O)NCc2c(C)cc(C)[nH]c2=O)c1C)C1CCOCC1] | 545.40 |
| 93 | 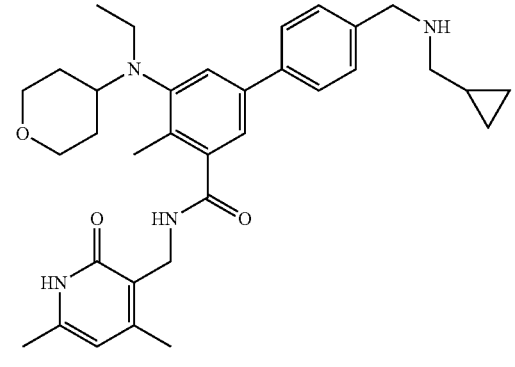 [SMILES: CCN(c1cc(-c2ccc(CNCC3CC3)cc2)cc(C(=O)NCc2c(C)cc(C)[nH]c2=O)c1C)C1CCOCC1] | 557.35 |
| 94 | 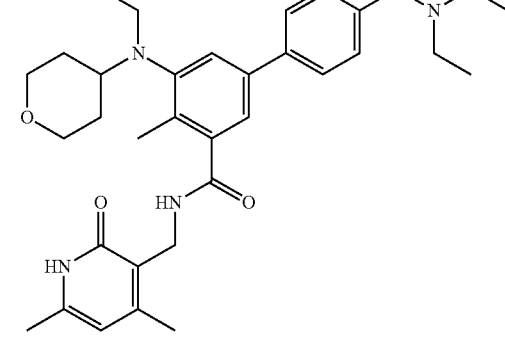 | 559.20 |

TABLE 1-continued

| Compound Number | Structure | MS (M + 1)+ |
|---|---|---|
| 95 | 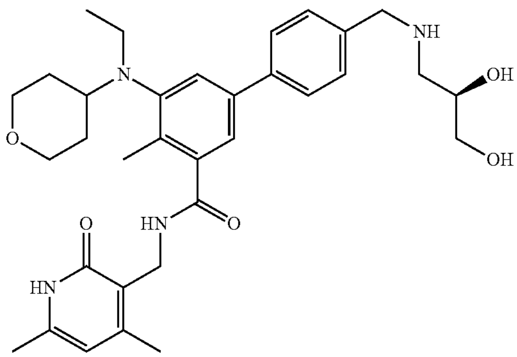 [SMILES: CCN(c1cc(-c2ccc(CNC[C@@H](O)CO)cc2)cc(C(=O)NCc2c(C)cc(C)[nH]c2=O)c1C)C1CCOCC1] | 599.35 (M + Na) |
| 96 | 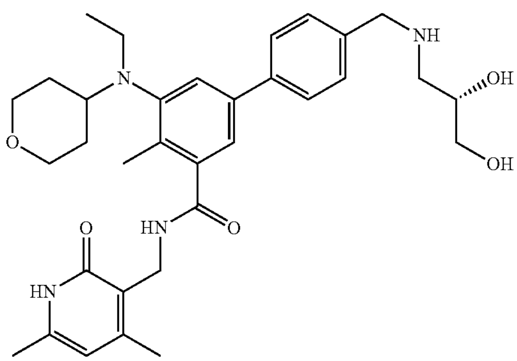 [SMILES: CCN(c1cc(-c2ccc(CNC[C@H](O)CO)cc2)cc(C(=O)NCc2c(C)cc(C)[nH]c2=O)c1C)C1CCOCC1] | 577.25 |
| 97 | 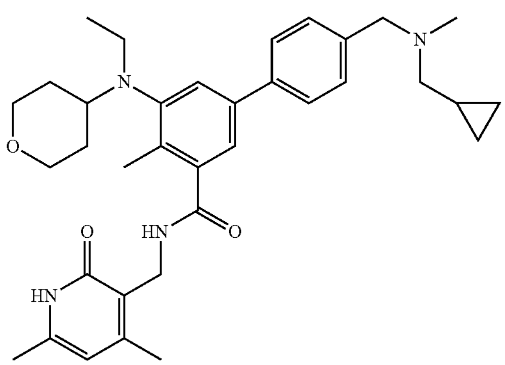 [SMILES: CCN(c1cc(-c2ccc(CN(C)CC3CC3)cc2)cc(C(=O)NCc2c(C)cc(C)[nH]c2=O)c1C)C1CCOCC1] | 571.40 |
| 98 | 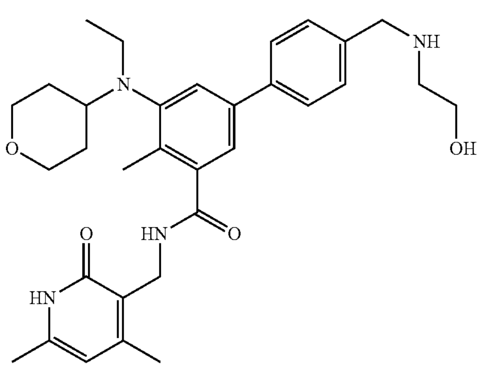 [SMILES: CCN(c1cc(-c2ccc(CNCCO)cc2)cc(C(=O)NCc2c(C)cc(C)[nH]c2=O)c1C)C1CCOCC1] | 547.35 |

TABLE 1-continued

| Compound Number | Structure | MS (M + 1)+ |
|---|---|---|
| 99 | 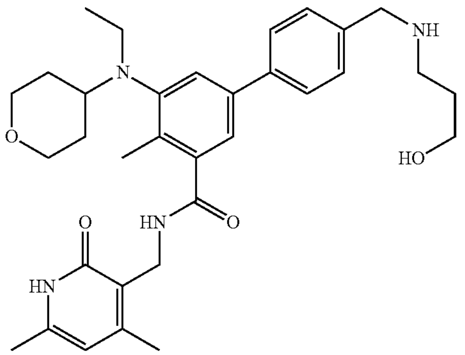 [SMILES: CCN(c1cc(-c2ccc(CNCCCO)cc2)cc(C(=O)NCc2c(C)cc(C)[nH]c2=O)c1C)C1CCOCC1] | 561.30 |
| 100 | 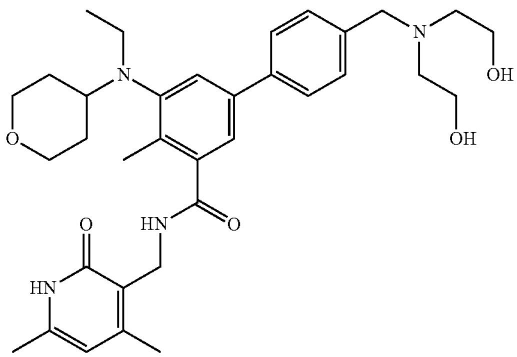 [SMILES: CCN(c1cc(-c2ccc(CN(CCO)CCO)cc2)cc(C(=O)NCc2c(C)cc(C)[nH]c2=O)c1C)C1CCOCC1] | 591.25 |
| 101 | 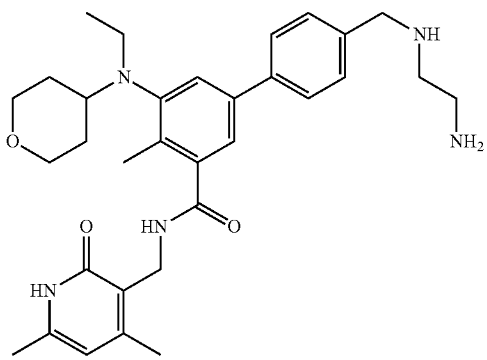 [SMILES: CCN(c1cc(-c2ccc(CNCCN)cc2)cc(C(=O)NCc2c(C)cc(C)[nH]c2=O)c1C)C1CCOCC1] | 546.35 |
| 102 | 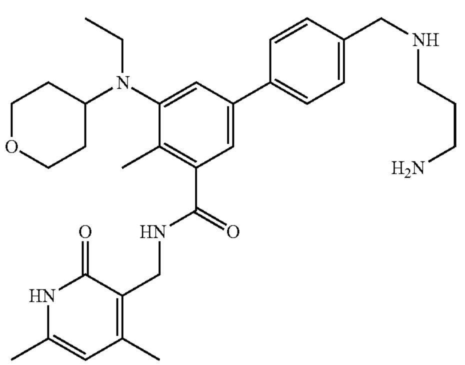 [SMILES: CCN(c1cc(-c2ccc(CNCCCN)cc2)cc(C(=O)NCc2c(C)cc(C)[nH]c2=O)c1C)C1CCOCC1] | 560.20 |

TABLE 1-continued

| Compound Number | Structure | MS (M + 1)+ |
|---|---|---|
| 103 | 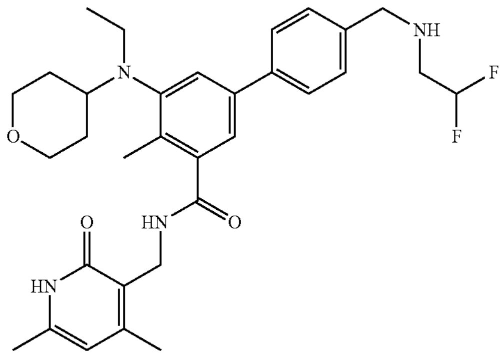 [SMILES: CCN(c1cc(-c2ccc(CNCC(F)F)cc2)cc(C(=O)NCc2c(C)cc(C)[nH]c2=O)c1C)C1CCOCC1] | 567.30 |
| 104 | 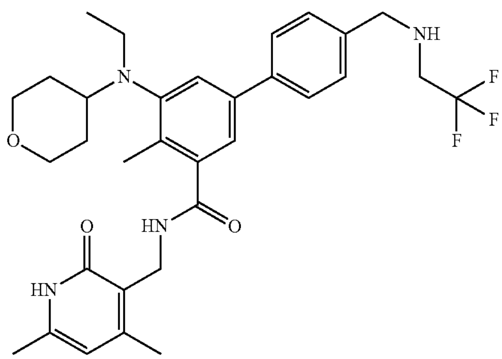 [SMILES: CCN(c1cc(-c2ccc(CNCC(F)(F)F)cc2)cc(C(=O)NCc2c(C)cc(C)[nH]c2=O)c1C)C1CCOCC1] | 585.25 |
| 105 | 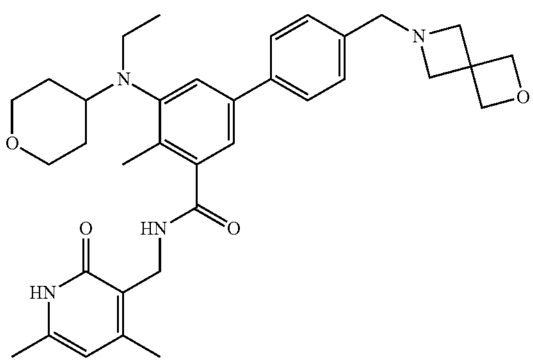 [SMILES: CCN(c1cc(-c2ccc(CN3CC4(COC4)C3)cc2)cc(C(=O)NCc2c(C)cc(C)[nH]c2=O)c1C)C1CCOCC1] | 585.40 |
| 107 | 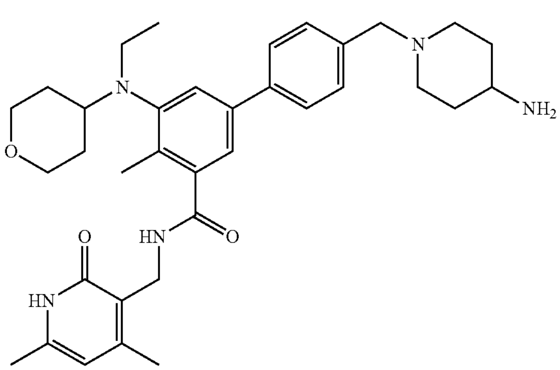 [SMILES: CCN(c1cc(-c2ccc(CN3CCC(N)CC3)cc2)cc(C(=O)NCc2c(C)cc(C)[nH]c2=O)c1C)C1CCOCC1] | |

TABLE 1-continued

| Compound Number | Structure | MS (M + 1)+ |
|---|---|---|
| 108 | 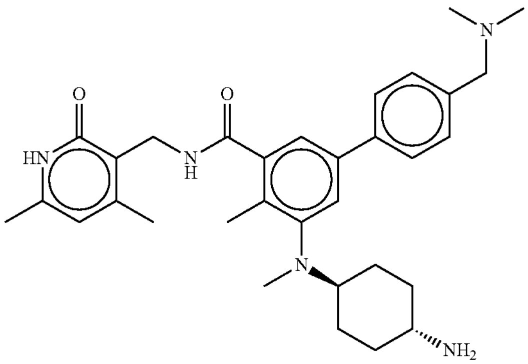 | 530.35 |
| 114 | 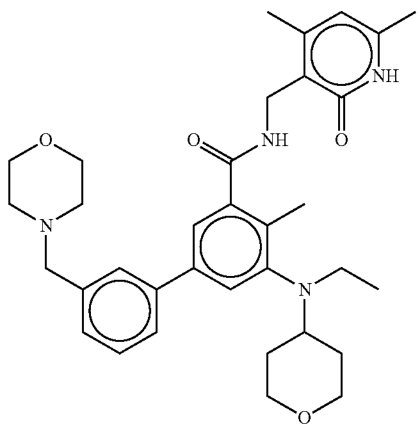 | 573.25 |
| 115 | 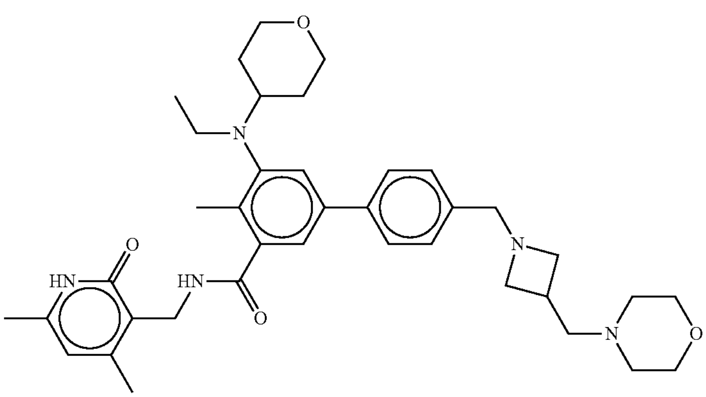 | 642.45 |
| 116 | 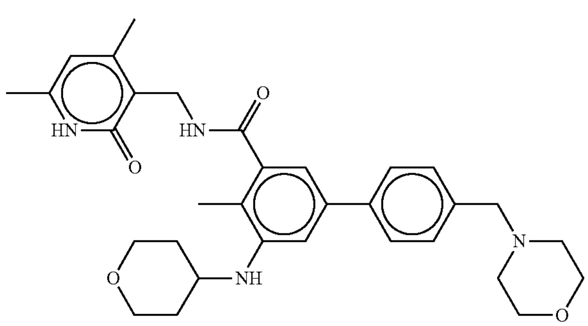 | 545.15 |

TABLE 1-continued

| Compound Number | Structure | MS (M + 1)+ |
|---|---|---|
| 117 | 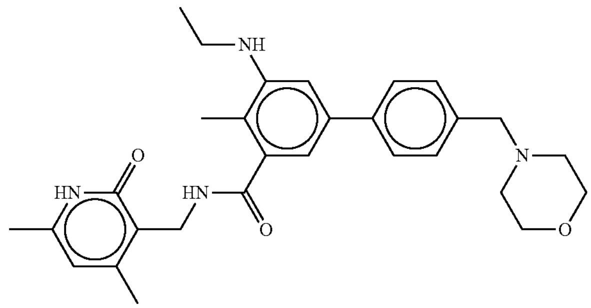 | 489.20 |
| 119 | 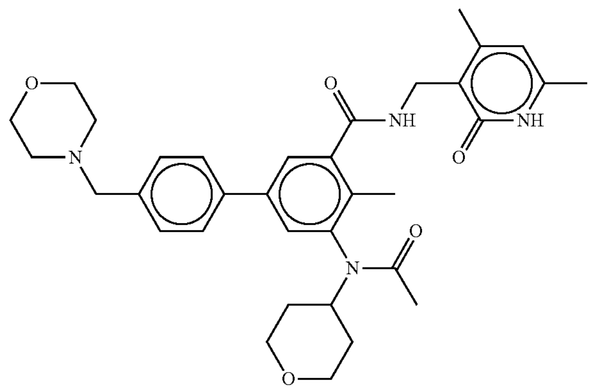 | 609.35 |
| 122 | 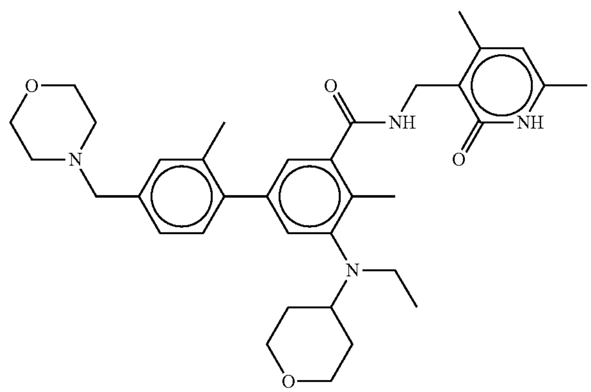 | 587.55 |
| 124 | 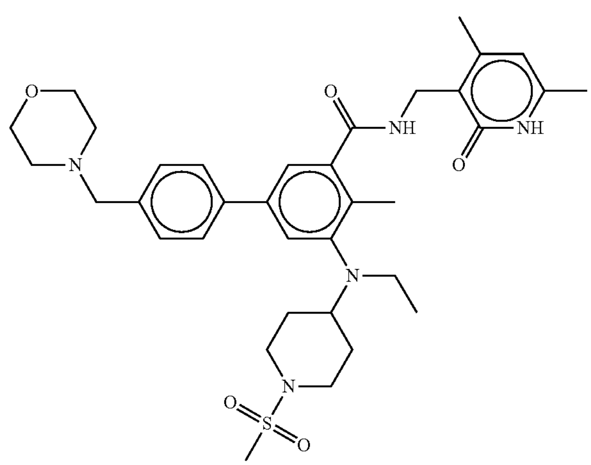 | 650.85 |

TABLE 1-continued
| Compound Number | Structure | MS (M + 1)+ |
|---|---|---|
| 125 | 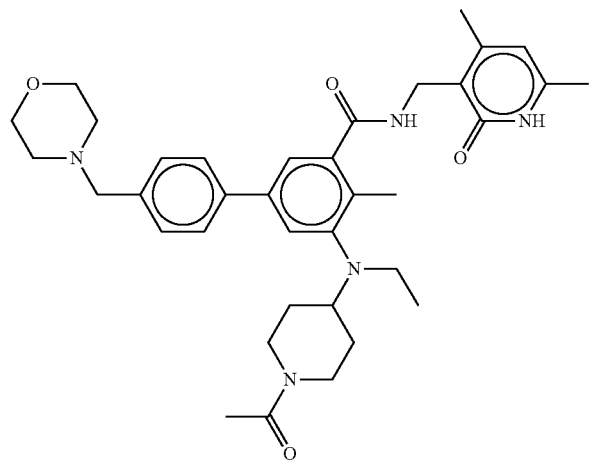 | 614.75 |
| 126 | 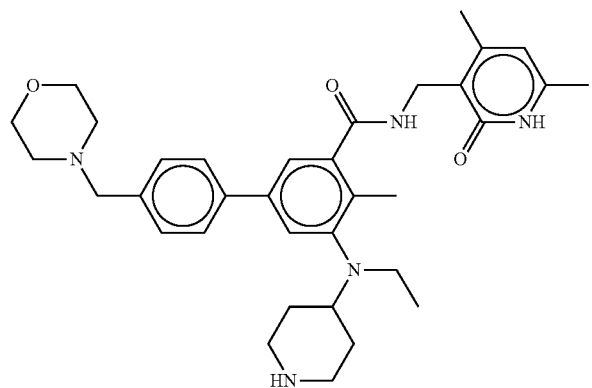 | 572.35 |
| 127 | 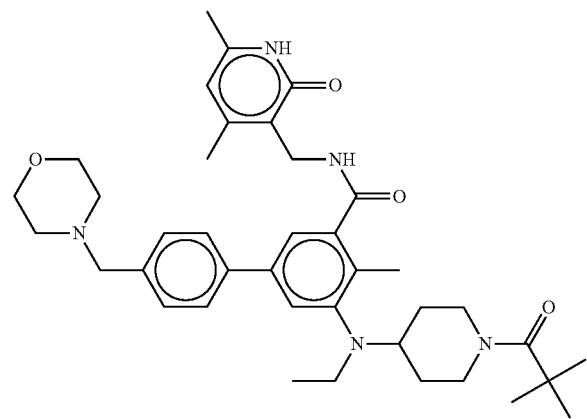 | 656.65 |

TABLE 1-continued

| Compound Number | Structure | MS (M + 1)+ |
|---|---|---|
| 128 | 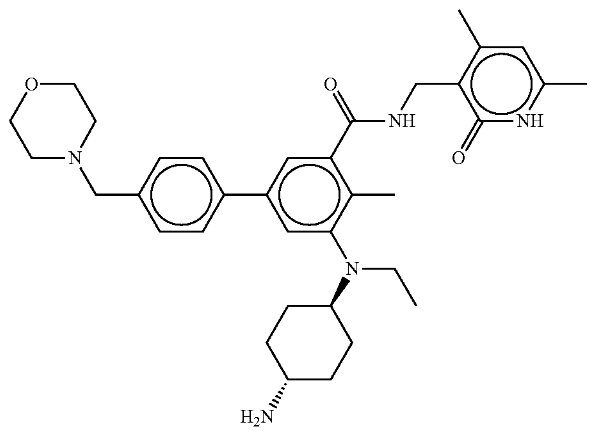 | 586.45 |
| 129 | 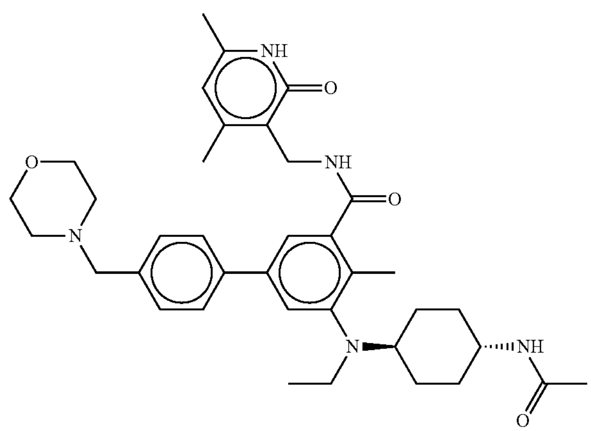 | 628.35 |
| 130 | 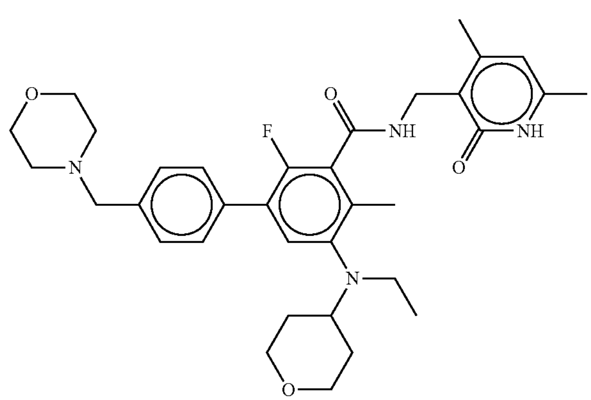 | 591.2 |

TABLE 1-continued

| Compound Number | Structure | MS (M + 1)+ |
|---|---|---|
| 131 | 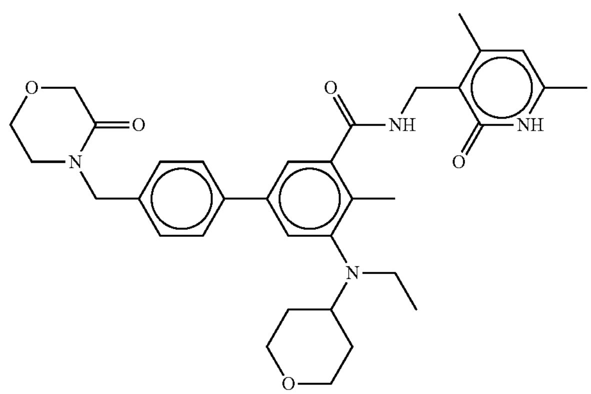 | 587.35 |
| 132 | 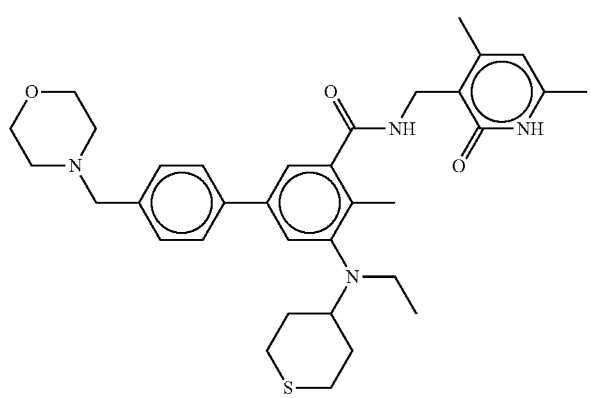 | 589.25 |
| 133 | 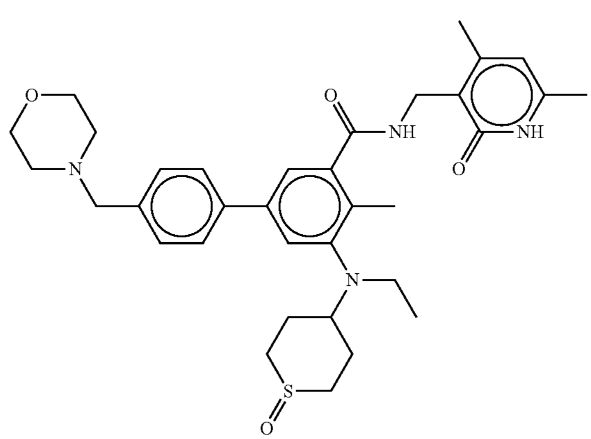 | 605.25 |

TABLE 1-continued
| Compound Number | Structure | MS (M + 1)+ |
|---|---|---|
| 135 | 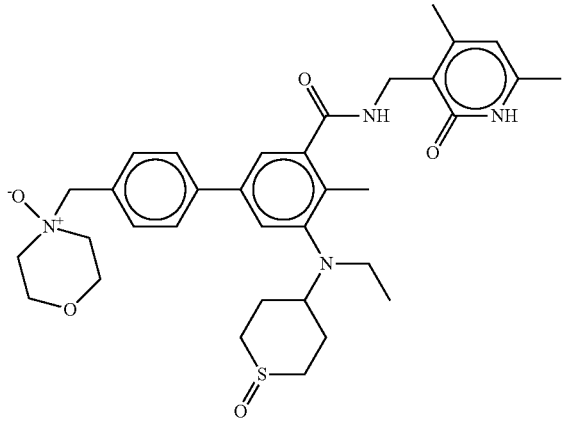 | 621.40 |
| 136 | 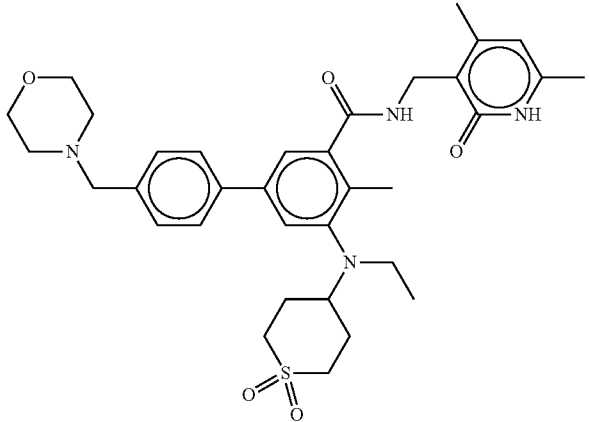 | 621.45 |
| 137 | 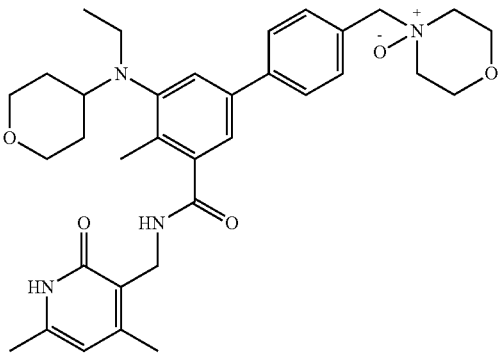 | 589.35 |

TABLE 1-continued

| Compound Number | Structure | MS (M + 1)+ |
|---|---|---|
| 138 | 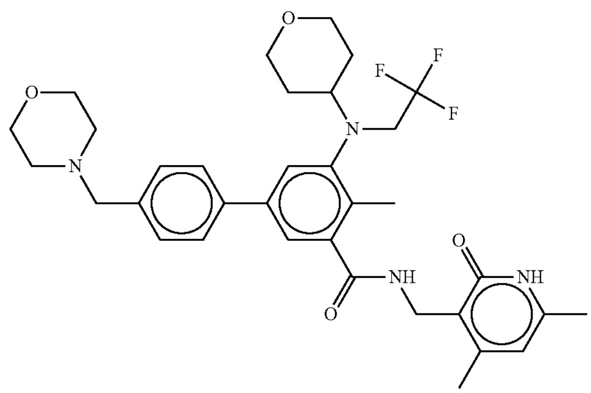 | 627.5 |
| 141 | 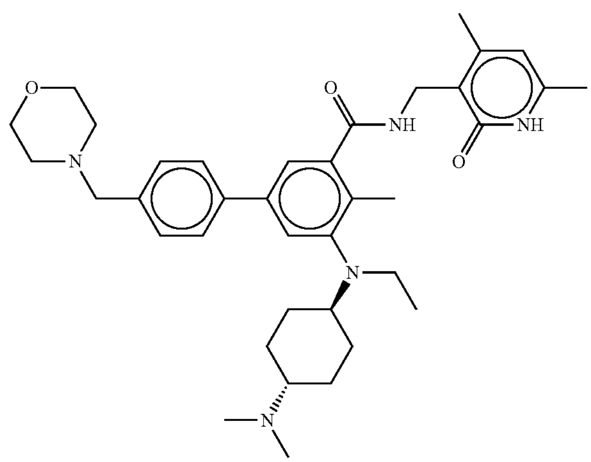 | 614.65 |
| 142 | 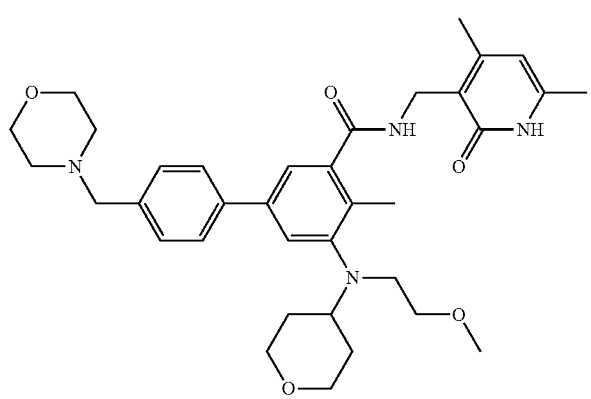 [SMILES: COCCN(c1cc(-c2ccc(CN3CCOCC3)cc2)cc(C(=O)NCc2c(C)cc(C)[nH]c2=O)c1C)C1CCOCC1] | 603.45 |

TABLE 1-continued

| Compound Number | Structure | MS (M + 1)+ |
|---|---|---|
| 143 | 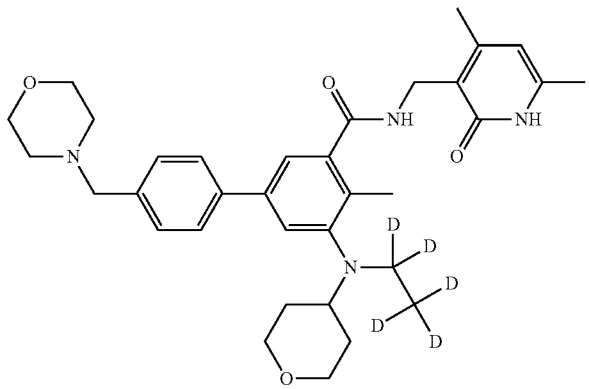 [SMILES: [2H]C([2H])([2H])C([2H])([2H])N(c1cc(-c2ccc(CN3CCOCC3)cc2)cc(C(=O)NCc2c(C)cc(C)[nH]c2=O)c1C)C1CCOCC1] | 578.35 |
| 144 | 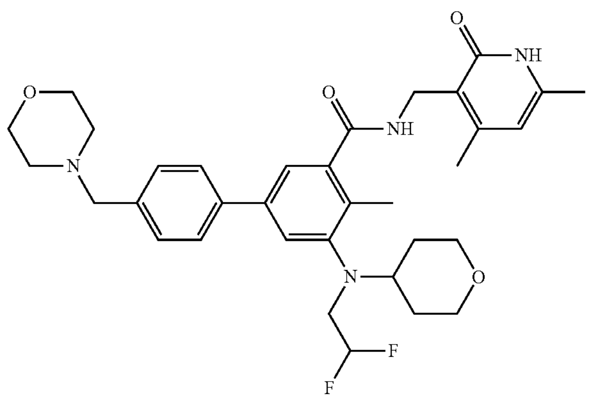 [SMILES: Cc1cc(C)c(CNC(=O)c2cc(-c3ccc(CN4CCOCC4)cc3)cc(N(CC(F)F)C3CCOCC3)c2C)c(=O)[nH]1] | 609.15 |
| 146 | 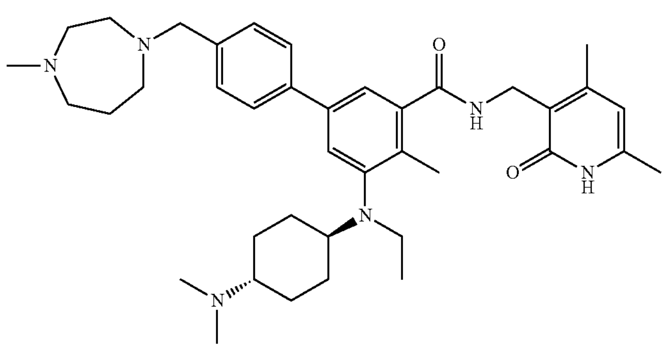 | 641.50 |
| 178 | 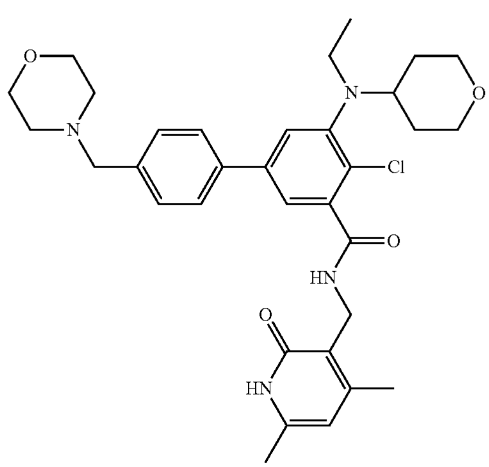 [SMILES: CCN(c1cc(-c2ccc(CN3CCOCC3)cc2)cc(C(=O)NCc2c(C)cc(C)[nH]c2=O)c1Cl)C1CCOCC1] | 593.60 |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—CHCH3$CH_2$—), n-butyl (—$CH_2CH_2CH_2CH_2$—), s-butyl (—CHCH$_3$CH$_2$CH$_2$—), i-butyl (—C(CH$_3$)2CH$_2$—), n-pentyl (—CH$_2$CH$_2$CH$_2$CH$_2$CH$_2$—), s-pentyl (—CHCH$_3$CH$_2$CH$_2$CH$_2$—) or n-hexyl (—CH$_2$CH$_2$CH$_2$CH$_2$CH$_2$CH$_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O—.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —NH$_2$. "Alkylamino" includes groups of compounds wherein nitrogen of —NH$_2$ is bound to at least one alkyl group. Examples of alkylamino groups include benzylamino, methylamino, ethylamino, phenethylamino, etc. "Dialkylamino" includes groups wherein the nitrogen of —NH$_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present disclosure that contain nitrogens can be converted to N-oxides by treatment with an oxidizing agent (e.g., 3-chloroperoxybenzoic acid (mCPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It should also be understood that when compounds have chiral isomeric or geometric isomeric forms, all isomeric forms are intended to be included in the scope of the present disclosure, and the naming of the compounds does not exclude any isomeric forms.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

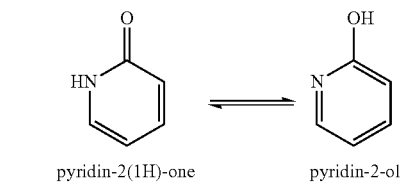 [SMILES: O=c1cccc[nH]1 ; Oc1ccccn1]

pyridin-2(1H)-one      pyridin-2-ol

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form.

The compounds of Formulae (I)-(VIa) disclosed herein include the compounds themselves, as well as their salts and their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms. In the salt form, it is understood that the ratio of the compound to the cation or anion of the salt can be 1:1, or any ration other than 1:1, e.g., 3:1, 2:1, 1:2, or 1:3.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

Any compound of Formulae (I)-(VIa) of the present disclosure, as described herein, may be an EZH2 inhibitor.

In certain aspects of the disclosure an inhibitor of EZH2 "selectively inhibits" histone methyltransferase activity of the mutant EZH2 when it inhibits histone methyltransferase activity of the mutant EZH2 more effectively than it inhibits histone methyltransferase activity of wild-type EZH2. For example, in one embodiment the selective inhibitor has an IC50 for the mutant EZH2 that is at least 40 percent lower than the IC50 for wild-type EZH2. In one embodiment the selective inhibitor has an IC50 for the mutant EZH2 that is at least 50 percent lower than the IC50 for wild-type EZH2. In one embodiment the selective inhibitor has an IC50 for the mutant EZH2 that is at least 60 percent lower than the IC50 for wild-type EZH2. In one embodiment the selective inhibitor has an IC50 for the mutant EZH2 that is at least 70 percent lower than the IC50 for wild-type EZH2. In one embodiment the selective inhibitor has an IC50 for the mutant EZH2 that is at least 80 percent lower than the IC50 for wild-type EZH2. In one embodiment the selective inhibitor has an IC50 for the mutant EZH2 that is at least 90 percent lower than the IC50 for wild-type EZH2.

In one embodiment, the selective inhibitor of a mutant EZH2 exerts essentially no inhibitory effect on wild-type EZH2.

In certain aspects of the disclosure the inhibitor inhibits conversion of H3-K27me2 to H3-K27me3. In one embodiment the inhibitor is said to inhibit trimethylation of H3-K27. Since conversion of H3-K27me1 to H3-K27me2 precedes conversion of H3-K27me2 to H3-K27me3, an inhibitor of conversion of H3-K27me1 to H3-K27me2 naturally also inhibits conversion of H3-K27me2 to H3-K27me3, i.e., it inhibits trimethylation of H3-K27. It is also possible to inhibit conversion of H3-K27me2 to H3-K27me3 without inhibition of conversion of H3-K27me1 to H3-K27me2. Inhibition of this type would also result in inhibition of trimethylation of H3-K27, albeit without inhibition of dimethylation of H3-K27.

In one embodiment the inhibitor inhibits conversion of H3-K27me1 to H3-K27me2 and the conversion of H3-K27me2 to H3-K27me3. Such inhibitor may directly inhibit the conversion of H3-K27me1 to H3-K27me2 alone. Alternatively, such inhibitor may directly inhibit both the conversion of H3-K27me1 to H3-K27me2 and the conversion of H3-K27me2 to H3-K27me3.

In certain aspects of the disclosure, the inhibitor compound inhibits histone methyltransferase activity. Inhibition of histone methyltransferase activity can be detected using any suitable method. The inhibition can be measured, for example, either in terms of rate of histone methyltransferase activity or as product of histone methyltransferase activity.

The inhibition is a measurable inhibition compared to a suitable control. In one embodiment, inhibition is at least 10 percent inhibition compared to a suitable control. That is, the rate of enzymatic activity or the amount of product with the inhibitor is less than or equal to 90 percent of the corresponding rate or amount made without the inhibitor. In various other embodiments, inhibition is at least 20, 25, 30, 40, 50, 60, 70, 75, 80, 90, or 95 percent inhibition compared to a suitable control. In one embodiment, inhibition is at least 99 percent inhibition compared to a suitable control. That is, the rate of enzymatic activity or the amount of product with the inhibitor is less than or equal to 1 percent of the corresponding rate or amount made without the inhibitor.

A composition of the present disclosure comprises a compound of Formulae (I)-(VIa), or a pharmaceutically acceptable salt thereof, and one or more other therapeutic agents, or a pharmaceutically acceptable salt thereof. The present disclosure provides for the administration of a compound of Formulae (I)-(VIa) or a pharmaceutically acceptable salt thereof, and one or more therapeutic agents or a pharmaceutically acceptable salt thereof, as a co-formulation or separate formulations, wherein the administration of formulations is simultaneous, sequential, or in alternation. In certain embodiments, the other therapeutic agents can be an agent that is recognized in the art as being useful to treat the disease or condition being treated by the composition of the present disclosure. In other embodiment, the other therapeutic agent can be an agent that is not recognized in the art as being useful to treat the disease or condition being treated by the composition of the present disclosure. In one aspect, the other therapeutic agents can be an agent that imparts a beneficial attribute to the composition of the present disclosure (e.g., an agent that affects the viscosity of the composition). The beneficial attribute to the composition of the present disclosure includes, but is not limited to, pharmacokinetic or pharmacodynamic co-action resulting from the combination of a compound of Formulae (I)-(VIa) and one or more other therapeutic agents. For example, the one or more other therapeutic agents can be anticancer agents or chemotherapeutic agents. For example, the one or more other therapeutic agents can be glucocorticoids. For example, the one or more other therapeutic agents can be selected from prednisone, prednisolone, cyclophosphamide, vincristine, doxorubicin, mafosfamide, cisplatin, AraC, everolimus, decitabine, dexamethasone, or functional analogs, derivatives, produgs, and metabolites thereof. In another aspect, the other therapeutic agent can be Prednisone or its active metabolite, Prednisolone.

The therapeutic agents set forth below are for illustrative purposes and not intended to be limiting. The present disclosure includes at least one other therapeutic agent selected from the lists below. The present disclosure can include more than one other therapeutic agent, e.g., two, three, four, or five other therapeutic agents such that the composition of the present disclosure can perform its intended function.

In one embodiment, the other therapeutic agent is an anticancer agent. In one embodiment, the anticancer agent is a compound that affects histone modifications, such as an HDAC inhibitor. In certain embodiments, an anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, *Bacillus* Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™ Thalomid®, Tykerb®, Velcade® and Zevalin™); corticosteroids, (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

In another embodiment, the other therapeutic agent is a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodinel 31 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristine, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate), or lovastatin.

In another aspect, the other therapeutic agent is a chemotherapeutic agent or a cytokine such as G-CSF (granulocyte colony stimulating factor).

In yet another aspect, the other therapeutic agents can be standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R—CHOP (rituximab, cyclophosphamide, hydroxydaunorubicin, oncovin, prednisone or prednisolone), or CMFP (cyclophosphamide, methotrexate, 5-fluorouracil and prednisone).

In another aspect, the other therapeutic agents can be an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-ß, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets P13K), VX-680 (targets Aurora kinase), Azdl 1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888. More examples of the other therapeutic agents suitable to be used in combination with a compounds of Formulae (I)-(VIa) or a pharmaceutically acceptable salt thereof are disclosed in U.S. Application No. 61/992,881 filed May 13, 2014 and International Application No. PCT/US2014/069167 filed Dec. 8, 2014, the contents of each of which are incorporated herein by reference in their entireties.

The present disclosure provides methods for combination therapy in which a composition comprising a compound of Formulae (I)-(VIa) or a pharmaceutically acceptable salt thereof, and one or more other therapeutic agents are administered to a subject in need for treatment of a disease or cancer. The combination therapy can also be administered to cancer cells to inhibit proliferation or induce cell death. In one aspect, a compound of Formulae (I)-(VIa) or a pharmaceutically acceptable salt thereof is administered subsequent to administration of the composition of the present disclosure comprising a compound of Formulae (I)-(VIa) or a pharmaceutically acceptable salt thereof, and one or more other therapeutic agents. In one aspect, a compound of Formulae (I)-(VIa) or a pharmaceutically acceptable salt thereof is administered prior to administration of the composition of the present disclosure comprising a compound of Formulae (I)-(VIa) or a pharmaceutically acceptable salt thereof, and one or more other therapeutic agents. In one aspect, a compound of Formulae (I)-(VIa) or a pharmaceutically acceptable salt thereof is administered subsequent to administration of one or more therapeutic agents, such that the other therapeutic agents are administered either in a single composition or in two or more compositions, e.g. administered simultaneously, sequentially, or in alternation. In one aspect, a compound of Formulae (I)-(VIa) or a pharmaceutically acceptable salt thereof is administered prior to administration of one or more therapeutic agents, such that the other therapeutic agents are administered either in a single composition or in two or more compositions, e.g. administered simultaneously, sequentially, or in alternation.

In one embodiment, a composition of the present disclosure includes a compound of Formulae (I)-(VIa) or a pharmaceutically acceptable salt thereof, and one or more anticancer agents, e.g., CHOP (cyclophosphamide, hydroxydaunorubicin, oncovin, and prednisone or prednisolone) or R—CHOP (rituximab, cyclophosphamide, hydroxydaunorubicin, oncovin, prednisone or prednisolone). In one embodiment, a composition of the present disclosure includes a compound of Formulae (I)-(VIa) or a pharmaceutically acceptable salt thereof, and prednisone or prednisolone. Methods of the present disclosure include the combination therapy of administering a compound of Formulae (I)-(VIa) or a pharmaceutically acceptable salt thereof, and anticancer agents, wherein the anticancer agents are CHOP, R—CHOP, prednisone, or prednisolone.

In certain embodiments, "combination therapy" is intended to embrace administration of these therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation.

In certain aspects of the disclosure, the combination therapies featured in the present disclosure can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

In certain aspects of the disclosure "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, a composition of the present disclosure, or a pharmaceutically acceptable salt, solvate, analog or derivative thereof, may be administered in combination with radiation therapy. Radiation therapy can also be administered in combination with a composition of the present disclosure and another chemotherapeutic agent described herein as part of a multiple agent therapy.

Combination therapy can be achieved by administering two or more agents, e.g., a compound of Formulae (I)-(VIa) and one or more other therapeutic agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7,8,9,10,12,14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The present disclosure also provides pharmaceutical compositions comprising a compound of Formulae (I)-(VIa) or pharmaceutically acceptable salts thereof, and one or more other therapeutic agents disclosed herein, mixed with pharmaceutically suitable carriers or excipient(s) at doses to treat or prevent a disease or condition as described herein. In one aspect, the present disclosure also provides pharmaceutical compositions comprising any compound of Table I or pharmaceutically acceptable salts thereof, and one or more therapeutic agents, mixed with pharmaceutically suitable carriers or excipient (s) at doses to treat or prevent a disease or condition as described herein. In another aspect, the present disclosure also provides pharmaceutical compositions comprising Compound 44

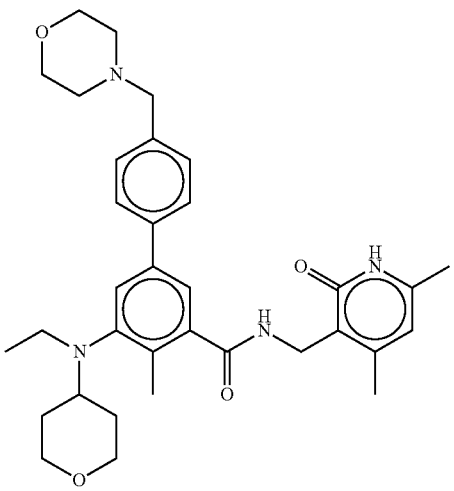

or pharmaceutically acceptable salts thereof, and one or more therapeutic agents, mixed with pharmaceutically suitable carriers or excipient(s) at doses to treat or prevent a disease or condition as described herein. The pharmaceutical compositions of the present disclosure can also be administered in combination with other therapeutic agents or therapeutic modalities simultaneously, sequentially, or in alternation.

Mixtures of compositions of the present disclosure can also be administered to the patient as a simple mixture or in suitable formulated pharmaceutical compositions. For example, one aspect of the disclosure relates to a pharmaceutical composition comprising a therapeutically effective dose of an EZH2 inhibitor of Formulae (I)-(VIa), or a pharmaceutically acceptable salt, hydrate, enantiomer or stereoisomer thereof; one or more other therapeutic agents, and a pharmaceutically acceptable diluent or carrier.

A "pharmaceutical composition" is a formulation containing the compounds of the present disclosure in a form suitable for administration to a subject. A compound of Formulae (I)-(VIa) and one or more other therapeutic agents described herein each can be formulated individually or in multiple pharmaceutical compositions in any combinations of the active ingredients. Accordingly, one or more administration routes can be properly elected based on the dosage form of each pharmaceutical composition. Alternatively, a compound of Formulae (I)-(VIa) and one or more other therapeutic agents described herein can be formulated as one pharmaceutical composition.

In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition of the disclosure can be administered to a subject in many of the well-known methods currently used for chemotherapeutic treatment. For example, for treatment of cancers, a compound of the disclosure may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the EZH2 inhibitor compounds described herein, other therapeutic agents described herein, compositions comprising a compound of Formulae (I)-(VIa) and one or more other therapeutic agents, or the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The composition of the present disclosure is capable of further forming salts. The composition of the present disclosure is capable of forming more than one salt per molecule, e.g., mono-, di-, tri-. All of these forms are also contemplated within the scope of the claimed disclosure.

As used herein, "pharmaceutically acceptable salts" refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates), of the same salt.

The composition of the present disclosure may also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The composition, or pharmaceutically acceptable salts or solvatesthereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in Remington: the Science and Practice of Pharmacy, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

The present disclosure provides compositions and methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a composition of the present disclosure or a pharmaceutically acceptable salt or solvate thereof, to a subject in need of such treatment.

Based at least on the fact that abnormal histone methylation has been found to be associated with certain cancers and precancerous conditions, a method for treating cancer or a precancerous condition with a mutant EZH2 in a subject comprises administering to the subject in need thereof a therapeutically effective amount of a compound that inhibits methylation. In one embodiment a method for treating cancer or a precancerous condition in a subject comprises administering to the subject in need thereof a therapeutically effective amount of a compound that inhibits conversion of unmethylated H3-K27 to monomethylated H3-K27 (H3-K27me1). In one embodiment a method for treating cancer or a precancerous condition in a subject comprises administering to the subject in need thereof a therapeutically effective amount of a compound that inhibits conversion of monomethylated H3-K27 (H3-K27me1) to dimethylated H3-K27 (H3-K27me2). In one embodiment a method for treating cancer or a precancerous condition in a subject comprises administering to the subject in need thereof a therapeutically effective amount of a compound that inhibits conversion of H3-K27me2 to trimethylated H3-K27 (H3-K27me3). In one embodiment a method for treating cancer or a precancerous condition in a subject comprises administering to the subject in need thereof a therapeutically effective amount of a compound that inhibits both conversion of H3-K27me1 to H3-K27me2 and conversion of H3-K27me2 to H3-K27me3. It is important to note that disease-specific increase in methylation can occur at chromatin in key genomic loci in the absence of a global increase in cellular levels of histone or protein methylation. For example, it is possible for aberrant hypermethylation at key disease-relevant genes to occur against a backdrop of global histone or protein hypomethylation.

Modulators of methylation can be used for modulating cell proliferation, generally. For example, in some cases excessive proliferation may be reduced with agents that decrease methylation, whereas insufficient proliferation may be stimulated with agents that increase methylation. Accordingly, diseases that may be treated include hyperproliferative diseases, such as benign cell growth and malignant cell growth (cancer).

The disorder in which EZH2-mediated protein methylation plays a part can be cancer, a cell proliferative disorder, or a precancerous condition. The present disclosure further provides the use of a composition of the present disclosure, or a pharmaceutically acceptable salt or solvate thereof, to a subject in need of such treatment, for the preparation of a medicament useful for the treatment of cancer. Exemplary cancers that may be treated include lymphomas, including non-Hodgkin lymphoma, follicular lymphoma (FL) and diffuse large B-cell lymphoma (DLBCL); melanoma; and leukemia, including CML. Exemplary precancerous condition includes myelodisplastic syndrome (MDS; formerly known as preleukemia).

In general, compounds that are methylation modulators can be used for modulating cell proliferation, generally. For example, in some cases excessive proliferation may be reduced with agents that decrease methylation, whereas insufficient proliferation may be stimulated with agents that increase methylation. Accordingly, diseases that may be treated by the compounds of the disclosure include hyperproliferative diseases, such as benign cell growth and malignant cell growth.

As used herein, a "subject in need thereof" is a subject having a disorder in which EZH2-mediated protein methylation plays a part, or a subject having an increased risk of developing such disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

The subject of the present disclosure includes any human subject who has been diagnosed with, has symptoms of, or is at risk of developing a cancer or a precancerous condition. The subject of the present disclosure includes any human subject expressing a mutant EZH2. For example, a mutant EZH2 comprises one or more mutations, wherein the mutation is a substitution, a point mutation, a nonsense mutation, a missense mutation, a deletion, or an insertion or any other EZH2 mutation described herein.

A subject in need thereof may have refractory or resistant cancer. "Refractory or resistant cancer" means cancer that does not respond to treatment. The cancer may be resistant at the beginning of treatment or it may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In certain embodiments the prior therapy is monotherapy. In certain embodiments the prior therapy is combination therapy.

In some embodiments, a subject in need thereof may have a secondary cancer as a result of a previous therapy. "Secondary cancer" means cancer that arises due to or as a result from previous carcinogenic therapies, such as chemotherapy.

The subject may also exhibit resistance to EZH2 histone methyltransferase inhibitors or any other therapeutic agent.

The disclosure also features a method of selecting a combination therapy for a subject having cancer. The method includes the steps of: detecting one or more EZH2 mutations described herein in a sample from the subject; and selecting, based on the presence of the one or more EZH2 mutations, a combination therapy for treating cancer. In one embodiment, the therapy includes administering to the subject a composition of the disclosure. In one embodiment, the method further includes administrating to the subject a therapeutically effective amount of a composition of the disclosure. An EZH2 mutation can be detected using any suitable method known in the art. More methods are described in U.S. patent publication US 20130040906, which is incorporated herein by reference in their entireties.

The methods and uses described herein may include steps of detecting one or more EZH2 mutations described herein in a sample from a subject in need thereof prior to and/or after the administration of a composition of the disclosure (e.g., a composition comprising a compound of Formulae (I)-(VIa) or pharmaceutically acceptable salts thereof, and one or more therapeutic agents) to the subject. The presence of the one or more EZH2 mutations described herein in the tested sample indicates the subject is responsive to the combination therapy of the disclosure.

The present disclosure provides personalized medicine, treatment and/or cancer management for a subject by genetic screening of one or more EZH2 mutations described herein in the subject. For example, the present disclosure provides methods for treating or alleviating a symptom of cancer or a precancerous condition in a subject in need thereof by determining responsiveness of the subject to a combination therapy and when the subject is responsive to the combination therapy, administering to the subject a composition of the disclosure. The responsiveness is determined by obtaining a sample from the subject and detecting one or more EZH2 mutations described herein, and the presence of such one or more EZH2 mutations described herein indicates that the subject is responsive to the composition of the disclosure. Once the responsiveness of a subject is determined, a therapeutically effective amount of a composition, for example, a composition comprising a compound of Formulae (I)-(VIa) or pharmaceutically acceptable salts thereof, and one or more therapeutic agents, can be administered. The therapeutically effective amount of a composition can be determined by one of ordinary skill in the art.

As used herein, the term "responsiveness" is interchangeable with terms "responsive", "sensitive", and "sensitivity", and it is meant that a subject is showing therapeutic responses when administered a composition of the disclosure, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered a composition of the disclosure, e.g., tumor cells or tumor tissues of the subject undergo apoptosis and/or necrosis, and/or display reduced growing, dividing, or proliferation.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the disclosure encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present disclosure may be used to treat a cancer selected from the group consisting of a hematologic cancer of the present disclosure or a hematologic cell proliferative disorder of the present disclosure. A hematologic cancer of the present disclosure can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present disclosure may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructural heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present disclosure may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructural heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present disclosure may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the present disclosure may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphocytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructural heterogeneity (e.g., mixed cell types).

Preferably, compound of the present disclosure, or a pharmaceutically acceptable salt or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present disclosure, or a pharmaceutically acceptable salt or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can be histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2,N2a, N2b, N3,N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present disclosure, or a pharmaceutically acceptable salt or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present disclosure, or a pharmaceutically acceptable salt or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "treating" or "treat" describes the management and care of a patient for the purpose of combating a disease, condition, or disorder and includes the administration of a compound of the present disclosure, or a pharmaceutically acceptable salt or solvate thereof, to alleviate the symptoms or complications of a disease, condition or disorder, or to eliminate the disease, condition or disorder.

A composition of the present disclosure, or a pharmaceutically acceptable salt or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the disclosure leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the disclosure, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/ nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

The disorder in which EZH2-mediated protein methylation plays a part can be a neurological disease. The compound of this disclosure can thus also be used for treating neurologic diseases such as epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Any other disease in which epigenetic methylation, which is mediated by EZH2, plays a role may be treatable or preventable using compositions and methods described herein.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present disclosure, or a pharmaceutically acceptable salt, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means.

An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present disclosure, or a pharmaceutically acceptable salt, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present disclosure, or a pharmaceutically acceptable salt or solvate thereof, acts selectively on a cancer or precancerous cell but not on a normal cell. Preferably, a compound of the present disclosure, or a pharmaceutically acceptable salt or solvate thereof, acts selectively to modulate one molecular target (e.g., a target protein methyltransferase) but does not significantly modulate another molecular target (e.g., a non-target protein methyltransferase). The disclosure also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition of the present disclosure, e.g., a composition comprising any compound of Formulae (I)-(VIa) or pharmaceutically acceptable salt thereof, and one or more other therapeutic agents, such as prednisone, can modulate the activity of a molecular target (e.g., a target protein methyltransferase). Modulating refers to stimulating or inhibiting an activity of a molecular target. Preferably, a compound of the present disclosure, or a pharmaceutically acceptable salt or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present disclosure, or a pharmaceutically acceptable salt or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A composition of the present disclosure does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present disclosure, or a pharmaceutically acceptable salt or solvate thereof, demonstrates a minimum of a fourfold differential, preferably a tenfold differential, more preferably a fifty fold differential, in the dosage required to achieve a biological effect. Preferably, a compound of the present disclosure, or a pharmaceutically acceptable salt or solvate thereof, demonstrates this differential across the range of inhibition, and the differential is exemplified at the $IC_{50}$, i.e., a 50% inhibition, for a molecular target of interest.

Administering a composition of the present disclosure to a cell or a subject in need thereof can result in modulation (i.e., stimulation or inhibition) of an activity of a protein methyltransferase of interest.

Administering a compound of the present disclosure, e.g., a composition comprising any compound of Formulae (I)-(VIa) or pharmaceutically acceptable salt thereof, and one or more other therapeutic agents, such as prednisone, to a cell or a subject in need thereof results in modulation (i.e., stimulation or inhibition) of an activity of an intracellular target (e.g., substrate). Several intracellular targets can be modulated with the compounds of the present disclosure, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA.* 100(5): 2674-8, 2003. In an aspect, cell death occurs by apoptosis.

Preferably, an effective amount of a composition of the present disclosure, or a pharmaceutically acceptable salt or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a composition of the present disclosure, or a pharmaceutically acceptable salt or solvate thereof, can induce or activate cell death selectively in cancer cells. Administering to a subject in need thereof a compound of the present disclosure, or a pharmaceutically acceptable salt or solvate thereof, can induce or activate cell death selectively in cancer cells. Contacting a cell with a composition of the present disclosure, or a pharmaceutically acceptable salt or solvate thereof, can induce cell death selectively in one or more cells affected by a cell proliferative disorder. Preferably, administering to a subject in need thereof a composition of the present disclosure, or a pharmaceutically acceptable salt or solvate thereof, induces cell death selectively in one or more cells affected by a cell proliferative disorder.

The present disclosure relates to a method of treating or preventing cancer by administering a composition of the present disclosure, or a pharmaceutically acceptable salt or solvate thereof, to a subject in need thereof, where administration of the composition of the present disclosure, or a pharmaceutically acceptable salt or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3rd edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., 18th edition (1990). These texts can, of course, also be referred to in making or using an aspect of the disclosure.

Example 1

Preclinical data have suggested that small molecule inhibitors for the histone methyltransferase EZH2 represent potential new treatment modalities for Non-Hodgkin lymphomas (NHL) expressing EZH2 change of function mutations. It has been previously reported that selective inhibition of EZH2 results in specific killing of lymphoma cells bearing EZH2 mutations in vitro and in vivo, with minimal effects on non-mutant lymphoma cells [Knutson et al. Nature Chemical Biology 2012[1]; Keilhack et al. Blood (ASH Annual Meeting Abstracts) 2012, 120, Abstract 3712[2]]. Since epigenetic changes have been suggested to be involved in resistance of cancer cells to many anticancer agents, Compound 44 in combination with standard of care agents for NHL, second line therapies or targeted therapies that are being explored in this indication was studied. With continuous exposure to Compound 44, cell-based assays of two different EZH2 mutant cell lines demonstrated combination benefits with all components of the CHOP chemotherapy regime, second line therapies but also with several targeted therapies (for instance other epigenetic drugs, PI3K pathway or other inhibitors). These effects were not observed in an EZH2 wild type lymphoma cell line of the activated B cell type. Strong combination benefit with CHOP was also observed in two different EZH2 mutant xenograft models. For instance, in the SUDHL6 Y646N xenograft model neither Compound 44 nor CHOP chemotherapy alone induced a significant antitumor effect, yet their combination produced durable tumor regressions even after cessation of dosing. Importantly, this effect was preserved when doxorubicin was omitted from the CHOP chemotherapy regime in a third study with another EZH2 mutant xenograft model. Subsequently data presented herein showed that glucocorticoid receptor agonism may be a key mechanism of the combination benefit observed with CHOP, as the anti-proliferative effect of Compound 44 was enhanced by either prednisolone or dexamethasone alone, in several EZH2 mutant lymphoma cell lines (in vitro). Taken together these data suggest that the single agent activity of Compound 44 in EZH2 mutant NHL may be further enhanced and expanded through rational combination strategies.

The data presented herein demonstrate that:

Compound 44 and glucocorticoid receptor agonists cooperate to dramatically enhance the antiproliferative activity in EZH2 mutant and wild type GCB lymphoma lines, including EZH2i insensitive mutant lines, but not those of the activated B-cell type in vitro.

In mutant EZH2 GCB lymphoma cells, combination benefit was also observed with all the single components of the CHOP chemotherapy regime, second line and other targeted therapies, including strong synergy with the BCL2 inhibitor, navitoclax and mTOR inhibitor everolimus.

Strong combination benefit with CHOP was observed in two different EZH2 mutant xenograft models, and this effect was preserved in a study in a third EZH2 mutant xenograft model in which doxorubicin was omitted from the chemotherapy regime.

Taken together these results suggest that glucocorticoid receptor agonist may play a key role in the amplified anti-tumor activity observed with combinations of Compound 44 and CHOP in EZH2 mutant lymphoma xenografts and that the observed strong in vitro synergy, with several novel therapies currently evaluated in NHL warrant further investigation of rational combinatorial approaches.

Example 2: Synergistic Anti-Tumor Activity of EZH2 Inhibitors and Glucocorticoid Receptor Agonists in Germinal Center Non-Hodgkin Lymphomas Results Dramatic synergy was observed when Compound 44 is combined just with the glucocorticoid receptor agonist (GRag) prednisolone of CHOP or with other GRag, such as dexamethasone. When combined with CHOP, the antiproliferative effects of Compound 44 are greatly enhanced and most of this synergy can be ascribed to the GRag component of CHOP, prednisolone (the active metabolite of prednisone). Remarkably, the combination of Compound 44 and prednisolone extends the range of cells that are sensitive to EZH2 inhibition, from mutant-bearing only to all GCB NHL cells.

Two EZH2 mutant cell lines, WSU-DLCL2 and SU-DHL10, were pre-treated with Compound 44 for 4 days and then co-treated with the combination of Compound 44 plus individual CHOP components for 3 additional days (4+3 model). Mafosfamide (an analog of cyclophosphamide), doxorubicin, and vincristine, all showed concentration-dependent growth inhibition in the mutant cell lines by themselves. Hence, combination indices (CI, calculated using Calcusyn software) were obtained for these drugs in combination with Compound 44. These cell lines, however, showed no sensitivity to prednisolone (the active metabolite of prednisone) by itself. Thus, in this case a CI could not be determined and instead an enhancement of potency was calculated based on the shift in $IC_{50}$ of Compound 44 seen with a concentration-response curve of prednisolone.

Figure 1:
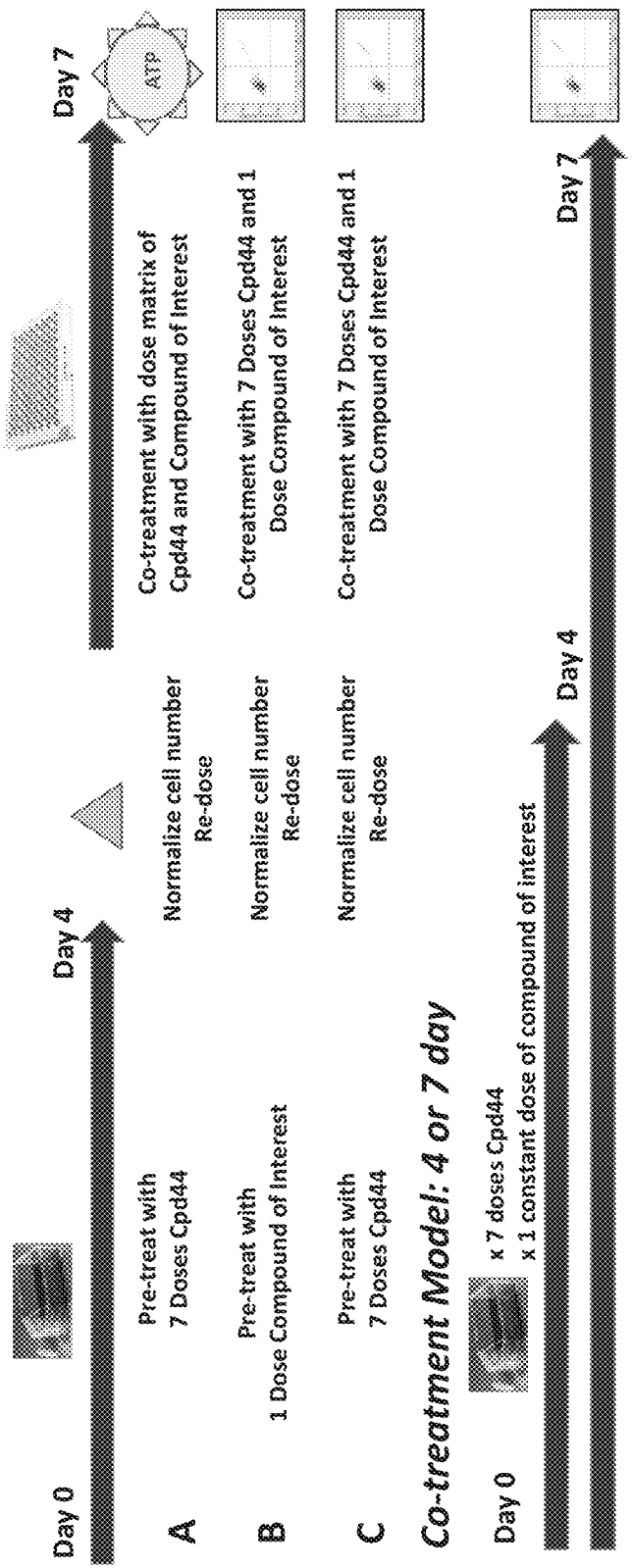
Figure 2:
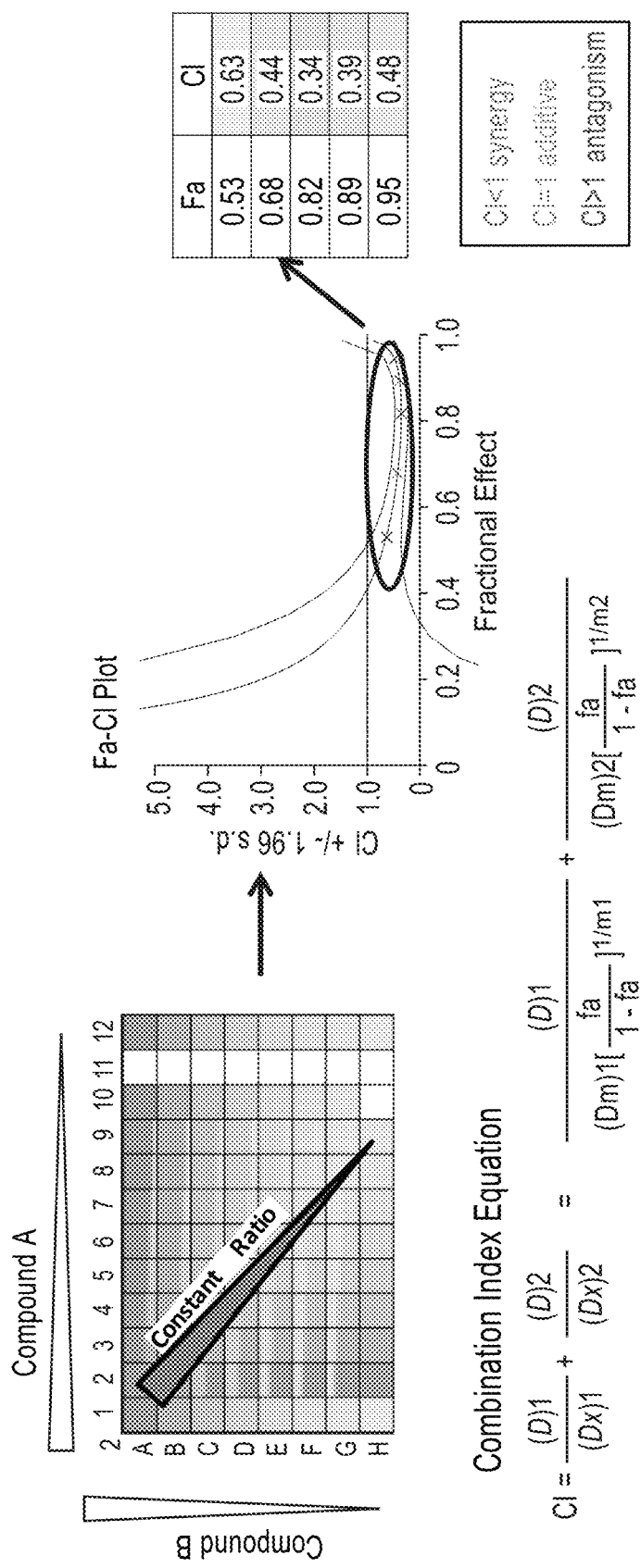
Figure 4A:
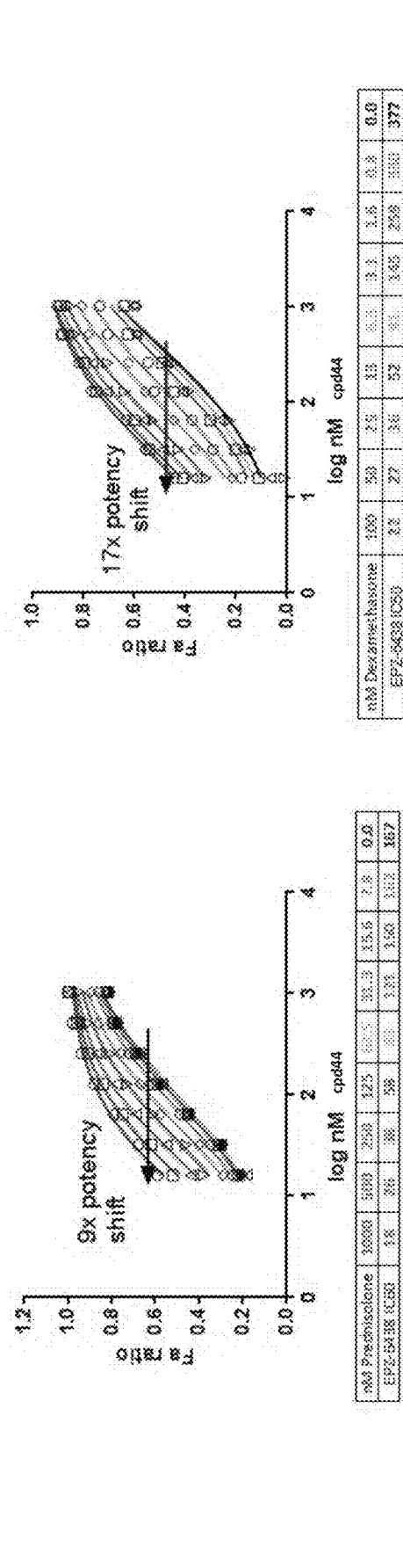
Figure 4B:
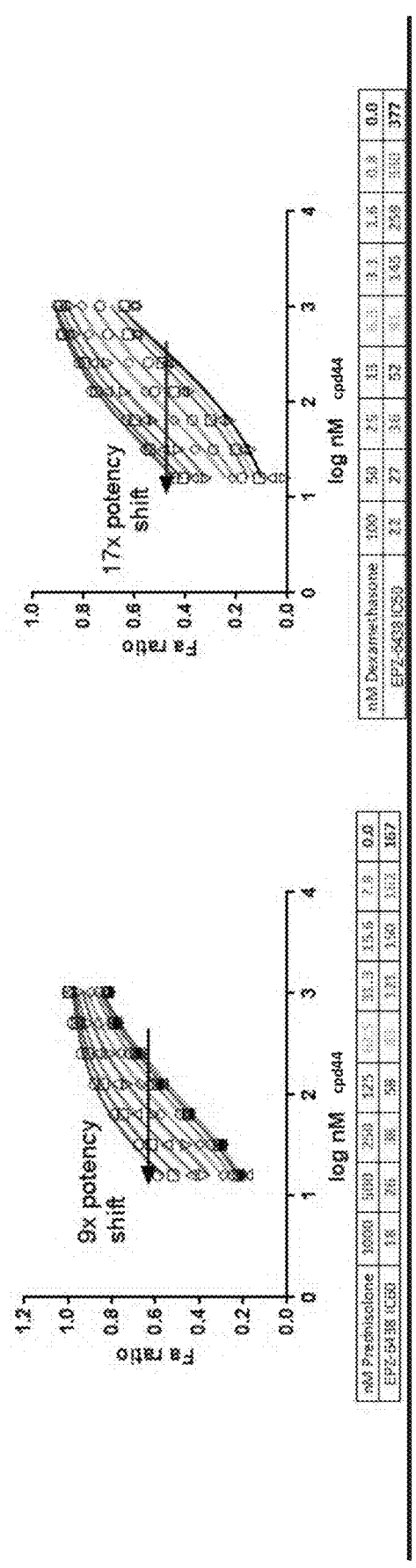
Figure 4C:
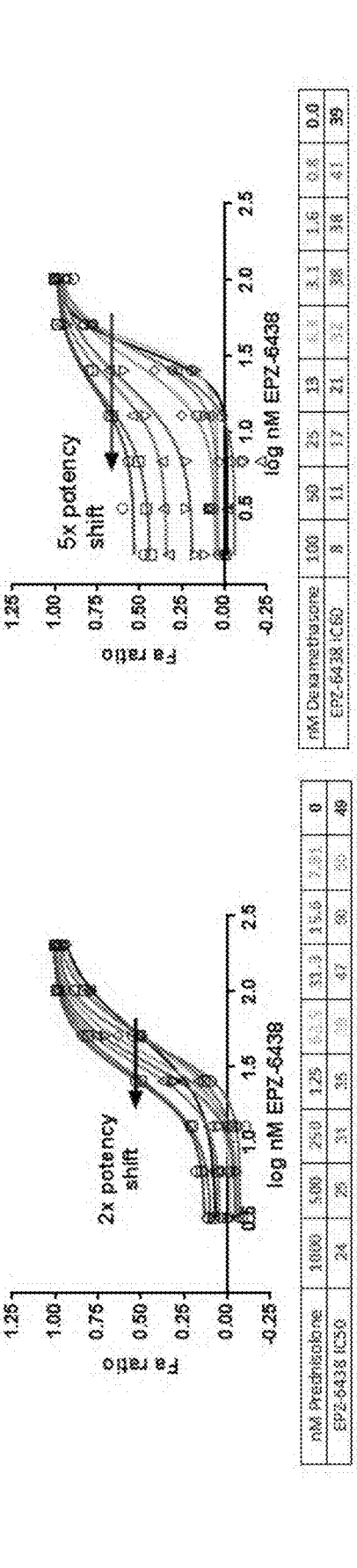
Figure 4D:
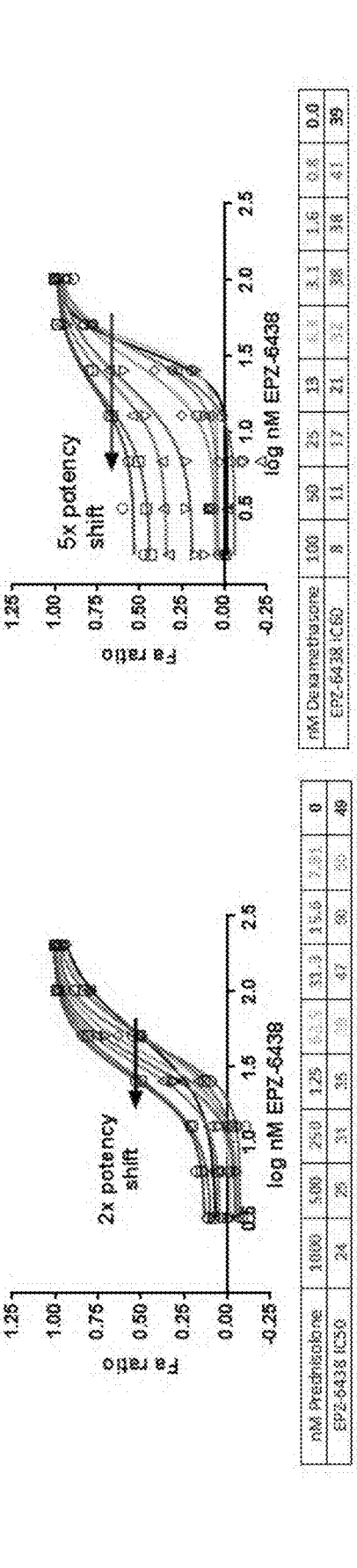
Figure 7B:
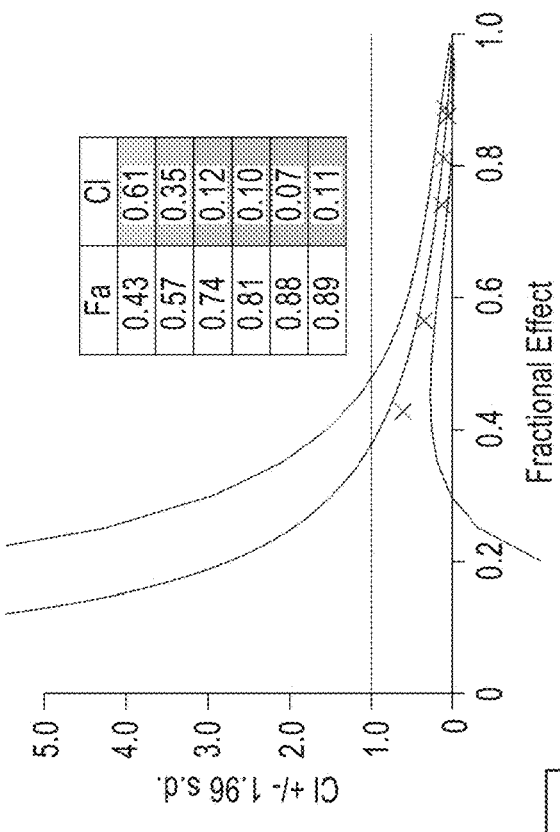
Figure 7A:
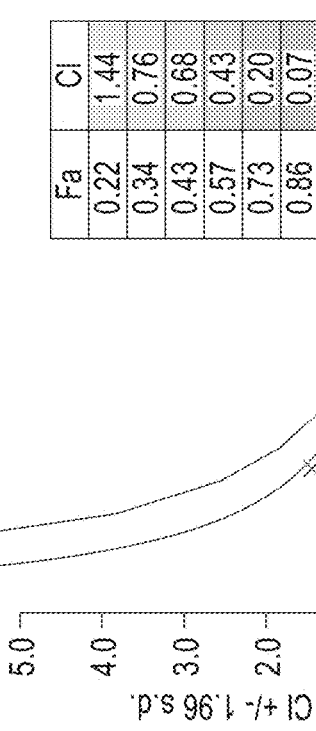

The combination of Compound 44+mafosfamide led to an overall additive combination benefit in both EZH2 mutant cell lines (FIGS. 3C and 3F). In WSU-DLCL2 cells, Compound 44+doxorubicin acted synergistically in the 4+3 model (FIG. 3A), while this combination was additive in SU-DHL10 cells (FIG. 3D). The combination of Compound 44+vincristine also demonstrated additivity in both EZH2 mutant cell lines (FIGS. 3B and 3E). When WSU-DLCL2 cells were treated with prednisolone+ Compound 44, a 9-fold shift to greater potency was observed for Compound 44. Treatment with a different GRag, dexamethasone, resulted in an even greater shift in the $IC_{50}$ of Compound 44 of 17-fold (FIGS. 4A and 4B). A similar trend in potency shift for Compound 44 was observed in SU-DHL10 cells (FIGS. 4C and 4D).

Whether the combination effect of Compound 44+CHOP could render WT EZH2 lymphoma cell lines, both of the GCB and ABC subtype, sensitive to Compound 44 was investigated next. Since Compound 44 treatment alone does not induce growth inhibition in EZH2 WT lymphoma lines, shifts in potency were calculated based on the concentration-response curves of the individual CHOP components. Of the When EZH2 mutant, Compound 44 sensitive cell lines were co-treated for 4 days, a 30-60 fold lower $IC_{50}$ of Compound 44 was observed, demonstrating similar trends to that of the 4+3 treatment schedule (Table 2). Similar results were observed with 7 day co-treatment, and the 4+3 model (Table 2). In EZH2 WT GCB cell lines, despite yielding no measureable Compound 44 $IC_{50}$ after 4 days, both cell lines exhibited decreased proliferation and a measurable Compound 44 $IC_{50}$ after 4 days of co-treatment with prednisolone (Table 2). EZH2 WT GCB cells also responded to the 4+3 model and/or 7 day co-treatment schedules (Table 2). Strikingly, EZH2 mutant, Compound 44 insensitive cell lines, which also exhibit no measurable Compound 44 $IC_{50}$ after 4 day treatment, demonstrated decreased proliferation with 4 day co-treatment, with even greater response to the combination with the 4+3 treatment schedule as well as with 7 day co-treatment (Table 2). Only 1 of the 6 cell lines demonstrated a combination benefit when cells were pre-treated with prednisolone, then co-treated with Compound 44+prednisolone, suggesting that the order of drug addition is important for the synergy effect (Table 2). Table 2. Compound 44/GRag Combination Increases EZH2i Sensitivity in EZH2 Y646 Cell Lines and Overcomes EZH2i Insensitivity in Cell Lines Resistant to EZH2i

| Cell Line | 4 Day Cpd44 $IC_{50}$ (uM) | | 7 Day Cpd44 $IC_{50}$ (uM) | | |
| --- | --- | --- | --- | --- | --- |
| | Cpd44 Alone | Cpd44 Co-treatment | 4 d Cpd44 Pre/ 3 d Co-treat | 4 d Pred Pre/ 3 d Co-treat | 7 d Co-treatment |
| WSU (Y646-Sens) | 0.53 +/− 0.014 | 0.020 +/− 0.021 | 0.011 +/− 0.0062 | >1 | 0.014 +/− 0.0049 |
| SU-DHL10 (Y646-Sens) | 0.64 +/− 0.26 | 0.0092 +/− 0.0044 | 0.0027 +/− 0.0013 | 0.52, >1 | 0.020 +/− 0.0057 |
| RL (Y646-Res) | >1 | 0.0096 +/− 0.0066 | <<0.004 | 0.38 | <0.004 |
| SU-DHL4 (Y646-Res) | >1 | >1, 0.2, >1 | 0.035 +/− 0.043 | >1 | 0.51 +/− 0.35 |
| DOHH2 (WT) | >1 | 0.20 +/− 0.25 | >1, 0.03, >1 | >1 | 0.34 +/− 0.078 |
| OCI-Ly19 (WT) | >1 | 0.19 +/− 0.11 | 0.0055 +/− 0.0047 | >1 | 0.026, <0.004 | four CHOP components tested, only the combination of GRag+ Compound 44 led to a potency shift in a WT GCB lymphoma cell line (FIGS. 5A and 5B and Table 3). In contrast, no potency shift was observed in a WT ABC lymphoma line with any of the 4 CHOP components (FIGS. 5C and 5D and Table 3), suggesting that the GRag+EZH2i combination benefit is specific to the biology of the GCB subtype of lymphoma.

Given that only the GRag+EZH2i combination induced dramatically enhanced antiproliferative effects, compared to either single agent, in EZH2 WT and mutant GCB lymphoma cell lines, whether duration of treatment and/or sequence of addition of compounds affected sensitivity was determined. The cell line panel was also extended to include two EZH2 WT, two EZH2 mutant, Compound 44 sensitive, and two EZH2 mutant, Compound 44 insensitive cell lines (previously reported by McCabe et al, and unpublished internal data). In the previous 4+3 model, the potency shift was based on either Compound 44 (in EZH2 Y646 sensitive cell lines) or prednisolone (in EZH2 WT cell lines) exposure. For this set of experiments, the Compound 44 $IC_{50}$ shift at a fixed concentration of prednisolone was used to determine the combination benefit in cell lines treated with either the 4+3 model, 4 day or 7 day co-treatment, or 4 day prednisolone pre-treatment plus 3 days of co-treatment.

Figure 11A:
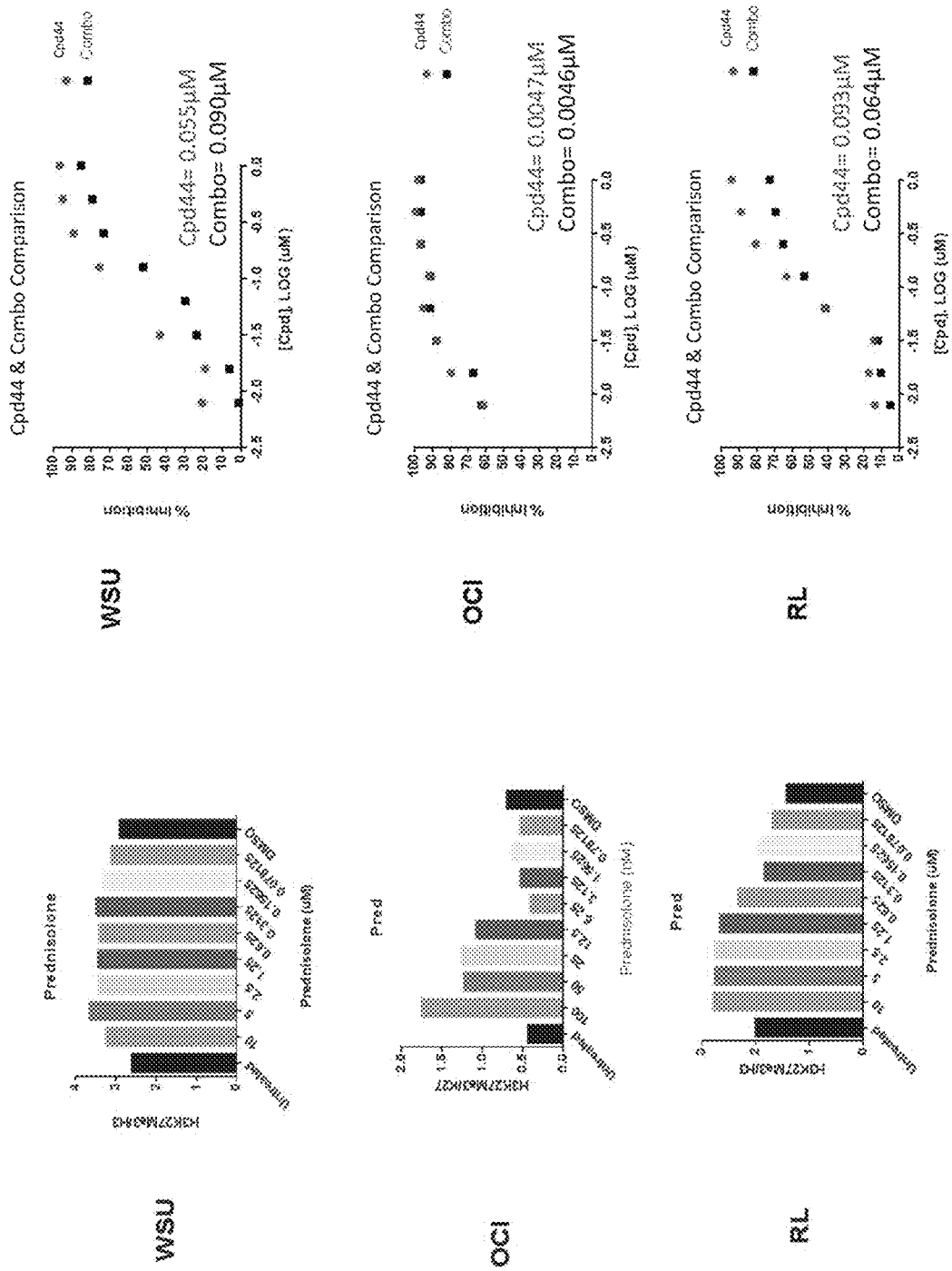
Figure 11B:
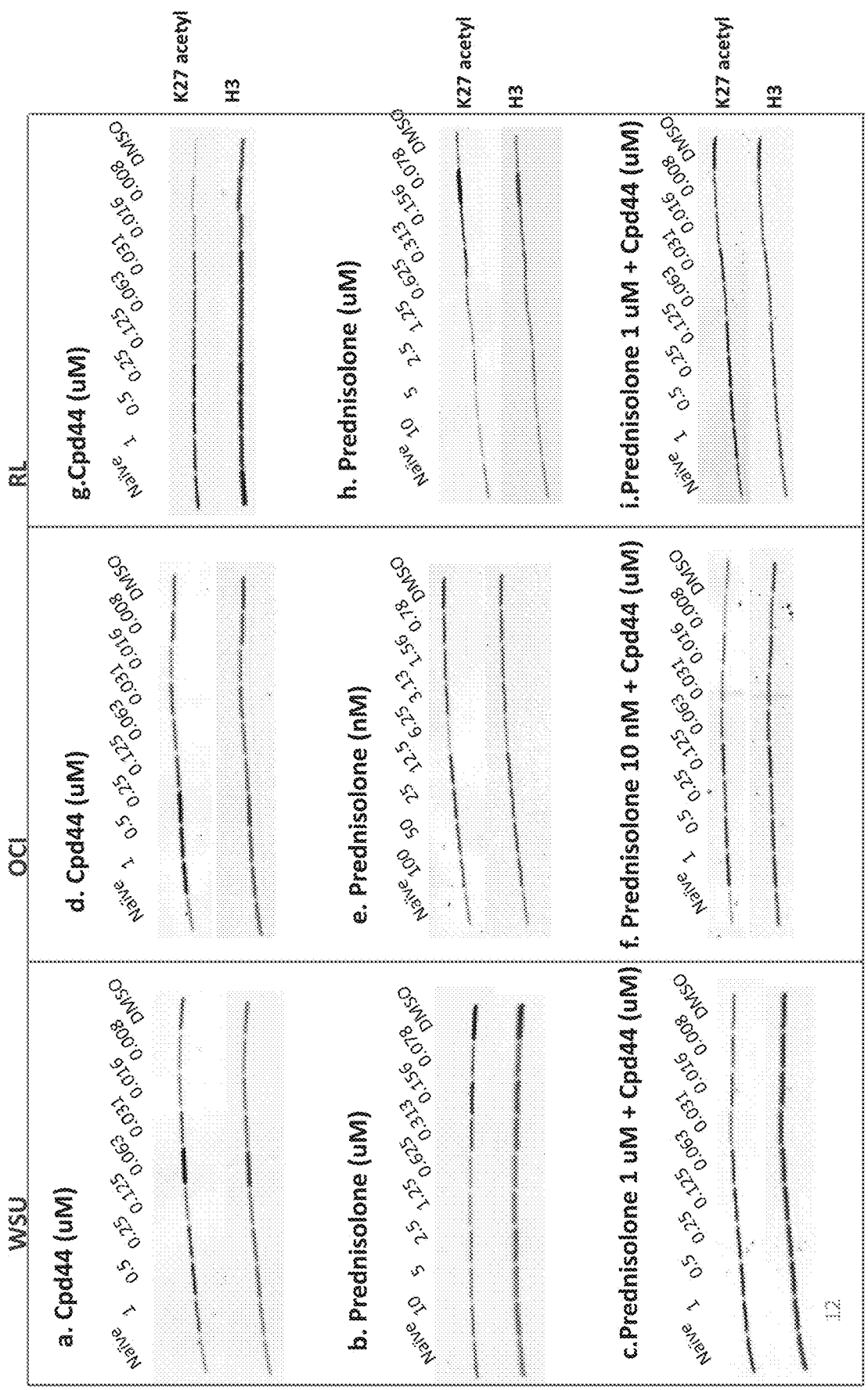
Figure 12:
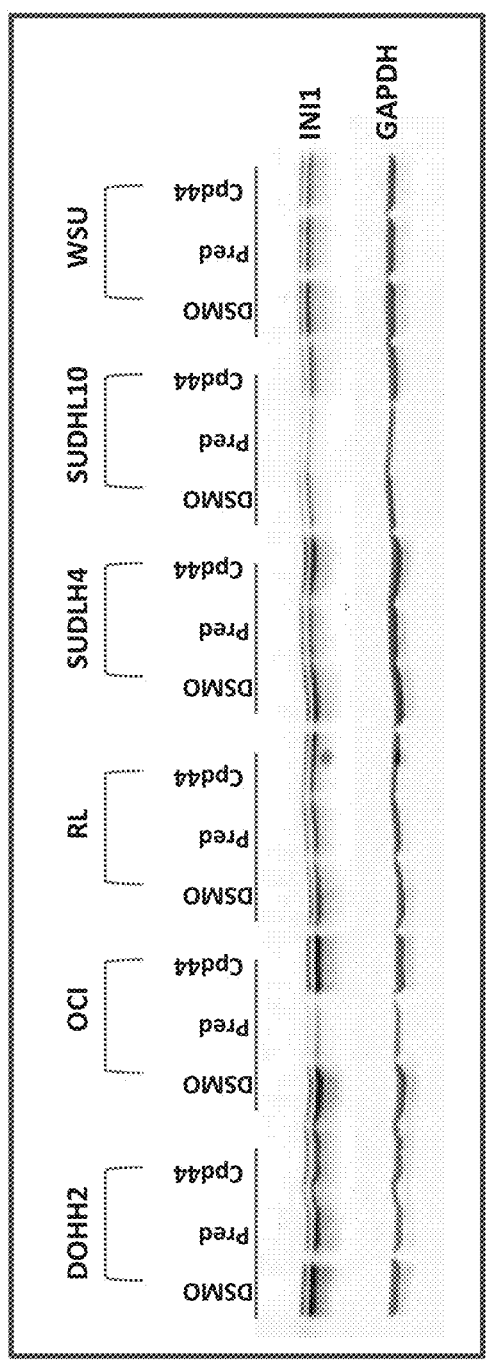
FIG. 12 is a western blot showing that single agent treatment with Compound 44 or prednisolone has no effect on SMARCB1 protein levels.
Figure 13:
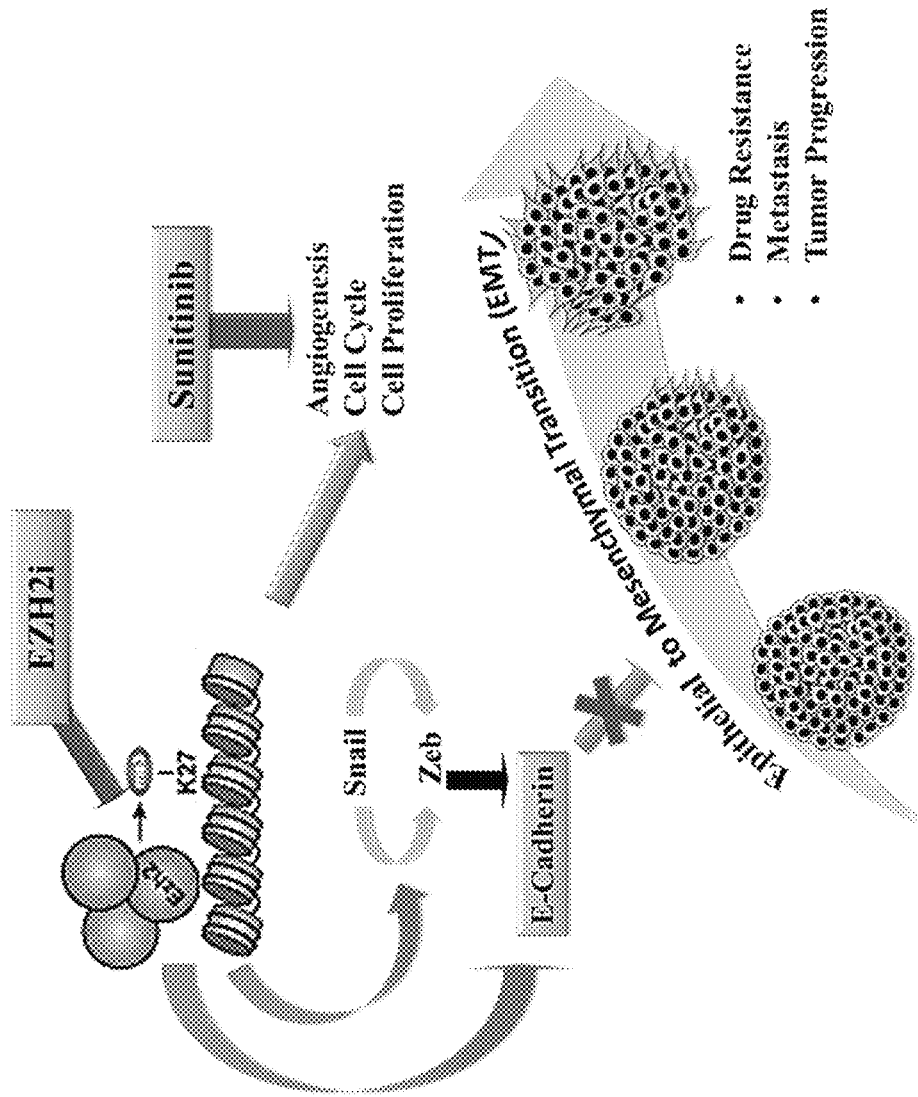
FIG. 13 is a scheme showing involvement of EZH2 in drug resistance to anti-VEGF therapy, which continues to be a challenge in patients with metastatic renal cell carcinoma as patients who initially respond to treatment eventually develop resistance and tumor progress.
Figure 14:
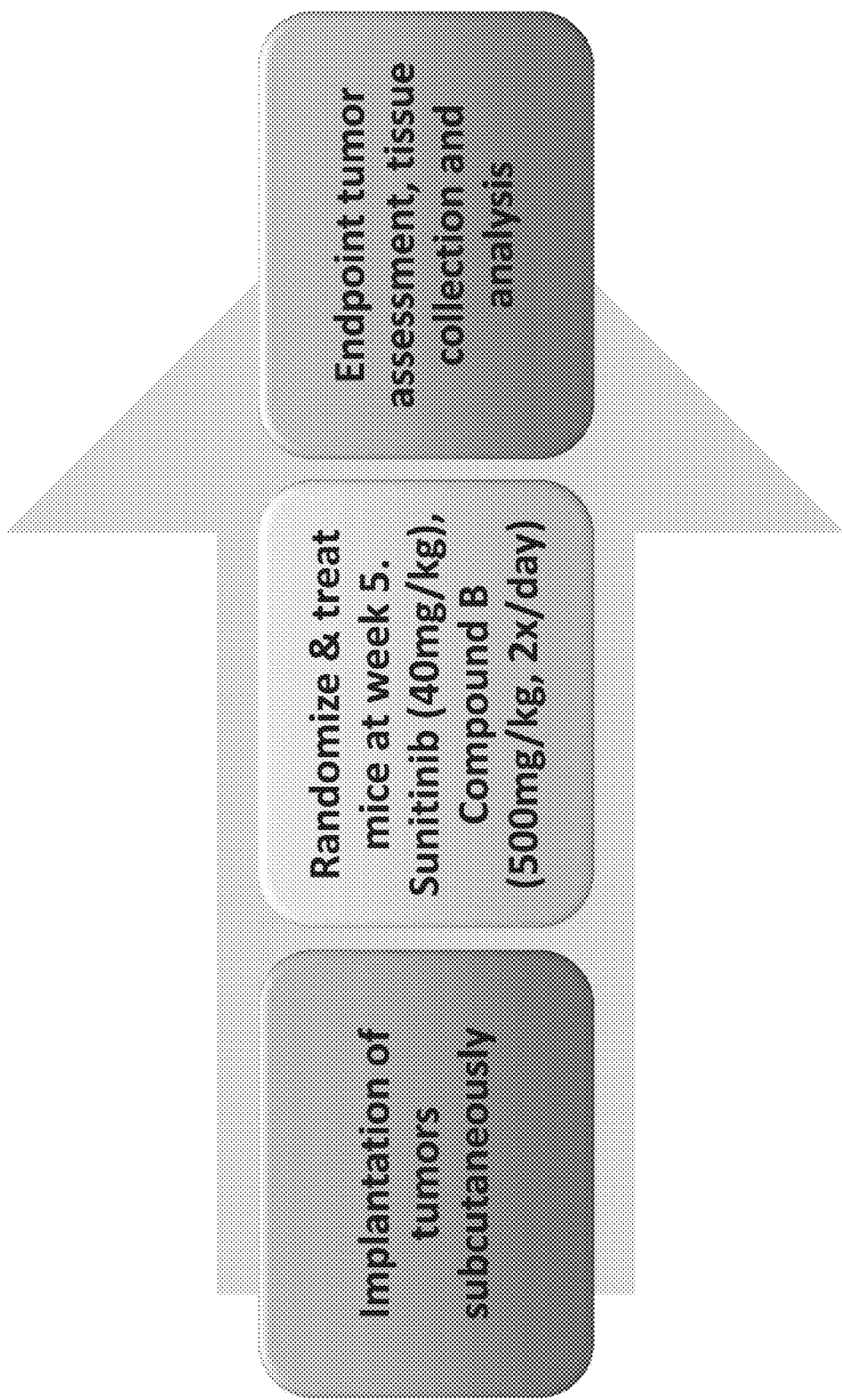
FIG. 14 is a scheme showing the design of in vivo combination assays.

To investigate the mechanism of action through which this combination benefit of Compound 44+GRag acts in these cell lines, global methylation and acetylation of the histone H3 lysine 27 (H3K27) residue was analyzed. WSU-DLCL2, OCI-LY19, and RL cells were treated with either Compound 44, prednisolone, or their combination for 4 days, and H3K27 modifications were assessed by ELISA or western blot. Prednisolone alone did not have any effect on H3K27 trimethylation (H3K27me3) in either WSU-DCL2 or RL cells, but did result in a modest increase of H3K27me3 at higher doses in OCI-LY19 cells. The combination of Compound 44+prednisolone did not shift the Compound 44 $IC_{50}$ for H3K27me3 inhibition in any cell line (FIG. 11A). Similarly, H3K27 acetylation levels were not globally affected by prednisolone alone or the combination of Compound 44+prednisolone (FIG. 11B).

Figure 10A:
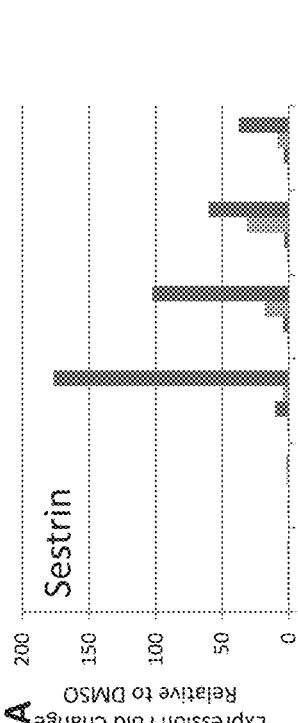
Figure 10B:
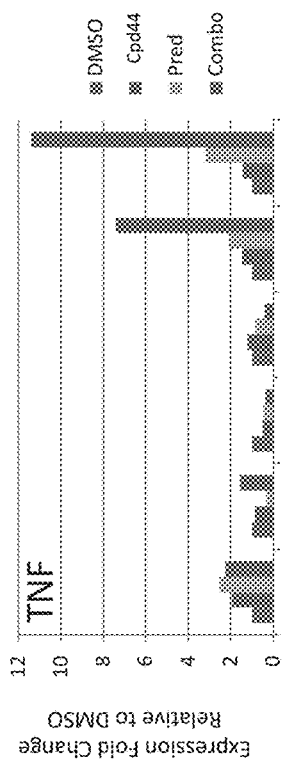
Figure 10C:
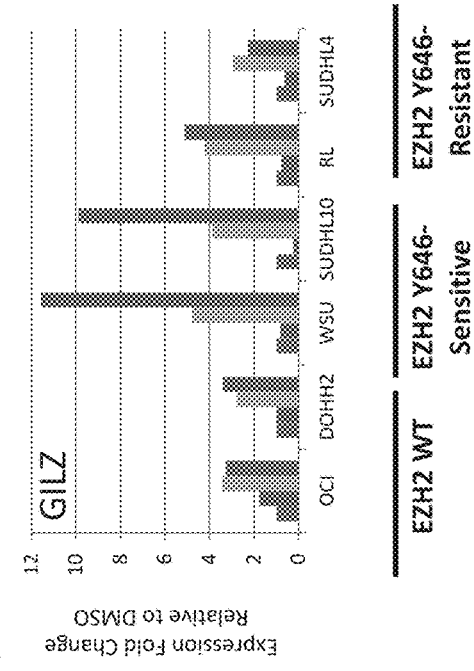

Having found that global levels of H3K27 acetylation or trimethylation were unaffected, transcriptional regulation of GR signaling pathways was studied. WSU-DLCL2, SU-DHL10, RL, SU-DHL4, OCI-LY19, and DOHH2 cells were treated with a single concentration of Compound 44, prednisolone, or the combination for 4 days, and gene expression was analyzed using a glucocorticoid signaling PCR array (Table 4). Overall, a larger number of genes were down-regulated with both prednisolone and combination treatments in all cell lines, pointing to a role of GR as both activator and repressor of gene expression. Here, the activating function of GR was focused on and 3 genes which have a synergistic up-regulation in the panel of cell lines with combination treatment were described. Sestrin, a putative tumor suppressor that inhibits mTOR signaling (ref), was identified as a gene commonly up-regulated among the 4 EZH2 mutant cell lines in a synergistic manner with combination treatment, but not in EZH2 WT cell lines (FIG. 10A). TNF expression was synergistically up-regulated only in the EZH2 mutant, Compound 44 insensitive cell lines (FIG. 10B), and TSC22D3/GILZ, while up-regulated in all cell lines by prednisolone, is only synergistically enhanced by combination treatment in EZH2 mutant, Compound 44 sensitive cell lines (FIG. 10C).

TABLE 3

Summary of Combinations with Compound 44

| | | WSU-DLCL2 (EZH2 mutant GCB) | SU-DHL10 (EZH2 mutant GCB) | Toledo (WT EZH2 ABC) | DOHH2 (WT EZH2 GCB) |
|---|---|---|---|---|---|
| Standard of Care DLBCL | Prednisolone | potency enhanced 7x | potency enhanced 3x | no effect | potency enhanced 2x |
| | Doxorubicin | synergy | additive | no effect | no effect |
| | Mafosfamide | additive | additive | no effect | no effect |
| | Vincristine | additive | additive | no effect | no effect |
| Other Therapies | Dexamethasone | potency enhanced 15x | potency enhanced 5x | no effect | potency enhanced 4x | no effect = No change in drug $IC_{50}$ upon addition of EPZ-6438

| | |
|---|---|
| CI < 1 | synergy |
| CI = 1 | additive |
| CI > 1 | antagonism |

Figure 9A:
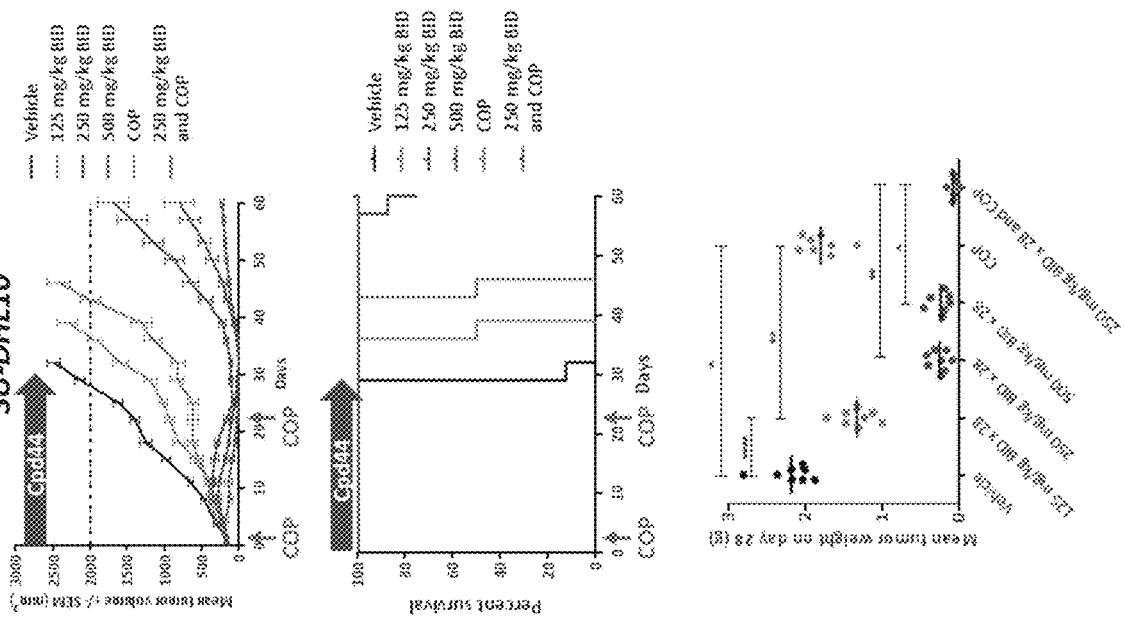

Finally, tumor growth inhibition was assessed in 3 different EZH2 mutant lymphoma xenograft models. SCID or nude mice bearing subcutaneous lymphoma xenografts were co-dosed with Compound 44 and chemotherapy, either CHOP or COP (CHOP without doxorubicin), and compared to single agent treatments. In WSU-DLCL2 xenograft bearing mice, tumor growth inhibition was achieved at all Compound 44 doses and schedules employed, and was better than CHOP chemotherapy alone (FIG. 9A). Moreover, the combination therapy of Compound 44 and CHOP induced a robust anti-tumor response and significantly ($p<0.001$) better tumor growth inhibition (93%) than with either single agent alone (45% and 71%, for CHOP and Compound 44, respectively). All single treatments were tolerated; there was minor body weight loss (11.3%) in the Compound 44/CHOP combo group after the first cycle after which the mice recovered before the next cycle of treatment.

Figure 9B:
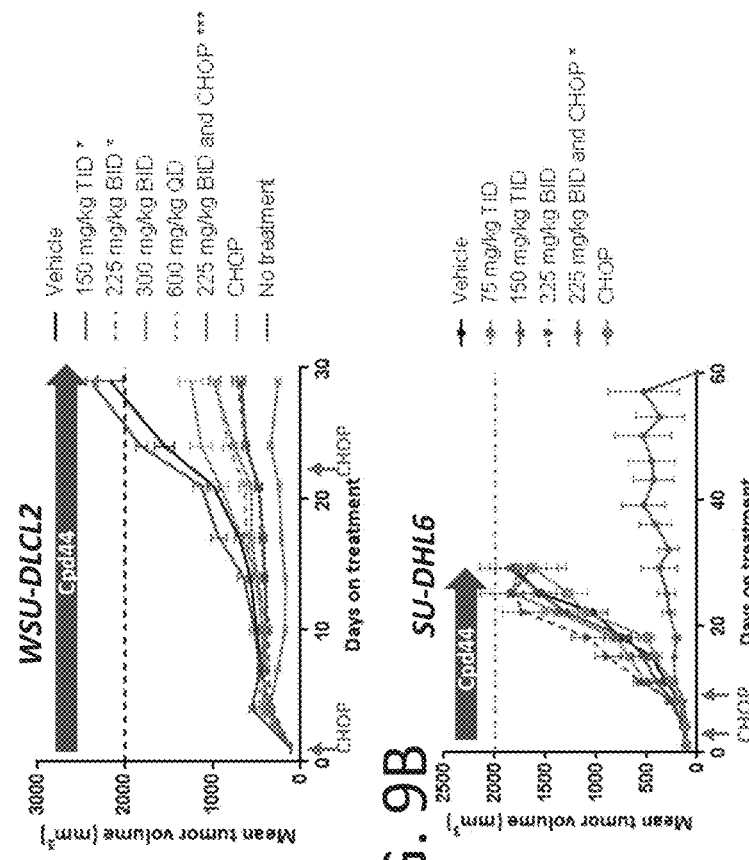

In a SU-DHL6 xenograft model, significant tumor growth inhibition was not observed with CHOP alone, nor with Compound 44 (FIG. 9B, top panel), in contrast to results previously published by Beguelin et al. using the EZH2 inhibitor GSK503. Strikingly, the combination of Compound 44/CHOP resulted in tumor regression. When dosing was stopped at day 28 and mice were observed out to day 60 for tumor growth delay, this combination resulted in tumor free survival in 58% of the mice (FIG. 9B, bottom panel).

Figure 9C:
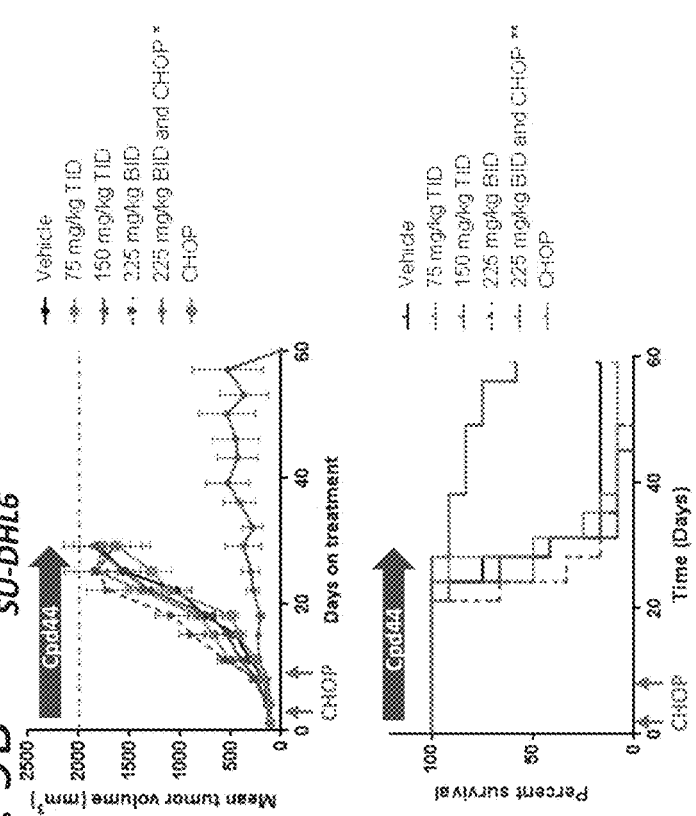

The doxorubicin component of CHOP has a lifetime cumulative dosing limit of <550 mg/m$^2$ due to its cardiotoxicity. Therefore, the combination benefit of a Compound 44/chemotherapy regimen that eliminated this component was investigated. In a third study, SU-DHL10 xenograft bearing mice were treated for 28 days with either increasing doses of Compound 44 (BID), doxorubicin-free chemotherapy regimen (COP), or a combination of COP and Compound 44 Tumor growth inhibition was observed at all Compound 44 doses as well as with COP (FIG. 9C, top panel). The 266 mg/kg, 532 mg/kg and COP/Compound 44 combination treatments resulted in regressions that were statistically different from vehicle ($p>0.001$) as assessed by repeated measures ANOVA and Dunnett's post test, with the Compound 44/COP combination group demonstrating the best overall response. After the 28 day dosing, a sub-group of mice with the smallest tumor burden (8 mice per group) were kept alive without further dosing for a tumor growth delay endpoint. There was a clear dose dependent tumor growth delay benefit for mice treated with Compound 44, while COP treated tumors progressed faster than those treated with Compound 44 (FIG. 9C, middle panel). While mice treated with the maximal tolerated dose of Compound 44 or with the Compound 44/COP combination showed 100% survival on Day 60, the combination group showed the smallest terminal tumor weights, statistically different ($p>0.05$) from all other treatment groups, including the maximal tolerated dose for Compound 44 (FIG. 9C, bottom panel).

Standard treatments for B-cell NHL are combination chemotherapy regimens composed of cyclophosphamide, doxorubicin, vincristine and prednisolone. While complete response rates of 40-50% can be achieved, a substantial proportion of patients relapse, with 3-year overall survival rates of only about 30%. Relapsed lymphomas can exhibit resistance to a wide range of anticancer drugs, which poses a severe challenge in the clinic to manage these aggressive malignancies. Acquisition of drug resistance in lymphoma is partly driven by the genetic heterogeneity and instability of the tumor cells. Successful treatment of chemoresistant NHL will thus require rational combinations of drugs targeting multiple pathways specific to the different subtypes of B-cell NHL. For instance, in lymphomas of the activated B cell type, constitutive activation of the NFkB pathway has been implicated in therapy resistance, and several novel targeted therapies have shown promise in this subtype.

Epigenetic effectors, such as polycomb, have also been implicated in cancer cell chemo-resistance. EZH2, the catalytic subunit of polycomb repressive complex 2 (PRC2) is a critical oncogenic driver in germinal center derived B-cell lymphomas. These more primitive B-cell malignancies, especially variants expressing EZH2 mutants with altered catalytic activity, require EZH2 for proliferation and survival. Results from preclinical studies forecast great promise for EZH2 catalytic inhibitors for the treatment of such genetically defined cancers, and EZH2 inhibitors may also mitigate chemotherapy resistance. The data presented herein show that Compound 44, a clinical stage EZH2 inhibitor, shows various degrees of combination benefit, ranging from additivity to synergy, with the components of CHOP. Those combination effects were specifically found in lymphomas of the germinal center origin, and, in the case of cyclophosphamide, doxorubicin and vincristine, were restricted to EZH2 mutant-bearing cells. Significant synergy in lymphoma cell killing was also found when Compound 44 was co-dosed with CHOP in vivo. This was especially true in the SU-DHL6 xenograft model where neither single agent showed any significant antitumor actvity, but the combination induced durable regressions in >50% of mice. This reiterates the potential importance of overactive EZH2 in chemoresistance of EZH2 mutant lymphoma. Among the CHOP components, Compound 44 combinations with prednisone induced the strongest antiproliferative activity, and this combination could also render insensitive GCB lymphoma cell lines sensitive to EZH2 inhibition, regardless of the EZH2 mutational status. Additionally, this combination benefit is more apparent when Compound 44 and prednisolone are either dosed together or in a sequence specific manner; thus, priming cells with an EZH2 inhibitor, followed by treatment with GR agonists proved particularly effective. This surprising finding has potentially important implications for the application of EZH2 inhibitors in the clinic. First, the widely used GRag are frequently co-administrated with anticancer drugs to prevent drug-induced allergic reactions and to relieve pain, nausea, and emesis, and are pivotal in the treatment of hematopoietic malignancies owing to their ability to induce apoptosis in these cancers. Compared to the other CHOP components, GRag induces the least severe adverse effects. Further, the opportunity to eliminate doxorubicin from the CHOP regime while preserving a combination benefit with Compound 44, as suggested by the data in the SU-DHL10 xenograft model, could spare patients from the dose-limiting cardiotoxic side effects of doxorubicin. Finally, preclinical studies have shown that single agent EZH2 inhibitors induce significant cell killing only in EZH2 mutant-bearing lymphomas, which represent a fraction (20%) of GCB lymphoma patients with high unmet clinical need. The results here demonstrate that GRag/EZH2 inhibitor combinations may have clinical utility in all germinal center derived B cell lymphomas.

Glucocorticoid bound GR molecules move to the nucleus and can act as either transcriptional activator or repressor, depending on the cellular environment. It has been suggested that GR constantly samples the nucleosome for a productive interaction, and the purpose of chromatin-modifying enzymes is to provide regulated access of GR, its cofactors and the basal transcription machinery to DNA. Other studies show that GR often binds to preexisting regions of open chromatin, and the chromatin architecture in a given cell type is organized such that GR can act in a tissue specific manner. Accessibility to GR binding sites can further be enhanced by ATP-dependent chromatin remodeling, and the SWI/SNF complex plays a key role in this activity. Not wishing to be bound by a particular theory or a specific mechanism of action, it is conceivable that aberrant chromatin repression, induced by EZH2 mediated hypertrimethylation of H3K27, can block some of the otherwise accessible GR binding sites, interfering with normal GR mediated gene induction or repression. Indeed, all EZH2 mutant lymphoma cell lines are insensitive to GRag treatment, while concentration-dependent cell killing is observed in EZH2 WT cells. The observation that pretreatment with prednisolone, followed by Compound 44 treatment, cannot induce synergy in almost all cell lines tested, points towards the possibility of EZH2 inhibitor induced chromatin remodeling being the rate limiting step for the enhanced action of GR. Also, PRC2 is known to antagonize with SWI/SNF function and the down-regulation of core subunits of the SWI/SNF complex—SMARCA4, ARIDIA, and INI1—have been associated with resistance to prednisolone in acute lymphoblastic T-cell leukemia. Since the relationship of INI1 loss and EZH2 over-activation has been established in rhabdoid tumors, whether global INI1 protein levels would increase in various lymphoma cells exposed to Compound 44 or prednisolone, potentially allowing greater accessibility of GR to its binding sites after increased SWI/SNF function, was investigated.

GR pathway gene expression arrays revealed both increased and decreased gene expression after treatment of several GCB lymphoma cells (both EZH2 WT and mutant) with either Compound 44, prednisolone or their combination, confirming the dual function of GR. The only gene that was synergistically up-regulated with the combination in all EZH2 mutant lymphoma cells was SESN1, a TP53 tumor suppressor with functions in cellular response to DNA damage and oxidative stress. Sestrins inhibit cell growth by activating AMP-activated protein kinase, resulting in the inhibition of the mTOR pathway. Hence SESN1 mediated mTOR pathway inhibition may be an important mechanism of reintroducing GRag sensitivity in EZH2 mutant lymphoma cells after Compound 44 treatment.

Conversely, GRag/Compound 44 combination treatment could also induce cell killing in those EZH2 mutant lymphoma cell lines that have been reported as refractory to EZH2 inhibitor treatment (RL, SU-DHL4). SESN1 was induced with combination treatment in those cell lines as well, but an additional synergistic up-regulation of TNF, a potent inflammatory cytokine, was observed specifically in RL and SU-DHL4 cells. This observation seems surprising as TNF and glucocorticoids usually act antagonistically. TNF, through its receptor TNFR-1, can induce apoptosis, but also has the ability to transduce survival signals, mainly through the NFkB pathway. It is thus possible that increased TNF expression, induced by the Compound 44/prednisolone combination, may shift TNF action towards apoptosis in the context of GR agonist repression of NFkB-mediated transcription. It is unclear, however, why this mechanism would result in synergistic cell killing in Compound 44 insensitive EZH2 mutant cells. The potential importance of aberrant repression of negative regulators of the NFkB pathway in GRag resistance and the potential role of EZH2 mediating that is further supported by the observation that GILZ is synergistically up-regulated in 2 out of 6 cells lines with the combination.

Methods

Medium Throughput Assay

Lymphoma cells were seeded into flasks (50,000 cells/mL for WSU-DLCL2 and DOHH2, 10,000 cells/mL for SU-DHL10, and 100,000 cells/mL for Toledo) and pretreated with 7 doses of Compound 44 or DMSO for 4 days or 6 days for Toledo assays. Cells were then split back to 50,000 cells/mL for WSU-DLCL2 and DOHH2 or 30,000 cells/mL for SU-DHL-10 and co-treated with Compound 44 and compound of interest using the HP D300 digital dispenser (Tecan). Both drugs were serially diluted two-fold and combined in a matrix with constant ratios diagonally across the plate with a final DMSO content of 0.11% (v/v). After 3 days of co-treatment (5 days for Toledo assays), cell viability was measured via ATP content using CellTiter-Glo® (Promega) and luminescence was detected using a Spectra-Max M5 microplate reader (Molecular Devices).

Synergy quantification is performed using the Chou-Talalay method for drug combination (Ref 1). The Combination Index (CI) equation offers a quantitative definition for additivity (CI=1), synergism (CI<1), and antagonism (CI>1). This equation used fractional effect (Fa) values from a constant ratio of drug combination to determine CI values. The resulting plot (Fa-CI) plot shows the resultant CI values bracketed by 95% confidence intervals. These Fa-CI plots are generated using the Calcusyn for Windows software (Ref 2). CI values<1 with confidence interval lines also below 1 indicate statistically significant synergism.

For drug combinations where only one drug showed more than 50% inhibition, Potency shifts were determined. Dose responses were plotted using Graphpad Prism and either 50% or 60% inhibitory concentrations were interpolated from the dose response curves. Potency shifts were considered significant when confidence intervals for dose responses did not overlap.

Cell Lines, Compounds, and Treatment Outline

WSU-DLCL2, SU-DHL10, RL, SU-DHL4, OCI-Ly19, and DOHH2 were previously described (NatChemBio 2012). For combination studies, a modified version of the proliferation assay in suspension cells was used, as previously described (Daigle et al). Briefly, on day 0, cells were plated in triplicate in 96-well plates at initial densities to ensure linear log phase growth over 4 days. Cells were treated with either a dose curve of Compound 44 (starting at a top dose of 1 µM), a single dose of prednisolone (Catalog # and Manufacturer) at a concentration 10-fold lower than the 4-day IC50 of the drug, or a combination of Compound 44+prednisolone. On day 4, cells were counted using Viacount reagent in the guava easyCyte flow cytometer, and the viable cell number was used to replate cells at the original densities for 3 additional days. Cells that were pre-treated with Compound 44 either received continuous Compound 44 alone, or Compound 44+prednisolone (constant dose); cells pre-treated with prednisolone either received continuous prednisolone, or prednisolone+ Compound 44; cells co-treated for 4 days continued to receive co-treatment through 7 days.

Xenograft Studies

All the procedures related to animal handling, care and the treatment in this study were performed according to the guidelines approved by the Institutional Animal Care and Use Committee (IACUC) of CRL Piedmont and Shanghai ChemPartner following the guidance of the Association for Assessment and Accreditation of Laboratory Animal Care (AAALAC). WSU-DLCL2, SU-DHL6, or SU-DHL10 cells were harvested during mid-log phase growth, and re-suspended in PBS with 50% Matrigel™ (BD Biosciences), and injected into immune-compromised mice. Each mouse received 1×107 cells (0.2 mL cell suspension) subcutaneously in the right flank, and once tumors reached a predetermined size, mice were orally dosed with different doses of Compound 44 at various schedules for up to 28 days and/or CHOP/COP on the following schedules: Cyclophosphamide was administered intraperitoneally (i.p.), and doxorubicin and vincristine were each administered via bolus tail vein injections (i.v.); each was given once daily on Days 1 and 8 in the SU-DHL6 study, and on Days 1 and 22 in the WSU-DLCL2 and SU-DHL10 studies. Prednisone was administered p.o. on two cycles of five daily doses, starting on Days 1 and 8 ((qd×5)×2, Days 1, 8) in the SU-DHL6 study, and on Days 1 and 22 ((qd×5)×2, Days 1, 22) in the WSU-DLCL2 and SU-DHL10 studies. Each dose was delivered in a volume of 0.2 mL/20 g mouse (10 mL/kg), and adjusted for the last recorded weight of individual animals. Tumor measurements and body weights were collected twice-weekly for 28 days for all studies. To determine tumor growth delay in the SU-DHL10 and SU-DHL6 studies, each test animal was euthanized when its neoplasm reached the endpoint volume of 2000 mm3 or on the last day of the study (day 60), whichever came first.

Quantitative PCR

WSU-DLCL2, SU-DHL10, RL, SU-DHL4, OCI-LY19, and DOHH2 cells were treated in parallel with DMSO, 1 uM of Compound 44 (SU-DHL10 treated with 100 nM Compound 44), a dose of prednisolone at a concentration 10-fold lower than the 4-day $IC_{50}$, or the combination of drugs for 4 days. Cells were harvested and total mRNA was extracted from cell pellets using the RNeasy Plus Mini Kit (Qiagen; 74134). For the RT2 Glucocorticoid Signaling PCR array (Qiagen; PAHS-154ZE-4), cDNA was made by RT2 First Strand Kit (Qiagen; 330401). Array RT-PCR was performed using ViiA 7 Real-Time PCR Systems [Applied Biosystems (AB)] with RT2 SYBR Green ROX qPCR Mastermix (Qiagen; 330521). Gene expression was normalized to array's B2M and fold change compared to DMSO was calculated using the ΔΔCt method. To validate array data, TaqMan probe based qPCR was carried out using TaqMan Fast Advanced Master Mix (AB; 4444964) and TaqMan primer/probe sets for Sestrin (AB; Hs00902787_m1) and TNF (AB; Hs01113624_m1). Fold change was calculated as above, normalizing to RPLPO (AB; 4333761F).

ELISA

Histones were extracted from tumor samples as described above. Histones were prepared in equivalent concentrations in coating buffer (PBS+0.05% BSA) yielding 0.5 ng/ul of sample, and 100 ul of sample or standard was added in duplicate to 2 96-well ELISA plates (Thermo Labsystems, Immulon 4HBX #3885). The plates were sealed and incubated overnight at 4° C. The following day, plates were washed 3x with 300 ul/well PBST (PBS+0.05% Tween 20; 10X PBST, KPL #51-14-02) on a Bio Tek plate washer. Plates were blocked with 300 ul/well of diluent (PBS+2% BSA+0.05% Tween 20), incubated at RT for 2 hours, and washed 3x with PBST. All antibodies were diluted in diluent. 100 ul/well of anti-H3K27me3 (CST #9733, 50% glycerol stock 1:1,000) or anti-total H3 (Abcam ab1791, 50% glycerol 1:10,000) was added to each plate. Plates were incubated for 90 min at RT and washed 3x with PBST. 100 ul/well of anti-Rb-IgG-HRP (Cell Signaling Technology, 7074) was added 1:2,000 to the H3K27Me3 plate and 1:6,000 to the H3 plate and incubated for 90 min at RT. Plates were washed 4X with PBST. For detection, 100 ul/well of TMB substrate (BioFx Laboratories, #TMBS) was added and plates incubated in the dark at RT for 5 min. Reaction was stopped with 100 ul/well 1N $H_2SO_4$ Absorbance at 450 nm was read on SpectaMax M5 Microplate reader.

TABLE 4a

Ct values and fold changes from the RT2 Glucocorticoid signaling PCR array analysis for OCI cell line.

| Gene | Ct Values | | | | ΔCT (B2M) | | | |
|---|---|---|---|---|---|---|---|---|
| | DMSO | Cpd44 | Pred | Combo | DMSO | Cpd44 | Pred | Combo |
| ADARB1 | 24.373 | 23.799 | 24.946 | 24.323 | 7.368 | 6.580 | 7.319 | 7.177 |
| AFF1 | 21.574 | 21.780 | 21.892 | 21.613 | 4.569 | 4.561 | 4.265 | 4.467 |
| AK2 | 20.300 | 20.497 | 20.859 | 20.656 | 3.295 | 3.278 | 3.232 | 3.510 |
| AMPD3 | 27.424 | 26.984 | 27.937 | 27.892 | 10.419 | 9.765 | 10.310 | 10.746 |
| ANGPTL4 | 30.465 | 30.374 | 30.333 | 29.769 | 13.460 | 13.155 | 12.706 | 12.623 |
| ANXA4 | 23.319 | 23.379 | 24.130 | 23.394 | 6.314 | 6.160 | 6.503 | 6.248 |
| AQP1 | Undetermined | 31.992 | Undetermined | Undetermined | N/A | 14.773 | N/A | N/A |
| ARID5B | 22.092 | 22.537 | 22.635 | 22.538 | 5.087 | 5.318 | 5.008 | 5.392 |
| ASPH | 27.926 | 27.556 | 28.894 | 27.701 | 10.921 | 10.337 | 11.267 | 10.555 |
| ATF4 | 18.500 | 18.838 | 19.578 | 19.368 | 1.495 | 1.619 | 1.951 | 2.222 |
| BCL6 | 27.421 | 26.240 | 28.282 | 26.459 | 10.416 | 9.021 | 10.655 | 9.313 |
| BMPER | Undetermined | 34.674 | Undetermined | 32.290 | N/A | 17.455 | N/A | 15.144 |
| CALCR | Undetermined | Undetermined | Undetermined | Undetermined | N/A | N/A | N/A | N/A |
| CEBPA | 30.199 | 27.522 | 30.852 | 28.731 | 13.194 | 10.303 | 13.225 | 11.585 |
| CEBPB | 23.119 | 23.723 | 24.427 | 24.678 | 6.114 | 6.504 | 6.800 | 7.532 |
| COL4A2 | 32.777 | 33.300 | 35.000 | 32.293 | 15.772 | 16.081 | 17.373 | 15.147 |
| CREB1 | 22.477 | 22.697 | 23.159 | 22.702 | 5.472 | 5.478 | 5.532 | 5.556 |
| CREB3 | 24.708 | 24.979 | 25.174 | 24.863 | 7.703 | 7.760 | 7.547 | 7.717 |
| CREB3L4 | 24.162 | 24.000 | 24.936 | 24.497 | 7.157 | 6.781 | 7.309 | 7.351 |
| CTGF | 21.557 | 21.719 | 21.099 | 20.311 | 4.552 | 4.500 | 3.472 | 3.165 |
| CYB561 | Undetermined | 33.134 | Undetermined | 32.534 | N/A | 15.915 | N/A | 15.388 |
| DDIT4 | 24.102 | 23.567 | 23.551 | 23.195 | 7.097 | 6.348 | 5.924 | 6.049 |
| DIRAS2 | Undetermined | Undetermined | Undetermined | Undetermined | N/A | N/A | N/A | N/A |
| DUSP1 | 20.981 | 20.800 | 21.767 | 21.200 | 3.976 | 3.581 | 4.140 | 4.054 |
| EDN1 | Undetermined | Undetermined | 33.433 | 32.487 | N/A | N/A | 15.806 | 15.341 |
| EHD3 | 28.984 | 28.117 | 28.833 | 27.236 | 11.979 | 10.898 | 11.206 | 10.090 |
| ERRFI1 | Undetermined | Undetermined | 32.824 | Undetermined | N/A | N/A | 15.197 | N/A |
| FKBP5 | 22.604 | 22.499 | 22.353 | 21.699 | 5.599 | 5.280 | 4.726 | 4.553 |
| FOSL2 | 26.226 | 26.214 | 26.368 | 25.547 | 9.221 | 8.995 | 8.741 | 8.401 |
| GDPD1 | 26.444 | 26.638 | 27.196 | 26.808 | 9.439 | 9.419 | 9.569 | 9.662 |
| GHRHR | 37.467 | 33.641 | 35.486 | 36.113 | 20.462 | 16.422 | 17.859 | 18.967 |
| GLUL | 22.916 | 22.385 | 23.448 | 22.402 | 5.911 | 5.166 | 5.821 | 5.256 |
| GOT1 | 23.094 | 23.224 | 23.810 | 23.450 | 6.089 | 6.005 | 6.183 | 6.304 |
| H6PD | 26.842 | 26.141 | 26.981 | 26.440 | 9.837 | 8.922 | 9.354 | 9.294 |
| HAS2 | Undetermined | Undetermined | Undetermined | Undetermined | N/A | N/A | N/A | N/A |
| HNRPLL | 29.840 | 29.708 | 30.306 | 29.439 | 12.835 | 12.489 | 12.679 | 12.293 |
| IL10 | Undetermined | Undetermined | 34.155 | Undetermined | N/A | N/A | 16.528 | N/A |
| IL1RN | 33.932 | 32.902 | Undetermined | Undetermined | 16.927 | 15.683 | N/A | N/A |
| IL6 | Undetermined | Undetermined | Undetermined | 32.602 | N/A | N/A | N/A | 15.456 |
| IL6R | Undetermined | Undetermined | Undetermined | Undetermined | N/A | N/A | N/A | N/A |
| KLF13 | 23.416 | 23.178 | 23.963 | 23.145 | 6.411 | 5.959 | 6.336 | 5.999 |
| KLF9 | 29.546 | 28.545 | 28.597 | 27.791 | 12.541 | 11.326 | 10.970 | 10.546 |
| LOX | 33.344 | 32.825 | 32.787 | 31.904 | 16.339 | 15.606 | 15.160 | 14.758 |
| MERTK | 29.340 | 28.749 | 29.685 | 28.885 | 12.335 | 11.530 | 12.058 | 11.739 |
| MT1E | Undetermined | Undetermined | Undetermined | Undetermined | N/A | N/A | N/A | N/A |
| MT2A | 22.845 | 22.941 | 23.298 | 22.515 | 5.840 | 5.722 | 5.671 | 5.369 |
| NFKBIA | 21.672 | 21.905 | 22.337 | 21.755 | 4.667 | 4.686 | 4.710 | 4.609 |
| NR3C1 | 20.940 | 21.131 | 21.276 | 20.605 | 3.935 | 3.912 | 3.649 | 3.459 |
| PDCD7 | 23.121 | 23.359 | 28.314 | 23.491 | 6.116 | 6.140 | 10.687 | 6.345 |
| PDGFRB | 32.160 | 33.308 | 30.540 | 30.932 | 15.155 | 16.089 | 12.913 | 13.786 |
| PDP1 | 26.092 | 25.788 | 26.292 | 25.520 | 9.087 | 8.569 | 8.665 | 8.374 |
| PER1 | 24.615 | 25.503 | 25.500 | 26.016 | 7.610 | 8.284 | 7.873 | 8.870 |
| PER2 | Undetermined | 23.177 | 23.707 | 23.482 | N/A | 5.958 | 6.080 | 6.336 |
| PIK3R1 | 23.175 | 23.115 | 23.678 | 23.317 | 6.170 | 5.896 | 6.051 | 6.171 |
| PLD1 | Undetermined | Undetermined | Undetermined | 33.540 | N/A | N/A | N/A | 16.394 |
| PLEKHF1 | 30.216 | 29.694 | 30.977 | 30.285 | 13.211 | 12.475 | 13.350 | 13.139 |
| POU2F1 | 24.562 | 24.656 | 25.232 | 24.555 | 7.557 | 7.437 | 7.605 | 7.409 |
| POU2F2 | 31.495 | 31.740 | 31.543 | 31.643 | 14.490 | 14.521 | 13.916 | 14.497 |
| RASA3 | 23.112 | 23.251 | 23.743 | 23.462 | 6.107 | 6.032 | 6.115 | 6.316 |
| RGS2 | 28.455 | 27.701 | 29.467 | 28.122 | 11.450 | 10.482 | 11.840 | 10.976 |
| RHOB | 22.108 | 20.944 | 20.967 | 19.659 | 5.103 | 3.725 | 3.340 | 2.513 |
| RHOJ | Undetermined | Undetermined | Undetermined | Undetermined | N/A | N/A | N/A | N/A |
| SESN1 | 22.463 | 22.424 | 23.126 | 22.491 | 5.458 | 5.205 | 5.499 | 5.345 |
| SGK1 | 26.351 | 26.107 | 25.819 | 24.816 | 9.346 | 8.888 | 8.192 | 7.670 |
| SLC10A6 | 31.403 | 30.432 | 31.656 | 32.746 | 14.398 | 13.213 | 14.029 | 15.600 |
| SLC19A2 | 24.878 | 24.881 | 25.910 | 25.274 | 7.873 | 7.662 | 8.283 | 8.128 |
| SLC22A5 | 29.254 | 29.101 | 30.112 | 29.115 | 12.249 | 11.882 | 12.485 | 11.969 |
| SNTA1 | 28.151 | 27.457 | 28.892 | 28.483 | 11.146 | 10.238 | 11.265 | 11.337 |
| SPHK1 | 28.555 | 28.787 | 29.199 | 29.124 | 11.550 | 11.568 | 11.572 | 11.978 |
| SPSB1 | 27.338 | 27.455 | 28.347 | 28.097 | 10.333 | 10.236 | 10.720 | 10.951 |
| STAT5A | 22.115 | 22.442 | 22.673 | 22.391 | 5.110 | 5.223 | 5.046 | 5.245 |
| STAT5B | 22.886 | 22.979 | 23.838 | 23.297 | 5.881 | 5.760 | 6.211 | 6.151 |
| TBL1XR1 | 21.317 | 21.488 | 21.705 | 21.430 | 4.312 | 4.269 | 4.078 | 4.284 |
| TNF | 24.763 | 24.377 | 24.612 | 23.620 | 7.758 | 7.158 | 6.985 | 6.474 |

TABLE 4a-continued

Ct values and fold changes from the RT2 Glucocorticoid signaling PCR array analysis for OCI cell line.

| | | | | | | | | |
|---|---|---|---|---|---|---|---|---|
| TNFAIP3 | 22.296 | 22.827 | 23.168 | 23.327 | 5.291 | 5.608 | 5.541 | 6.181 |
| TSC22D3 | 25.692 | 25.235 | 24.619 | 24.219 | 8.687 | 8.016 | 6.992 | 7.073 |
| USP2 | 33.949 | 31.341 | 33.986 | 32.493 | 16.944 | 14.122 | 16.359 | 15.347 |
| USP54 | 24.856 | 25.235 | 25.764 | 24.989 | 7.851 | 8.016 | 8.137 | 7.843 |
| VDR | 25.093 | 24.754 | 24.985 | 24.651 | 8.088 | 7.535 | 7.358 | 7.505 |
| VLDLR | 28.968 | 28.902 | 29.671 | 29.488 | 11.963 | 11.683 | 12.044 | 12.342 |
| XDH | Undetermined | Undetermined | Undetermined | Undetermined | N/A | N/A | N/A | N/A |
| ZFP36 | 24.550 | 25.191 | Undetermined | 25.349 | 7.545 | 7.972 | N/A | 8.203 |
| ZHX3 | 24.941 | 24.761 | 24.833 | 24.322 | 7.936 | 7.542 | 7.206 | 7.176 |
| ZNF281 | 22.504 | 23.249 | 23.997 | 23.695 | 5.499 | 6.030 | 6.370 | 6.549 |
| ACTB | 15.098 | 14.892 | 16.093 | 14.987 | −1.907 | −2.327 | −1.534 | −2.159 |
| B2M | 17.005 | 17.219 | 17.627 | 17.146 | 0.000 | 0.000 | 0.000 | 0.000 |
| GAPDH | 15.880 | 16.149 | 16.519 | 16.647 | −1.125 | −1.070 | −1.108 | −0.499 |
| HPRT1 | 21.462 | 21.828 | 22.125 | 21.813 | 4.457 | 4.609 | 4.498 | 4.667 |
| RPLP0 | 14.351 | 14.350 | 15.011 | 14.197 | −2.654 | −2.869 | −2.616 | −2.949 |
| HGDC | Undetermined | Undetermined | Undetermined | Undetermined | N/A | N/A | N/A | N/A |
| RTC | 22.174 | 21.961 | 21.962 | 22.251 | 5.169 | 4.742 | 4.335 | 5.105 |
| RTC | 22.089 | 21.953 | 22.140 | 22.008 | 5.084 | 4.734 | 4.513 | 4.862 |
| RTC | 22.195 | 21.961 | 22.167 | 21.993 | 5.190 | 4.742 | 4.540 | 4.847 |
| PPC | 18.397 | 18.268 | 18.432 | 18.371 | 1.392 | 1.049 | 0.805 | 1.225 |
| PPC | 18.426 | 18.330 | 18.320 | 18.347 | 1.421 | 1.111 | 0.693 | 1.201 |
| PPC | 18.301 | 17.672 | 18.372 | 18.378 | 1.296 | 0.453 | 0.745 | 1.232 |

| | Cpd44 | | Pred | | Combo | |
|---|---|---|---|---|---|---|
| Gene | ΔΔCT | Fold Change | ΔΔCT | Fold Change | ΔΔCT | Fold Change |
| ADARB1 | −0.788 | 1.727 | −0.049 | 1.035 | −0.191 | 1.142 |
| AFF1 | −0.008 | 1.006 | −0.304 | 1.235 | −0.102 | 1.073 |
| AK2 | −0.017 | 1.012 | −0.063 | 1.045 | 0.215 | 0.862 |
| AMPD3 | −0.654 | 1.574 | −0.109 | 1.078 | 0.327 | 0.797 |
| ANGPTL4 | −0.305 | 1.235 | −0.754 | 1.686 | −0.837 | 1.786 |
| ANXA4 | −0.154 | 1.113 | 0.189 | 0.877 | −0.066 | 1.047 |
| AQP1 | N/A | N/A | N/A | N/A | N/A | N/A |
| ARID5B | 0.231 | 0.852 | −0.079 | 1.056 | 0.305 | 0.809 |
| ASPH | −0.584 | 1.499 | 0.346 | 0.787 | −0.366 | 1.289 |
| ATF4 | 0.124 | 0.918 | 0.456 | 0.729 | 0.727 | 0.604 |
| BCL6 | −1.395 | 2.630 | 0.239 | 0.847 | −1.103 | 2.148 |
| BMPER | N/A | N/A | N/A | N/A | N/A | N/A |
| CALCR | N/A | N/A | N/A | N/A | N/A | N/A |
| CEBPA | −2.891 | 7.418 | 0.031 | 0.979 | −1.609 | 3.050 |
| CEBPB | 0.390 | 0.763 | 0.686 | 0.622 | 1.418 | 0.374 |
| COL4A2 | 0.309 | 0.807 | 1.601 | 0.330 | −0.625 | 1.542 |
| CREB1 | 0.006 | 0.996 | 0.060 | 0.959 | 0.084 | 0.943 |
| CREB3 | 0.057 | 0.961 | −0.156 | 1.114 | 0.014 | 0.990 |
| CREB3L4 | −0.376 | 1.298 | 0.152 | 0.900 | 0.194 | 0.874 |
| CTGF | −0.052 | 1.037 | −1.080 | 2.114 | −1.387 | 2.615 |
| CYB561 | N/A | N/A | N/A | N/A | N/A | N/A |
| DDIT4 | −0.749 | 1.681 | −1.173 | 2.255 | −1.048 | 2.068 |
| DIRAS2 | N/A | N/A | N/A | N/A | N/A | N/A |
| DUSP1 | −0.395 | 1.315 | 0.164 | 0.893 | 0.078 | 0.947 |
| EDN1 | N/A | N/A | N/A | N/A | N/A | N/A |
| EHD3 | −1.081 | 2.116 | −0.773 | 1.709 | −1.889 | 3.704 |
| ERRFI1 | N/A | N/A | N/A | N/A | N/A | N/A |
| FKBP5 | −0.319 | 1.247 | −0.873 | 1.831 | −1.046 | 2.065 |
| FOSL2 | −0.226 | 1.170 | −0.480 | 1.395 | −0.820 | 1.765 |
| GDPD1 | −0.020 | 1.014 | 0.130 | 0.914 | 0.223 | 0.857 |
| GHRHR | −4.040 | 16.450 | −2.603 | 6.075 | −1.495 | 2.819 |
| GLUL | −0.745 | 1.675 | −0.090 | 1.064 | −0.655 | 1.575 |
| GOT1 | −0.084 | 1.060 | 0.094 | 0.937 | 0.215 | 0.862 |
| H6PD | −0.915 | 1.886 | −0.483 | 1.398 | −0.543 | 1.457 |
| HAS2 | N/A | N/A | N/A | N/A | N/A | N/A |
| HNRPLL | −0.346 | 1.271 | −0.156 | 1.114 | −0.542 | 1.456 |
| IL10 | N/A | N/A | N/A | N/A | N/A | N/A |
| IL1RN | −1.244 | 2.369 | N/A | N/A | N/A | N/A |
| IL6 | N/A | N/A | N/A | N/A | N/A | N/A |
| IL6R | N/A | N/A | N/A | N/A | N/A | N/A |
| KLF13 | −0.452 | 1.368 | −0.075 | 1.053 | −0.412 | 1.331 |
| KLF9 | −1.215 | 2.321 | −1.571 | 2.971 | −1.896 | 3.722 |
| LOX | −0.733 | 1.662 | −1.179 | 2.264 | −1.581 | 2.992 |
| MERTK | −0.805 | 1.747 | −0.277 | 1.212 | −0.596 | 1.512 |
| MT1E | N/A | N/A | N/A | N/A | N/A | N/A |
| MT2A | −0.118 | 1.085 | −0.169 | 1.124 | −0.471 | 1.386 |
| NFKBIA | 0.019 | 0.987 | 0.043 | 0.971 | −0.058 | 1.041 |
| NR3C1 | −0.023 | 1.016 | −0.286 | 1.219 | −0.476 | 1.391 |
| PDCD7 | 0.024 | 0.984 | 4.571 | 0.042 | 0.229 | 0.853 |
| PDGFRB | 0.934 | 0.523 | −2.242 | 4.731 | −1.369 | 2.583 |
| PDP1 | −0.518 | 1.432 | −0.422 | 1.340 | −0.713 | 1.639 |

TABLE 4a-continued

Ct values and fold changes from the RT2 Glucocorticoid signaling PCR array analysis for OCI cell line.

| | | | | | | |
|---|---|---|---|---|---|---|
| PER1 | 0.674 | 0.627 | 0.263 | 0.833 | 1.260 | 0.418 |
| PER2 | N/A | N/A | N/A | N/A | N/A | N/A |
| PIK3R1 | −0.274 | 1.209 | −0.119 | 1.086 | 0.001 | 0.999 |
| PLD1 | N/A | N/A | N/A | N/A | N/A | N/A |
| PLEKHF1 | −0.736 | 1.666 | 0.139 | 0.908 | −0.072 | 1.051 |
| POU2F1 | −0.120 | 1.087 | 0.048 | 0.967 | −0.148 | 1.108 |
| POU2F2 | 0.031 | 0.979 | −0.574 | 1.489 | 0.007 | 0.995 |
| RASA3 | −0.075 | 1.053 | 0.009 | 0.994 | 0.209 | 0.865 |
| RGS2 | −0.968 | 1.956 | 0.390 | 0.763 | −0.474 | 1.389 |
| RHOB | −1.378 | 2.599 | −1.763 | 3.394 | −2.590 | 6.021 |
| RHOJ | N/A | N/A | N/A | N/A | N/A | N/A |
| SESN1 | −0.253 | 1.192 | 0.041 | 0.972 | −0.113 | 1.081 |
| SGK1 | −0.458 | 1.374 | −1.154 | 2.225 | −1.676 | 3.195 |
| SLC10A6 | −1.185 | 2.274 | −0.369 | 1.291 | 1.202 | 0.435 |
| SLC19A2 | −0.211 | 1.157 | 0.410 | 0.753 | 0.255 | 0.838 |
| SLC22A5 | −0.367 | 1.290 | 0.236 | 0.849 | −0.280 | 1.214 |
| SNTA1 | −0.908 | 1.876 | 0.119 | 0.921 | 0.191 | 0.876 |
| SPHK1 | 0.018 | 0.988 | 0.022 | 0.985 | 0.428 | 0.743 |
| SPSB1 | −0.097 | 1.070 | 0.387 | 0.765 | 0.618 | 0.652 |
| STAT5A | 0.113 | 0.925 | −0.064 | 1.045 | 0.135 | 0.911 |
| STAT5B | −0.121 | 1.087 | 0.330 | 0.796 | 0.270 | 0.829 |
| TBL1XR1 | −0.043 | 1.030 | −0.234 | 1.176 | −0.028 | 1.020 |
| TNF | −0.600 | 1.516 | −0.773 | 1.709 | −1.284 | 2.435 |
| TNFAIP3 | 0.317 | 0.803 | 0.250 | 0.841 | 0.890 | 0.540 |
| TSC22D3 | −0.671 | 1.592 | −1.695 | 3.238 | −1.614 | 3.061 |
| USP2 | −2.822 | 7.071 | −0.585 | 1.500 | −1.597 | 3.025 |
| USP54 | 0.165 | 0.892 | 0.286 | 0.820 | −0.008 | 1.006 |
| VDR | −0.553 | 1.467 | −0.730 | 1.659 | −0.583 | 1.498 |
| VLDLR | −0.280 | 1.214 | 0.081 | 0.945 | 0.379 | 0.769 |
| XDH | N/A | N/A | N/A | N/A | N/A | N/A |
| ZFP36 | 0.427 | 0.744 | N/A | N/A | 0.658 | 0.634 |
| ZHX3 | −0.394 | 1.314 | −0.730 | 1.659 | −0.760 | 1.693 |
| ZNF281 | 0.531 | 0.692 | 0.871 | 0.547 | 1.050 | 0.483 |
| ACTB | | | | | | |
| B2M | | | | | | |
| GAPDH | | | | | | |
| HPRT1 | | | | | | |
| RPLP0 | | | | | | |
| HGDC | | | | | | |
| RTC | | | | | | |
| RTC | | | | | | |
| RTC | | | | | | |
| PPC | | | | | | |
| PPC | | | | | | |
| PPC | | | | | | |

TABLE 4b

Ct values and fold changes from the RT2 Glucocorticoid signaling PCR array analysis for DOHH2 cell line.

| | Ct Values | | | | ΔCT (B2M) | | | |
|---|---|---|---|---|---|---|---|---|
| Gene | DMSO | Cpd44 | Pred | Combo | DMSO | Cpd44 | Pred | Combo |
| ADARB1 | 31.818 | 31.431 | 33.560 | 30.189 | 12.809 | 12.855 | 14.676 | 12.038 |
| AFF1 | 24.684 | 23.888 | 23.992 | 23.224 | 5.675 | 5.312 | 5.108 | 5.073 |
| AK2 | 20.334 | 20.173 | 20.262 | 19.961 | 1.325 | 1.597 | 1.378 | 1.810 |
| AMPD3 | 26.401 | 26.146 | 27.535 | 26.852 | 7.392 | 7.570 | 8.651 | 8.701 |
| ANGPTL4 | 31.134 | 30.820 | 31.538 | 30.854 | 12.125 | 12.244 | 12.654 | 12.703 |
| ANXA4 | 24.817 | 24.273 | 24.997 | 24.268 | 5.808 | 5.697 | 6.113 | 6.117 |
| AQP1 | Undetermined | Undetermined | Undetermined | Undetermined | N/A | N/A | N/A | N/A |
| ARID5B | 23.881 | 23.782 | 23.885 | 23.886 | 4.872 | 5.206 | 5.001 | 5.735 |
| ASPH | 22.970 | 22.823 | 23.369 | 22.996 | 3.961 | 4.247 | 4.485 | 4.845 |
| ATF4 | 19.156 | 19.190 | 19.313 | 18.983 | 0.147 | 0.614 | 0.429 | 0.832 |
| BCL6 | 21.529 | 21.323 | 21.801 | 21.773 | 2.520 | 2.747 | 2.917 | 3.622 |
| BMPER | 38.037 | 39.092 | 39.378 | 39.656 | 19.028 | 20.516 | 20.494 | 21.505 |
| CALCR | Undetermined | 33.630 | Undetermined | Undetermined | N/A | 15.054 | N/A | N/A |
| CEBPA | 34.654 | 30.676 | 32.188 | 30.646 | 15.645 | 12.100 | 13.304 | 12.495 |
| CEBPB | 23.911 | 23.925 | 24.317 | 24.001 | 4.902 | 5.349 | 5.433 | 5.850 |
| COL4A2 | 32.314 | 34.119 | 38.993 | 34.143 | 13.305 | 15.543 | 20.109 | 15.992 |
| CREB1 | 22.930 | 22.746 | 22.890 | 22.730 | 3.921 | 4.170 | 4.006 | 4.579 |
| CREB3 | 24.929 | 24.840 | 24.865 | 24.647 | 5.920 | 6.264 | 5.981 | 6.496 |
| CREB3L4 | 24.405 | 24.110 | 24.616 | 24.373 | 5.396 | 5.534 | 5.732 | 6.222 |
| CTGF | 33.711 | 32.760 | 33.728 | 33.696 | 14.702 | 14.184 | 14.844 | 15.545 |
| CYB561 | 37.790 | 31.945 | 39.582 | 34.331 | 18.781 | 13.369 | 20.698 | 16.180 |

TABLE 4b-continued

Ct values and fold changes from the RT2 Glucocorticoid signaling PCR array analysis for DOHH2 cell line.

| | | | | | | | | |
|---|---|---|---|---|---|---|---|---|
| DDIT4 | 23.934 | 23.508 | 24.105 | 22.948 | 4.925 | 4.932 | 5.221 | 4.797 |
| DIRAS2 | Undetermined | Undetermined | Undetermined | Undetermined | N/A | N/A | N/A | N/A |
| DUSP1 | 27.604 | 27.132 | 27.866 | 27.262 | 8.595 | 8.556 | 8.982 | 9.111 |
| EDN1 | 31.233 | 32.260 | 32.263 | 31.224 | 12.224 | 13.684 | 13.379 | 13.073 |
| EHD3 | 32.315 | 28.852 | 31.098 | 28.674 | 13.306 | 10.276 | 12.214 | 10.523 |
| ERRFI1 | 32.525 | 30.163 | 32.635 | 29.588 | 13.516 | 11.587 | 13.751 | 11.437 |
| FKBP5 | 21.985 | 21.520 | 20.912 | 20.512 | 2.976 | 2.944 | 2.028 | 2.361 |
| FOSL2 | 31.767 | 29.872 | 31.543 | 29.925 | 12.758 | 11.296 | 12.659 | 11.774 |
| GDPD1 | 27.532 | 27.570 | 27.884 | 27.396 | 8.523 | 8.994 | 9.000 | 9.245 |
| GHRHR | 37.684 | 39.644 | 36.095 | 37.813 | 18.675 | 21.068 | 17.211 | 19.662 |
| GLUL | 36.133 | 36.671 | 34.574 | 36.099 | 17.124 | 18.095 | 15.690 | 17.948 |
| GOT1 | 23.427 | 23.126 | 23.532 | 22.880 | 4.418 | 4.550 | 4.648 | 4.729 |
| H6PD | 24.717 | 24.377 | 24.969 | 24.453 | 5.708 | 5.801 | 6.085 | 6.302 |
| HAS2 | Undetermined | Undetermined | Undetermined | Undetermined | N/A | N/A | N/A | N/A |
| HNRPLL | 30.324 | 29.151 | 33.284 | 31.380 | 11.315 | 10.575 | 14.400 | 13.229 |
| IL10 | Undetermined | Undetermined | Undetermined | Undetermined | N/A | N/A | N/A | N/A |
| IL1RN | Undetermined | 32.271 | 33.560 | 31.586 | N/A | 13.695 | 14.676 | 13.435 |
| IL6 | Undetermined | Undetermined | 34.758 | 37.608 | N/A | N/A | 15.874 | 19.457 |
| IL6R | Undetermined | 31.962 | Undetermined | 32.383 | N/A | 13.386 | N/A | 14.232 |
| KLF13 | 22.951 | 22.420 | 22.546 | 21.765 | 3.942 | 3.844 | 3.662 | 3.614 |
| KLF9 | 28.691 | 28.439 | 28.547 | 27.741 | 9.682 | 9.863 | 9.663 | 9.590 |
| LOX | 33.562 | 32.997 | 34.158 | 32.855 | 14.553 | 14.421 | 15.274 | 14.704 |
| MERTK | 32.997 | 32.456 | 32.892 | 31.474 | 13.988 | 13.880 | 14.008 | 13.323 |
| MT1E | 39.692 | Undetermined | Undetermined | Undetermined | 20.683 | N/A | N/A | N/A |
| MT2A | 39.646 | Undetermined | Undetermined | Undetermined | 20.637 | N/A | N/A | N/A |
| NFKBIA | 22.891 | 22.625 | 22.830 | 22.625 | 3.882 | 4.049 | 3.946 | 4.474 |
| NR3C1 | 22.602 | 22.430 | 22.794 | 22.573 | 3.593 | 3.854 | 3.910 | 4.422 |
| PDCD7 | 23.656 | 23.417 | 23.552 | 23.397 | 4.647 | 4.841 | 4.668 | 5.246 |
| PDGFRB | Undetermined | 35.193 | 34.934 | 31.552 | N/A | 16.617 | 16.050 | 13.401 |
| PDP1 | 25.863 | 25.175 | 25.682 | 25.330 | 6.854 | 6.599 | 6.798 | 7.179 |
| PER1 | 24.944 | 24.717 | 25.142 | 25.289 | 5.935 | 6.141 | 6.258 | 7.138 |
| PER2 | 24.642 | 23.835 | 24.159 | 23.476 | 5.633 | 5.259 | 5.275 | 5.325 |
| PIK3R1 | 24.177 | 23.712 | 23.850 | 23.610 | 5.168 | 5.136 | 4.966 | 5.459 |
| PLD1 | 37.038 | Undetermined | 37.120 | 38.323 | 18.029 | N/A | 18.236 | 20.172 |
| PLEKHF1 | 29.886 | 28.946 | 29.414 | 28.738 | 10.877 | 10.370 | 10.530 | 10.587 |
| POU2F1 | 24.378 | 24.003 | 24.648 | 23.667 | 5.369 | 5.427 | 5.764 | 5.516 |
| POU2F2 | 22.469 | 22.167 | 22.489 | 21.930 | 3.460 | 3.591 | 3.605 | 3.779 |
| RASA3 | 27.152 | 27.636 | 27.803 | 28.392 | 8.143 | 9.060 | 8.919 | 10.241 |
| RGS2 | 24.790 | 24.861 | 25.514 | 25.639 | 5.781 | 6.285 | 6.630 | 7.488 |
| RHOB | 32.661 | 30.745 | 33.162 | 30.702 | 13.652 | 12.169 | 14.278 | 12.551 |
| RHOJ | Undetermined | Undetermined | Undetermined | Undetermined | N/A | N/A | N/A | N/A |
| SESN1 | 24.226 | 23.848 | 22.839 | 21.993 | 5.217 | 5.272 | 3.955 | 3.842 |
| SGK1 | 27.633 | 27.821 | 29.628 | 29.125 | 8.624 | 9.245 | 10.744 | 10.974 |
| SLC10A6 | 34.483 | 36.435 | 36.176 | 32.738 | 15.474 | 17.859 | 17.292 | 14.587 |
| SLC19A2 | 25.600 | 24.859 | 25.455 | 24.769 | 6.591 | 6.283 | 6.571 | 6.618 |
| SLC22A5 | 28.392 | 27.992 | 28.915 | 27.835 | 9.383 | 9.416 | 10.031 | 9.684 |
| SNTA1 | 24.584 | 24.550 | 25.124 | 25.000 | 5.575 | 5.974 | 6.240 | 6.849 |
| SPHK1 | 30.677 | 28.863 | 29.971 | 28.646 | 11.668 | 10.287 | 11.087 | 10.495 |
| SPSB1 | 27.110 | 26.652 | 26.911 | 26.621 | 8.101 | 8.076 | 8.027 | 8.470 |
| STAT5A | 24.237 | 23.771 | 23.885 | 23.477 | 5.228 | 5.195 | 5.001 | 5.326 |
| STAT5B | 22.503 | 22.328 | 22.632 | 22.414 | 3.494 | 3.752 | 3.748 | 4.263 |
| TBL1XR1 | 21.397 | 20.994 | 21.304 | 21.133 | 2.388 | 2.418 | 2.420 | 2.982 |
| TNF | 31.328 | 31.849 | 31.956 | 31.194 | 12.319 | 13.273 | 13.072 | 13.043 |
| TNFAIP3 | 28.260 | 27.520 | Undetermined | 30.586 | 9.251 | 8.944 | N/A | 12.435 |
| TSC22D3 | 25.176 | 24.752 | 23.310 | 22.374 | 6.167 | 6.176 | 4.426 | 4.223 |
| USP2 | 24.104 | 23.684 | 23.501 | 22.971 | 5.095 | 5.108 | 4.617 | 4.820 |
| USP54 | 26.599 | 25.892 | 26.683 | 25.856 | 7.590 | 7.316 | 7.799 | 7.705 |
| VDR | 27.406 | 26.426 | 26.847 | 26.577 | 8.397 | 7.850 | 7.963 | 8.426 |
| VLDLR | 27.166 | 27.232 | 28.584 | 27.543 | 8.157 | 8.656 | 9.700 | 9.392 |
| XDH | Undetermined | Undetermined | Undetermined | Undetermined | N/A | N/A | N/A | N/A |
| ZFP36 | 24.170 | 23.980 | 24.270 | 24.094 | 5.161 | 5.404 | 5.386 | 5.943 |
| ZHX3 | 25.200 | 24.611 | 24.418 | 23.897 | 6.191 | 6.035 | 5.534 | 5.746 |
| ZNF281 | 24.066 | 23.541 | 23.828 | 23.343 | 5.057 | 4.965 | 4.944 | 5.192 |
| ACTB | 14.843 | 14.519 | 14.721 | 14.509 | −4.166 | −4.057 | −4.163 | −3.642 |
| B2M | 19.009 | 18.576 | 18.884 | 18.151 | 0.000 | 0.000 | 0.000 | 0.000 |
| GAPDH | 16.513 | 16.197 | 16.551 | 16.157 | −2.496 | −2.379 | −2.333 | −1.994 |
| HPRT1 | 21.698 | 21.561 | 21.777 | 21.657 | 2.689 | 2.985 | 2.893 | 3.506 |
| RPLP0 | 15.187 | 14.935 | 15.128 | 14.595 | −3.822 | −3.641 | −3.756 | −3.556 |
| HGDC | Undetermined | Undetermined | Undetermined | Undetermined | N/A | N/A | N/A | N/A |
| RTC | 21.284 | 21.345 | 21.449 | 21.483 | 2.275 | 2.769 | 2.565 | 3.332 |
| RTC | 21.287 | 21.410 | 21.464 | 21.371 | 2.278 | 2.834 | 2.580 | 3.220 |
| RTC | 21.358 | 21.384 | 21.483 | 21.483 | 2.349 | 2.808 | 2.599 | 3.332 |
| PPC | 18.611 | 18.672 | 18.684 | 18.624 | −0.398 | 0.096 | −0.200 | 0.473 |
| PPC | 18.638 | 19.142 | 18.699 | 18.587 | −0.371 | 0.566 | −0.185 | 0.436 |
| PPC | 18.646 | 18.711 | 19.076 | 18.685 | −0.363 | 0.135 | 0.192 | 0.534 |

TABLE 4b-continued

Ct values and fold changes from the RT2 Glucocorticoid signaling PCR array analysis for DOHH2 cell line.

| Gene | Cpd44 | | Pred | | Combo | |
|---|---|---|---|---|---|---|
| | ΔΔCT | Fold Change | ΔΔCT | Fold Change | ΔΔCT | Fold Change |
| ADARB1 | 0.046 | 0.969 | 1.867 | 0.274 | −0.771 | 1.706 |
| AFF1 | −0.363 | 1.286 | −0.567 | 1.481 | −0.602 | 1.518 |
| AK2 | 0.272 | 0.828 | 0.053 | 0.964 | 0.485 | 0.714 |
| AMPD3 | 0.178 | 0.884 | 1.259 | 0.418 | 1.309 | 0.404 |
| ANGPTL4 | 0.119 | 0.921 | 0.529 | 0.693 | 0.578 | 0.670 |
| ANXA4 | −0.111 | 1.080 | 0.305 | 0.809 | 0.309 | 0.807 |
| AQP1 | N/A | N/A | N/A | N/A | N/A | N/A |
| ARID5B | 0.334 | 0.793 | 0.129 | 0.914 | 0.863 | 0.550 |
| ASPH | 0.286 | 0.820 | 0.524 | 0.695 | 0.884 | 0.542 |
| ATF4 | 0.467 | 0.723 | 0.282 | 0.822 | 0.685 | 0.622 |
| BCL6 | 0.227 | 0.854 | 0.397 | 0.759 | 1.102 | 0.466 |
| BMPER | 1.488 | 0.357 | 1.466 | 0.362 | 2.477 | 0.180 |
| CALCR | N/A | N/A | N/A | N/A | N/A | N/A |
| CEBPA | −3.545 | 11.672 | −2.341 | 5.067 | −3.150 | 8.877 |
| CEBPB | 0.447 | 0.734 | 0.531 | 0.692 | 0.948 | 0.518 |
| COL4A2 | 2.238 | 0.212 | 6.804 | 0.009 | 2.687 | 0.155 |
| CREB1 | 0.249 | 0.841 | 0.085 | 0.943 | 0.658 | 0.634 |
| CREB3 | 0.344 | 0.788 | 0.061 | 0.959 | 0.576 | 0.671 |
| CREB3L4 | 0.138 | 0.909 | 0.336 | 0.792 | 0.826 | 0.564 |
| CTGF | −0.518 | 1.432 | 0.142 | 0.906 | 0.843 | 0.557 |
| CYB561 | −5.412 | 42.577 | 1.917 | 0.265 | −2.601 | 6.067 |
| DDIT4 | 0.007 | 0.995 | 0.296 | 0.815 | −0.128 | 1.093 |
| DIRAS2 | N/A | N/A | N/A | N/A | N/A | N/A |
| DUSP1 | −0.039 | 1.027 | 0.387 | 0.765 | 0.516 | 0.699 |
| EDN1 | 1.460 | 0.363 | 1.155 | 0.449 | 0.849 | 0.555 |
| EHD3 | −3.030 | 8.168 | −1.092 | 2.132 | −2.783 | 6.883 |
| ERRFI1 | −1.929 | 3.808 | 0.235 | 0.850 | −2.079 | 4.225 |
| FKBP5 | −0.032 | 1.022 | −0.948 | 1.929 | −0.615 | 1.532 |
| FOSL2 | −1.462 | 2.755 | −0.099 | 1.071 | −0.984 | 1.978 |
| GDPD1 | 0.471 | 0.721 | 0.477 | 0.718 | 0.722 | 0.606 |
| GHRHR | 2.393 | 0.190 | −1.464 | 2.759 | 0.987 | 0.505 |
| GLUL | 0.971 | 0.510 | −1.434 | 2.702 | 0.824 | 0.565 |
| GOT1 | 0.132 | 0.913 | 0.230 | 0.853 | 0.311 | 0.806 |
| H6PD | 0.093 | 0.938 | 0.377 | 0.770 | 0.594 | 0.663 |
| HAS2 | N/A | N/A | N/A | N/A | N/A | N/A |
| HNRPLL | −0.740 | 1.670 | 3.085 | 0.118 | 1.914 | 0.265 |
| IL10 | N/A | N/A | N/A | N/A | N/A | N/A |
| IL1RN | N/A | N/A | N/A | N/A | N/A | N/A |
| IL6 | N/A | N/A | N/A | N/A | N/A | N/A |
| IL6R | N/A | N/A | N/A | N/A | N/A | N/A |
| KLF13 | −0.098 | 1.070 | −0.280 | 1.214 | −0.328 | 1.255 |
| KLF9 | 0.181 | 0.882 | −0.019 | 1.013 | −0.092 | 1.066 |
| LOX | −0.132 | 1.096 | 0.721 | 0.607 | 0.151 | 0.901 |
| MERTK | −0.108 | 1.078 | 0.020 | 0.986 | −0.665 | 1.586 |
| MT1E | N/A | N/A | N/A | N/A | N/A | N/A |
| MT2A | N/A | N/A | N/A | N/A | N/A | N/A |
| NFKBIA | 0.167 | 0.891 | 0.064 | 0.957 | 0.592 | 0.663 |
| NR3C1 | 0.261 | 0.835 | 0.317 | 0.803 | 0.829 | 0.563 |
| PDCD7 | 0.194 | 0.874 | 0.021 | 0.986 | 0.599 | 0.660 |
| PDGFRB | N/A | N/A | N/A | N/A | N/A | N/A |
| PDP1 | −0.255 | 1.193 | −0.056 | 1.040 | 0.325 | 0.798 |
| PER1 | 0.206 | 0.867 | 0.323 | 0.799 | 1.203 | 0.434 |
| PER2 | −0.374 | 1.296 | −0.358 | 1.282 | −0.308 | 1.238 |
| PIK3R1 | −0.032 | 1.022 | −0.202 | 1.150 | 0.291 | 0.817 |
| PLD1 | N/A | N/A | 0.207 | 0.866 | 2.143 | 0.226 |
| PLEKHF1 | −0.507 | 1.421 | −0.347 | 1.272 | −0.290 | 1.223 |
| POU2F1 | 0.058 | 0.961 | 0.395 | 0.760 | 0.147 | 0.903 |
| POU2F2 | 0.131 | 0.913 | 0.145 | 0.904 | 0.319 | 0.802 |
| RASA3 | 0.917 | 0.530 | 0.776 | 0.584 | 2.098 | 0.234 |
| RGS2 | 0.504 | 0.705 | 0.849 | 0.555 | 1.707 | 0.306 |
| RHOB | −1.483 | 2.795 | 0.626 | 0.648 | −1.101 | 2.145 |
| RHOJ | N/A | N/A | N/A | N/A | N/A | N/A |
| SESN1 | 0.055 | 0.963 | −1.262 | 2.398 | −1.375 | 2.594 |
| SGK1 | 0.621 | 0.650 | 2.120 | 0.230 | 2.350 | 0.196 |
| SLC10A6 | 2.385 | 0.191 | 1.818 | 0.284 | −0.887 | 1.849 |
| SLC19A2 | −0.308 | 1.238 | −0.020 | 1.014 | 0.027 | 0.981 |
| SLC22A5 | 0.033 | 0.977 | 0.648 | 0.638 | 0.301 | 0.812 |
| SNTA1 | 0.399 | 0.758 | 0.665 | 0.631 | 1.274 | 0.414 |
| SPHK1 | −1.381 | 2.604 | −0.581 | 1.496 | −1.173 | 2.255 |
| SPSB1 | −0.025 | 1.017 | −0.074 | 1.053 | 0.369 | 0.774 |
| STAT5A | −0.033 | 1.023 | −0.227 | 1.170 | 0.098 | 0.934 |
| STAT5B | 0.258 | 0.836 | 0.254 | 0.839 | 0.769 | 0.587 |
| TBL1XR1 | 0.030 | 0.979 | 0.032 | 0.978 | 0.594 | 0.663 |
| TNF | 0.954 | 0.516 | 0.753 | 0.593 | 0.724 | 0.605 |

TABLE 4b-continued

Ct values and fold changes from the RT2 Glucocorticoid signaling PCR array analysis for DOHH2 cell line.

| | | | | | | | |
|---|---|---|---|---|---|---|---|
| TNFAIP3 | −0.307 | 1.237 | N/A | N/A | 3.184 | 0.110 |
| TSC22D3 | 0.009 | 0.994 | −1.741 | 3.343 | −1.944 | 3.848 |
| USP2 | 0.013 | 0.991 | −0.478 | 1.393 | −0.275 | 1.210 |
| USP54 | −0.274 | 1.209 | 0.209 | 0.865 | 0.115 | 0.923 |
| VDR | −0.547 | 1.461 | −0.434 | 1.351 | 0.029 | 0.980 |
| VLDLR | 0.499 | 0.708 | 1.543 | 0.343 | 1.235 | 0.425 |
| XDH | N/A | N/A | N/A | N/A | N/A | N/A |
| ZFP36 | 0.243 | 0.845 | 0.225 | 0.856 | 0.782 | 0.582 |
| ZHX3 | −0.156 | 1.114 | −0.657 | 1.577 | −0.445 | 1.361 |
| ZNF281 | −0.092 | 1.066 | −0.113 | 1.081 | 0.135 | 0.911 |
| ACTB | | | | | | |
| B2M | | | | | | |
| GAPDH | | | | | | |
| HPRT1 | | | | | | |
| RPLP0 | | | | | | |
| HGDC | | | | | | |
| RTC | | | | | | |
| RTC | | | | | | |
| RTC | | | | | | |
| PPC | | | | | | |
| PPC | | | | | | |
| PPC | | | | | | |

TABLE 4c

Ct values and fold changes from the RT2 Glucocorticoid signaling PCR array analysis for WSU cell line.

| | Ct Values | | | | ΔCT (B2M) | | | |
|---|---|---|---|---|---|---|---|---|
| Gene | DMSO | Cpd44 | Pred | Combo | DMSO | Cpd44 | Pred | Combo |
| ADARB1 | 26.316 | 25.386 | 26.108 | 26.018 | 6.866 | 5.701 | 6.963 | 5.845 |
| AFF1 | 28.103 | 27.925 | 27.334 | 26.727 | 8.653 | 8.240 | 8.189 | 6.554 |
| AK2 | 20.644 | 21.365 | 20.433 | 22.069 | 1.194 | 1.680 | 1.288 | 1.896 |
| AMPD3 | 28.467 | 27.162 | 27.943 | 26.847 | 9.017 | 7.477 | 8.798 | 6.674 |
| ANGPTL4 | 31.444 | 30.487 | 30.810 | 31.510 | 11.994 | 10.802 | 11.665 | 11.337 |
| ANXA4 | 27.736 | 24.659 | 27.406 | 25.013 | 8.286 | 4.974 | 8.261 | 4.840 |
| AQP1 | Undetermined | 33.645 | 33.595 | 32.796 | N/A | 13.960 | 14.450 | 12.623 |
| ARID5B | 26.244 | 26.126 | 26.721 | 27.140 | 6.794 | 6.441 | 7.576 | 6.967 |
| ASPH | 22.285 | 22.415 | 21.939 | 22.834 | 2.835 | 2.730 | 2.794 | 2.661 |
| ATF4 | 19.874 | 20.470 | 19.659 | 20.871 | 0.424 | 0.785 | 0.514 | 0.698 |
| BCL6 | 20.954 | 20.795 | 20.898 | 21.133 | 1.504 | 1.110 | 1.753 | 0.960 |
| BMPER | 39.814 | Undetermined | Undetermined | 38.494 | 20.364 | N/A | N/A | 18.321 |
| CALCR | Undetermined | Undetermined | Undetermined | Undetermined | N/A | N/A | N/A | N/A |
| CEBPA | 28.438 | 27.014 | 27.838 | 27.647 | 8.988 | 7.329 | 8.693 | 7.474 |
| CEBPB | 25.266 | 26.770 | 25.775 | 27.187 | 5.816 | 7.085 | 6.630 | 7.014 |
| COL4A2 | Undetermined | Undetermined | 34.328 | Undetermined | N/A | N/A | 15.183 | N/A |
| CREB1 | 23.170 | 23.413 | 22.732 | 23.778 | 3.720 | 3.728 | 3.587 | 3.605 |
| CREB3 | 25.309 | 25.459 | 24.551 | 25.393 | 5.859 | 5.774 | 5.406 | 5.220 |
| CREB3L4 | 25.072 | 24.392 | 24.437 | 24.344 | 5.622 | 4.707 | 5.292 | 4.171 |
| CTGF | Undetermined | Undetermined | Undetermined | Undetermined | N/A | N/A | N/A | N/A |
| CYB561 | 36.874 | 31.478 | 32.971 | 33.799 | 17.424 | 11.793 | 13.826 | 13.626 |
| DDIT4 | 24.229 | 24.404 | 22.252 | 22.739 | 4.779 | 4.719 | 3.107 | 2.566 |
| DIRAS2 | Undetermined | Undetermined | Undetermined | Undetermined | N/A | N/A | N/A | N/A |
| DUSP1 | 25.679 | 27.284 | 25.828 | 26.552 | 6.229 | 7.599 | 6.683 | 6.379 |
| EDN1 | Undetermined | 26.349 | 30.819 | 26.407 | N/A | 6.664 | 11.674 | 6.234 |
| EHD3 | 29.674 | 24.270 | 27.724 | 24.166 | 10.224 | 4.585 | 8.579 | 3.993 |
| ERRFI1 | Undetermined | 32.771 | Undetermined | 32.896 | N/A | 13.086 | N/A | 12.723 |
| FKBP5 | 22.873 | 23.267 | 21.321 | 21.824 | 3.423 | 3.582 | 2.176 | 1.651 |
| FOSL2 | 31.109 | 34.140 | 33.647 | 34.690 | 11.659 | 14.455 | 14.502 | 14.517 |
| GDPD1 | 28.371 | 27.494 | 28.235 | 27.303 | 8.921 | 7.809 | 9.090 | 7.130 |
| GHRHR | 34.636 | 39.957 | 37.789 | Undetermined | 15.186 | 20.272 | 18.644 | N/A |
| GLUL | Undetermined | 28.395 | 31.475 | 30.591 | N/A | 8.710 | 12.330 | 10.418 |
| GOT1 | 22.884 | 23.827 | 22.841 | 24.411 | 3.434 | 4.142 | 3.696 | 4.238 |
| H6PD | 26.360 | 25.976 | 26.197 | 25.435 | 6.910 | 6.291 | 7.052 | 5.262 |
| HAS2 | Undetermined | Undetermined | Undetermined | Undetermined | N/A | N/A | N/A | N/A |
| HNRPLL | 23.972 | 24.170 | 24.750 | 26.864 | 4.522 | 4.485 | 5.605 | 6.691 |
| IL10 | Undetermined | 34.229 | 34.306 | 35.010 | N/A | 14.544 | 15.161 | 14.837 |
| IL1RN | 32.606 | 28.388 | 33.599 | 29.393 | 13.156 | 8.703 | 14.454 | 9.220 |
| IL6 | Undetermined | Undetermined | Undetermined | Undetermined | N/A | N/A | N/A | N/A |
| IL6R | Undetermined | 33.814 | Undetermined | Undetermined | N/A | 14.129 | N/A | N/A |
| KLF13 | 24.539 | 23.800 | 23.792 | 23.671 | 5.089 | 4.115 | 4.647 | 3.498 |
| KLF9 | 30.841 | 28.881 | 30.105 | 28.187 | 11.391 | 9.196 | 10.960 | 8.014 |
| LOX | 34.266 | 34.399 | 34.511 | 34.207 | 14.816 | 14.714 | 15.366 | 14.034 |
| MERTK | Undetermined | 31.323 | 32.524 | Undetermined | N/A | 11.638 | 13.379 | N/A |

TABLE 4c-continued

Ct values and fold changes from the RT2 Glucocorticoid signaling PCR array analysis for WSU cell line.

| | | | | | | | | |
|---|---|---|---|---|---|---|---|---|
| MT1E | Undetermined | Undetermined | Undetermined | Undetermined | N/A | N/A | N/A | N/A |
| MT2A | 24.717 | 23.499 | 24.518 | 24.350 | 5.267 | 3.814 | 5.373 | 4.177 |
| NFKBIA | 22.371 | 23.807 | 22.895 | 23.454 | 2.921 | 4.122 | 3.750 | 3.281 |
| NR3C1 | 23.250 | 23.121 | 23.110 | 23.300 | 3.800 | 3.436 | 3.965 | 3.127 |
| PDCD7 | 24.179 | 24.740 | 23.874 | 25.248 | 4.729 | 5.055 | 4.729 | 5.075 |
| PDGFRB | Undetermined | Undetermined | Undetermined | Undetermined | N/A | N/A | N/A | N/A |
| PDP1 | 25.371 | 25.226 | 24.957 | 25.536 | 5.921 | 5.541 | 5.812 | 5.363 |
| PER1 | 25.109 | 25.820 | 24.989 | 26.651 | 5.659 | 6.135 | 5.844 | 6.478 |
| PER2 | 24.451 | 24.837 | 24.218 | 25.563 | 5.001 | 5.152 | 5.073 | 5.390 |
| PIK3R1 | 23.734 | 24.332 | 23.429 | 24.080 | 4.284 | 4.647 | 4.284 | 3.907 |
| PLD1 | Undetermined | Undetermined | 35.266 | Undetermined | N/A | N/A | 16.121 | N/A |
| PLEKHF1 | 27.205 | 28.660 | 26.977 | 29.585 | 7.755 | 8.975 | 7.832 | 9.412 |
| POU2F1 | 24.234 | 24.671 | 24.368 | 24.732 | 4.784 | 4.986 | 5.223 | 4.559 |
| POU2F2 | 23.123 | 22.678 | 22.565 | 22.920 | 3.673 | 2.993 | 3.420 | 2.747 |
| RASA3 | 23.952 | 23.208 | 23.454 | 23.293 | 4.502 | 3.523 | 4.309 | 3.120 |
| RGS2 | 22.902 | 24.869 | 23.962 | 27.302 | 3.452 | 5.184 | 4.817 | 7.129 |
| RHOB | 29.724 | 27.234 | 28.803 | 27.392 | 10.274 | 7.549 | 9.658 | 7.219 |
| RHOJ | Undetermined | Undetermined | Undetermined | Undetermined | N/A | N/A | N/A | N/A |
| SESN1 | 28.689 | 25.215 | 25.915 | 21.378 | 9.239 | 5.530 | 6.770 | 1.205 |
| SGK1 | 25.579 | 28.624 | 27.309 | 30.174 | 6.129 | 8.939 | 8.164 | 10.001 |
| SLC10A6 | 36.617 | 35.684 | 37.200 | 39.653 | 17.167 | 15.999 | 18.055 | 19.480 |
| SLC19A2 | 26.638 | 26.125 | 25.887 | 26.101 | 7.188 | 6.440 | 6.742 | 5.928 |
| SLC22A5 | 28.901 | 26.640 | 29.427 | 27.488 | 9.451 | 6.955 | 10.282 | 7.315 |
| SNTA1 | 24.438 | 24.181 | 24.329 | 25.156 | 4.988 | 4.496 | 5.184 | 4.993 |
| SPHK1 | 29.643 | 29.333 | 29.804 | 29.702 | 10.193 | 9.648 | 10.659 | 9.529 |
| SPSB1 | 29.613 | 26.952 | 29.963 | 27.294 | 10.163 | 7.267 | 10.818 | 7.121 |
| STAT5A | 25.567 | 25.495 | 25.699 | 24.956 | 6.117 | 5.810 | 6.554 | 4.783 |
| STAT5B | 23.414 | 23.453 | 23.270 | 23.985 | 3.964 | 3.768 | 4.125 | 3.812 |
| TBL1XR1 | 21.602 | 22.111 | 21.479 | 22.588 | 2.152 | 2.426 | 2.334 | 2.415 |
| TNF | 23.694 | 25.079 | 24.151 | 25.675 | 4.244 | 5.394 | 5.006 | 5.502 |
| TNFAIP3 | 24.946 | 26.903 | 26.733 | 28.675 | 5.496 | 7.218 | 7.588 | 8.502 |
| TSC22D3 | 25.514 | 25.390 | 22.481 | 21.679 | 6.064 | 5.705 | 3.336 | 1.506 |
| USP2 | 22.646 | 21.903 | 20.884 | 20.640 | 3.196 | 2.218 | 1.739 | 0.467 |
| USP54 | 26.549 | 26.807 | 26.453 | 27.306 | 7.099 | 7.122 | 7.308 | 7.133 |
| VDR | 30.102 | 27.293 | 29.232 | 27.319 | 10.652 | 7.608 | 10.087 | 7.146 |
| VLDLR | 28.252 | 32.346 | 30.596 | Undetermined | 8.802 | 12.661 | 11.451 | N/A |
| XDH | Undetermined | Undetermined | Undetermined | Undetermined | N/A | N/A | N/A | N/A |
| ZFP36 | 24.367 | 25.541 | 25.166 | 26.450 | 4.917 | 5.856 | 6.021 | 6.277 |
| ZHX3 | 25.774 | 24.831 | 25.570 | 25.485 | 6.324 | 5.146 | 6.425 | 5.312 |
| ZNF281 | 24.007 | 23.913 | 23.608 | 24.577 | 4.557 | 4.228 | 4.463 | 4.404 |
| ACTB | 14.801 | 15.450 | 14.572 | 16.143 | −4.649 | −4.235 | −4.573 | −4.030 |
| B2M | 19.450 | 19.685 | 19.145 | 20.173 | 0.000 | 0.000 | 0.000 | 0.000 |
| GAPDH | 16.528 | 17.275 | 16.349 | 17.416 | −2.922 | −2.410 | −2.796 | −2.757 |
| HPRT1 | 21.509 | 22.793 | 21.361 | 23.732 | 2.059 | 3.108 | 2.216 | 3.559 |
| RPLP0 | 15.697 | 15.681 | 15.330 | 15.349 | −3.753 | −4.004 | −3.815 | −4.824 |
| HGDC | Undetermined | Undetermined | Undetermined | Undetermined | N/A | N/A | N/A | N/A |
| RTC | 21.199 | 20.891 | 21.392 | 21.368 | 1.749 | 1.206 | 2.247 | 1.195 |
| RTC | 21.219 | 20.949 | 21.293 | 21.425 | 1.769 | 1.264 | 2.148 | 1.252 |
| RTC | 21.216 | 20.945 | 21.237 | 21.320 | 1.766 | 1.260 | 2.092 | 1.147 |
| PPC | 18.984 | 18.798 | 18.835 | 18.992 | −0.466 | −0.887 | −0.310 | −1.181 |
| PPC | 18.832 | 18.877 | 18.870 | 18.841 | −0.618 | −0.808 | −0.275 | −1.332 |
| PPC | 18.869 | 19.007 | 18.873 | 18.835 | −0.581 | −0.678 | −0.272 | −1.338 |

| | Cpd44 | | Pred | | Combo | |
|---|---|---|---|---|---|---|
| Gene | ΔΔCT | Fold Change | ΔΔCT | Fold Change | ΔΔCT | Fold Change |
| ADARB1 | −1.165 | 2.242 | 0.097 | 0.935 | −1.021 | 2.029 |
| AFF1 | −0.413 | 1.331 | −0.464 | 1.379 | −2.099 | 4.284 |
| AK2 | 0.486 | 0.714 | 0.094 | 0.937 | 0.702 | 0.615 |
| AMPD3 | −1.540 | 2.908 | −0.219 | 1.164 | −2.343 | 5.074 |
| ANGPTL4 | −1.192 | 2.285 | −0.329 | 1.256 | −0.657 | 1.577 |
| ANXA4 | −3.312 | 9.931 | −0.025 | 1.017 | −3.446 | 10.898 |
| AQP1 | N/A | N/A | N/A | N/A | N/A | N/A |
| ARID5B | −0.353 | 1.277 | 0.782 | 0.582 | 0.173 | 0.887 |
| ASPH | −0.105 | 1.075 | −0.041 | 1.029 | −0.174 | 1.128 |
| ATF4 | 0.361 | 0.779 | 0.090 | 0.940 | 0.274 | 0.827 |
| BCL6 | −0.394 | 1.314 | 0.249 | 0.841 | −0.544 | 1.458 |
| BMPER | N/A | N/A | N/A | N/A | −2.043 | 4.121 |
| CALCR | N/A | N/A | N/A | N/A | N/A | N/A |
| CEBPA | −1.659 | 3.158 | −0.295 | 1.227 | −1.514 | 2.856 |
| CEBPB | 1.269 | 0.415 | 0.814 | 0.569 | 1.198 | 0.436 |
| COL4A2 | N/A | N/A | N/A | N/A | N/A | N/A |
| CREB1 | 0.008 | 0.994 | −0.133 | 1.097 | −0.115 | 1.083 |
| CREB3 | −0.085 | 1.061 | −0.453 | 1.369 | −0.639 | 1.557 |
| CREB3L4 | −0.915 | 1.886 | −0.330 | 1.257 | −1.451 | 2.734 |
| CTGF | N/A | N/A | N/A | N/A | N/A | N/A |
| CYB561 | −5.631 | 49.556 | −3.598 | 12.109 | −3.798 | 13.910 |

TABLE 4c-continued

Ct values and fold changes from the RT2 Glucocorticoid signaling PCR array analysis for WSU cell line.

| | | | | | | |
|---|---|---|---|---|---|---|
| DDIT4 | −0.060 | 1.042 | −1.672 | 3.187 | −2.213 | 4.636 |
| DIRAS2 | N/A | N/A | N/A | N/A | N/A | N/A |
| DUSP1 | 1.370 | 0.387 | 0.454 | 0.730 | 0.150 | 0.901 |
| EDN1 | N/A | N/A | N/A | N/A | N/A | N/A |
| EHD3 | −5.639 | 49.832 | −1.645 | 3.127 | −6.231 | 75.113 |
| ERRFI1 | N/A | N/A | N/A | N/A | N/A | N/A |
| FKBP5 | 0.159 | 0.896 | −1.247 | 2.373 | −1.772 | 3.415 |
| FOSL2 | 2.796 | 0.144 | 2.843 | 0.139 | 2.858 | 0.138 |
| GDPD1 | −1.112 | 2.161 | 0.169 | 0.889 | −1.791 | 3.461 |
| GHRHR | 5.086 | 0.029 | 3.458 | 0.091 | N/A | N/A |
| GLUL | N/A | N/A | N/A | N/A | N/A | N/A |
| GOT1 | 0.708 | 0.612 | 0.262 | 0.834 | 0.804 | 0.573 |
| H6PD | −0.619 | 1.536 | 0.142 | 0.906 | −1.648 | 3.134 |
| HAS2 | N/A | N/A | N/A | N/A | N/A | N/A |
| HNRPLL | −0.037 | 1.026 | 1.083 | 0.472 | 2.169 | 0.222 |
| IL10 | N/A | N/A | N/A | N/A | N/A | N/A |
| IL1RN | −4.453 | 21.902 | 1.298 | 0.407 | −3.936 | 15.306 |
| IL6 | N/A | N/A | N/A | N/A | N/A | N/A |
| IL6R | N/A | N/A | N/A | N/A | N/A | N/A |
| KLF13 | −0.974 | 1.964 | −0.442 | 1.358 | −1.591 | 3.013 |
| KLF9 | −2.195 | 4.579 | −0.431 | 1.348 | −3.377 | 10.389 |
| LOX | −0.102 | 1.073 | 0.550 | 0.683 | −0.782 | 1.720 |
| MERTK | N/A | N/A | N/A | N/A | N/A | N/A |
| MT1E | N/A | N/A | N/A | N/A | N/A | N/A |
| MT2A | −1.453 | 2.738 | 0.106 | 0.929 | −1.090 | 2.129 |
| NFKBIA | 1.201 | 0.435 | 0.829 | 0.563 | 0.360 | 0.779 |
| NR3C1 | −0.364 | 1.287 | 0.165 | 0.892 | −0.673 | 1.594 |
| PDCD7 | 0.326 | 0.798 | 0.000 | 1.000 | 0.346 | 0.787 |
| PDGFRB | N/A | N/A | N/A | N/A | N/A | N/A |
| PDP1 | −0.380 | 1.301 | −0.109 | 1.078 | −0.558 | 1.472 |
| PER1 | 0.476 | 0.719 | 0.185 | 0.880 | 0.819 | 0.567 |
| PER2 | 0.151 | 0.901 | 0.072 | 0.951 | 0.389 | 0.764 |
| PIK3R1 | 0.363 | 0.778 | 0.000 | 1.000 | −0.377 | 1.299 |
| PLD1 | N/A | N/A | N/A | N/A | N/A | N/A |
| PLEKHF1 | 1.220 | 0.429 | 0.077 | 0.948 | 1.657 | 0.317 |
| POU2F1 | 0.202 | 0.869 | 0.439 | 0.738 | −0.225 | 1.169 |
| POU2F2 | −0.680 | 1.602 | −0.253 | 1.192 | −0.926 | 1.900 |
| RASA3 | −0.979 | 1.971 | −0.193 | 1.143 | −1.382 | 2.606 |
| RGS2 | 1.732 | 0.301 | 1.365 | 0.388 | 3.677 | 0.078 |
| RHOB | −2.725 | 6.612 | −0.616 | 1.533 | −3.055 | 8.311 |
| RHOJ | N/A | N/A | N/A | N/A | N/A | N/A |
| SESN1 | −3.709 | 13.077 | −2.469 | 5.537 | −8.034 | 262.105 |
| SGK1 | 2.810 | 0.143 | 2.035 | 0.244 | 3.872 | 0.068 |
| SLC10A6 | −1.168 | 2.247 | 0.888 | 0.540 | 2.313 | 0.201 |
| SLC19A2 | −0.748 | 1.679 | −0.446 | 1.362 | −1.260 | 2.395 |
| SLC22A5 | −2.496 | 5.641 | 0.831 | 0.562 | −2.136 | 4.395 |
| SNTA1 | −0.492 | 1.406 | 0.196 | 0.873 | 0.005 | 0.997 |
| SPHK1 | −0.545 | 1.459 | 0.466 | 0.724 | −0.664 | 1.584 |
| SPSB1 | −2.896 | 7.444 | 0.655 | 0.635 | −3.042 | 8.236 |
| STAT5A | −0.307 | 1.237 | 0.437 | 0.739 | −1.334 | 2.521 |
| STAT5B | −0.196 | 1.146 | 0.161 | 0.894 | −0.152 | 1.111 |
| TBL1XR1 | 0.274 | 0.827 | 0.182 | 0.881 | 0.263 | 0.833 |
| TNF | 1.150 | 0.451 | 0.762 | 0.590 | 1.258 | 0.418 |
| TNFAIP3 | 1.722 | 0.303 | 2.092 | 0.235 | 3.006 | 0.124 |
| TSC22D3 | −0.359 | 1.283 | −2.728 | 6.625 | −4.558 | 23.556 |
| USP2 | −0.978 | 1.970 | −1.457 | 2.745 | −2.729 | 6.630 |
| USP54 | 0.023 | 0.984 | 0.209 | 0.865 | 0.034 | 0.977 |
| VDR | −3.044 | 8.248 | −0.565 | 1.479 | −3.506 | 11.361 |
| VLDLR | 3.859 | 0.069 | 2.649 | 0.159 | N/A | N/A |
| XDH | N/A | N/A | N/A | N/A | N/A | N/A |
| ZFP36 | 0.939 | 0.522 | 1.104 | 0.465 | 1.360 | 0.390 |
| ZHX3 | −1.178 | 2.263 | 0.101 | 0.932 | −1.012 | 2.017 |
| ZNF281 | −0.329 | 1.256 | −0.094 | 1.067 | −0.153 | 1.112 |
| ACTB | | | | | | |
| B2M | | | | | | |
| GAPDH | | | | | | |
| HPRT1 | | | | | | |
| RPLP0 | | | | | | |
| HGDC | | | | | | |
| RTC | | | | | | |
| RTC | | | | | | |
| RTC | | | | | | |
| PPC | | | | | | |
| PPC | | | | | | |
| PPC | | | | | | |

TABLE 4d

Ct values and fold changes from the RT2 Glucocorticoid signaling PCR array analysis for SUDHL10 cell line.

| Gene | | | | | | |
|---|---|---|---|---|---|---|
| H6PD | 26.184 | 28.126 | 26.256 | 26.915 | 7.758 | 8.979 |
| HAS2 | Undetermined | Undetermined | Undetermined | Undetermined | N/A | N/A |
| HNRPLL | 22.972 | 23.764 | 22.692 | 24.016 | 4.546 | 4.617 |
| IL10 | Undetermined | 32.505 | Undetermined | 32.875 | N/A | 13.358 |
| IL1RN | Undetermined | 32.182 | Undetermined | Undetermined | N/A | 13.035 |
| IL6 | Undetermined | Undetermined | Undetermined | Undetermined | N/A | N/A |
| IL6R | Undetermined | 33.807 | 33.801 | Undetermined | N/A | 14.660 |
| KLF13 | 25.451 | 24.536 | 22.488 | 22.832 | 7.025 | 5.389 |
| KLF9 | 32.931 | 32.525 | 30.255 | 29.691 | 14.505 | 13.378 |
| LOX | 33.500 | 35.385 | 32.223 | 32.465 | 15.074 | 16.238 |
| MERTK | Undetermined | 34.652 | Undetermined | 33.161 | N/A | 15.505 |
| MT1E | Undetermined | Undetermined | Undetermined | 34.503 | N/A | N/A |
| MT2A | 34.844 | 37.225 | 35.909 | 35.849 | 16.418 | 18.078 |
| NFKBIA | 22.331 | 23.654 | 21.628 | 22.744 | 3.905 | 4.507 |
| NR3C1 | 22.516 | 23.754 | 22.000 | 22.835 | 4.090 | 4.617 |
| PDCD7 | 23.600 | 25.123 | 23.256 | 24.731 | 5.174 | 5.976 |
| PDGFRB | Undetermined | Undetermined | Undetermined | Undetermined | N/A | N/A |
| PDP1 | 25.438 | 26.175 | 25.178 | 26.259 | 7.012 | 7.028 |
| PER1 | 26.209 | 27.710 | 24.762 | 26.686 | 7.783 | 8.563 |
| PER2 | 23.618 | 24.780 | 22.642 | 24.465 | 5.192 | 5.633 |
| PIK3R1 | 23.509 | 24.661 | 22.697 | 23.585 | 5.083 | 5.514 |
| PLD1 | Undetermined | Undetermined | Undetermined | Undetermined | N/A | N/A |
| PLEKHF1 | 27.789 | 28.979 | 26.691 | 27.331 | 9.363 | 9.832 |
| POU2F1 | 25.115 | 25.842 | 24.283 | 24.827 | 6.689 | 6.695 |
| POU2F2 | 23.953 | 25.098 | 22.977 | 24.098 | 5.527 | 5.951 |
| RASA3 | 23.171 | 24.277 | 22.449 | 23.649 | 4.745 | 5.130 |
| RGS2 | 24.794 | 25.587 | 25.390 | 26.161 | 6.368 | 6.440 |
| RHOB | 28.583 | 27.829 | 27.968 | 26.383 | 10.157 | 8.682 |
| RHOJ | Undetermined | 36.530 | Undetermined | Undetermined | N/A | 17.383 |
| SESN1 | 28.405 | 27.480 | 24.220 | 22.646 | 9.979 | 8.333 |
| SGK1 | 22.694 | 25.358 | 22.897 | 24.642 | 4.268 | 6.211 |
| SLC10A6 | 36.987 | 37.060 | 34.670 | 36.258 | 18.561 | 17.913 |
| SLC19A2 | 31.019 | 30.597 | 31.940 | 31.354 | 12.593 | 11.450 |
| SLC22A5 | 31.275 | 30.263 | 32.426 | 29.324 | 12.849 | 11.116 |
| SNTA1 | 25.751 | 27.003 | 24.913 | 26.374 | 7.325 | 7.856 |
| SPHK1 | 26.852 | 27.804 | 25.801 | 27.082 | 8.426 | 8.657 |
| SPSB1 | 25.856 | 26.133 | 24.455 | 24.642 | 7.430 | 6.986 |
| STAT5A | 24.170 | 25.275 | 23.779 | 24.550 | 5.744 | 6.128 |
| STAT5B | 23.533 | 24.281 | 23.480 | 24.231 | 5.107 | 5.134 |
| TBL1XR1 | 20.891 | 21.846 | 20.224 | 21.815 | 2.465 | 2.699 |
| TNF | 23.208 | 23.725 | 22.657 | 24.669 | 4.782 | 4.578 |
| TNFAIP3 | 26.832 | 27.677 | 27.010 | 26.749 | 8.406 | 8.530 |
| TSC22D3 | 25.441 | 28.871 | 23.160 | 22.809 | 7.015 | 9.724 |
| USP2 | 22.643 | 23.434 | 21.579 | 22.360 | 4.217 | 4.287 |
| USP54 | 27.132 | 27.789 | 26.401 | 27.379 | 8.706 | 8.642 |
| VDR | 29.507 | 29.514 | 28.490 | 28.525 | 11.081 | 10.367 |
| VLDLR | 27.937 | 32.904 | 31.762 | 32.093 | 9.511 | 13.757 |
| XDH | Undetermined | Undetermined | Undetermined | Undetermined | N/A | N/A |
| ZFP36 | 25.707 | 26.643 | 24.515 | 25.887 | 7.281 | 7.496 |
| ZHX3 | 26.753 | 26.305 | 26.008 | 26.393 | 8.327 | 7.158 |
| ZNF281 | 23.573 | 23.857 | 22.336 | 23.665 | 5.147 | 4.710 |
| ACTB | 14.330 | 14.828 | 13.138 | 14.548 | −4.096 | −4.319 |
| B2M | 18.426 | 19.147 | 17.654 | 18.834 | 0.000 | 0.000 |
| GAPDH | 16.544 | 17.793 | 15.669 | 16.935 | −1.882 | −1.354 |
| HPRT1 | 19.452 | 20.615 | 18.679 | 20.706 | 1.026 | 1.468 |
| RPLP0 | 15.746 | 16.821 | 15.169 | 15.785 | −2.680 | −2.326 |
| HGDC | Undetermined | Undetermined | Undetermined | Undetermined | N/A | N/A |
| RTC | 22.619 | 22.346 | 22.496 | 23.181 | 4.193 | 3.199 |
| RTC | 22.626 | 22.362 | 22.621 | 23.201 | 4.200 | 3.215 |
| RTC | 22.662 | 22.313 | 22.484 | 23.114 | 4.236 | 3.166 |
| PPC | 18.253 | 18.442 | 17.960 | 18.476 | −0.173 | −0.705 |
| PPC | 18.527 | 18.474 | 18.434 | 18.446 | 0.101 | −0.673 |
| PPC | 18.410 | 18.623 | 18.515 | 18.482 | −0.016 | −0.524 |

| Gene | | | | | | | | |
|---|---|---|---|---|---|---|---|---|
| H6PD | 8.602 | 8.081 | 1.221 | 0.429 | 0.844 | 0.557 | 0.323 | 0.799 |
| HAS2 | N/A | N/A | N/A | N/A | N/A | N/A | N/A | N/A |
| HNRPLL | 5.038 | 5.182 | 0.071 | 0.952 | 0.492 | 0.711 | 0.636 | 0.643 |
| IL10 | N/A | 14.041 | N/A | N/A | N/A | N/A | N/A | N/A |
| IL1RN | N/A | N/A | N/A | N/A | N/A | N/A | N/A | N/A |
| IL6 | N/A | N/A | N/A | N/A | N/A | N/A | N/A | N/A |
| IL6R | 16.147 | N/A | N/A | N/A | N/A | N/A | N/A | N/A |
| KLF13 | 4.834 | 3.998 | −1.636 | 3.108 | −2.191 | 4.566 | −3.027 | 8.151 |
| KLF9 | 12.601 | 10.857 | −1.127 | 2.184 | −1.904 | 3.742 | −3.648 | 12.536 |
| LOX | 14.569 | 13.631 | 1.164 | 0.446 | −0.505 | 1.419 | −1.443 | 2.719 |
| MERTK | N/A | 14.327 | N/A | N/A | N/A | N/A | N/A | N/A |
| MT1E | N/A | 15.669 | N/A | N/A | N/A | N/A | N/A | N/A |
| MT2A | 18.255 | 17.015 | 1.660 | 0.316 | 1.837 | 0.280 | 0.597 | 0.661 |

TABLE 4d-continued

Ct values and fold changes from the RT2 Glucocorticoid signaling PCR array analysis for SUDHL10 cell line.

| | | | | | | | | |
|---|---|---|---|---|---|---|---|---|
| NFKBIA | 3.974 | 3.910 | 0.602 | 0.659 | 0.069 | 0.953 | 0.005 | 0.997 |
| NR3C1 | 4.346 | 4.001 | 0.527 | 0.694 | 0.256 | 0.837 | −0.089 | 1.064 |
| PDCD7 | 5.602 | 5.897 | 0.802 | 0.574 | 0.428 | 0.743 | 0.723 | 0.606 |
| PDGFRB | N/A | N/A | N/A | N/A | N/A | N/A | N/A | N/A |
| PDP1 | 7.524 | 7.425 | 0.016 | 0.989 | 0.512 | 0.701 | 0.413 | 0.751 |
| PER1 | 7.108 | 7.852 | 0.780 | 0.582 | −0.675 | 1.597 | 0.069 | 0.953 |
| PER2 | 4.988 | 5.631 | 0.441 | 0.737 | −0.204 | 1.152 | 0.439 | 0.738 |
| PIK3R1 | 5.043 | 4.751 | 0.431 | 0.742 | −0.040 | 1.028 | −0.332 | 1.259 |
| PLD1 | N/A | N/A | N/A | N/A | N/A | N/A | N/A | N/A |
| PLEKHF1 | 9.037 | 8.497 | 0.469 | 0.722 | −0.326 | 1.254 | −0.866 | 1.823 |
| POU2F1 | 6.629 | 5.993 | 0.006 | 0.996 | −0.060 | 1.042 | −0.696 | 1.620 |
| POU2F2 | 5.323 | 5.264 | 0.424 | 0.745 | −0.204 | 1.152 | −0.263 | 1.200 |
| RASA3 | 4.795 | 4.815 | 0.385 | 0.766 | 0.050 | 0.966 | 0.070 | 0.953 |
| RGS2 | 7.736 | 7.327 | 0.072 | 0.951 | 1.368 | 0.387 | 0.959 | 0.514 |
| RHOB | 10.314 | 7.549 | −1.475 | 2.780 | 0.157 | 0.897 | −2.608 | 6.097 |
| RHOJ | N/A | N/A | N/A | N/A | N/A | N/A | N/A | N/A |
| SESN1 | 6.566 | 3.812 | −1.646 | 3.130 | −3.413 | 10.652 | −6.167 | 71.854 |
| SGK1 | 5.243 | 5.808 | 1.943 | 0.260 | 0.975 | 0.509 | 1.540 | 0.344 |
| SLC10A6 | 17.016 | 17.424 | −0.648 | 1.567 | −1.545 | 2.918 | −1.137 | 2.199 |
| SLC19A2 | 14.286 | 12.520 | −1.143 | 2.208 | 1.693 | 0.309 | −0.073 | 1.052 |
| SLC22A5 | 14.772 | 10.490 | −1.733 | 3.324 | 1.923 | 0.264 | −2.359 | 5.130 |
| SNTA1 | 7.259 | 7.540 | 0.531 | 0.692 | −0.066 | 1.047 | 0.215 | 0.862 |
| SPHK1 | 8.147 | 8.248 | 0.231 | 0.852 | −0.279 | 1.213 | −0.178 | 1.131 |
| SPSB1 | 6.801 | 5.808 | −0.444 | 1.360 | −0.629 | 1.546 | −1.622 | 3.078 |
| STAT5A | 6.125 | 5.716 | 0.384 | 0.766 | 0.381 | 0.768 | −0.028 | 1.020 |
| STAT5B | 5.826 | 5.397 | 0.027 | 0.981 | 0.719 | 0.608 | 0.290 | 0.818 |
| TBL1XR1 | 2.570 | 2.981 | 0.234 | 0.850 | 0.105 | 0.930 | 0.516 | 0.699 |
| TNF | 5.003 | 5.835 | −0.204 | 1.152 | 0.221 | 0.858 | 1.053 | 0.482 |
| TNFAIP3 | 9.356 | 7.915 | 0.124 | 0.918 | 0.950 | 0.518 | −0.491 | 1.405 |
| TSC22D3 | 5.506 | 3.975 | 2.709 | 0.153 | −1.509 | 2.846 | −3.040 | 8.225 |
| USP2 | 3.925 | 3.526 | 0.070 | 0.953 | −0.292 | 1.224 | −0.691 | 1.614 |
| USP54 | 8.747 | 8.545 | −0.064 | 1.045 | 0.041 | 0.972 | −0.161 | 1.118 |
| VDR | 10.836 | 9.691 | −0.714 | 1.640 | −0.245 | 1.185 | −1.390 | 2.621 |
| VLDLR | 14.108 | 13.259 | 4.246 | 0.053 | 4.597 | 0.041 | 3.748 | 0.074 |
| XDH | N/A | N/A | N/A | N/A | N/A | N/A | N/A | N/A |
| ZFP36 | 6.861 | 7.053 | 0.215 | 0.862 | −0.420 | 1.338 | −0.228 | 1.171 |
| ZHX3 | 8.354 | 7.559 | −1.169 | 2.249 | 0.027 | 0.981 | −0.768 | 1.703 |
| ZNF281 | 4.682 | 4.831 | −0.437 | 1.354 | −0.465 | 1.380 | −0.316 | 1.245 |
| ACTB | −4.516 | −4.286 | | | | | | |
| B2M | 0.000 | 0.000 | | | | | | |
| GAPDH | −1.985 | −1.899 | | | | | | |
| HPRT1 | 1.025 | 1.872 | | | | | | |
| RPLP0 | −2.485 | −3.049 | | | | | | |
| HGDC | N/A | N/A | | | | | | |
| RTC | 4.842 | 4.347 | | | | | | |
| RTC | 4.967 | 4.367 | | | | | | |
| RTC | 4.830 | 4.280 | | | | | | |
| PPC | 0.306 | −0.358 | | | | | | |
| PPC | 0.780 | −0.388 | | | | | | |
| PPC | 0.861 | −0.352 | | | | | | |

TABLE 4e

Ct values and fold changes from the RT2 Glucocorticoid signaling PCR array analysis for RI cell line.

| | Ct Values | | | | ΔCT (B2M) | | | |
|---|---|---|---|---|---|---|---|---|
| Gene | DMSO | Cpd44 | Pred | Combo | DMSO | Cpd44 | Pred | Combo |
| ADARB1 | 27.745 | 26.650 | 28.557 | 28.623 | 8.964 | 7.292 | 9.377 | 9.377 |
| AFF1 | 28.249 | 26.820 | 27.258 | 26.977 | 9.468 | 7.462 | 8.078 | 7.731 |
| AK2 | 19.425 | 20.270 | 20.510 | 21.466 | 0.644 | 0.912 | 1.330 | 2.220 |
| AMPD3 | 27.499 | 27.191 | 27.354 | 27.238 | 8.718 | 7.833 | 8.174 | 7.992 |
| ANGPTL4 | 30.178 | 29.820 | 32.245 | 29.596 | 11.397 | 10.462 | 13.065 | 10.350 |
| ANXA4 | 24.380 | 24.395 | | 24.910 | 5.599 | 5.037 | 5.730 | 5.525 |
| AQP1 | Undetermined | Undetermined | Undetermined | 33.328 | N/A | N/A | N/A | 14.082 |
| ARID5B | 27.976 | 27.333 | 29.208 | 28.495 | 9.195 | 7.975 | 10.028 | 9.249 |
| ASPH | 22.413 | 23.466 | 23.583 | 24.410 | 3.632 | 4.108 | 4.403 | 5.164 |
| ATF4 | 17.689 | 18.269 | 19.452 | 20.540 | −1.092 | −1.089 | 0.272 | 1.294 |
| BCL6 | 19.449 | 20.289 | 20.785 | 20.772 | 0.668 | 0.931 | 1.605 | 1.526 |
| BMPER | Undetermined | Undetermined | Undetermined | Undetermined | N/A | N/A | N/A | N/A |
| CALCR | Undetermined | Undetermined | Undetermined | Undetermined | N/A | N/A | N/A | N/A |
| CEBPA | Undetermined | 36.511 | Undetermined | Undetermined | N/A | 17.153 | N/A | N/A |
| CEBPB | 23.192 | 23.765 | 26.229 | 27.211 | 4.411 | 4.407 | 7.049 | 7.965 |

TABLE 4e-continued

Ct values and fold changes from the RT2 Glucocorticoid signaling PCR array analysis for RI cell line.

| | | | | | | | | |
|---|---|---|---|---|---|---|---|---|
| COL4A2 | 31.978 | 31.782 | Undetermined | 35.212 | 13.197 | 12.424 | N/A | 15.966 |
| CREB1 | 22.435 | 23.217 | 23.317 | 23.470 | 3.654 | 3.859 | 4.137 | 4.224 |
| CREB3 | 23.790 | 24.178 | 24.951 | 24.735 | 5.009 | 4.820 | 5.771 | 5.489 |
| CREB3L4 | 23.683 | 23.500 | 24.211 | 23.870 | 4.902 | 4.142 | 5.031 | 4.624 |
| CTGF | Undetermined | Undetermined | Undetermined | Undetermined | N/A | N/A | N/A | N/A |
| CYB561 | 39.352 | 38.452 | 38.088 | 37.618 | 20.571 | 19.094 | 18.908 | 18.372 |
| DDIT4 | 21.641 | 22.679 | 23.471 | 22.583 | 2.860 | 3.321 | 4.291 | 3.337 |
| DIRAS2 | Undetermined | Undetermined | Undetermined | Undetermined | N/A | N/A | N/A | N/A |
| DUSP1 | 25.166 | 25.422 | 25.412 | 24.981 | 6.385 | 6.064 | 6.232 | 5.735 |
| EDN1 | 32.446 | 31.815 | 39.440 | 30.700 | 13.665 | 12.457 | 20.260 | 11.454 |
| EHD3 | 24.957 | 24.572 | 25.411 | 23.975 | 6.176 | 5.214 | 6.231 | 4.729 |
| ERRFI1 | Undetermined | 31.705 | 32.655 | 31.791 | N/A | 12.347 | 13.475 | 12.545 |
| FKBP5 | 20.792 | 21.757 | 20.858 | 20.881 | 2.011 | 2.399 | 1.678 | 1.635 |
| FOSL2 | 31.458 | 30.761 | 34.157 | 36.459 | 12.677 | 11.403 | 14.977 | 17.213 |
| GDPD1 | 27.589 | 27.394 | 28.699 | 28.110 | 8.808 | 8.036 | 9.519 | 8.864 |
| GHRHR | Undetermined | 37.546 | 33.555 | 29.797 | N/A | 18.188 | 14.375 | 10.551 |
| GLUL | 30.775 | 28.738 | 32.181 | 32.961 | 11.994 | 9.380 | 13.001 | 13.715 |
| GOT1 | 21.489 | 22.584 | 23.355 | 24.551 | 2.708 | 3.226 | 4.175 | 5.305 |
| H6PD | 25.108 | 25.012 | 26.442 | 24.742 | 6.327 | 5.654 | 7.262 | 5.496 |
| HAS2 | Undetermined | Undetermined | Undetermined | Undetermined | N/A | N/A | N/A | N/A |
| HNRPLL | 21.958 | 22.844 | 23.146 | 24.289 | 3.177 | 3.486 | 3.966 | 5.043 |
| IL10 | 32.353 | 31.498 | 32.669 | Undetermined | 13.572 | 12.140 | 13.489 | N/A |
| IL1RN | 29.709 | 28.405 | 29.300 | 29.204 | 10.928 | 9.047 | 10.120 | 9.958 |
| IL6 | Undetermined | Undetermined | Undetermined | Undetermined | N/A | N/A | N/A | N/A |
| IL6R | 29.184 | 29.246 | 30.468 | 31.321 | 10.403 | 9.888 | 11.288 | 12.075 |
| KLF13 | 22.843 | 22.854 | 23.590 | 23.322 | 4.062 | 3.496 | 4.410 | 4.076 |
| KLF9 | 34.469 | Undetermined | Undetermined | Undetermined | 15.688 | N/A | N/A | N/A |
| LOK | 33.918 | 33.915 | 34.185 | 33.948 | 15.137 | 14.557 | 15.005 | 14.702 |
| MERTK | 34.533 | 30.691 | Undetermined | 31.272 | 15.752 | 11.333 | N/A | 12.026 |
| MT1E | Undetermined | 34.215 | Undetermined | Undetermined | N/A | 14.857 | N/A | N/A |
| MT2A | 23.125 | 24.279 | 25.570 | 25.570 | 4.344 | 4.921 | 6.000 | 6.324 |
| NFKBIA | 22.279 | 23.710 | 23.531 | 23.442 | 3.498 | 4.352 | 4.351 | 4.196 |
| NR3C1 | 21.972 | 22.616 | 23.323 | 23.237 | 3.191 | 3.258 | 4.143 | 3.991 |
| PDCD7 | 23.823 | 24.406 | 24.616 | 24.925 | 5.042 | 5.048 | 5.436 | 5.679 |
| PDGFRB | Undetermined | Undetermined | Undetermined | Undetermined | N/A | N/A | N/A | N/A |
| PDP1 | 25.799 | 25.387 | 26.940 | 25.667 | 7.018 | 6.029 | 7.760 | 6.421 |
| PER1 | 24.531 | 25.492 | 27.160 | 26.707 | 5.750 | 6.134 | 7.980 | 7.461 |
| PER2 | 24.162 | 24.378 | 24.811 | 24.547 | 5.381 | 5.020 | 5.631 | 5.301 |
| PIK3R1 | 22.958 | 23.908 | 24.331 | 24.602 | 4.177 | 4.550 | 5.151 | 5.356 |
| PLD1 | Undetermined | Undetermined | Undetermined | Undetermined | N/A | N/A | N/A | N/A |
| PLEKHF1 | 29.893 | 30.520 | 31.367 | 34.212 | 11.112 | 11.162 | 12.187 | 14.966 |
| POU2F1 | 23.693 | 24.243 | 25.222 | 25.607 | 4.912 | 4.885 | 6.042 | 6.361 |
| POU2F2 | 21.776 | 21.769 | 22.972 | 22.359 | 2.995 | 2.411 | 3.792 | 3.113 |
| RASA3 | 25.711 | 26.279 | 27.653 | 26.571 | 6.930 | 6.921 | 8.473 | 7.325 |
| RGS2 | 25.306 | 25.721 | 26.477 | 28.212 | 6.525 | 6.363 | 7.297 | 8.966 |
| RHOB | Undetermined | Undetermined | Undetermined | 38.682 | N/A | N/A | N/A | 19.436 |
| RHOJ | Undetermined | Undetermined | Undetermined | Undetermined | N/A | N/A | N/A | N/A |
| SESN1 | 25.545 | 24.425 | 21.882 | 20.973 | 6.764 | 5.067 | 2.702 | 1.727 |
| SGK1 | 24.884 | 26.262 | 26.131 | 26.411 | 6.103 | 6.904 | 6.951 | 7.165 |
| SLC10A6 | 35.730 | Undetermined | 34.404 | 35.950 | 16.949 | N/A | 15.224 | 16.704 |
| SLC19A2 | 25.756 | 25.536 | 26.202 | 25.342 | 6.975 | 6.178 | 7.022 | 6.096 |
| SLC22A5 | 32.280 | Undetermined | Undetermined | 38.888 | 13.499 | N/A | N/A | 19.642 |
| SNTA1 | 24.937 | 25.554 | 26.480 | 26.133 | 6.156 | 6.196 | 7.300 | 6.887 |
| SPHK1 | 31.323 | 31.119 | 34.340 | Undetermined | 12.542 | 11.761 | 15.160 | N/A |
| SPSB1 | 26.573 | 26.285 | 28.977 | 28.200 | 7.792 | 6.927 | 9.797 | 8.954 |
| STAT5A | 22.191 | 22.769 | 23.379 | 22.666 | 3.410 | 3.411 | 4.199 | 3.420 |
| STAT5B | 22.200 | 22.683 | 23.111 | 23.737 | 3.419 | 3.325 | 3.931 | 4.491 |
| TBL1XR1 | 20.394 | 21.663 | 21.587 | 21.692 | 1.613 | 2.305 | 2.407 | 2.446 |
| TNF | 24.972 | 24.712 | 24.773 | 22.812 | 6.191 | 5.354 | 5.593 | 3.566 |
| TNFAIP3 | 25.433 | 26.896 | 27.393 | 28.474 | 6.652 | 7.538 | 8.213 | 9.228 |
| TSC22D3 | 22.534 | 23.300 | 21.502 | 21.179 | 3.753 | 3.942 | 2.322 | 1.933 |
| USP2 | 20.982 | 21.420 | 20.720 | 20.616 | 2.201 | 2.062 | 1.540 | 1.370 |
| USP54 | 26.748 | 26.364 | 27.638 | 26.992 | 7.967 | 7.006 | 8.458 | 7.746 |
| VDR | 29.817 | 27.736 | 31.463 | 29.508 | 11.036 | 8.378 | 12.283 | 10.262 |
| VLDLR | 35.442 | Undetermined | 33.979 | Undetermined | 16.661 | N/A | 14.799 | N/A |
| XDH | Undetermined | Undetermined | Undetermined | Undetermined | N/A | N/A | N/A | N/A |
| ZFP36 | 23.833 | 24.374 | 25.160 | 24.997 | 5.052 | 5.016 | 5.980 | 5.751 |
| ZHX3 | 24.547 | 29.785 | 25.114 | 24.601 | 5.766 | 10.427 | 5.934 | 5.355 |
| ZNF281 | 23.044 | 23.667 | 23.814 | 23.669 | 4.263 | 4.309 | 4.634 | 4.423 |
| ACTB | 14.794 | 15.664 | 15.466 | 15.976 | −3.987 | −3.694 | −3.714 | −3.270 |
| B2M | 18.781 | 19.358 | 19.180 | 19.246 | 0.000 | 0.000 | 0.000 | 0.000 |
| GAPDH | 15.388 | 15.720 | 16.234 | 17.444 | −3.393 | −3.638 | −2.946 | −1.802 |
| HPRT1 | 21.297 | 22.013 | 21.626 | 22.777 | 2.516 | 2.655 | 2.446 | 3.531 |
| RPLP0 | 15.092 | 14.837 | 15.994 | 15.962 | −3.689 | −4.521 | −3.186 | −3.284 |
| HGDC | Undetermined | Undetermined | Undetermined | Undetermined | N/A | N/A | N/A | N/A |
| RTC | 20.832 | 21.659 | 20.818 | 20.383 | 2.051 | 2.301 | 1.638 | 1.137 |
| RTC | 20.752 | 21.713 | 20.681 | 20.380 | 1.971 | 2.355 | 1.501 | 1.134 |
| RTC | 20.792 | 21.629 | 20.780 | 20.481 | 2.011 | 2.271 | 1.600 | 1.235 |

TABLE 4e-continued

Ct values and fold changes from the RT2 Glucocorticoid signaling PCR array analysis for RI cell line.

| | | | | | | | | |
|---|---|---|---|---|---|---|---|---|
| PPC | 18.493 | 18.197 | 18.424 | 18.380 | −0.288 | −1.161 | −0.756 | −0.866 |
| PPC | 18.567 | 18.303 | 18.491 | 18.255 | −0.214 | −1.055 | −0.689 | −0.991 |
| PPC | 18.444 | 18.435 | 18.381 | 18.325 | −0.337 | −0.923 | −0.799 | −0.921 |

| | Cpd44 | | Pred | | Combo | |
|---|---|---|---|---|---|---|
| Gene | ΔΔCT | Fold Change | ΔΔCT | Fold Change | ΔΔCT | Fold Change |
| ADARB1 | −1.672 | 3.187 | 0.413 | 0.751 | 0.413 | 0.751 |
| AFF1 | −2.006 | 4.017 | −1.390 | 2.621 | −1.737 | 3.333 |
| AK2 | 0.268 | 0.830 | 0.686 | 0.622 | 1.576 | 0.335 |
| AMPD3 | −0.885 | 1.847 | −0.544 | 1.458 | −0.726 | 1.654 |
| ANGPTL4 | −0.935 | 1.912 | 1.668 | 0.315 | −1.047 | 2.066 |
| ANXA4 | −0.562 | 1.476 | 0.131 | 0.913 | −0.074 | 1.053 |
| AQP1 | N/A | N/A | N/A | N/A | N/A | N/A |
| ARID5B | −1.220 | 2.329 | 0.833 | 0.561 | 0.054 | 0.963 |
| ASPH | 0.476 | 0.719 | 0.771 | 0.586 | 1.532 | 0.346 |
| ATF4 | 0.003 | 0.998 | 1.364 | 0.389 | 2.386 | 0.191 |
| BCL6 | 0.263 | 0.833 | 0.937 | 0.522 | 0.858 | 0.552 |
| BMPER | N/A | N/A | N/A | N/A | N/A | N/A |
| CALCR | N/A | N/A | N/A | N/A | N/A | N/A |
| CEBPA | N/A | N/A | N/A | N/A | N/A | N/A |
| CEBPB | −0.004 | 1.003 | 2.638 | 0.161 | 3.554 | 0.085 |
| COL4A2 | −0.773 | 1.709 | N/A | N/A | 2.769 | 0.147 |
| CREB1 | 0.205 | 0.868 | 0.483 | 0.715 | 0.570 | 0.674 |
| CREB3 | −0.189 | 1.140 | 0.762 | 0.590 | 0.480 | 0.717 |
| CREB3L4 | −0.760 | 1.693 | 0.129 | 0.914 | −0.278 | 1.213 |
| CTGF | N/A | N/A | N/A | N/A | N/A | N/A |
| CYB561 | −1.477 | 2.784 | −1.663 | 3.167 | −2.199 | 4.592 |
| DDIT4 | 0.461 | 0.726 | 1.431 | 0.371 | 0.477 | 0.718 |
| DIRAS2 | N/A | N/A | N/A | N/A | N/A | N/A |
| DUSP1 | −0.321 | 1.249 | −0.153 | 1.112 | −0.650 | 1.569 |
| EDN1 | −1.208 | 2.310 | 6.595 | 0.010 | −2.211 | 4.630 |
| EHD3 | −0.962 | 1.948 | 0.055 | 0.963 | −1.447 | 2.726 |
| ERRFI1 | N/A | N/A | N/A | N/A | N/A | N/A |
| FKBP5 | 0.388 | 0.764 | −0.333 | 1.260 | −0.376 | 1.298 |
| FOSL2 | −1.274 | 2.418 | 2.300 | 0.203 | 4.536 | 0.043 |
| GDPD1 | −0.772 | 1.708 | 0.711 | 0.611 | 0.056 | 0.962 |
| GHRHR | N/A | N/A | N/A | N/A | N/A | N/A |
| GLUL | −2.614 | 6.122 | 1.007 | 0.498 | 1.721 | 0.303 |
| GOT1 | 0.518 | 0.698 | 1.467 | 0.362 | 2.597 | 0.165 |
| H6PD | −0.673 | 1.594 | 0.935 | 0.523 | −0.831 | 1.779 |
| HAS2 | N/A | N/A | N/A | N/A | N/A | N/A |
| HNRPLL | 0.309 | 0.807 | 0.789 | 0.579 | 1.866 | 0.274 |
| IL10 | −1.432 | 2.698 | −0.083 | 1.059 | N/A | N/A |
| IL1RN | −1.881 | 3.683 | −0.808 | 1.751 | −0.970 | 1.959 |
| IL6 | N/A | N/A | N/A | N/A | N/A | N/A |
| IL6R | −0.515 | 1.429 | 0.885 | 0.541 | 1.672 | 0.314 |
| KLF13 | −0.566 | 1.480 | 0.348 | 0.786 | 0.014 | 0.990 |
| KLF9 | N/A | N/A | N/A | N/A | N/A | N/A |
| LOK | −0.580 | 1.495 | −0.132 | 1.096 | −0.435 | 1.352 |
| MERTK | −4.419 | 21.392 | N/A | N/A | −3.726 | 13.232 |
| MT1E | N/A | N/A | N/A | N/A | N/A | N/A |
| MT2A | 0.577 | 0.670 | 1.656 | 0.317 | 1.980 | 0.253 |
| NFKBIA | 0.854 | 0.553 | 0.853 | 0.554 | 0.698 | 0.616 |
| NR3C1 | 0.067 | 0.955 | 0.952 | 0.517 | 0.800 | 0.574 |
| PDCD7 | 0.006 | 0.996 | 0.394 | 0.761 | 0.637 | 0.643 |
| PDGFRB | N/A | N/A | N/A | N/A | N/A | N/A |
| PDP1 | −0.989 | 1.985 | 0.742 | 0.598 | −0.597 | 1.513 |
| PER1 | 0.384 | 0.766 | 2.230 | 0.213 | 1.711 | 0.305 |
| PER2 | −0.361 | 1.284 | 0.250 | 0.841 | −0.080 | 1.057 |
| PIK3R1 | 0.373 | 0.772 | 0.974 | 0.509 | 1.179 | 0.442 |
| PLD1 | N/A | N/A | N/A | N/A | N/A | N/A |
| PLEKHF1 | 0.050 | 0.966 | 1.075 | 0.475 | 3.854 | 0.069 |
| POU2F1 | −0.027 | 1.019 | 1.130 | 0.457 | 1.449 | 0.366 |
| POU2F2 | −0.584 | 1.499 | 0.797 | 0.576 | 0.118 | 0.921 |
| RASA3 | −0.009 | 1.006 | 1.543 | 0.343 | 0.395 | 0.760 |
| RGS2 | −0.162 | 1.119 | 0.772 | 0.586 | 2.441 | 0.184 |
| RHOB | N/A | N/A | N/A | N/A | N/A | N/A |
| RHOJ | N/A | N/A | N/A | N/A | N/A | N/A |
| SESN1 | −1.697 | 3.242 | −4.062 | 16.703 | −5.037 | 32.831 |
| SGK1 | 0.801 | 0.574 | 0.848 | 0.556 | 1.062 | 0.479 |
| SLC10A6 | N/A | N/A | −1.725 | 3.306 | −0.245 | 1.185 |
| SLC19A2 | −0.797 | 1.737 | 0.047 | 0.968 | −0.879 | 1.839 |
| SLC22A5 | N/A | N/A | N/A | N/A | 6.143 | 0.014 |
| SNTA1 | 0.040 | 0.973 | 1.144 | 0.453 | 0.731 | 0.602 |
| SPHK1 | −0.781 | 1.718 | 2.618 | 0.163 | N/A | N/A |
| SPSB1 | −0.865 | 1.821 | 2.005 | 0.249 | 1.162 | 0.447 |

TABLE 4e-continued

Ct values and fold changes from the RT2 Glucocorticoid signaling PCR array analysis for RI cell line.

| | | | | | | |
|---|---|---|---|---|---|---|
| STAT5A | 0.001 | 0.999 | 0.789 | 0.579 | 0.010 | 0.993 |
| STAT5B | −0.094 | 1.067 | 0.512 | 0.701 | 1.072 | 0.476 |
| TBL1XR1 | 0.692 | 0.619 | 0.794 | 0.577 | 0.833 | 0.561 |
| TNF | −0.837 | 1.786 | −0.598 | 1.514 | −2.625 | 6.169 |
| TNFAIP3 | 0.886 | 0.541 | 1.561 | 0.339 | 2.576 | 0.168 |
| TSC22D3 | 0.189 | 0.877 | −1.431 | 2.696 | −1.820 | 3.531 |
| USP2 | −0.139 | 1.101 | −0.661 | 1.581 | −0.831 | 1.779 |
| USP54 | −0.961 | 1.947 | 0.491 | 0.712 | −0.221 | 1.166 |
| VDR | −2.658 | 6.312 | 1.247 | 0.421 | −0.774 | 1.710 |
| VLDLR | N/A | N/A | −1.862 | 3.635 | N/A | N/A |
| XDH | N/A | N/A | N/A | N/A | N/A | N/A |
| ZFP36 | −0.036 | 1.025 | 0.928 | 0.526 | 0.699 | 0.616 |
| ZHX3 | 4.661 | 0.040 | 0.168 | 0.890 | −0.411 | 1.330 |
| ZNF281 | 0.046 | 0.969 | 0.371 | 0.773 | 0.160 | 0.895 |
| ACTB | | | | | | |
| B2M | | | | | | |
| GAPDH | | | | | | |
| HPRT1 | | | | | | |
| RPLP0 | | | | | | |
| HGDC | | | | | | |
| RTC | | | | | | |
| RTC | | | | | | |
| RTC | | | | | | |
| PPC | | | | | | |
| PPC | | | | | | |
| PPC | | | | | | |

TABLE 4f

Ct values and fold changes from the RT2 Glucocorticoid signaling PCR array analysis for SUDHL4 cell line.

| | Ct Values | | | | ΔCT (B2M) | | | |
|---|---|---|---|---|---|---|---|---|
| Gene | DMSO | Cpd44 | Pred | Combo | DMSO | Cpd44 | Pred | Combo |
| ADARB1 | 27.696 | 28.562 | 27.634 | 28.373 | 10.107 | 8.878 | 9.591 | 8.992 |
| AFF1 | 26.492 | 25.874 | 25.660 | | 7.394 | 7.118 | 6.965 | 7.788 |
| AK2 | 19.861 | 20.311 | 20.602 | 20.682 | 2.416 | 1.846 | 1.340 | 1.157 |
| AMPD3 | 25.234 | 25.553 | 24.780 | 25.739 | 7.473 | 6.024 | 6.582 | 6.530 |
| ANGPTL4 | 29.764 | 29.825 | 29.326 | 30.167 | 11.901 | 10.570 | 10.854 | 11.060 |
| ANXA4 | 26.847 | 28.717 | 26.973 | 28.902 | 10.636 | 8.217 | 9.746 | 8.143 |
| AQP1 | Undetermined | Undetermined | 32.982 | 32.161 | 13.895 | 14.226 | N/A | N/A |
| ARID5B | 25.120 | 25.129 | 24.504 | 24.555 | 6.289 | 5.748 | 6.158 | 6.416 |
| ASPH | 22.618 | 23.348 | 22.741 | 23.094 | 4.828 | 3.985 | 4.377 | 3.914 |
| ATF4 | 19.323 | 18.778 | 18.988 | 18.352 | 0.086 | 0.232 | −0.193 | 0.619 |
| BCL6 | 20.521 | 21.075 | 20.634 | 21.163 | 2.897 | 1.878 | 2.104 | 1.817 |
| BMPER | Undetermined | Undetermined | Undetermined | Undetermined | N/A | N/A | N/A | N/A |
| CALCR | Undetermined | Undetermined | Undetermined | Undetermined | N/A | N/A | N/A | N/A |
| CEBPA | 28.837 | 31.206 | 28.782 | 30.802 | 12.536 | 10.026 | 12.235 | 10.133 |
| CEBPB | 24.507 | 23.911 | 23.944 | 22.678 | 4.412 | 5.188 | 4.940 | 5.803 |
| COL4A2 | Undetermined | Undetermined | Undetermined | 33.904 | 15.638 | N/A | N/A | N/A |
| CREB1 | 22.906 | 22.973 | 22.993 | 22.816 | 4.550 | 4.237 | 4.002 | 4.202 |
| CREB3 | 24.330 | 24.566 | 24.421 | 24.421 | 6.155 | 5.665 | 5.595 | 5.626 |
| CREB3L4 | 24.709 | 25.089 | 24.418 | 24.583 | 6.317 | 5.662 | 6.118 | 6.005 |
| CTGF | Undetermined | Undetermined | Undetermined | Undetermined | N/A | N/A | N/A | N/A |
| CYB561 | 33.993 | 36.737 | 33.006 | 36.752 | 18.486 | 14.250 | 17.766 | 15.289 |
| DDIT4 | 21.247 | 21.455 | 21.854 | 22.681 | 4.415 | 3.098 | 2.484 | 2.543 |
| DIRAS2 | Undetermined | Undetermined | 33.382 | Undetermined | N/A | 14.626 | N/A | N/A |
| DUSP1 | 26.436 | 26.325 | 26.754 | 26.713 | 8.447 | 7.998 | 7.354 | 7.732 |
| EDN1 | 32.440 | 33.297 | 32.372 | Undetermined | N/A | 13.616 | 14.326 | 13.736 |
| EHD3 | 24.298 | 25.766 | 24.878 | 26.386 | 8.120 | 6.122 | 6.795 | 5.594 |
| ERRFI1 | Undetermined | Undetermined | Undetermined | Undetermined | N/A | N/A | N/A | N/A |
| FKBP5 | 20.533 | 20.494 | 21.869 | 21.371 | 3.105 | 3.113 | 1.523 | 1.829 |
| FOSL2 | 35.083 | 31.757 | 33.362 | Undetermined | N/A | 14.606 | 12.786 | 16.379 |
| GDPD1 | 27.358 | 28.134 | 26.972 | 27.838 | 9.572 | 8.216 | 9.163 | 8.654 |
| GHRHR | 36.313 | 37.623 | Undetermined | 36.734 | 18.468 | N/A | 18.652 | 17.609 |
| GLUL | 35.436 | 35.795 | 34.414 | Undetermined | N/A | 15.658 | 16.824 | 16.732 |
| GOT1 | 22.400 | 22.607 | 22.859 | 22.304 | 4.038 | 4.103 | 3.636 | 3.696 |
| H6PD | 25.209 | 25.743 | 24.819 | 24.878 | 6.612 | 6.063 | 6.772 | 6.505 |
| HAS2 | Undetermined | 35.628 | 31.961 | Undetermined | N/A | 13.205 | 16.657 | N/A |
| HNRPLL | 22.667 | 22.977 | 22.577 | 22.558 | 4.292 | 3.821 | 4.006 | 3.963 |
| IL10 | 32.210 | 33.099 | 31.119 | 32.524 | 14.258 | 12.363 | 14.128 | 13.506 |
| IL1RN | Undetermined | Undetermined | 36.259 | Undetermined | N/A | 17.503 | N/A | N/A |
| IL6 | Undetermined | Undetermined | Undetermined | Undetermined | N/A | N/A | N/A | N/A |
| IL6R | 32.607 | 33.589 | 31.995 | 33.408 | 15.142 | 13.239 | 14.618 | 13.903 |

TABLE 4f-continued

Ct values and fold changes from the RT2 Glucocorticoid signaling PCR array analysis for SUDHL4 cell line.

| Gene | | | | | | | | |
|---|---|---|---|---|---|---|---|---|
| KLF13 | 22.256 | 22.649 | 22.834 | 22.878 | 4.612 | 4.078 | 3.678 | 3.552 |
| KLF9 | 26.816 | 27.456 | 26.769 | 27.572 | 9.306 | 8.013 | 8.485 | 8.112 |
| LOX | 33.947 | Undetermined | Undetermined | Undetermined | N/A | N/A | N/A | 15.243 |
| MERTK | 33.257 | Undetermined | 33.859 | 31.392 | 13.126 | 15.103 | N/A | 14.553 |
| MT1E | Undetermined | Undetermined | Undetermined | Undetermined | N/A | N/A | N/A | N/A |
| MT2A | 23.416 | 24.175 | 23.522 | 23.341 | 5.075 | 4.766 | 5.204 | 4.712 |
| NFKBIA | 22.744 | 22.909 | 23.016 | 22.914 | 4.648 | 4.260 | 3.938 | 4.040 |
| NR3C1 | 22.602 | 22.803 | 22.781 | 22.525 | 4.259 | 4.025 | 3.832 | 3.898 |
| PDCD7 | 23.859 | 24.858 | 24.113 | 23.750 | 5.484 | 5.357 | 5.887 | 5.155 |
| PDGFRB | Undetermined | Undetermined | 35.205 | Undetermined | N/A | 16.449 | N/A | N/A |
| PDP1 | 25.255 | 26.112 | 25.507 | 25.928 | 7.662 | 6.751 | 7.141 | 6.551 |
| PER1 | 24.612 | 24.926 | 24.973 | 25.007 | 6.741 | 6.217 | 5.955 | 5.908 |
| PER2 | 23.794 | 24.371 | 24.403 | 24.767 | 6.501 | 5.647 | 5.400 | 5.090 |
| PIK3R1 | 23.210 | 23.440 | 23.615 | 23.627 | 5.361 | 4.859 | 4.469 | 4.506 |
| PLD1 | Undetermined | Undetermined | Undetermined | Undetermined | N/A | N/A | N/A | N/A |
| PLEKHF1 | 27.292 | 27.868 | 27.684 | 28.448 | 10.182 | 8.928 | 8.897 | 8.588 |
| POU2F1 | 23.799 | 24.224 | 23.866 | 23.951 | 5.685 | 5.110 | 5.253 | 5.095 |
| POU2F2 | 21.502 | 21.920 | 21.841 | 21.890 | 3.624 | 3.085 | 2.949 | 2.798 |
| RASA3 | 22.754 | 23.207 | 22.984 | 23.225 | 4.959 | 4.228 | 4.236 | 4.050 |
| RGS2 | 24.883 | 25.145 | 24.670 | 24.812 | 6.546 | 5.914 | 6.174 | 6.179 |
| RHOB | 30.760 | 32.584 | 30.084 | 31.155 | 12.889 | 11.328 | 13.613 | 12.056 |
| RHOJ | Undetermined | Undetermined | 38.493 | Undetermined | N/A | 19.737 | N/A | N/A |
| SESN1 | 22.189 | Undetermined | 25.195 | 26.963 | 8.697 | 6.439 | N/A | 3.485 |
| SGK1 | 25.886 | 25.808 | 26.513 | 25.449 | 7.183 | 7.757 | 6.837 | 7.182 |
| SLC10A6 | 37.655 | 34.857 | 34.336 | 38.026 | 19.760 | 15.580 | 15.886 | 18.951 |
| SLC19A2 | 26.295 | 27.465 | 26.633 | 27.755 | 9.489 | 7.877 | 8.494 | 7.591 |
| SLC22A5 | 27.847 | 28.544 | 27.725 | 28.010 | 9.744 | 8.969 | 9.573 | 9.143 |
| SNTA1 | 24.008 | 24.797 | 24.422 | 24.779 | 6.513 | 5.666 | 5.826 | 5.304 |
| SPHK1 | 29.372 | 30.619 | 29.007 | 29.583 | 11.317 | 10.251 | 11.648 | 10.668 |
| SPSB1 | 25.736 | 26.495 | 25.588 | 25.722 | 7.456 | 6.832 | 7.524 | 7.032 |
| STAT5A | 24.652 | 25.174 | 24.761 | 24.858 | 6.592 | 6.005 | 6.203 | 5.948 |
| STAT5B | 21.986 | 22.153 | 21.908 | 21.716 | 3.450 | 3.152 | 3.182 | 3.282 |
| TBL1XR1 | 20.756 | 20.805 | 20.855 | 20.821 | 2.555 | 2.099 | 1.834 | 2.052 |
| TNF | 27.723 | 29.337 | 29.509 | 31.477 | 13.211 | 10.753 | 10.366 | 9.019 |
| TNFAIP3 | 28.965 | 28.521 | 27.807 | 26.978 | 8.712 | 9.051 | 9.550 | 10.261 |
| TSC22D3 | 21.819 | 21.432 | 23.384 | 22.896 | 4.630 | 4.628 | 2.461 | 3.115 |
| USP2 | 20.842 | 21.342 | 22.120 | 22.318 | 4.052 | 3.364 | 2.371 | 2.138 |
| USP54 | 26.333 | 26.952 | 33.990 | 27.307 | 9.041 | 15.234 | 7.981 | 7.629 |
| VDR | 27.497 | 28.330 | 26.956 | 28.621 | 10.355 | 8.200 | 9.359 | 8.793 |
| VLDLR | 30.410 | 28.792 | 27.824 | 26.896 | 8.630 | 9.068 | 9.821 | 11.706 |
| XDH | Undetermined | Undetermined | Undetermined | Undetermined | N/A | N/A | N/A | N/A |
| ZFP36 | 24.716 | 24.706 | 24.770 | 24.542 | 6.276 | 6.014 | 5.735 | 6.012 |
| ZHX3 | 24.009 | 24.719 | 24.325 | 24.882 | 6.616 | 5.569 | 5.748 | 5.305 |
| ZNF281 | 23.423 | 23.881 | 23.813 | 23.935 | 5.669 | 5.057 | 4.910 | 4.719 |
| ACTB | 13.717 | 14.247 | 14.284 | 14.272 | -3.994 | -4.472 | -4.724 | -4.987 |
| B2M | 18.704 | 18.971 | 18.756 | 18.266 | 0.000 | 0.000 | 0.000 | 0.000 |
| GAPDH | 15.435 | 15.835 | 15.790 | 15.782 | -2.484 | -2.966 | -3.136 | -3.269 |
| HPRT1 | 21.349 | 21.358 | 21.582 | 21.214 | 2.948 | 2.826 | 2.387 | 2.645 |
| RPLP0 | 15.192 | 15.469 | 15.266 | 15.194 | -3.072 | -3.490 | -3.502 | -3.512 |
| HGDC | Undetermined | Undetermined | Undetermined | Undetermined | N/A | N/A | N/A | N/A |
| RTC | 21.372 | 21.163 | 21.388 | 21.673 | 3.407 | 2.632 | 2.192 | 2.668 |
| RTC | 21.441 | 21.008 | 21.369 | 21.554 | 3.288 | 2.613 | 2.037 | 2.737 |
| RTC | 21.504 | 21.137 | 21.357 | 21.500 | 3.234 | 2.601 | 2.166 | 2.800 |
| PPC | 18.529 | 18.295 | 18.338 | 18.368 | 0.102 | -0.418 | -0.676 | -0.175 |
| PPC | 18.544 | 18.326 | 19.432 | 18.405 | 0.139 | 0.676 | -0.645 | -0.160 |
| PPC | 18.784 | 18.935 | 18.081 | 18.679 | 0.413 | -0.675 | -0.036 | 0.080 |

| Gene | Cpd44 | | Pred | | Combo | |
|---|---|---|---|---|---|---|
| | ΔΔCT | Fold Change | ΔΔCT | Fold Change | ΔΔCT | Fold Change |
| ADARB1 | -1.229 | 2.344 | -0.516 | 1.430 | -1.115 | 2.166 |
| AFF1 | -0.276 | 1.211 | -0.429 | 1.346 | 0.394 | 0.761 |
| AK2 | -0.570 | 1.485 | -1.076 | 2.108 | -1.259 | 2.393 |
| AMPD3 | -1.449 | 2.730 | -0.891 | 1.854 | -0.943 | 1.923 |
| ANGPTL4 | -1.331 | 2.516 | -1.047 | 2.066 | -0.841 | 1.791 |
| ANXA4 | -2.419 | 5.348 | -0.890 | 1.853 | -2.493 | 5.629 |
| AQP1 | 0.331 | 0.795 | N/A | N/A | N/A | N/A |
| ARID5B | -0.541 | 1.455 | -0.131 | 1.095 | 0.127 | 0.916 |
| ASPH | -0.843 | 1.794 | -0.451 | 1.367 | -0.914 | 1.884 |
| ATF4 | 0.146 | 0.904 | -0.279 | 1.213 | 0.533 | 0.691 |
| BCL6 | -1.019 | 2.027 | -0.793 | 1.733 | -1.080 | 2.114 |
| BMPER | N/A | N/A | N/A | N/A | N/A | N/A |
| CALCR | N/A | N/A | N/A | N/A | N/A | N/A |
| CEBPA | -2.510 | 5.696 | -0.301 | 1.232 | -2.403 | 5.289 |
| CEBPB | 0.776 | 0.584 | 0.528 | 0.694 | 1.391 | 0.381 |
| COL4A2 | N/A | N/A | N/A | N/A | N/A | N/A |
| CREB1 | -0.313 | 1.242 | -0.548 | 1.462 | -0.348 | 1.273 |

TABLE 4f-continued

Ct values and fold changes from the RT2 Glucocorticoid signaling PCR array analysis for SUDHL4 cell line.

| | | | | | | |
|---|---|---|---|---|---|---|
| CREB3 | −0.490 | 1.404 | −0.560 | 1.474 | −0.529 | 1.443 |
| CREB3L4 | −0.655 | 1.575 | −0.199 | 1.148 | −0.312 | 1.241 |
| CTGF | N/A | N/A | N/A | N/A | N/A | N/A |
| CYB561 | −4.236 | 18.844 | −0.720 | 1.647 | −3.197 | 9.170 |
| DDIT4 | −1.317 | 2.491 | −1.931 | 3.813 | −1.872 | 3.660 |
| DIRAS2 | N/A | N/A | N/A | N/A | N/A | N/A |
| DUSP1 | −0.449 | 1.365 | −1.093 | 2.133 | −0.715 | 1.641 |
| EDN1 | N/A | N/A | N/A | N/A | N/A | N/A |
| EHD3 | −1.998 | 3.994 | −1.325 | 2.505 | −2.526 | 5.760 |
| ERRFI1 | N/A | N/A | N/A | N/A | N/A | N/A |
| FKBP5 | 0.008 | 0.994 | −1.582 | 2.994 | −1.276 | 2.422 |
| FOSL2 | N/A | N/A | N/A | N/A | N/A | N/A |
| GDPD1 | −1.356 | 2.560 | −0.409 | 1.328 | −0.918 | 1.889 |
| GHRHR | N/A | N/A | 0.184 | 0.880 | −0.859 | 1.814 |
| GLUL | N/A | N/A | N/A | N/A | N/A | N/A |
| GOT1 | 0.065 | 0.956 | −0.402 | 1.321 | −0.342 | 1.268 |
| H6PD | −0.549 | 1.463 | 0.160 | 0.895 | −0.107 | 1.077 |
| HAS2 | N/A | N/A | N/A | N/A | N/A | N/A |
| HNRPLL | −0.471 | 1.386 | −0.286 | 1.219 | −0.329 | 1.256 |
| IL10 | −1.895 | 3.719 | −0.130 | 1.094 | −0.752 | 1.684 |
| IL1RN | N/A | N/A | N/A | N/A | N/A | N/A |
| IL6 | N/A | N/A | N/A | N/A | N/A | N/A |
| IL6R | −1.903 | 3.740 | −0.524 | 1.438 | −1.239 | 2.360 |
| KLF13 | −0.534 | 1.448 | −0.934 | 1.911 | −1.060 | 2.085 |
| KLF9 | −1.293 | 2.450 | −0.821 | 1.767 | −1.194 | 2.288 |
| LOX | N/A | N/A | N/A | N/A | N/A | N/A |
| MERTK | 1.977 | 0.254 | N/A | N/A | 1.427 | 0.372 |
| MT1E | N/A | N/A | N/A | N/A | N/A | N/A |
| MT2A | −0.309 | 1.239 | 0.129 | 0.914 | −0.363 | 1.286 |
| NFKBIA | −0.388 | 1.309 | −0.710 | 1.636 | −0.608 | 1.524 |
| NR3C1 | −0.234 | 1.176 | −0.427 | 1.344 | −0.361 | 1.284 |
| PDCD7 | −0.127 | 1.092 | 0.403 | 0.756 | −0.329 | 1.256 |
| PDGFRB | N/A | N/A | N/A | N/A | N/A | N/A |
| PDP1 | −0.911 | 1.880 | −0.521 | 1.435 | −1.111 | 2.160 |
| PER1 | −0.524 | 1.438 | −0.786 | 1.724 | −0.833 | 1.781 |
| PER2 | −0.854 | 1.808 | −1.101 | 2.145 | −1.411 | 2.659 |
| PIK3R1 | −0.502 | 1.416 | −0.892 | 1.856 | −0.855 | 1.809 |
| PLD1 | N/A | N/A | N/A | N/A | N/A | N/A |
| PLEKHF1 | −1.254 | 2.385 | −1.285 | 2.437 | −1.594 | 3.019 |
| POU2F1 | −0.575 | 1.490 | −0.432 | 1.349 | −0.590 | 1.505 |
| POU2F2 | −0.539 | 1.453 | −0.675 | 1.597 | −0.826 | 1.773 |
| RASA3 | −0.731 | 1.660 | −0.723 | 1.651 | −0.909 | 1.878 |
| RGS2 | −0.632 | 1.550 | −0.372 | 1.294 | −0.367 | 1.290 |
| RHOB | −1.561 | 2.951 | 0.724 | 0.605 | −0.833 | 1.781 |
| RHOJ | N/A | N/A | N/A | N/A | N/A | N/A |
| SESN1 | −2.258 | 4.783 | N/A | N/A | −5.212 | 37.065 |
| SGK1 | 0.574 | 0.672 | −0.346 | 1.271 | −0.001 | 1.001 |
| SLC10A6 | −4.180 | 18.126 | −3.874 | 14.662 | −0.809 | 1.752 |
| SLC19A2 | −1.612 | 3.057 | −0.995 | 1.993 | −1.898 | 3.727 |
| SLC22A5 | −0.775 | 1.711 | −0.171 | 1.126 | −0.601 | 1.517 |
| SNTA1 | −0.847 | 1.799 | −0.687 | 1.610 | −1.209 | 2.312 |
| SPHK1 | −1.066 | 2.094 | 0.331 | 0.795 | −0.649 | 1.568 |
| SPSB1 | −0.624 | 1.541 | 0.068 | 0.954 | −0.424 | 1.342 |
| STAT5A | −0.587 | 1.502 | −0.389 | 1.309 | −0.644 | 1.563 |
| STAT5B | −0.298 | 1.229 | −0.268 | 1.204 | −0.168 | 1.123 |
| TBL1XR1 | −0.456 | 1.372 | −0.721 | 1.648 | −0.503 | 1.417 |
| TNF | −2.458 | 5.495 | −2.845 | 7.185 | −4.192 | 18.278 |
| TNFAIP3 | 0.339 | 0.791 | 0.838 | 0.559 | 1.549 | 0.342 |
| TSC22D3 | −0.002 | 1.001 | −2.169 | 4.497 | −1.515 | 2.858 |
| USP2 | −0.688 | 1.611 | −1.681 | 3.207 | −1.914 | 3.769 |
| USP54 | 6.193 | 0.014 | −1.060 | 2.085 | −1.412 | 2.661 |
| VDR | −2.155 | 4.454 | −0.996 | 1.994 | −1.562 | 2.953 |
| VLDLR | 0.438 | 0.738 | 1.191 | 0.438 | 3.076 | 0.119 |
| XDH | N/A | N/A | N/A | N/A | N/A | N/A |
| ZFP36 | −0.262 | 1.199 | −0.541 | 1.455 | −0.264 | 1.201 |
| ZHX3 | −1.047 | 2.066 | −0.868 | 1.825 | −1.311 | 2.481 |
| ZNF281 | −0.612 | 1.528 | −0.759 | 1.692 | −0.950 | 1.932 |
| ACTB | | | | | | |
| B2M | | | | | | |
| GAPDH | | | | | | |
| HPRT1 | | | | | | |
| RPLP0 | | | | | | |

TABLE 4f-continued

Ct values and fold changes from the RT2 Glucocorticoid signaling PCR array analysis for SUDHL4 cell line.

HGDC
RTC
RTC
RTC
PPC
PPC
PPC

Example 3: Inhibition of EZH2 Overcomes Resistance to Sunitinib in Clear Cell Renal Cell Carcinoma Models Alterations in epigenetic mechanisms including histone modification and hypermethylation at gene promoter regions have been implicated as mechanisms of drug resistance in cancer. Alternation of epigenetic regulators such histone methyltransferase, EZH2, has been reported in numerous cancer types including advanced renal cell carcinoma (RCC). Previous studies suggest that sunitinib may have a direct anti-tumor effect and that acquired sunitinib resistance may be induced in tumor cells rather than just in endothelial cells. In this study, the role of EZH2 was investigated in sunitinib resistance in clear cell renal cell carcinoma.

Methods:

Human RCC cell lines 786-0 were treated and exposed to increasing concentrations of sunitinib to develop a resistant cell line, 786-0R. Parental and resistant cell lines were treated with either sunitinib, GSK126 (EZH2 inhibitor) or both. In parallel, EZH2 was knocked down in 786-0 cells and exposed to increasing concentrations of sunitinib. Cell viability was quantitated by absorbance of crystal violet stained cells using a spectrometer at 570 nm. In a second set of experiments, control and treated cells were collected for western analysis. Mice bearing human ccRCC patient derived xenograft (PDXs); RP-R-01, RP-R-02 and RP-R-02LM (a metastatic ccRCC model established from RP-R-02) were implanted into SCID mice. When tumors reached an average volume of 50 mm$^3$, mice were randomly grouped into 2 arms; control, sunitinib treatment (40 mg/kg, 5 days/week) or EZH2i EPZ011989 (500 mg/kg, 2×/day, 5 days/week). Tumors volumes and body weight were assessed once per week. Tumor tissues and lungs were collected for immunohistochemistry analysis. All assessments and quantification were done blindly.

Results:

The in vitro and in vivo data showed an increased expression of EZH2 with resistance to sunitinib. Furthermore, inhibition of EZH2 in the in vitro and in vivo studies correlated with a significant increase in the anti-tumor effect of sunitinib in both parental and resistant cell lines.

CONCLUSION

Overall, the data suggest the potential role of epigenetic alterations, specifically EZH2 overexpression and its association with resistance to sunitinib.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for treating clear cell renal cell carcinoma in a patient in need thereof comprising administering a therapeutically effective amount of an EZH2 inhibitor and one or more tyrosine kinase inhibitors, wherein the EZH2 inhibitor is GSK-126 having the following formula:

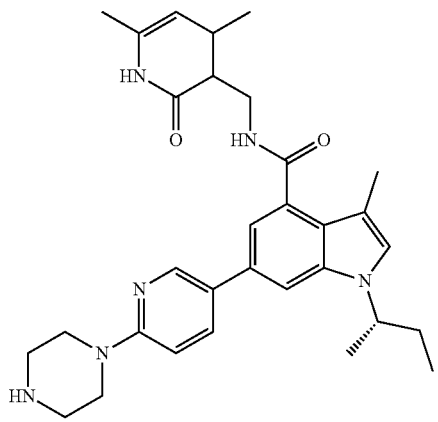

(GSK-126)

or a pharmaceutically acceptable salt thereof; or
a compound of Formula (I):

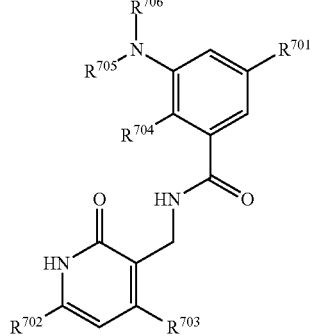

(I)

or a pharmaceutically acceptable salt thereof;
wherein:
$R^{701}$ is H, F, $OR^{707}$, $NHR^{707}$, —(C≡C)—$(CH_2)_{n7}$-$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl alkyl;

each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo;

each of $R^{704}$ and $R^{705}$, independently is $C_{1-4}$ alkyl;

$R^{706}$ is cyclohexyl substituted by $N(C_{1-4}$ alkyl$)_2$ wherein one or both of the $C_{1-4}$ alkyl is substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and n7 is 0, 1 or 2.

2. The method of claim 1, wherein the clear cell renal cell carcinoma is resistant to tyrosine kinase inhibitor treatment.

3. The method of claim 2, wherein the one or more tyrosine kinase inhibitors are VEGF/VEGFR inhibitors.

4. A method for treating renal cell carcinoma in a patient in need thereof comprising administering a therapeutically effective amount of an EZH2 inhibitor and one or more VEGF/VEGFR inhibitors, wherein the EZH2 inhibitor is GSK-126 having the following formula:

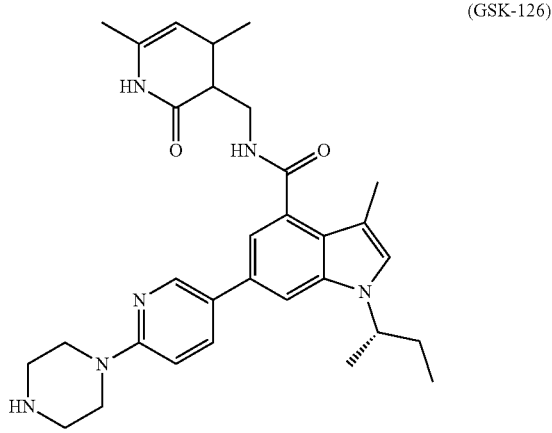 [SMILES: CC[C@H](C)n1cc(C)c2c(C(=O)NCC3C(=O)NC(C)=CC3C)cc(-c3ccc(N4CCNCC4)nc3)cc21]

(GSK-126)

or a pharmaceutically acceptable salt thereof;
or
a compound of Formula (I):

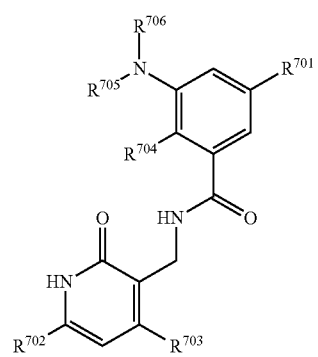

(I)

or a pharmaceutically acceptable salt thereof;
wherein:
$R^{701}$ is H, F, $OR^{707}$, $NHR^{707}$, —(C≡C)—(CH$_2$)$_{n7}$-$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl;
each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo;
each of $R^{704}$ and $R^{705}$, independently is $C_{1-4}$ alkyl;
$R^{706}$ is cyclohexyl substituted by N($C_{1-4}$ alkyl)$_2$ wherein one or both of the $C_{1-4}$ alkyl is substituted with $C_{1-6}$ alkoxy; or $R^{706}$ is tetrahydropyranyl;
$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;
$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and
n7 is 0, 1 or 2.

5. The method of claim 4, wherein the renal cell carcinoma is resistant to VEGF/VEGFR inhibitor treatment.

6. The method of claim 1, wherein the EZH2 inhibitor is Compound 44 having the following formula:

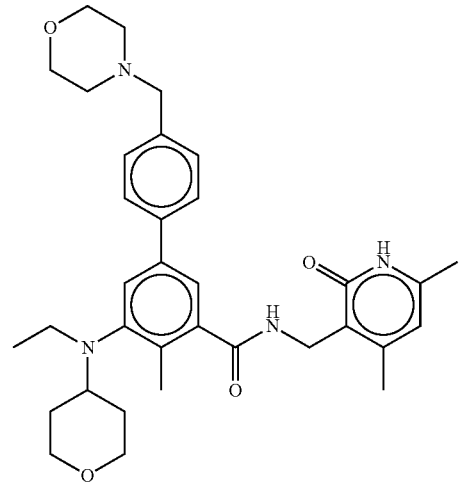

(Compound 44)

or pharmaceutically acceptable salt thereof.

7. The method of claim 1, wherein the EZH2 inhibitor is:

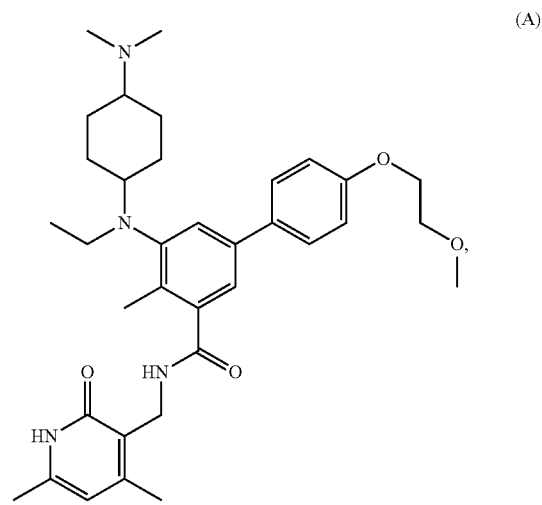

(A)

-continued (B)

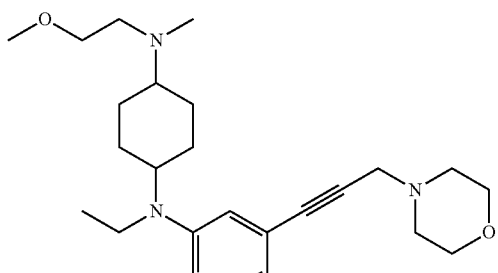

or (C)

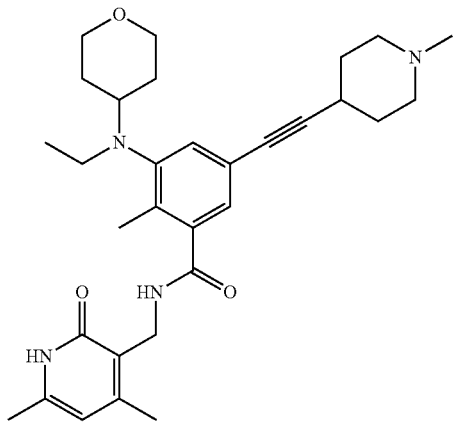

or pharmaceutically acceptable salt thereof.

8. The method of claim 1, wherein the EZH2 inhibitor is GSK-126.

9. The method of claim 1, wherein the one or more tyrosine kinase inhibitors are selected from erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; and AMG888.

10. The method of claim 1, wherein the one or more tyrosine kinase inhibitors include sunitinib.

11. The method of claim 4, wherein the one or more VEGF/VEGFR inhibitors are selected from bevacizumab (Avastin); sorafenib (Nexavar);
sunitinib (Sutent); ranibizumab; pegaptanib; vandetinib; E7080; Zd6474; PKC-412; Vatalanib (Ptk787 or ZK222584); and motesanib diphosphate.

12. The method of claim 4, wherein the one or more VEGF/VEGFR inhibitors include sunitinib.

13. The method of claim 1, wherein the EZH2 inhibitor and the one or more tyrosine kinase inhibitors are administered simultaneously or sequentially.

14. The method of claim 1, wherein the EZH2 inhibitor is administered prior to administration of the one or more tyrosine kinase inhibitors.

15. The method of claim 4, wherein the EZH2 inhibitor and the one or more VEGF/VEGFR inhibitors are administered simultaneously or sequentially.

16. The method of claim 4, wherein the EZH2 inhibitor is administered prior to administration of the one or more VEGF/VEGFR inhibitors.

17. The method of claim 4, wherein the renal cell carcinoma is clear cell renal cell carcinoma.

18. The method of claim 4, wherein the EZH2 inhibitor is Compound 44 having the following formula:

(Compound 44)

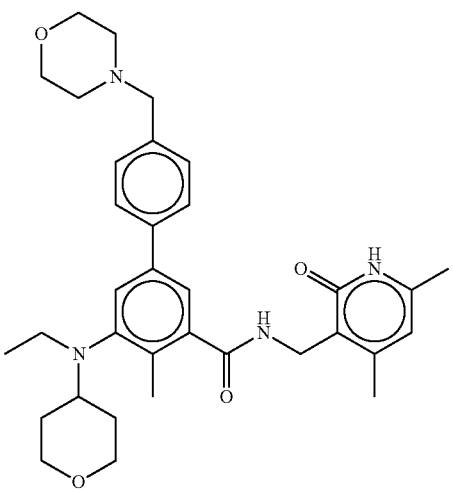

or pharmaceutically acceptable salt thereof.

19. The method of claim 4, wherein the EZH2 inhibitor is:

(A)

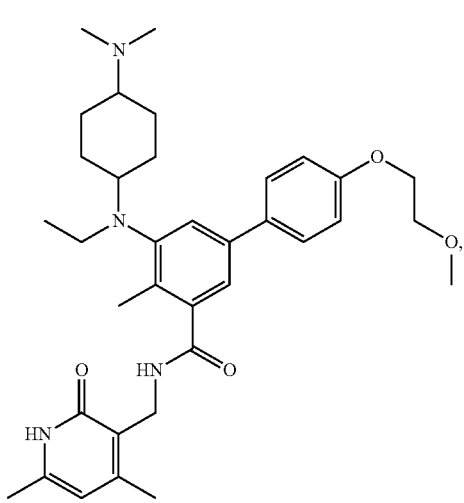

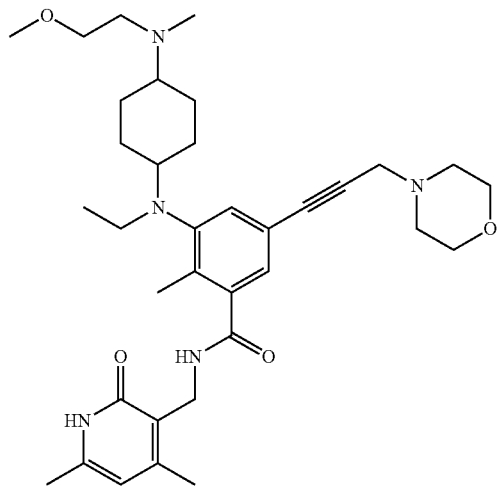
(B)
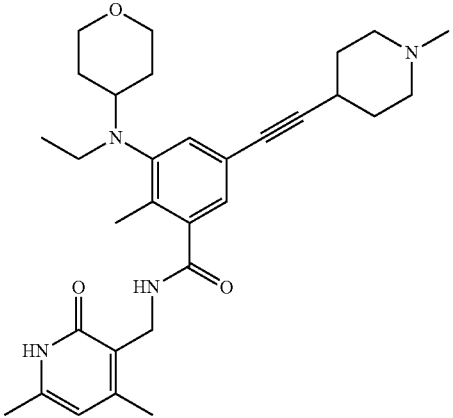
(C)
or pharmaceutically acceptable salt thereof.
20. The method of claim 4, wherein the EZH2 inhibitor is GSK-126.
* * * * *

UNITED STATES PATENT AND TRADEMARK OFFICE
CERTIFICATE OF CORRECTION

PATENT NO. : 11,026,949 B2
APPLICATION NO. : 16/562683
DATED : June 8, 2021
INVENTOR(S) : Heike Keilhack et al.

It is certified that error appears in the above-identified patent and that said Letters Patent is hereby corrected as shown below:

In the Claims

At Column 196, Claim number 1, Line number 31, replace:
"with O-$C_{1-3}$ alkyl or NH-$C_{1-3}$ alkyl alkyl;"
With:
--with O-$C_{1-3}$ alkyl or NH-$C_{1-3}$ alkyl;--

At Column 196, Claim number 1, Line number 56, replace:
"n7 is 0, 1 or 2."
With:
--$n_7$ is 0, 1 or 2.--

At Column 198, Claim number 4, Line number 12, replace:
"n7 is 0, 1 or 2."
With:
--$n_7$ is 0, 1 or 2.--

Signed and Sealed this
Nineteenth Day of April, 2022

Katherine Kelly Vidal
*Director of the United States Patent and Trademark Office*